US011859191B2

(12) United States Patent
Flasinski et al.

(10) Patent No.: US 11,859,191 B2
(45) Date of Patent: Jan. 2, 2024

(54) COMPOSITIONS AND METHODS FOR GENOME EDITING IN PLANTA

(71) Applicant: Monsanto Technology LLC, St. Louis, MO (US)

(72) Inventors: Stanislaw Flasinski, Ballwin, MO (US); Elysia Krieger, Kirkwood, MO (US); Ervin Nagy, Lake Saint Louis, MO (US); Krishnakumar Sridharan, Cary, NC (US); Xudong Ye, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 17/817,196

(22) Filed: Aug. 3, 2022

(65) Prior Publication Data

US 2023/0193302 A1    Jun. 22, 2023

Related U.S. Application Data

(63) Continuation of application No. 16/563,581, filed on Sep. 6, 2019, now Pat. No. 11,414,669.

(60) Provisional application No. 62/727,784, filed on Sep. 6, 2018.

(51) Int. Cl.
*C12N 15/82* (2006.01)

(52) U.S. Cl.
CPC ..... *C12N 15/8213* (2013.01); *C12N 15/8205* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| 7,022,896 | B1 | 4/2006 | Weeks et al. |
| 9,938,535 | B2 | 4/2018 | Chittoor et al. |
| 2009/0029861 | A1 | 1/2009 | Feng et al. |
| 2014/0283200 | A1 | 9/2014 | Chittoor et al. |
| 2017/0166912 | A1 | 6/2017 | Brower-toland et al. |
| 2018/0105823 | A1 | 4/2018 | Flasinski |

FOREIGN PATENT DOCUMENTS

| WO | 9741228 | A2 | 11/1997 | |
| WO | 2015131101 | A1 | 9/2015 | |
| WO | 2018138385 | A1 | 8/2018 | |
| WO | WO-2018138385 | A1 * | 8/2018 | ............. A61P 35/00 |
| WO | 2019084148 | A1 | 5/2019 | |

OTHER PUBLICATIONS

Gao, Linyi, et al. "Engineered Cpf1 variants with altered PAM specificities." Nature biotechnology 35.8 (2017): 789-792. (Year: 2017 ).*
Begemann, M. B. et al. (e-pub Sep. 14, 2017). "Precise Insertion and Guided Editing of Higher Plant Genomes Using Cpf1 CRISPR Nucleases," Scientific Reports 7:11606, 6 pages.
Chandrashekhar, P. J. et al. (1997). "Context Sequences of Translation Initiation Codon in Plants," Plant Molecular Biology 35:993-1001.
Christensen, A. J. et al. (1996). "Ubiquitin Promoter-Based Vectors for High-Level Expression of Selectable and/or Screenable Marker Genes in Monocotyledonous Plants," Transgenic Research 5:213-218.
Endo, A. et al. (Dec. 1, 2016). "Efficient Targeted Mutagenesis of Rice and Tobacco Genomes Using Cpf1 from Francisella Novicida," Scientific Reports 6:38169, 9 pages.
Gao, L. et al. (Aug. 2017). "Engineered Cpf1 Variants with Altered PAM Specificities," Nature biotechnology 35(8)789-792.
Kim, G. B. et al. (2013). "Isolation and Characterization of Medicago Truncatula U6 Promoters for the Construction of Small Hairpin RNA-Mediated Gene Silencing Vectors," Plant Molecular Biology 31:581-593.
Misawa, N. et al. (Nov. 1993). "Functional Expression of the Erwinia Uredovora Carotenoid Biosynthesis Gene Crtl In Transgenic Plants Showing an Increase of Beta-carotene Biosynthesis Activity and Resistance to the Bleaching Heroicide Norflurazon," The Plant Journal 4(5) 833-840.
Sahoo, D. K. et al. (2015). "Analysis of Dahlia Mosaic Virus Full-length Transcript Promoter-Driven Gene Expression in Transgenic Plants," Plant Molecular Biology 33:178-199.
Scharf, K. D. et al. (Apr. 1998). "The Tomato Hsf System: HsfA2 Needs Interaction with HsfA1 for Efficient Nuclear Import and May Be Localized in Cytoplasmic Heat Stress Granules, "Molecular and Cellular Biology 18(4):2240-2251.
Takebe, Y. et al. (Jan. 1988). "SR Alpha Promoter: An Efficient and Versatile Mammalian CDNA Expression System Composed of the Simian Virus 40 Early Promoter and the R-U5 Segment of human T-cell Leukemia virus type Long Terminal Repeat," Molecular and Cellular Biology 8(1):466-472.
Tang, X. et al. (Feb. 17, 2017). "A CRISPR-Cpf1 System for Efficient Genome Editing and Transcriptional Repression in Plants," Nature Plants 3:17018, 22 pages.
Thompson, J.D. (Nov. 11, 1994). "Clustal W: Improving the Sensitivity of Progressive Multiple Sequence Alignment Through Sequence Weighting, Position-Specific Gap Penalties and Weight Matrix Choice," Nucleic Acids Res. 22(22):4673-4680.
Xu, R. et al. (2017). "Generation of Targeted Mutant Rice Using a CRISPR-Cpf1 System," Plant Biotechnology Journal 15:713-717.

(Continued)

*Primary Examiner* — Weihua Fan
*Assistant Examiner* — Brian James Sullivan
(74) *Attorney, Agent, or Firm* — Morrison & Foerster LLP

(57) ABSTRACT

This disclosure is related to plant-optimized recombinant nucleic acids encoding Cpf1 and their use in planta. Also disclosed are compositions, expression cassettes, and plant cells comprising the recombinant nucleic acids as well as methods and kits for modifying a target sequence in a plant genome using the recombinant nucleic acids.

20 Claims, 2 Drawing Sheets

Specification includes a Sequence Listing.

(56) References Cited

OTHER PUBLICATIONS

Yang, L. et al. (2009). "The 3'-untranslated Region of Rice Glutelin GluB-1 Affects Accumulation of Heterologous Protein in Transgenic Rice," Biotechnology Letters 31:1625-1631.

Zetsche, B. et al. (Oct. 22, 2015). "Cpf1 Is A Single RNA-Guided Endonuclease Of A Class 2 CRISPR-Cas System," Cell 163:759-771.

* cited by examiner

COMPOSITIONS AND METHODS FOR GENOME EDITING IN PLANTA

CROSS-REFERENCE TO RELATED APPLICATIONS

This application is a continuation of U.S. patent application Ser. No. 16/563,581, filed Sep. 6, 2019, which claims the benefit of U.S. Provisional Application No. 62/727,784, filed Sep. 6, 2018, which are thereby incorporated by reference in their entirety herein.

INCORPORATION OF SEQUENCE LISTING

A sequence listing contained in the file named 777052058701SUBSEQLIST.xml, which is 339,611 bytes (measured in MS Windows®) and created on Oct. 14, 2022, and comprises 76 sequences, is filed electronically herewith and incorporated by reference in its entirety.

FIELD

This disclosure relates to plant-optimized recombinant nucleic acids encoding Cpf1 and their use in planta.

BACKGROUND

Clustered Regularly Interspaced Short Palindromic Repeats from *Prevotella* and *Francisella* 1 or CRISPR/Cpf1 (also known as Cas12a) was first demonstrated for genome editing in mammalian cells in 2015 (Zetsche et al., 2015, Cell 163, 759-771). Cpf1 (CRISPR from *Prevotella* and *Francisella* 1) is a large, 1,300 amino acid protein, belonging to class 2 CRISPR system. Different from Cas9 nuclease, the PAM motif of Cpf1 is located at 5' of the target site and the mature gRNA is a single strand of approximately 44 bp.

Cpf1 genome editing in plants was first observed in rice (Xu et al., 2017, Plant Biotechnology Journal 15, 713-717), where up to 41% mutation rate was achieved at OsBel locus using pre-crRNA gRNA structure and LbCpf1. Subsequently, Cpf1 genome editing of rice and tobacco were observed in different laboratories using both LbCpf1 and FnCpf1 (Endo et al., Scientific Reports volume 6, Article number: 38169 (2016); Hu et al., 2017, Journal of Genetics and Genomics 44, 71-73; Tang et al., Nature Plants volume 3, Article number: 17018 (2017); Begemann et al., 2017, Sci Rep. 7, 11606). However, there remains a need for more effective Cpf1-based genome editing technologies in plants.

SUMMARY

Several embodiments relate to a recombinant nucleic acid comprising a sequence selected from the group consisting of: SEQ ID NOs 1, 10, 38, 45-51 and 75. In some embodiments, the recombinant nucleic acid further comprises a nucleic acid sequence encoding one or more nuclear localization signals operably linked to the recombinant nucleic acid comprising a sequence selected from the group consisting of: SEQ ID NOs 1, 10, 38, 45-51 and 75. In some embodiments, the nuclear localization signal is provided on the 5' end of Cpf1. In some embodiments, the nuclear localization signal is provided on the 3' end of Cpf1. In some embodiments, the nuclear localization signal is provided on the 5' and 3' end of Cpf1. In some embodiments, the recombinant nucleic acid further comprises a promoter operably linked to the recombinant nucleic acid comprising a sequence selected from the group consisting of: SEQ ID NOs 1, 10, 38, 45-51 and 75. In some embodiments, the promoter comprises a sequence selected from the group consisting of SEQ ID NOs 7, 22, 27, and 32. In some embodiments, the recombinant nucleic acid further comprising one or more of an intron, a kozak sequence, a leader sequence and a terminator sequence. Several embodiments relate to a recombinant nucleic acid comprising a sequence selected from the group consisting of SEQ ID NOs 4, 6, 12, 14, 41, 63, 66, 68, 70, and 72.

Several embodiments relate to a plant cell comprising a recombinant nucleic acid comprising a sequence selected from the group consisting of: SEQ ID NOs 1, 10, 38, 45-51 and 75. Several embodiments relate to a plant cell comprising a recombinant nucleic acid comprising a nucleic acid sequence encoding one or more nuclear localization signals operably linked to the recombinant nucleic acid comprising a sequence selected from the group consisting of: SEQ ID NOs 1, 10, 38, 45-51 and 75. In some embodiments, the nuclear localization signal is provided on the 5' end of Cpf1. In some embodiments, the nuclear localization signal is provided on the 3' end of Cpf1. In some embodiments, the nuclear localization signal is provided on the 5' and 3' end of Cpf1. Several embodiments relate to a plant cell comprising a promoter operably linked to a recombinant nucleic acid comprising a sequence selected from the group consisting of: SEQ ID NOs 1, 10, 38, 45-51 and 75, and optionally one or more nuclear localization signals, an intron, a kozak sequence, a leader sequence and a terminator sequence. In some embodiments, the promoter comprises a sequence selected from the group consisting of SEQ ID NOs 7, 22, 27, and 32. Several embodiments relate to a plant cell comprising recombinant nucleic acid comprising a sequence selected from the group consisting of SEQ ID NOs 4, 6, 12, 14, 41, 63, 66, 68, 70, and 72. In some embodiments, the plant cell is a monocot or a dicot. In some embodiments, the plant cell is a maize, cotton, soybean, canola, wheat, tomato, rice, brassica, melon, cucurbit, or lettuce cell.

Several embodiments relate to an expression cassette comprising a recombinant nucleic acid sequence selected from the group consisting of SEQ ID NOs 15, 20, 26, 31, 36, 40, 56, 59, 65, 67, 69, 71, and 73. Several embodiments relate to a plant cell comprising an expression cassette comprising a recombinant nucleic acid sequence selected from the group consisting of SEQ ID NOs 15, 20, 26, 31, 36, 40, 56, 59, 65, 67, 69, 71, and 73. Several embodiments relate to an *Agrobacterium* T-DNA vector comprising an expression SEQ ID NOs 15, 20, 26, 31, 36, 40, 56, 59, 65, 67, 69, 71, and 73. Several embodiments relate to an *Agrobacterium* cell comprising an *Agrobacterium* T-DNA vector comprising an expression SEQ ID NOs 15, 20, 26, 31, 36, 40, 56, 59, 65, 67, 69, 71, and 73. In some embodiments, the *Agrobacterium* T-DNA vector further comprises an expression cassette for a selectable marker gene. In some embodiments, the *Agrobacterium* T-DNA vector further comprising a promoter operably linked to a one or more crRNA sequences and one or more spacer sequences, where in the spacer sequence is complementary to at least 23 base pairs of a target site. In some embodiments, the crRNA sequence is a pre-crRNA or a mature crRNA.

Several embodiments relate to a composition comprising: (a) recombinant nucleic acid comprising a sequence selected from the group consisting of: SEQ ID NOs 1, 10, 38, 45-51 and 75, and (b) a recombinant nucleic acid encoding a guide RNA comprised of at least one crRNA and at least one spacer RNA sequence. Several embodiments relate to a composition comprising: (a) recombinant nucleic acid comprising a sequence selected from the group consisting of: SEQ ID NOs 6, 12, 14, 41, 63, 66, 68, 70, and 72, and (b) a recombinant nucleic acid encoding a guide RNA comprised of at least one crRNA and at least one spacer RNA sequence. In some embodiments, the composition is provided on a particle suitable for biolistic delivery to a plant cell.

Several embodiments relate to a method for modifying a target sequence in the genome of a plant cell, comprising: introducing into the plant cell a recombinant nucleic acid comprising a sequence selected from the group consisting of: SEQ ID NOs 1, 10, 38, 45-51 and 75 operably linked to a promoter, and introducing into the plant cell a guide polynucleotide comprising a nucleic acid sequence that is complementary to a target sequence or a recombinant nucleic acid encoding the guide polynucleotide, wherein the guide polynucleotide and a Cpf1 nuclease expressed from the recombinant nucleic acid comprising a sequence selected from the group consisting of: SEQ ID NOs 1, 10, 38, 45-51 and 75 form a complex that can bind to and modify the target sequence. Several embodiments relate to a method for modifying a target sequence in the genome of a plant cell, comprising: introducing into the plant cell a recombinant nucleic acid comprising a sequence selected from the group consisting of: SEQ ID NOs 1, 10, 38, 45-51 and 75 operably linked to a promoter, and introducing into the plant cell a guide polynucleotide comprising a nucleic acid sequence that is complementary to a target sequence or a recombinant nucleic acid encoding the guide polynucleotide, wherein the guide polynucleotide and a Cpf1 nuclease expressed from the recombinant nucleic acid comprising a sequence selected from the group consisting of: SEQ ID NOs 1, 10, 38, 45-51 and 75 form a complex that can bind to and modify the target sequence, wherein the recombinant nucleic acid comprising a sequence selected from the group consisting of: SEQ ID NOs 1, 10, 38, 45-51 and 75 is operably linked to a promoter comprising a sequence selected from the group consisting of SEQ ID NOs 7, 22, 27, and 32. In some embodiments, the method further comprises incubating the plant cell at temperatures between 24° C. and 35° C. for a period of at least about 1-8 hours. In some embodiments, the method further comprises incubating the plant cell at temperatures between 28° C. and 35° C. for a period of at least about 4 hours. In some embodiments, the plant cell is a monocot or a dicot. In some embodiments, the plant cell is a maize, cotton, soybean, canola, wheat, tomato, rice, *brassica*, melon, cucurbit, or lettuce cell. In some embodiments, the method further comprises introducing a donor DNA to the plant cell. In some embodiments, the method further comprises identifying at least one plant cell comprising in its genome the donor DNA, or a portion thereof, integrated into or near said target sequence.

Several embodiments relate to a method for modifying a target sequence in the genome of a plant cell, the method comprising: introducing a guide polynucleotide comprising a nucleic acid sequence that is substantially complementary to the target sequence, or a recombinant nucleic acid encoding the guide polynucleotide, into a plant cell comprising in its genome a recombinant nucleic acid comprising a sequence selected from the group consisting of: SEQ ID NOs 1, 10, 38, 45-51 and 75 operably linked to a promoter, wherein the guide polynucleotide and a Cpf1 nuclease expressed from the recombinant nucleic acid comprising a sequence selected from the group consisting of: SEQ ID NOs 1, 10, 38, 45-51 and 75 form a complex that can bind to and modify the target sequence. Several embodiments relate to a method for modifying a target sequence in the genome of a plant cell, the method comprising: introducing a guide polynucleotide comprising a nucleic acid sequence that is substantially complementary to the target sequence, or a recombinant nucleic acid encoding the guide polynucleotide, into a plant cell comprising in its genome a recombinant nucleic acid comprising a sequence selected from the group consisting of: SEQ ID NOs 1, 10, 38, 45-51 and 75 operably linked to a promoter comprising a sequence selected from the group consisting of SEQ ID NOs 7, 22, 27, and 32, wherein the guide polynucleotide and a Cpf1 nuclease expressed from the recombinant nucleic acid comprising a sequence selected from the group consisting of: SEQ ID NOs 1, 10, 38, 45-51 and 75 form a complex that can bind to and modify the target sequence. In some embodiments, the method further comprises incubating the plant cell at temperatures between 24° C. and 35° C. for a period of at least about 1-8 hours. In some embodiments, the method further comprises incubating the plant cell at temperatures between 28° C. and 35° C. for a period of at least about 4 hours. In some embodiments, the plant cell is a monocot or a dicot. In some embodiments, the plant cell is a maize, cotton, soybean, canola, wheat, tomato, rice, brassica, melon, cucurbit, or lettuce cell. In some embodiments, the method further comprises introducing a donor DNA to the plant cell. In some embodiments, the method further comprises identifying at least one plant cell comprising in its genome the donor DNA, or a portion thereof, integrated into or near said target sequence.

Several embodiments relate to a kit for modifying a target sequence in the genome of a plant cell, the kit comprising a guide polynucleotide comprising a nucleic acid sequence that is complementary to a target sequence or a recombinant nucleic acid encoding the guide polynucleotide, and recombinant nucleic acid comprising a sequence selected from the group consisting of: SEQ ID NOs 1, 10, 38, 45-51 and 75. Several embodiments relate to a kit for modifying a target sequence in the genome of a plant cell, the kit comprising a guide polynucleotide comprising a nucleic acid sequence that is complementary to a target sequence or a recombinant nucleic acid encoding the guide polynucleotide, and recombinant nucleic acid comprising a sequence selected from the group consisting of: SEQ ID NOs 4, 6, 7, 12, 14, 15, 20, 22, 26, 27, 31, 32, 36, 40, 41, 56, 59, 63, 65, 66, 67, 68, 69, 70, 71, 72 and 73. Several embodiments relate to a kit for modifying a target sequence in the genome of a plant cell, the kit comprising a guide polynucleotide comprising a nucleic acid sequence that is complementary to a target sequence or a recombinant nucleic acid encoding the guide polynucleotide, a recombinant nucleic acid comprising a sequence selected from the group consisting of: SEQ ID NOs 1, 4, 6, 7, 10, 12, 14, 15, 20, 22, 26, 27, 31, 32, 36, 40, 41, 56, 59, 63, 65, 66, 67, 68, 69, 70, 71, 72, 73 and 75, and a recombinant nucleic acid encoding a selectable marker.

BRIEF DESCRIPTION OF THE DRAWINGS

The accompanying drawings, which are incorporated in and form a part of the specification, illustrate the aspects of this disclosure and together with the description, serve to explain the principles of the disclosure. In the drawings.

DETAILED DESCRIPTION

Figure 1:
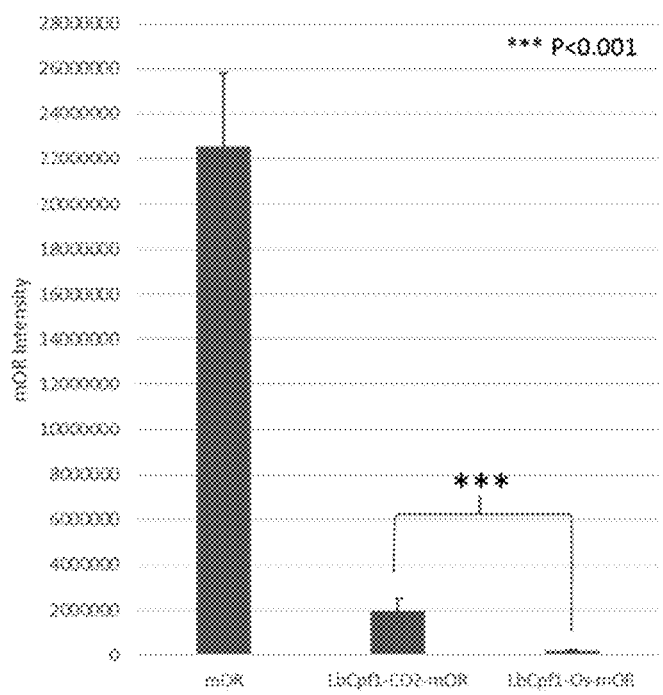
FIG. 1 illustrates the expression of LbCpf1-mOrange fluorescent proteins in corn protoplasts denoted by average mOrange intensities.

Unless defined otherwise, all technical and scientific terms used herein have the same meaning as commonly understood by one of ordinary skill in the art to which this disclosure belongs. Where a term is provided in the singular, the inventors also contemplate aspects of the disclosure described by the plural of that term. Where there are discrepancies in terms and definitions used in references that are incorporated by reference, the terms used in this application shall have the definitions given herein. Other technical terms used have their ordinary meaning in the art in which they are used.

The practice of the present disclosure employs, unless otherwise indicated, conventional techniques of biochemistry, chemistry, molecular biology, microbiology, cell biology, genomics, plant breeding, and biotechnology, which are within the skill of the art. See, e.g., Green and Sambrook, MOLECULAR CLONING: A LABORATORY MANUAL, 4th edition (2012); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)); Harlow and Lane, eds. (1988) ANTIBODIES, A LABORATORY MANUAL; ANIMAL CELL CULTURE (R. I. Freshney, ed. (1987)); RECOMBINANT PROTEIN PURIFICATION: PRINCIPLES AND METHODS, 18-1142-75, GE Healthcare Life Sciences; C. N. Stewart, A. Touraev, V. Citovsky, T. Tzfira eds. (2011) PLANT TRANSFORMATION TECHNOLOGIES (Wiley-Blackwell); and R. H. Smith (2013) PLANT TISSUE CULTURE. TECHNIQUES AND EXPERIMENTS (Academic Press, Inc.). The inventors do not intend to be limited to a mechanism or mode of action. Reference thereto is provided for illustrative purposes only.

Any references cited herein are incorporated by reference in their entireties.

As used herein, the singular form "a," "an," and "the" include plural references unless the context clearly dictates otherwise. For example, the term "a compound" or "at least one compound" may include a plurality of compounds, including mixtures thereof. Thus, for example, reference to "plant," "the plant," or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule.

As used herein, the term "about" indicates that a value includes the inherent variation of error for the method being employed to determine a value, or the variation that exists among experiments.

As used herein, "encoding" refers either to a polynucleotide (DNA or RNA) encoding for the amino acids of a polypeptide or a DNA encoding for the nucleotides of an RNA. As used herein, "coding sequence" and "coding region" are used interchangeably and refer to a polynucleotide that encodes a polypeptide. The boundaries of a coding region are generally determined by a translation start codon at its 5' end and a translation stop codon at its 3' end.

As used herein, the term "identity" when used in relation to nucleic acids, describes the degree of similarity between two or more nucleotide sequences. The percentage of "sequence identity" between two sequences can be determined by comparing two optimally aligned sequences over a comparison window, such that the portion of the sequence in the comparison window may comprise additions or deletions (gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. An alignment of two or more sequences may be performed using any suitable computer program. For example, a widely used and accepted computer program for performing sequence alignments is CLUSTALW v1.6 (Thompson, et al. (1994) Nucl. Acids Res., 22: 4673-4680).

As used herein, the terms "nucleic acid," "polynucleotide," and "oligonucleotide are used interchangeably and refer to deoxyribonuclotides (DNA), ribonucleotides (RNA), and functional analogues thereof, such as complementary DNA (cDNA) in linear or circular conformation. Nucleic acid molecules provided herein can be single stranded or double stranded. Nucleic acid molecules comprise the nucleotide bases adenine (A), guanine (G), thymine (T), cytosine (C). Uracil (U) replaces thymine in RNA molecules. Analogues of the natural nucleotide bases, as well as nucleotide bases that are modified in the base, sugar, and/or phosphate moieties are also provided herein. The symbol "N" can be used to represent any nucleotide base (e.g., A, G, C, T, or U). The symbol "Y" can be used to represent thymine or cytosine bases. The symbol "V" can be used to represent the nucleotide bases A, C or G. As used herein, "complementary" in reference to a nucleic acid molecule or nucleotide bases refers to A being complementary to T (or U), and G being complementary to C. Two complementary nucleic acid molecules are capable of hybridizing with each other under appropriate conditions. In an aspect of the present disclosure, two nucleic acid sequences are homologous if they have at least 70%, at least 75%, at least 80%, at least 85%, at least 90%, at least 95%, at least 96%, at least 97%, at least 98%, at least 99% or 100% sequence identity with each other.

As used herein, the term "plant" refers to any photosynthetic, eukaryotic, unicellular or multicellular organism of the kingdom Plantae and includes a whole plant or a cell or tissue culture derived from a plant, comprising any of: whole plants, plant components or organs (e.g., leaves, stems, roots, etc.), plant tissues, seeds, plant cells, protoplasts and/or progeny of the same. A progeny plant can be from any filial generation, e.g., F1, F2, F3, F4, F5, F6, F7, etc. A "plant cell" is a biological cell of a plant, taken from a plant or derived through culture from a cell taken from a plant. The term plant encompasses monocotyledonous and dicotyledonous plants. The methods, systems, and compositions described herein are useful across a broad range of plants. Suitable plants in which the methods, systems, and compositions disclosed herein can be used include, but are not limited to, cereals and forage grasses (e.g., alfalfa, rice, maize, wheat, barley, oat, sorghum, pearl millet, finger millet, cool-season forage grasses, and bahiagrass), oilseed crops (e.g., soybean, oilseed brassicas including canola and oilseed rape, sunflower, peanut, flax, sesame, and safflower), legume grains and forages (e.g., common bean, cowpea, pea, faba bean, lentil, tepary bean, Asiatic beans, pigeonpea, vetch, chickpea, lupine, alfalfa, and clovers), temperate fruits and nuts (e.g., apple, pear, peach, plums, berry crops, cherries, grapes, olive, almond, and Persian walnut), tropical and subtropical fruits and nuts (e.g., citrus including limes, oranges, and grapefruit; banana and plantain, pineapple, papaya, mango, avocado, kiwifruit, passionfruit, and persimmon), vegetable crops (e.g., solanaceous plants including tomato, eggplant, and peppers; vegetable brassicas; radish, carrot, cucurbits, alliums, asparagus, and leafy vegetables), sugar cane, tubers (e.g., beets, parsnips, potatoes, turnips, sweet potatoes), and fiber crops (sugarcane, sugar beet, stevia, potato, sweet potato, cassava, and cotton), plantation crops, ornamentals, and turf grasses (tobacco, coffee, cocoa, tea, rubber tree, medicinal plants, ornamentals, and turf grasses), and forest tree species.

As used herein, "plant genome" refers to a nuclear genome, a mitochondrial genome, or a plastid (e.g., chloroplast) genome of a plant cell. In some embodiments, a plant genome may comprise a parental genome contributed by the male and a parental genome contributed by the female. In some embodiments, a plant genome may comprise only one parental genome.

As used herein, "polynucleotide" refers to a nucleic acid molecule containing multiple nucleotides and generally refers both to "oligonucleotides" (a polynucleotide molecule of 18-25 nucleotides in length) and polynucleotides of 26 or more nucleotides. Aspects of this disclosure include compositions including oligonucleotides having a length of 18-25 nucleotides (e.g., 18-mers, 19-mers, 20-mers, 21-mers, 22-mers, 23-mers, 24-mers, or 25-mers), or medium-length polynucleotides having a length of 26 or more nucleotides (e.g., polynucleotides of 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides), or long polynucleotides having a length greater than about 300 nucleotides (e.g., polynucleotides of between about 300 to about 400 nucleotides, between about 400 to about 500 nucleotides, between about 500 to about 600 nucleotides, between about 600 to about 700 nucleotides, between about 700 to about 800 nucleotides, between about 800 to about 900 nucleotides, between about 900 to about 1000 nucleotides, between about 300 to about 500 nucleotides, between about 300 to about 600 nucleotides, between about 300 to about 700 nucleotides, between about 300 to about 800 nucleotides, between about 300 to about 900 nucleotides, or about 1000 nucleotides in length, or even greater than about 1000 nucleotides in length, for example up to the entire length of a target gene including coding or non-coding or both coding and non-coding portions of the target gene). Where a polynucleotide is double-stranded, its length can be similarly described in terms of base pairs.

As used herein, terms "polypeptide", "peptide" and "protein" are used interchangeably to refer to a polymer of amino acid residues. The term also applies to amino acid polymers in which one or more amino acids are chemical analogues or modified derivatives of a corresponding naturally-occurring amino acids.

As used herein, "protoplast" refers to a plant cell that has had its protective cell wall completely or partially removed using, for example, mechanical or enzymatic means resulting in an intact biochemical competent unit of living plant that can reform their cell wall, proliferate and regenerate grow into a whole plant under proper growing conditions.

As used herein, a "recombinant nucleic acid" refers to a nucleic acid molecule (DNA or RNA) having a coding and/or non-coding sequence distinguishable from endogenous nucleic acids found in natural systems. In some aspects, a recombinant nucleic acid provided herein is used in any composition, system or method provided herein. In some aspects, a recombinant nucleic acid may encode any CRISPR enzyme provided herein can be used in any composition, system or method provided herein. In some aspects, a recombinant nucleic acid may comprise or encode any guide RNA provided herein can be used in any composition, system or method provided herein. In an aspect, a vector provided herein comprises any recombinant nucleic acid provided herein. In another aspect, a cell provided herein comprises a recombinant nucleic acid provided herein. In another aspect, a cell provided herein comprises a vector provided herein.

As used herein, the term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as meristem, or particular cell types (e.g., pollen). Regulatory elements may also direct expression in a temporal-dependent manner, such as in a cell-cycle dependent or developmental stage-dependent manner, which may or may not also be tissue or cell-type specific. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); and SV40 enhancer.

As used herein, the terms "target sequence" or "target site" refer to a nucleotide sequence against which a guide RNA is capable of hybridizing. A target sequence may be genic or non-genic. In some aspects, a target sequence provided herein comprises a genic region. In other aspects, a target sequence provided herein comprises an intergenic region. In yet another aspect, a target sequence provided herein comprises both a genic region and an intergenic region. In an aspect, a target sequence provided herein comprises a coding nucleic acid sequence. In another aspect, a target sequence provided herein comprises a non-coding nucleic acid sequence. In an aspect, a target sequence provided herein is located in a promoter. In another aspect, a target sequence provided herein comprises an enhancer sequence. In yet another aspect, a target sequence provided herein comprises both a coding nucleic acid sequence and a non-coding nucleic acid sequence. In one aspect, a target sequence provided herein is recognized and cleaved by a double-strand break inducing agent, such as a system comprising a Cpf1 enzyme and a guide RNA.

As used herein, the term "donor" or "donor DNA" means a single stranded or double stranded DNA that comprises a polynucleotide sequence to be inserted at or near the target site of a Cpf1 enzyme and guide system. In some embodiments, the donor DNA comprises a transgene for insertion into the plant cell genome. In some embodiments, the donor DNA comprises a first and a second region of homology that flank the transgene, where the first and second regions of homology share homology to a first and a second genomic region present in or flanking the target site. A region of homology can be of any length that is sufficient to promote homologous recombination at the target site. For example, a region of homology can comprise at least 5-10, 10-15, 15-20, 20-25, 25-30, 30-35, 35-40, 40-45, 45-50, 50-55, 55-60, 60-65, 65-70, 70-75, 75-80, 80-85, 85-90, 90-95, 95-100, 100-150, 150-200, 200-250, 250-300, 300-350, 350-400, 400-450, 450-500, 500-550, 550-600, 600-650, 650-700, 700-750, 750-800, 800-850, 850-900, 900-950, 950-1,000, 1,000-1,150, 1,150-1,200, 1,200-1,250, 1,250-1,300, 1,300-1,350, 1,350-1,400, 1,400-1,450, 1,450-1,500, 1,500-1,550, 1,550-1,600, 1,600-1,650, 1,650-1,700, 1,700-1,750, 1,750-1,800, 1,800-1,850, 1,850-1,900, 1,900-1,950, 1,950-2,000, or more bases in length. In some embodiments, the donor DNA comprises a polynucleotide sequence that comprises at least 1, 2, 3, 4, 5, 6, 7, 8, 9, 10 or more nucleotide modifications compared to the target site. In some embodiments, the donor DNA comprises a polynucleotide sequence that is at least 80%, 81%, 82%, 83%, 84%, 85%, 86%, 87%, 88%, 89%, 90%, 91%, 92%, 93%, 94%, 95%, 96%, 97%, 98%, 99% identical to a polynucleotide sequence at or adjacent to the target site. In some embodiments, the donor DNA is 20, 25, 26, 27, 28, 29, 30, 31, 30-35, 35-40, 40-45, 45-50, 50-55, 55-60, 60-65, 65-70, 70-75, 75-80, 80-85, 85-90, 90-95, 95-100, 100-150, 150-200, 200-250, 250-300, 300-350, 350-400, 400-450, 450-500, 500-550, 550-600, 600-650, 650-700, 700-750, 750-800, 800-850, 850-900, 900-950, 950-1,000, 1,000-1,150, 1,150-1,200, 1,200-1,250, 1,250-1,300, 1,300-1,350, 1,350-1,400, 1,400-1,450, 1,450-1,500, 1,500-1,550, 1,550-1,600, 1,600-1,650, 1,650-1,700, 1,700-1,750, 1,750-1,800, 1,800-1,850, 1,850-1,900, 1,900-1,950, 1,950-2,000, 2,000-2,100, 2,000-2,200, 2,000-2,300, 2,000-2,400, 2,000-2,500, 2,000-2,600, 2,000-2,700, 2,000-2,800, 2,000-2,900, 2,000-3,000, 3,000-3,100, 3,000-3,200, 3,000-3,300, 3,000-3,400, 3,000-3,500, 3,000-3,600, 3,000-3,700, 3,000-3,800, 3,000-3,900, 3,000-4,000, 4,000-4,100, 4,000-4,200, 4,000-4,300, 4,000-4,400, 4,000-4,500, 4,000-4,600, 4,000-4,700, 4,000-4,800, 4,000-4,900, 4,000-5,000, or more nucleotides in length.

In an aspect, a Cpf1 nuclease provided herein is a Lachnospiraceae bacterium Cpf1 (LbCpf1) nuclease. In another aspect, a Cpf1 nuclease provided herein is a *Francisella novicida* Cpf1 (FnCpf1) nuclease.

A prerequisite for cleavage of the target site by a CRISPR ribonucleoprotein is the presence of a conserved Protospacer Adjacent Motif (PAM) near the target site. Depending on the CRISPR nuclease, cleavage can occur within a certain number of nucleotides (e.g., between 18-23 nucleotides for Cpf1) from the PAM site. PAM sites are only required for type I and type II CRISPR associated proteins, and different CRISPR endonucleases recognize different PAM sites. Without being limiting, the Cpf1 from Lachnospiraceae bacterium can recognize at least the following PAM sites: TTTN, and YTN; (where T is thymine; Y is thymine or cytosine; and N is thymine, cytosine, guanine, or adenine). Without being limiting, the Cpf1 from *Francisella novicida* can recognize at least the following PAM sites: TTN (where T is thymine; and N is thymine, cytosine, guanine, or adenine). In certain embodiments, the LbCpf1 protein disclosed here has been modified to recognize a non-natural PAM. LbCpf1 variants comprising one or more amino acid substitutions resulting in altered PAM sequence specificities have been disclosed in the art (for example see Gao et. al., Nature Biotech., 2017 August; 35(8):789-792). Gao et. al. have disclosed two LbCpf1 variants: SEQ ID NO: 39 comprising the amino acid substitutions G532R/K595R that can recognize TYCV PAM (where T is thymine; Y is thymine or cytosine; C is cytosine and V is cytosine, guanine, or adenine) and SEQ ID NO: 76 comprising the amino acid substitutions G532R/K538V/Y542R that can recognize the TATV PAM (where T is thymine; A is adenine; and V is cytosine, guanine, or adenine). As used herein, LbCpf1(TYC) variant refers to an LbCpf1 nuclease comprising the amino acid substitutions G532R/K595R. As used herein, LbCpf1(TAT) variant (SEQ ID NO: 76) refers to an LbCpf1 nuclease comprising the mutations G532R/K538V/Y542R.

The instant disclosure provides a recombinant nucleic acid encoding the Cpf1 nuclease of SEQ ID NO 2, 39, 43, 76 or a fragment thereof, wherein the recombinant nucleic acid is optimized for expression in a plant cell. A sequence can be optimized for expression in a plant cell by modifying a nucleotide sequence encoding a protein such as, for example, the nucleic acid sequence encoding the Cpf1 nuclease of SEQ ID NO 2, 39, 43 or a fragment thereof, using one or more plant-preferred codons for improved expression. In some embodiments, the plant-optimized recombinant nucleic acid encoding the Cpf1 nuclease of SEQ ID NO 2, or a fragment thereof, comprises a sequence having at least 80% identity, at least 81% identity, at least 82% identity, at least 83% identity, at least 84% identity, at least 85% identity, at least 90% identity, at least 91% identity, at least 92% identity, at least 93% identity, at least 94% identity, at least 95% identity, at least 96% identity, at least 97% identity, at least 98% identity, at least 99%, or 100% identity to a sequence selected from SEQ ID NOs: 1 and 10, or a fragment thereof. In some embodiments, the plant-optimized recombinant nucleic acid encoding the LbCpf1(TYC) nuclease (SEQ ID NO: 39), or a fragment thereof, comprises a sequence having at least 80% identity, at least 81% identity, at least 82% identity, at least 83% identity, at least 84% identity, at least 85% identity, at least 90% identity, at least 91% identity, at least 92% identity, at least 93% identity, at least 94% identity, at least 95% identity, at least 96% identity, at least 97% identity, at least 98% identity, at least 99%, or 100% identity to a sequence selected from SEQ ID NOs: 38, or a fragment thereof. In some embodiments, the plant-optimized recombinant nucleic acid encoding the LbCpf1 (TAT) nuclease (SEQ ID NO: 76) or a fragment thereof, comprises a sequence having at least 80% identity, at least 81% identity, at least 82% identity, at least 83% identity, at least 84% identity, at least 85% identity, at least 90% identity, at least 91% identity, at least 92% identity, at least 93% identity, at least 94% identity, at least 95% identity, at least 96% identity, at least 97% identity, at least 98% identity, at least 99%, or 100% identity to a sequence selected from SEQ ID NOs: 75, or a fragment thereof.

In some embodiments, the plant-optimized recombinant nucleic acid encoding the FnCpf1 nuclease (SEQ ID NO 43), or a fragment thereof, comprises a sequence having at least 80% identity, at least 81% identity, at least 82% identity, at least 83% identity, at least 84% identity, at least 85% identity, at least 90% identity, at least 91% identity, at least 92% identity, at least 93% identity, at least 94% identity, at least 95% identity, at least 96% identity, at least 97% identity, at least 98% identity, at least 99%, or 100% identity to a sequence selected from SEQ ID NOs: 45-48, 50, 51 or a fragment thereof.

In some embodiments, the plant-optimized recombinant nucleic acid is operably linked to a heterologous promoter.

In one aspect, a recombinant nucleic acid provided herein comprises one or more, two or more, three or more, four or more, five or more, six or more, seven or more, eight or more, nine or more, or ten or more heterologous promoters operably linked to one or more, two or more, three or more, four or more, five or more, six or more, seven or more, eight or more, nine or more, or ten or more plant-optimized recombinant nucleic acids encoding a Cpf1 nuclease. In some embodiments, a plant-optimized recombinant nucleic acids encoding a Cpf1 nuclease provided herein is provided to a plant cell in combination with one or more, two or more, three or more, four or more, five or more, six or more, seven or more, eight or more, nine or more, or ten or more guide polynucleotides. As used herein, the term "guide polynucleotide" refers to a polynucleotide sequence that can form a complex with a Cpf1 endonuclease and enables the Cpf1 endonuclease to bind to, and optionally cleave, a target site. The guide polynucleotide sequence can be a RNA sequence, a DNA sequence, or any combination thereof (e.g., a RNA-DNA hybrid sequence). In one aspect, a guide polynucleotide provided herein comprises a CRISPR repeat sequence and a spacer sequence that is complementary to a target site. In one aspect, a guide polynucleotide provided herein comprises one or more repeats of a CRISPR repeat sequence, a spacer sequence, and a CRISPR repeat sequence. In some embodiments, the guide polynucleotide comprises two or more spacer sequences that are complementary to different target sites. In some embodiments, the guide polynucleotide comprises one or more CRISPR repeat sequences selected from a pre-crRNA and a mature cr-RNA. In some embodiments, the guide polynucleotide is operably linked to a promoter. In certain embodiments, recombinant nucleic acids encoding guide polynucleotides may be designed in an array format such that multiple guide polynucleotides can be simultaneously released. In some embodiments, expression of one or more guide polynucleotides is U6-driven. In some embodiments, Cpf1 enzymes complex with multiple guide polynucleotides to mediate genome editing and at multiple target sequences. Some embodiments relate to expression of singly or in tandem array format from 1 up to 4 or more different guide sequences; e.g. up to about 20 or about 30 guides sequences. Each individual guide sequence may target a different target sequence. Such may be processed from, e.g. one chimeric pol3 transcript. Pol3 promoters such as U6 or H1 promoters may be used.

In some embodiments, a plant-optimized recombinant nucleic acid as disclosed herein is expressed or delivered in a vector. As used herein, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is an *Agrobacterium* T-DNA. Another type of vector is a viral vector, wherein virally-derived DNA or RNA sequences are present in the vector for packaging into a virus (e.g., retroviruses, replication defective retroviruses, Tobacco mosaic virus (TMV), Potato virus X (PVX) and Cowpea mosaic virus (CPMV), tobamovirus, Gemini viruses, adenoviruses, replication defective adenoviruses, and adeno-associated viruses). Viral vectors also include polynucleotides carried by a virus for transfection into a host cell. In some embodiments, a viral vector may be delivered to a plant using *Agrobacterium*. Certain vectors are capable of autonomous replication in a host cell into which they are introduced. Other vectors are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). In some embodiments, an expression vector can comprise a plant-optimized recombinant nucleic acid in a form suitable for expression of the plant-optimized recombinant nucleic acid in a plant cell, which means that the expression vector comprises one or more regulatory elements that are operatively-linked to the plant-optimized recombinant nucleic acid to be expressed. Regulatory elements may include enhancers, termination sequences, introns, etc.

In certain embodiments, the plant-optimized recombinant nucleic acid may be operably linked to a nucleic acid sequence encoding one or more nuclear localization signal (NLS), nuclear export signal (NES), functional domains, and flexible linkers. The one or more of the NLS, the NES or the functional domain may be conditionally activated or inactivated. In particular embodiments it can be of interest to target the Cpf1 encoded by the plant-optimized recombinant nucleic acid to the chloroplast. In many cases, this targeting may be achieved by the operably linking the plant-optimized recombinant nucleic acid encoding Cpf1 to a nucleic acid encoding a chloroplast transit peptide (CTP) or plastid transit peptide. Other options for targeting to the chloroplast which have been described are the maize cab-m7 signal sequence (U.S. Pat. No. 7,022,896, WO 97/41228, incorporated by reference herein) a pea glutathione reductase signal sequence (WO 97/41228, incorporated by reference herein) and the CTP described in US2009029861, incorporated by reference herein.

Several embodiments relate to a method for modifying a target sequence in the genome of a plant cell, the method comprising: introducing a recombinant nucleic acid optimized for expression in a plant cell comprising one or more of SEQ ID NOs: 1, 4, 6, 10, 12, 14, 15, 26, 31, 36, 38, 40, 41, 45, 46, 47, 48, 49, 50, 51, 63, 65, 66, 67, 68, 68, 70, 71, 72, 73, and 75 and a guide polynucleotide comprising a targeting domain that is complementary to a target sequence into the plant cell, where the recombinant nucleic acid expresses Cpf1 endonuclease in the plant cell and the Cpf1 endonuclease and the guide polynucleotide are capable of forming a complex that can recognize, bind to, and optionally nick or cleave the target sequence. In some embodiments, the guide polynucleotide and/or the recombinant nucleic acid are introduced into the plant cell by biolistic delivery. Several embodiments relate to a method for modifying a target sequence in the genome of a plant cell, the method comprising: introducing a guide polynucleotide comprising a targeting domain that is complementary to a target sequence in the plant genome into a plant cell comprising a recombinant nucleic acid optimized for expression in a plant cell, wherein the recombinant nucleic acid comprises one or more of SEQ ID NOs: 11, 4, 6, 10, 12, 14, 15, 26, 31, 36, 38, 40, 41, 45, 46, 47, 48, 49, 50, 51, 63, 65, 66, 67, 68, 68, 70, 71, 72, 73, and 75 where the recombinant nucleic acid expresses Cpf1 endonuclease in the plant cell and the Cpf1 endonuclease and the guide polynucleotide are capable of forming a complex that can recognize, bind to, and optionally nick or cleave the target sequence. In some embodiments, the guide polynucleotide is introduced into the plant cell by biolistic delivery. In some embodiments, the method further comprises incubating the plant cell at temperatures between 24° C. and 25° C., 25° C. and 26° C., 26° C. and 27° C., 27° C. and 28° C., 28° C. and 29° C., 29° C. and 30° C., 30° C. and 31° C., 31° C. and 32° C., 32° C. and 33° C., 33° C. and 34° C., 34° C. and 35° C., 35° C. and 36° C., 36° C. and 37° C., 37° C. and 38° C., 38° C. and 39° C., 39° C. and 40° C., for a period of at least about 10 min., 15 min., 20 min., 25 min., 30 min., 35 min., 40 min., 45 min., 50 min., 55 min., 1 hr., 2 hrs., 3 hr., 4 hrs., 5 hrs., 6 hrs., 7 hrs., 8 hrs., 9 hrs., 10 hrs., 11 hrs., 12 hrs., 13 hrs., 14 hrs., 15 hrs., 16 hrs., 17 hrs., 18 hrs., 19 hrs., 20 hrs. 21 hrs., 22 hrs., 23 hrs., 24 hrs., 25 hrs., 26 hrs., 27 hrs., 28 hrs., 29 hrs., 30 hrs., 31 hrs., 32 hrs., 33 hrs., 34 hrs., 35 hrs., 36 hrs., 37 hrs., 38 hrs., 39 hrs., 40 hrs., 41 hrs., 42 hrs., 43 hrs. 44 hrs., 45 hrs., 46 hrs., 47 hrs., 48 hrs., 3 days, 4 days, 5 days, 6 days, or 7 days. In some embodiments, the methods described herein can further comprise identifying at least one plant cell, plant or progeny plant that has a modification at the target sequence, where the modification at the target sequence is selected from the group consisting of (i) a replacement of at least one nucleotide, (ii) a deletion of at least one nucleotide, (iii) an insertion of at least one nucleotide, and (iv) any combination of (i)-(iii). The method can further provide a donor DNA to the plant cell, where the donor DNA comprises a polynucleotide sequence of interest. This can produce a plant cell or plant having a detectable targeted genome modification.

Several embodiments relate to a method for modifying a target sequence in the genome of a plant cell, method comprising: obtaining a plant cell comprising in its genome a recombinant nucleic acid comprising a sequence selected from the group consisting of: SEQ ID NOs 1, 4, 6, 10, 12, 14, 15, 26, 31, 36, 38, 40, 41, 45, 46, 47, 48, 49, 50, 51, 63, 65, 66, 67, 68, 68, 70, 71, 72, 73, and 75 and introducing into the plant cell a guide polynucleotide comprising a targeting domain that is complementary to a target sequence in the plant genome or a recombinant nucleic acid encoding the guide polynucleotide, where the guide polynucleotide and Cpf1 endonuclease encoded by the recombinant nucleic acid are capable of forming a complex that can bind to, and modify the target sequence. In some embodiments, the guide polynucleotide is introduced into the plant cell by biolistic delivery. In some embodiments, the method further comprises incubating the plant cell at temperatures between 24° C. and 25° C., 25° C. and 26° C., 26° C. and 27° C., 27° C. and 28° C., 28° C. and 29° C., 29° C. and 30° C., 30° C. and 31° C., 31° C. and 32° C., 32° C. and 33° C., 33° C. and 34° C., 34° C. and 35° C., 35° C. and 36° C., 36° C. and 37° C., 37° C. and 38° C., 38° C. and 39° C., 39° C. and 40° C., for a period of at least about 10 min., 15 min., 20 min., 25 min., 30 min., 35 min., 40 min., 45 min., 50 min., 55 min., 1 hr., 2 hrs., 3 hr., 4 hrs., 5 hrs., 6 hrs., 7 hrs., 8 hrs., 9 hrs., 10 hrs., 11 hrs., 12 hrs., 13 hrs., 14 hrs., 15 hrs., 16 hrs., 17 hrs., 18 hrs., 19 hrs., 20 hrs. 21 hrs., 22 hrs., 23 hrs., 24 hrs., 25 hrs., 26 hrs., 27 hrs., 28 hrs., 29 hrs., 30 hrs., 31 hrs., 32 hrs., 33 hrs., 34 hrs., 35 hrs., 36 hrs., 37 hrs., 38 hrs., 39 hrs., 40 hrs., 41 hrs., 42 hrs., 43 hrs. 44 hrs., 45 hrs., 46 hrs., 47 hrs., 48 hrs., 3 days, 4 days, 5 days, 6 days, or 7 days. In some embodiments, the methods described herein can further comprise identifying at least one plant cell, plant or progeny plant that has a modification at the target sequence, where the modification at the target sequence is selected from the group consisting of (i) a replacement of at least one nucleotide, (ii) a deletion of at least one nucleotide, (iii) an insertion of at least one nucleotide, and (iv) any combination of (i)-(iii). The method can further provide a donor DNA to the plant cell, where the donor DNA comprises a polynucleotide sequence of interest. This can produce a plant cell or plant having a detectable targeted genome modification.

The plant cell may be of a monocot or dicot. In some embodiments, the plant cell may be from or of a crop or grain plant such as cassava, corn, sorghum, alfalfa, cotton, soybean, canola, wheat, oat or rice. The plant cell may also be of an algae, tree or production plant, fruit or vegetable (e.g., trees such as citrus trees, e.g., orange, grapefruit or lemon trees; peach or nectarine trees; apple or pear trees; nut trees such as almond or walnut or pistachio trees; nightshade plants; plants of the genus *Brassica*; plants of the genus *Lactuca*; plants of the genus *Spinacia*; plants of the genus *Capsicum*; cotton, tobacco, asparagus, avocado, *papaya*, cassava, carrot, cabbage, broccoli, cauliflower, tomato, eggplant, pepper, lettuce, spinach, strawberry, potato, squash, melon, blueberry, raspberry, blackberry, grape, coffee, cocoa, etc).

The methods for genome editing using the recombinant nucleic acid molecules as described herein can be used to confer desired traits on essentially any plant. A wide variety of plants and plant cell systems may be engineered for the desired physiological and agronomic characteristics described herein using the nucleic acid constructs of the present disclosure and the various transformation methods mentioned above.

EXAMPLES

The following examples are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); ss, single stranded; ds, double stranded and the like.

Example 1

Design and Analysis of LbCpf1-CO1, an Engineered Polynucleotide Optimized for Expression in Plant Cells This example describes the creation and testing of a synthetic polynucleotide encoding Lachnospiraceae bacterium ND2006 (LbCpf1) nuclease that is optimized for expression in plant cells.

A nucleotide sequence of Cpf1 from Lachnospiraceae bacterium ND2006 (LbCpf1) that was codon optimized for expression in human cells has been described by Zetsche et. al, (Cell 2015, 163, 759-771). The human codon optimized sequence disclosed by Zetsche et. al., was modified through algorithmic methods, partly based on corn codon preference, to design LbCpf1-CO1(Coding sequence Optimized version 1) (SEQ ID NO: 1) to optimize the sequence for expression of the LbCpf1 protein (SEQ ID NO: 2) in plant cells.

The plant-optimized LbCpf1-CO1 sequence was then incorporated into six different expression vectors to test its activity in corn cells. Three of the expression vectors were designed with an expression cassette (SEQ ID NO: 3) comprising the LbCpf1-CO1 nuclease and a nucleotide sequence encoding the Nuclear Localization Sequence (NLS) from the heat stress transcription factor 1 (HSFA1) gene from *Solanum lycopersicum* (SEQ ID NO:4) on the 5' and 3' ends. Three of the expression vectors were designed with an expression cassette (SEQ ID NO:5) comprising a processable potato LS1 intron sequence (SEQ ID NO: 6) introduced into the NLS-LbCpf1-CO1-NLS sequence to eliminate expression of the LbCpf1 protein in *Agrobacterium*. The NLS-LbCpf1-CO1-NLS expression cassettes also comprised a *Zea mays* Ubiquitin M1 promoter leader and intron sequence (SEQ ID NOs:7) operably linked to the NLS-LbCpf1-CO1-NLS nuclease and a transcription terminator sequence from a rice Lipid transfer protein (LTP) gene (SEQ ID NO:8). Each plant vector also comprised a gRNA expression array comprising either 2 or 4 guide RNA sequences (mature crRNA+spacer) positioned in tandem and targeting 2 or 4 sites on a corn chromosome. The first crRNA sequence was 35 nt while the remaining ones were 20 nt and the spacer sequence was 30 nt. The gRNA arrays were operably linked to the maize U6 Pol III promoter (SEQ ID NO:9) and a poly T terminator sequence. All the expression vectors also included a third expression cassette containing the selectable marker gene CP4 that provides resistance to the herbicide glyphosate. See Table 1.

Corn 01DKD2 cultivar embryos were transformed with *Agrobacterium* containing the plant expression vectors described in Table 1. Transformed plants were selected on glyphosate, leaf samples from regenerated plantlets were harvested after 2 weeks and genomic DNA was extracted for Fragment Length Analysis (FLA). FLA is a PCR-based molecular assay that can be used to identify indel (insertion or deletion) mutations introduced at the target site by NHEJ-mediated (Non Homologous End Joining) DNA repair following dsDNA cleavage by the Cpf1-guide complex. Genomic DNA was subjected to a PCR reaction with primers flanking the target site to generate amplicons. The amplicons fragment length was then compared to a wild type amplicon to identify mutants. PCR reactions were carried out using 5' FAM-labeled primer, a standard primer and Phusion™ polymerase (New England Biolabs, MA) according to manufactures instructions to generate 200 to 500 bp PCR fragments. 1 ul PCR product was combined with 0.5 ul GeneScan 1200 LIZ Size Standard (Thermo Fisher, MA), 8.5 ul formamide and run on ABI sequencer (Thermo Fisher, MA). Two FLA reactions were multiplexed and subsequently analyzed for fragment length variation to identify plants with mutations at the target sites. As shown in Table 1, 258 plants returned high quality FLA data, out of which only 1 plant was identified as having mutations at one of the target sites.

Example 2

Design and Analysis of LbCpf1-CO2, an Engineered Polynucleotide Optimized for Expression in Plant Cells This example describes the design and expression analysis of Lachnospiraceae bacterium ND2006 (LbCpf1) nuclease that is optimized for expression in plant cells.

The LbCpf1-CO1 nucleotide sequence described in Example 1 was manually analyzed for the presence of deleterious motifs that could potentially reduce gene expression. These deleterious motifs were given a higher priority for removal/replacement by nucleotide sequences coding for synonymous codons. Additionally, a monocot-specific codon frequency table was used for optimization of the nucleotide sequence for expression in monocots. Based on these criteria, a second optimized LbCpf1 (referred to as LbCpf1-CO2) nucleotide sequence was generated (SEQ ID NO: 10) for expression of the LbCpf1 protein (SEQ ID NO: 2) in planta. When compared to LbCpf1-CO1, the LbCpf1-CO2 sequence was determined to have a threefold reduction in the presence of deleterious motifs within its coding sequence. The full length LbCpf1-CO2 nucleotide sequence shows only 85.6% sequence identity with the human codon optimized LbCpf1 nucleotide sequence disclosed by Zetsche et. al., (Cell 2015, 163, 759-771), only 77.5% sequence identity with LbCpf1-CO1 and only 69.4% sequence identity with the native bacterial LbCpf1 sequence.

Three expression cassettes (Prom35S::HIStag:NLS:LbCpf1-CO2:mOrange:NLS::TermNOS; $Prom_{35S}$::HIStag:NLS:LbCpf1-Os:mOrange:NLS::TermNOS; and $Prom_{35S}$::HIStag:NLS:mOrange:NLS::$Term_{NOS}$) were generated by standard cloning techniques and as described below:

TABLE 1

SUMMARY OF RESULTS OF FRAGMENT LENGTH ANALYSIS (FLA) GENERATED FROM CORN PLANTS STABLY TRANSFORMED WITH LBCPF1-CO1 AND GRNAS TARGETING 8 UNIQUE GENOMIC TARGET SITES.

| Vector | Intron in Cpf1-CO1 cassette | Genomic sites targeted (TS) | Plants tested | Plants returning data | # Edited samples by FLA | Mutation efficiency (%) |
|---|---|---|---|---|---|---|
| 1 | No | ZmTS1, ZmTS2 | 47 | 34 | 0 | 0 |
| 2 | No | ZmTS3, ZmTS4, ZmTS5, ZmTS6 | 55 | 50 | 0 | 0 |
| 3 | No | ZmTS7, ZmTS8 | 45 | 44 | 0 | 0 |
| 4 | Yes | ZmTS7, ZmTS8 | 38 | 37 | 1 | 2.63 |
| 5 | Yes | ZmTS1, Zm TS2 | 65 | 64 | 0 | 0 |
| 6 | Yes | ZmTS3, ZmTS4, ZmTS5, ZmTS6 | 35 | 29 | 0 | 0 |
| Total | | | 285 | 258 | 1 | |

(1) Prom35S::HIS tag:NLS:LbCpf1-CO2:mOrange:NLS::TermNOS

The LbCpf1-CO2 coding sequence was fused 5' to the coding sequence of mOrange (mOr) from *Entacmaea quadricolor* (SEQ ID NO: 52). The LbCpf1-CO2:mOrange fusion gene was then flanked at the 5' and 3' ends with the NLS sequence from tomato HSFA1 gene (SEQ ID NO:3) and a nucleotide sequence encoding a HIS tag (MGSS7H) (SEQ ID NO: 54) was introduced to the 5' end. The nucleotide sequence was operably linked to the Cauliflower mosaic virus 35S promoter and an *Agrobacterium* NOS terminator.

(2) Prom$_{35S}$::HIS Tag:NLS:LbCpf1-Os:mOrange:NLS::Term$_{NOS}$

The rice codon-optimized Cpf1 (LbCpf1-Os) nucleotide sequence described by Xu et. al. (Plant Biotechnology Journal, 2017, 15, 713-717) (SEQ ID NO:11) was used as a control to compare in planta expression. The LbCpf1-Os coding sequence was fused 5' to the coding sequence of mOrange (mOr) from *Entacmaea quadricolor* (SEQ ID NO: 52). The LbCpf1-Os:mOrange fusion gene was then flanked at the 5' and 3' ends with the NLS sequence from tomato HSFA1 gene (SEQ ID NO:3) and a nucleotide sequence encoding a HIS tag (MGSS7H) (SEQ ID NO:54) was introduced to the 5' end. The nucleotide sequence was operably linked to the Cauliflower mosaic virus 35S promoter and an *Agrobacterium* NOS terminator.

(3) Prom$_{35S}$::HIS tag:NLS:mOrange:NLS::Term$_{NOS}$

The coding sequence of mOrange (mOr) gene (SEQ ID NO:52) from *Entacmaea quadricolor* was flanked at the 5' and 3' ends with the NLS sequence from tomato HSFA1 gene (SEQ ID NO:3) and a nucleotide sequence encoding a HIS tag (MGSS7H) (SEQ ID NO:54) was introduced to the 5' end. The nucleotide sequence was operably linked to the Cauliflower mosaic virus 35S promoter and an *Agrobacterium* NOS terminator.

The expression cassettes described above were cloned into plant expression constructs. Corn leaf protoplasts were transfected with either the LbCpf1-CO2-mOr construct, the LbCpf1-Os-mOr construct, or the control mOr construct to evaluate expression levels (Table 2). Since mOrange was fused to LbCpf1-CO2 and LbCpf1-Os, the relative mOrange fluorescence levels reflects LbCpf-CO2 and LbCpf1-Os expression levels. Transformations were carried out using standard polyethylene glycol (PEG) based transfection methods. To quantify transformation frequency, an expression vector comprising the luciferase gene was co-transfected. Following transformation, the protoplasts were incubated in the dark in incubation buffer and harvested after 48 hours. Transformation efficiency was calculated by quantifying luciferase expression. The average mOrange expression from 3 technical replicates was determined using Operetta™ (Perkin Elmer) analysis software. As shown in FIG. 1 and Table 2, mOrange intensity was significantly higher in protoplasts expressing LbCpf1-CO2-mOrange than in cells expressing LbCpf1-Os-mOrange.

TABLE 2

EXPRESSION ANALYSIS OF LBCPF1-CO2-MOR AND LBCPF1-OS-MOR FLUORESCENT PROTEINS IN CORN PROTOPLASTS

| Expression Construct | Fluorescence detected | Fold increase in expression compared to Cpf1-Os-mOr |
|---|---|---|
| Prom35S::HIStag:NLS:LbCpf1-CO2:mOrange:NLS::TermNOS | Yes | 14 |
| Prom35S::HIStag:NLS:LbCpf1-Os:mOrange:NLS::TermNOS | Yes | 1 |
| Prom$_{35S}$:: HIS tag:NLS:mOrange:NLS::Term$_{NOS}$ | Yes | 135 |

Example 3

Analysis of LbCpf1-CO2 Activity in Corn Plants

This example describes testing the LbCpf1-CO2 nucleotide sequence for activity at multiple genomic sites in corn plants using multiplexed guide RNAs.

An *Agrobacterium* LbCpf1-CO2 T-DNA vector comprising: an expression cassette for a selectable marker conferring resistance to the herbicide glyphosate; an expression cassette (SEQ ID NO:15) comprising NLS-LbCpf1-CO2-NLS (SEQ ID NO: 12) linked to a 5' Kozak sequence (SEQ ID NO:13) resulting in Koz-NLS-LbCpf1-CO2-NLS (SEQ ID NO: 14), which was operably linked to a *Zea mays* Ubiquitin M1 promoter cassette (SEQ ID NOs:7) and the transcription terminator sequence from rice LTP (SEQ ID NO:8); and an expression cassette comprising the *Zea mays* U6 promoter (SEQ ID NO:9) and a polyT terminator operably linked to gRNA expression array comprising three gRNAs positioned in tandem and targeting the three genomic sites, was created. Each gRNA comprised a 21 bp crRNA sequence linked to a 23 bp spacer sequence that was complementary to target site ZmTS9, ZmTS10 or ZmTS11 in the corn genome.

As a control, an *Agrobacterium* LbCpf1-Os T-DNA vector comprising: an expression cassette for a selectable marker conferring resistance to the herbicide glyphosate; an expression cassette (SEQ ID NO:18) comprising a Kozak sequence immediately upstream of the coding sequence of LbCpf1-Os (SEQ ID NO: 11) fused to the tomato HSFA NLS (SEQ ID NO:3) at the 5' end and the 3' end which was operably linked to the *Zea mays* Ubiquitin M1 promoter cassette (SEQ ID NO: 7) and to the rice LTP terminator (SEQ ID NO: 8); and an expression cassette comprising the *Zea mays* U6 promoter (SEQ ID NO:9) operably linked to gRNA expression array comprising three gRNAs positioned in tandem and targeting the three genomic sites, was created. Each gRNA comprised a 21 bp crRNA sequence linked to a 23 bp spacer sequence that was complementary to target site ZmTS9, ZmTS10 or ZmTS11 in the corn genome.

Corn 01DKD2 cultivar embryos were transformed with either the LbCpf1-CO2 or LbCpf1-Os T-DNA vectors described above by *Agrobacterium*-mediated transformation. Transformed plants were selected on glyphosate, leaf samples from regenerated plantlets were harvested after 2 weeks and genomic DNA was extracted for Fragment Length Analysis (FLA) to determine genome mutation rates, as described in Example 1. Table 3 summarizes the results and shows the mutation rate detected at each site in stably transformed corn plants.

TABLE 3

SUMMARY OF RESULTS OF FLA GENERATED FROM CORN PLANTS STABLY TRANSFORMED WITH EITHER LBCPF1-CO2 OR LBCPF1-OS AND GRNA ARRAY TARGETING 3 UNIQUE GENOMIC TARGET SITES

| T-DNA Vector | Target site | Plants assayed | # Edited plants by FLA analysis | Mutation frequency |
|---|---|---|---|---|
| LbCpf1-CO2 | ZmTS9 | 48 | 20 | 41.6% |
| | ZmTS10 | 47 | 6 | 12.7% |
| | ZmTS11 | 46 | 2 | 4.3% |
| LbCpf1-Os | ZmTS9 | 49 | 4 | 8% |
| | ZmTS10 | 49 | 1 | 2% |
| | ZmTS11 | 47 | 2 | 4.3% |

As shown in Table 3, all three sites targeted for cleavage with the guide/LbCpf1-CO2 system described above exhibited the presence of mutations which is indicative of DNA cleavage and repair. The frequency of mutations at the three sites ranged from 4.3% at ZmTS11, 12.7% for ZmTS10 to almost 42% at ZmTS9. 20 plants identified as having mutations in ZmTS9 were further analyzed to confirm the presence of mutations at the target site. PCR primers flanking the target site were used to generate amplicons which were cloned via Zero blunt-end Topo™ cloning (LifeTechnologies), sequenced and compared to the reference sequence. The presence of mutations was confirmed in all 20 events. For the guide/LbCpf1-Os system, mutations were identified at all three sites and the frequency of mutations at the three sites ranged from 2% at TS10, 4.3% for TS11 to almost 9% at TS1. Taken together, the data shows that the plant coding sequence optimized LbCpf1-CO2 is properly transcribed and translated in the corn host cell, is functional and can successfully promote gRNA directed chromosomal cleavage at target sites.

Example 4

Analysis of LbCpf1-CO2 Activity in Combination with a Single gRNA Expression System in Corn Plants This example describes the testing the LbCpf1-CO2 nucleotide sequence for the ability to induce cleavage and subsequent edits at a genomic target site in corn plants utilizing a single gRNA expression cassette.

An *Agrobacterium* T-DNA vector comprising: an expression cassette for a selectable marker gene that conferred resistance to the herbicide glyphosate; an expression cassette (SEQ ID NO:15) comprising a Kozak sequence introduced 5' to the NLS-LbCpf1-CO2-NLS nucleotide sequence and operably linked to a *Zea mays* Ubiquitin M1 promoter cassette and the transcription terminator sequence from rice LTP; and an expression cassette comprising the *Zea mays* U6 Pol III promoter (SEQ ID NO: 9) and a poly T terminator operably linked to a single guide RNA (gRNA) comprising a crRNA sequence linked to a 23 bp spacer sequence complementary to a unique target site (ZmTS12) in the corn chromosome.

Corn 01DKD2 cultivar embryos were transformed with *Agrobacterium* containing the T-DNA vector and stably transformed plants were selected on glyphosate. Leaf samples from regenerated plantlets were harvested after 2 weeks and genomic DNA was extracted for Fragment Length Analysis (FLA) to determine genome mutation rates, as described in Example 1.

TABLE 4

FLA RESULTS GENERATED FROM CORN PLANTS STABLY TRANSFORMED WITH LBCPF1-CO2 AND GRNA TARGETING ZMTS12 GENOMIC TARGET SITE.

| Nuclease sequence | Target site | Plants assayed | # Edited plants by FLA analysis | Mutation frequency |
|---|---|---|---|---|
| LbCpf1-CO2 | ZmTS12 | 247 | 158 | 64% |

As shown in Table 4, mutations were identified at the target site in 64% of corn plants stably transformed with a vector comprising the LbCp1-CO2 nucleotide sequence and a single guide RNA.

Example 5

Analysis of the Effect of the Addition of a Kozak Fragment Upstream of the LbCpf1-Os Nucleotide Sequence on Nuclease Activity in Plant Cells This example describes testing the addition of the Kozak sequence (SEQ ID NO:15) upstream of the LbCpf1-Os nucleotide sequence for the ability to enhance nuclease activity in corn plants.

An *Agrobacterium* LbCpf1-Os (Kozak minus) T-DNA vector comprising: an expression cassette for a selectable marker conferring resistance to the herbicide glyphosate; an expression cassette (SEQ ID NO:19) comprising NLS-LbCpf1-Os-NLS (SEQ ID NO:16), with an ATG sequence incorporated immediately 5' to SEQ ID NO:16 and operably linked to a *Zea mays* Ubiquitin M1 promoter cassette (SEQ ID NOs:7) and the transcription terminator sequence from rice LTP (SEQ ID NO:8); and an expression cassette comprising the *Zea mays* U6 promoter (SEQ ID NO:9) operably linked to gRNA expression array comprising three gRNAs positioned in tandem and targeting the three genomic sites, was created. Each gRNA comprised a 21 bp crRNA sequence linked to a 23 bp spacer sequence that was complementary to target site ZmTS9, ZmTS10 or ZmTS11 in the corn genome.

Corn plants were transformed with *Agrobacterium* containing either the T-DNA vector described above comprising the LbCpf1-Os (Kozak minus) expression cassette (SEQ ID NO:19) or the T-DNA vector described in Example 3 comprising a Kozak sequence immediately upstream of the coding sequence of LbCpf1-Os (SEQ ID NO:18). Transformed plants were selected on glyphosate, leaf samples from regenerated plantlets were harvested after 2 weeks and genomic DNA was extracted for Fragment Length Analysis (FLA) to determine genome mutation rates, as described in Example 1. Table 5 summarizes the results and shows the mutation rate for each site in stably transformed corn plants.

TABLE 5

SUMMARY OF FLA RESULTS GENERATED FROM CORN PLANTS STABLY TRANSFORMED WITH LBCPF1-OS AND GRNA ARRAY TARGETING 3 UNIQUE GENOMIC TARGET SITES

| Kozak sequence | Nuclease sequence | Target site | Plants assayed | # Edited plants by FLA analysis | Mutation frequency |
|---|---|---|---|---|---|
| + | LbCpf1-Os | ZmTS9 | 49 | 4 | 8% |
| | | ZmTS10 | 49 | 1 | 2% |
| | | ZmTS11 | 47 | 2 | 4.3% |

TABLE 5-continued

SUMMARY OF FLA RESULTS GENERATED FROM CORN
PLANTS STABLY TRANSFORMED WITH LBCPF1-OS AND
GRNA ARRAY TARGETING 3 UNIQUE GENOMIC TARGET SITES

| Kozak sequence | Nuclease sequence | Target site | Plants assayed | # Edited plants by FLA analysis | Mutation frequency |
|---|---|---|---|---|---|
| – | LbCpf1-Os | ZmTS9 | 33 | 0 | 0% |
|  |  | ZmTS10 | 35 | 0 | 0% |
|  |  | ZmTS11 | 35 | 0 | 0% |

Plants transformed with the LbCpf1-Os comprising a Kozak sequence upstream of the nuclease coding sequence exhibited mutations at all three target sites at frequency ranging from 2% at ZmTS10, 4.3% for ZmTS11 to almost 8% at ZmTS9. No mutants were identified at any of the three target sites in plants transformed with the LbCpf1-Os expression cassette lacking the Kozak sequence.

Example 6

Analysis of LbCpf1-CO2 Activity in Soybean Plants

This example describes testing the LbCpf1-CO2 nucleotide sequence for activity in soybean plants by assaying the ability of the nuclease to target cleavage at multiple unique genomic sites using multiplexed guides.

An *Agrobacterium* LbCpf1-CO2 T-DNA vector was created comprising: an expression cassette for a selectable marker conferring resistance to the antibiotic spectinomycin; an expression cassette (SEQ ID NO: 20) comprising NLS-LbCpf1-CO2-NLS (SEQ ID NO:12) with ATGGCG fused in frame 5' to SEQ ID NO 12 as the translational start site, which was operably linked to a promoter sequence (SEQ ID NO:37) and a transcriptional terminator sequence from *Medicago truncatula* (disclosed in US20140283200); and an expression cassette comprising the *Glycine max* U6 Pol III promoter (disclosed in US20170166912) and a polyT terminator operably linked to a gRNA array comprising three gRNAs arranged in tandem and a transcriptional terminator sequence. Each gRNA comprised a 21 bp mature crRNA sequence linked to a 23 bp spacer sequence that was complementary to either the GmFAD2-1A-TS, GmPDS-TS1 or GmPDS-TS2 target site.

An *Agrobacterium* LbCpf1-Os T-DNA control vector was created comprising: an expression cassette for a selectable marker conferring resistance to the antibiotic spectinomycin; an expression cassette (SEQ ID NO: 21) comprising NLS-LbCpf1-Os-NLS with ATGGCG fused in frame 5' as the translational start site, which was operably linked to a promoter sequence (SEQ ID NO:37) and a transcriptional terminator sequence from *Medicago truncatula* (disclosed in US20140283200); and an expression cassette comprising the *Glycine max* U6 Pol III promoter (disclosed in US20170166912) and polyT terminator operably linked to a gRNA array comprising three gRNAs arranged in tandem and a transcriptional terminator sequence. Each gRNA comprised a 21 bp mature crRNA sequence linked to a 23 bp spacer sequence that was complementary to either the GmFAD2-1A-TS, GmPDS-TS1 or GmPDS-TS2 target site.

Excised embryos from A3555 soybean plants were co-cultured with the *Agrobacterium* containing either the LbCpf1-CO2 T-DNA vector or the LbCpf1-Os T-DNA control vector described above. Transformed plants were selected on spectinomycin, leaf samples from regenerated plantlets were harvested after 4 weeks, and genomic DNA was extracted for Fragment Length Analysis (FLA) to determine genome mutation rates, as described in Example 1. A summary of FLA results generated from soy plants stably transformed with either LbCpf1-CO2 or LbCpf1-Os and gRNA array targeting 3 unique genomic target sites is provided in Table 6.

The plants were also scored for the albino phenotype typically associated with reduction/loss of PDS gene function (Table 7). PDS catalyzes a rate-limiting step in the biosynthesis of carotenoids in plants (Misawa, et. al., *The Plant Journal*, 1993, 4; 833-840). Reducing the endogenous PDS gene expression will therefore result in plants with a bleached phenotype and lowered chlorophyll content. Presence of an albino phenotype is therefore indicative of mutations at the PDS locus.

TABLE 6

SUMMARY OF FLA RESULTS GENERATED FROM SOY
PLANTS STABLY TRANSFORMED WITH EITHER LBCPF1-CO2
OR LBCPF1-OS AND GRNA ARRAY TARGETING 3 UNIQUE
GENOMIC TARGET SITES

| Nuclease seq variant | Target sites | Plants assayed | # Edited plants by FLA | Mutation rate |
|---|---|---|---|---|
| LbCpf1-CO2 | GmFAD2-1A | 62 | 22 | 36% |
|  | GmPDS-TS1 | 62 | 0 | 0% |
|  | GmPDS-TS2 | 62 | 28 | 45% |
| LbCpf1-Os | GmFAD2-1A | 88 | 20 | 22% |
|  | GmPDS-TS1 | 88 | 0 | 0% |
|  | GmPDS-TS2 | 88 | 37 | 42% |

TABLE 7

SUMMARY OF PLANTS SCORED FOR PDS GENE
MUTATIONS INDICATED BY AN ALBINO PHENOTYPE.

| Nuclease | Plants assayed | Albino plants | Albino frequency rate |
|---|---|---|---|
| LbCpf1-CO2 | 62 | 52 | 84% |
| LbCpf1-Os | 88 | 60 | 68% |

As summarized in Table 6, of the 3 sites targeted by LbCpf1-Os and LbCpf1-CO2, soybean plants were recovered where mutations were identified at FAD2 and PDS1-TS2 sites. The mutations at the PDS locus was further confirmed by scoring for the albino phenotype (see Table 7).

Example 7

Plant Expression Vectors with Unique Cpf1-CO2 Expression Cassettes $\text{Prom}_{Mt.Ubiq}$::NLS:LbCpf1-CO2:NLS::$\text{Term}_{Mt}$: An expression cassette (SEQ ID NO: 26) for the expression of a Cpf1-CO2 endonuclease was created comprising: a promoter (SEQ ID NO:22), leader (SEQ ID NO:23) and intron (SEQ ID NO:24) derived from *Medicago truncatula* Ubiquitin operably linked 5' to the NLS-LbCpf1-CO2-NLS coding sequence (SEQ ID NO: 12) wherein ATGGCG sequence was fused in frame 5' to SEQ ID NO 12 and served as the translational start site. The resulting sequence was in turn operably linked 5' to a UTR sequence from a gene from *Medicago truncatula* (SEQ ID NO:25).

The expression cassette was introduced into an *Agrobacterium* vector that also comprised a gRNA cassette designed to guide LbCpf1 to a unique GmTS1 target site on the soy chromosome. The gRNA comprised a 21 bp crRNA sequence linked to a 23 bp spacer sequence that was complementary to GmTS1 within the soy genome. The gRNA was operably linked to *Glycine max* U6 Pol III promoter (disclosed in US20170166912, incorporated by reference herein) and a poly T terminator. The vector also comprised an expression cassette for a selectable marker conferring resistance to the antibiotic spectinomycin.

Prom$_{EF1a}$::NLS:LbCpf1-CO2:NLS::Term$_{Mt}$: An expression cassette (SEQ ID NO: 31) for the expression of a Cpf1-CO2 endonuclease was created comprising: a promoter (SEQ ID NO:27), leader 5' (SEQ ID NO:28), intron (SEQ ID NO:29), leader 3' (SEQ ID NO:30) derived from *Cucumis melo* EIF1alpha gene operably linked 5' to the NLS-LbCpf1-CO2-NLS coding sequence (SEQ ID NO: 12) wherein ATGGCG sequence was fused in frame 5' to SEQ ID NO 12 and served as the translational start site. The resulting sequence was operably linked to a UTR sequence from a gene from *Medicago truncatula* (SEQ ID NO:25). The expression cassette was introduced into an *Agrobacterium* vector that also comprised a gRNA cassette designed to guide LbCpf1 to a unique GmTS2 target site on the soy chromosome. The gRNA comprised a 21 bp crRNA sequence linked to a 23 bp spacer sequence that was complementary to GmTS2 within the soy genome. The gRNA was operably linked to *Glycine max* U6 Pol III promoter (disclosed in US20170166912) and a poly T terminator. The vector also comprised an expression cassette for a selectable marker conferring resistance to the antibiotic spectinomycin.

Prom$_{At.Ubiq}$::NLS:LbCpf1-CO2:NLS::Term$_{Gb}$: An expression cassette (SEQ ID NO: 36) for the expression of a Cpf1-CO2 endonuclease was created comprising a promoter (SEQ ID NO:32), leader (SEQ ID NO:33) and intron (SEQ ID NO:34) derived from *Arabidopsis* Ubiquitin 10 gene operably linked 5' to the NLS-LbCpf1-CO2-NLS coding sequence (SEQ ID NO: 12) where ATGGCG sequence was fused in frame 5' to SEQ ID NO 12 and served as the translational start site. The resulting sequence was operably linked to a UTR sequence from a gene from *Gossypium barbadense* (SEQ ID NO: 35).

The expression cassette was introduced into an *Agrobacterium* vector that also comprised a gRNA cassette designed to guide LbCpf1 to a unique GmTS3 target site on the soy chromosome. The gRNA comprised a 21 bp crRNA sequence linked to a 23 bp spacer sequence that was complementary to GmTS3 within the soy genome. The gRNA was operably linked to *Glycine max* U6 Pol III promoter (disclosed in US20170166912) and a poly T terminator. The vector also comprised an expression cassette for a selectable marker conferring resistance to the antibiotic spectinomycin.

Example 8

Testing the Activity of LbCpf1-CO2 Expression Cassettes

The *Agrobacterium* T-DNA vectors described in Example 7, were introduced into *A. tumefaciens*. Excised embryos from A3555 Soybean plants were co-cultured with the *Agrobacterium* containing the vectors by standard methods known in the art and grown on spectinomycin to select for transformed plants. Leaf samples from regenerated plantlets were harvested after 2 weeks and genomic DNA was extracted for Fragment Length Analysis (FLA) to determine genome mutation rates at the target sites GmTS1, GmTS2 and GmTS3 as described in Example 1. A summary of FLA results generated from soy plants stably transformed with the three LbCpf1-CO2 expression cassettes and gRNAs targeting the unique soy genomic target sites is provided in Table 8.

TABLE 8

SUMMARY OF FLA RESULTS GENERATED FROM SOY PLANTS STABLY TRANSFORMED WITH LBCPF1-CO2 EXPRESSION CASSETTES AND GRNA TARGETING 3 UNIQUE GENOMIC TARGET SITES

| Expression vector with LbCpf1 cassette | Genomic target site | Plants assayed | # of edited plants by FLA | Target site mutation |
|---|---|---|---|---|
| Prom$_{Mt.Ubiq}$::NLS:LbCpf1-CO2:NLS::Term$_{Mt}$ | GmTS1 | 84 | 68 | 81% |
| Prom$_{EF1a}$::NLS:LbCpf1-CO2:NLS::Term$_{Mt}$ | GmTS2 | 84 | 58 | 69% |
| Prom$_{At.Ubiq}$::NLS:LbCpf1-CO2:NLS::Term$_{Gb}$ | GmTS3 | 84 | 72 | 86% |

As shown in Table 8, all three sites targeted for cleavage with the guide/LbCpf1-CO2 expression systems described above exhibited the presence of mutations which is indicative of DNA cleavage and repair.

Example 9

Analysis of LbCpf1(TYC)-CO2 Variant Activity in Corn Plants

This example describes the testing of a recombinant polynucleotide encoding Lachnospiraceae LbCpf1(TYC) PAM variant nuclease that is optimized for expression in plant cells.

LbCpf1 variants comprising amino acid mutations resulting in altered PAM sequence specificities have been described by Gao et. al. (see Nature Biotech., 2017 August; 35(8):789-792). For example, Gao et. al. have described an LbCpf1(TYC) variant comprising the mutations G532R/K595R that can be engineered to recognize TYCV PAM. Two nucleotide substitutions were introduced into the LbCpf1-CO2 sequence (SEQ ID NO:10) resulting in LbCpf1(TYC)-CO2 (SEQ ID NO:38) encoding the LbCpf1 (TYC) protein (SEQ ID NO:39) comprising the mutations G532R/K595R.

To test the activity of LbCpf1(TYC), an *Agrobacterium* T-DNA vector was generated. The vector comprised a Cpf1 expression cassette (SEQ ID NO:40) comprising the maize ubiquitin promoter (SEQ ID NO: 7) operably linked to a sequence (SEQ ID NO: 41) encoding LbCpf1(TYC)-CO2 comprising two nuclear localization signals (SEQ ID NOs: 42 and 3). The NLS-LbCpf1(TYC)-CO2-NLS was operably linked to a transcription terminator sequence from a rice Lipid transfer protein (LTP) gene (disclosed in US201801058230-0175, incorporated herein by reference). The vector also comprised a gRNA expression cassette encoding gRNAs designed to target two unique target sites in the corn genome, ZmTS13 and ZMTS14. The ZmTS13 and ZMTS14 sites were chosen since the TYCV PAM was present immediately upstream to each site. The 5'PAM for ZmTS13 was the sequence TTCA. The 5'PAM for ZmTS14 was the sequence TCCA. The gRNA expression cassette comprised the Zea mays U6 Pol III promoter (SEQ ID NO: 9) operably linked to two guide RNAs positioned in tandem and targeting the ZmTS13 and ZmTS14 sites. The expression vector also included a third expression cassette containing the selectable marker gene that provides resistance to the herbicide glyphosate.

Corn 01DKD2 cultivar embryos were transformed with the LbCpf1(TYC)-CO2 vector described above by *Agrobacterium*-mediated transformation. Transformed plants were selected on glyphosate, leaf samples from regenerated plantlets were harvested and genomic DNA was extracted for Fragment Length Analysis (FLA) to determine genome mutation rates specifically at ZmTS13 and ZmTS14 sites, as described in Example 1. ZmTS13 and ZmTS14 are arrayed in antisense orientation relative to each other in the genome and overlap by 8 nts, thus individual editing rates at each gRNA target site were not able to be ascertained. Table 9 summarizes the results and shows the cumulative mutation rate detected at or near the two sites in stably transformed corn plants. As shown in Table 9, 48% (40 of the 83) plants tested exhibited the presence of mutations at the expected region which is indicative of DNA cleavage by LbCpf1 (TYC) and subsequent repair.

TABLE 9

FLA RESULTS GENERATED FROM CORN PLANTS STABLY TRANSFORMED WITH LBCPF1(TYC)-CO2 EXPRESSION CASSETTE AND GRNA TARGETING 2 UNIQUE GENOMIC TARGET SITES.

| T-DNA Vector | Target sites tested | Plants assayed | # Edited plants by FLA analysis | Cumulative Mutation frequency |
| --- | --- | --- | --- | --- |
| LbCpf1(TYC)-CO2 | ZmTS13 ZmTS14 | 83 | 40 | 48% |

Example 10

Analysis of FnCpf1 Engineered Polynucleotides Optimized for Expression in Plant Cells This example describes the design and expression analysis of polynucleotide sequences encoding *Francisella novicida* (FnCpf1) nuclease that are optimized for expression in plant cells.

A nucleotide sequence of Cpf1 from *Francisella novicida* (FnCpf1) that was codon optimized for expression in human cells has been described by Zetsche et. al, (Cell 2015, 163, 759-771). To optimize the expression of the FnCpf1 protein (SEQ ID NO:43) in plant cells, the human codon optimized sequence disclosed by Zetsche et. al., (SEQ ID NO:44), described here as FnCpf1-Hs was modified through algorithmic methods, partly based on plant codon frequency tables, to design seven FnCpf1 CO (Codon optimized) sequences (see Table 10).

TABLE 10

CODON OPTIMIZED FNCPF1 AND THE CODON FREQUENCY TABLES USED TO DESIGN EACH SEQUENCE.

| Codon optimized FnCpf1 | Codon frequency table | SEQ ID NO: |
| --- | --- | --- |
| FnCpf1-CO1 | Glycine max | 45 |
| FnCpf1-CO2 | Monocot | 46 |
| FnCpf1-CO3 | Glycine max | 47 |
| FnCpf1-CO4 | Monocot | 48 |
| FnCpf1-CO5 | Oryza sativa | 49 |
| FnCpf1-CO6 | Oryza sativa | 50 |
| FnCpf1-CO7 | Zea mays | 51 |

Expression Analysis of FnCpf1-CO Variants Via Quantification of FnCpf1-mOr Intensity Three expression cassettes (Prom35S::HIStag:NLS:FnCpf1-CO1:mOrange:NLS::TermNOS; Prom35S::HIStag:NLS:FnCpf1-CO2:mOrange:NLS::TermNOS; and Prom$_{35S}$::HIStag:NLS:FnCpf1-Hs:mOrange:NLS::Term$_{NOS}$) were generated by standard cloning techniques and are described below:

(1) Prom$_{35S}$::HIS tag:NLS:FnCpf1-CO1:mOrange:NLS::Term$_{NOS}$

The FnCpf1-CO1 coding sequence (SEQ ID NO: 45) was fused 5' to the coding sequence of mOrange (mOr) from *Entacmaea quadricolor*(SEQ ID NO:52) The FnCpf1-CO1:mOrange fusion gene was flanked at the 5' end with an NLS sequence from potato (SEQ ID NO: 42) and at the 3' end with an NLS sequence from tomato HSFA1 gene (SEQ ID NO:3) resulting in NLS:FnCpf1-CO1:mOrange:NLS (SEQ ID NO: 53). A nucleotide sequence encoding a HIS tag (MGSS7H) (SEQ ID NO: 54) was introduced at the 5' end of SEQ ID NO:53. A 'TAG' termination codon was introduced to the 3' end of the resulting nucleotide sequence (SEQ ID NO: 55) which was then operably linked to the Cauliflower mosaic virus 35S promoter (disclosed in U.S. Pat. No. 9,938,535-0047, incorporated herein by reference) and an *Agrobacterium* NOS terminator (MK078637). The expression cassette (SEQ ID NO: 56) was cloned into a plant expression vector.

(2) Prom$_{35S}$::HIS tag:NLS:FnCpf1-CO2:mOrange:NLS::Term$_{NOS}$

The FnCpf1-CO2 coding sequence (SEQ ID NO: 46) was fused 5' to the coding sequence of mOrange (mOr) from *Entacmaea quadricolor*. (SEQ ID NO:52). The FnCpf1-CO2:mOrange fusion gene was flanked at the 5' end with an NLS sequence from potato (SEQ ID NO: 42) and at the 3' end with an NLS sequence from tomato HSFA1 gene (SEQ ID NO:3) resulting in NLS-FnCpf1-CO2-NLS(SEQ ID NO:57). A nucleotide sequence encoding a HIS tag (MGSS7H) (SEQ ID NO: 54) was introduced at the 5' end of SEQ ID NO:57. A 'TAG' termination codon was introduced to the 3' end of the resulting nucleotide sequence(SEQ ID NO:58) which was then operably linked to the Cauliflower mosaic virus 35S promoter and an *Agrobacterium* NOS terminator (MK078637). The expression cassette (SEQ ID NO:59) was cloned into a plant expression vector.

(3) Prom$_{35S}$::HIS tag:NLS:FnCpf1-Hs:mOrange:NLS::Term$_{NOS}$

The human codon-optimized Cpf1 (FnCpf1-Hs) nucleotide sequence described by Zetsche et. al, (Cell 2015, 163, 759-771) (SEQ ID NO:44) was fused 5' to the coding sequence of mOrange (mOr) from *Entacmaea quadricolor*. (SEQ ID NO:52). The FnCpf1-Hs:mOrange fusion gene was then flanked at the 5' end with an NLS sequence from potato (SEQ ID NO: 42) and at the 3' end with an NLS sequence from tomato HSFA1 gene (SEQ ID NO:3) resulting in NLS-FnCpf1-Hs:mOrange-NLS(SEQ ID NO: 60). A nucleotide sequence encoding a HIS tag (MGSS7H) (SEQ ID NO: 54) was introduced at the 5' end of SEQ ID NO:60. A 'TAG' termination codon was introduced to the 3' end of the resulting nucleotide sequence (SEQ ID NO:61) which was then operably linked to the Cauliflower mosaic virus 35S promoter and an *Agrobacterium* NOS terminator (MK078637). The expression cassette (SEQ ID NO:62) was cloned into a plant expression vector.

Figure 2:
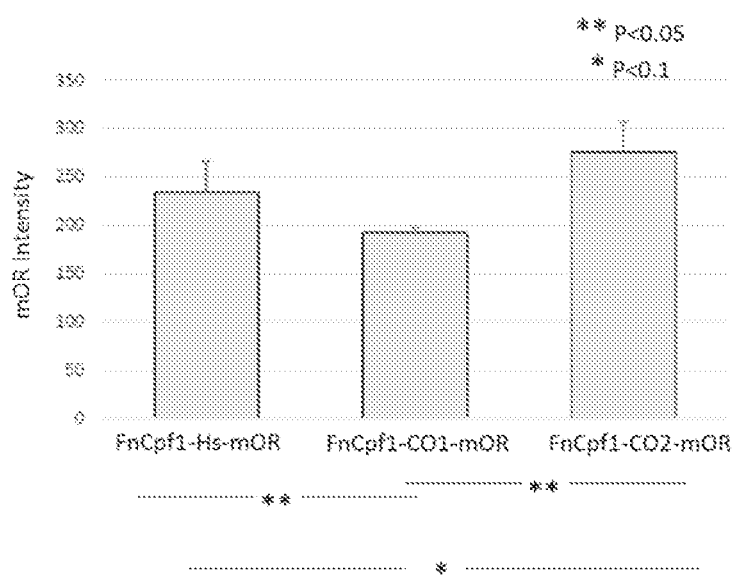
FIG. 2 illustrates the expression of FnCpf1-mOrange fluorescent proteins in corn protoplasts denoted by average mOrange intensities.

To evaluate and quantify the expression of the fusion proteins, corn leaf protoplasts were transfected with expression vectors comprising either of the three expression cassettes described above. Since mOrange was fused to FnCpf1-CO1, FnCpf1-CO2 and FnCpf1-Hs, the relative mOrange fluorescence levels reflects FnCpf1 expression levels. Transformations were carried out using standard polyethylene glycol (PEG) based transfection methods. To quantify transformation frequency, an expression vector comprising the luciferase gene was co-transfected. Following transformation, the protoplasts were incubated in the dark in incubation buffer and harvested after 48 hours. Transformation efficiency was calculated by quantifying luciferase expression. The average mOrange expression from 5 technical replicates was determined using Operetta™ (Perkin Elmer) analysis software. As shown in FIG. 2, mOrange fluorescence was detected from all three samples. The observed intensity was the highest in protoplasts expressing the FnCpf1-CO2-mOrange expression construct.

Expression Analysis FnCpf1-CO Variants Via Qualitative Western Blots:

In addition to the three expression constructs described above, five expression constructs were generated and are described below:

(4) $\text{Prom}_{Ubiq}$::NLS:FnCpf1-CO3:NLS::$\text{Term}_{Os}$:

The FnCpf1-CO3 sequence (SEQ ID NO:47) was flanked at the 5' end with an NLS sequence from potato (SEQ ID NO: 42) and at the 3' end with an NLS sequence from tomato HSFA1 gene (SEQ ID NO:3) resulting in NLS-FnCpf1-CO3-NLS (SEQ ID NO:63). An ATG sequence encoding the translation initiation codon was added 5' to the potato NLS sequence and a TGA termination codon sequence was introduced 3' to the tomato NLS sequence. The resulting sequence was operably linked to the maize ubiquitin promoter (SEQ ID NO: 7) and a transcription terminator sequence from a rice (SEQ ID NO:64). The FnCpf1-CO3 expression cassette sequence is set forth as SEQ ID NO:65. The expression cassette was cloned into a plant expression vector.

(5) $\text{Prom}_{Ubiq}$::NLS:FnCpf1-CO4:NLS::$\text{Term}_{Os}$:

The FnCpf1-CO4 sequence (SEQ ID NO:48) was flanked at the 5' end with an NLS sequence from potato (SEQ ID NO: 42) and at the 3' end with an NLS sequence from tomato HSFA1 gene (SEQ ID NO:3) resulting in NLS-FnCpf1-CO4-NLS(SEQ ID NO:66). An ATG sequence encoding the translation initiation codon was added 5' to the potato NLS sequence and a TAG termination codon sequence was introduced 3' to the tomato NLS sequence. The resulting sequence was operably linked to the maize ubiquitin promoter (SEQ ID NO: 7) and a transcription terminator sequence from a rice (SEQ ID NO: 64). The FnCpf1-CO4 expression cassette sequence is set forth as SEQ ID NO:67. The expression cassette was cloned into a plant expression vector.

(6) $\text{Prom}_{Ubiq}$::NLS:FnCpf1-CO5:NLS::$\text{Term}_{Os}$:

The FnCpf1-CO5 sequence (SEQ ID NO:49) was flanked at the 5' end with an NLS sequence from potato (SEQ ID NO: 42) and at the 3' end with an NLS sequence from tomato HSFA1 gene (SEQ ID NO:3) resulting in NLS-FnCpf1-CO5-NLS (SEQ ID NO:68). An ATG sequence encoding the translation initiation codon was added 5' to the potato NLS sequence and a TGA termination codon sequence was introduced 3' to the tomato NLS sequence. The resulting sequence was operably linked to the maize ubiquitin promoter (SEQ ID NO: 7) and a transcription terminator sequence from a rice (SEQ ID NO: 64). The FnCpf1-CO5 expression cassette sequence is set forth as SEQ ID NO:69. The expression cassette was cloned into a plant expression vector.

(7) $\text{Prom}_{Ubiq}$::NLS:FnCpf1-CO6:NLS::$\text{Term}_{Os}$:

The FnCpf1-CO6 sequence (SEQ ID NO:50) was flanked at the 5' end with an NLS sequence from potato (SEQ ID NO: 42) and at the 3' end with an NLS sequence from tomato HSFA1 gene (SEQ ID NO:3) resulting in NLS-FnCpf1-CO6-NLS (SEQ ID NO:70). An ATG sequence encoding the translation initiation codon was added 5' to the potato NLS sequence and a TGA termination codon sequence was introduced 3' to the tomato NLS sequence. The resulting sequence was operably linked to the maize ubiquitin promoter (SEQ ID NO: 7) and a transcription terminator sequence from a rice (SEQ ID NO: 64). The FnCpf1-CO6 expression cassette sequence is set forth as SEQ ID NO:71. The expression cassette was cloned into a plant expression vector.

(8) $\text{Prom}_{Ubiq}$::NLS:FnCpf1-CO7:NLS::$\text{Term}_{Os}$:

The FnCpf1-CO7 sequence (SEQ ID NO:51) was flanked at the 5' end with an NLS sequence from potato (SEQ ID NO: 42) and at the 3' end with an NLS sequence from tomato HSFA1 gene (SEQ ID NO:3) resulting in NLS-FnCpf1-CO7-NLS (SEQ ID NO:72). An ATG sequence encoding the translation initiation codon was added 5' to the potato NLS sequence and a TGA termination codon sequence was introduced 3' to the tomato NLS sequence. The resulting sequence was operably linked to the maize ubiquitin promoter (SEQ ID NO: 7) and a transcription terminator sequence from a rice (SEQ ID NO: 64). The FnCpf1-CO7 expression cassette sequence is set forth as SEQ ID NO:73. The expression cassette was cloned into a plant expression vector.

Corn protoplast cells were transformed with the eight plant expression vectors described above and in Table 11. As a negative control, cells were transformed with an expression vector for GFP. Transformations were carried out using standard polyethylene glycol (PEG) based transfection methods. Following transformation, the protoplasts were incubated in the dark in incubation buffer and harvested after 48 hours. $32*10^4$ cells from each transformation were lysed using 50 uL of lysis buffer. Total protein was extracted from each of the lysed samples and 30 ug protein per sample was resolved on an SDS-PAGE gel and electro-blotted onto nitrocellulose membranes by standard methods. 5 ng, 1 ng and 500 pg of purified FnCpf1 protein were loaded as positive controls. Western blots using anti-FnCpf1 antibody (Cell Signaling Technology, Danvers, MA) were performed to detect the presence of FnCpf1 proteins using standard methods. As noted in Table 11, a band corresponding to the FnCpf1-mOr was visually observed in the lanes containing protein extract from protoplasts expressing FnCpf1-CO2-mOr (Sample 3). Similarly, bands corresponding to FnCpf1 were visually observed in the lanes containing protein extract from protoplasts expressing FnCpf1-CO3 and FnCpf1-CO4 (Samples 4 and 5).

TABLE 11

EXPRESSION ANALYSIS FNCPF1-CODON OPTIMIZED VARIANTS VIA QUALITATIVE WESTERN BLOTS

| Sample | Expression cassette | Protein band observed |
|---|---|---|
| 1 | $Prom_{35S}$::HIStag:NLS:FnCpf1Hs:mOrange:NLS::$Term_{NOS}$ | No |
| 2 | $Prom_{35S}$:: HIS tag:NLS:FnCpf1-CO1:mOrange:NLS::$Term_{NOS}$ | No |
| 3 | $Prom_{35S}$:: HIS tag:NLS:FnCpf1-CO2:mOrange:NLS::$Term_{NOS}$ | Yes |
| 4 | $Prom_{Ubiq}$::NLS:FnCpf1-CO3:NLS::$Term_{Os}$ | Yes |
| 5 | $Prom_{Ubiq}$::NLS:FnCpf1-CO4:NLS::$Term_{Os}$ | Yes |
| 6 | $Prom_{Ubiq}$::NLS:FnCpf1-CO5:NLS::$Term_{Os}$ | No |
| 7 | $Prom_{Ubiq}$::NLS:FnCpf1-CO6:NLS::$Term_{Os}$ | No |
| 8 | $Prom_{Ubiq}$::NLS:FnCpf1-CO7:NLS::$Term_{Os}$ | No |
| 9 | 5 ng purified FnCpf1 protein (Positive control) | Yes |
| 10 | 1 ng purified FnCpf1 protein (Positive control) | Yes |
| 11 | 500 pg purified FnCpf1 protein (Positive control) | Yes |
| 12 | $Prom_{35S}$::GFP::$Term_{NOS}$ (Negative control) | No |

Example 11

Analysis of FnCpf1 Activity in Corn Protoplasts

The assay used to evaluate FnCpf1 activity in corn protoplasts was integration of a blunt-end, double-stranded DNA (dsDNA) fragment into the DSB (Double stranded break) created by FnCpf1 protein at a specific target site.

The blunt-end dsDNA fragment (disclosed in WO2019084148-021, incorporated herein by reference) was prepared by pre-annealing complementary ssDNA oligonucleotides. The ZmTS9 target site was chosen as the insertion site and a gRNA expression cassette targeting TS9 was designed. The expression cassette comprised a synthetic U6 promoter operably linked to a 21 bp crRNA sequence linked to a 23 bp spacer sequence that was complementary to ZmTS9 in the corn genome. The gRNA expression cassette was introduced into a plant expression vector. The gRNA vector and the eight plant vectors described in Example 11, each containing an expression cassette for a codon optimized FnCpf1 variant were co-transformed into isolated corn leaf protoplasts along with the double-stranded DNA (dsDNA) fragment essentially as described in patent application publication WO2015131101 (incorporated herein by reference), with minor modifications. Approximately $3.2 \times 10^5$ protoplasts were transformed using PEG with a total of 12 μg of plasmid DNA and 50 pmoles of the dsDNA fragment (assays 2-9 in Table 12). Protoplast samples lacking the nuclease expressing plasmids served as a negative control (see assay 10 in Table 12). Additionally, protoplast samples transformed with nuclease vectors and gRNA cassettes lacking the spacer sequence were used as negative controls (see assays 11-19 in Table 12). As a positive control (assay 1 in Table 12), protoplasts were transformed with the gRNA cassette and a vector comprising an expression cassette (SEQ ID NO:74) for LbCpf1-CO2 that has been shown to be active in corn (see Examples 3-4). The expression cassette (SEQ ID NO: 20) comprised NLS-LbCpf1-CO2-NLS (SEQ ID NO:12) with ATGGCG fused in frame 5' to SEQ ID NO 12 as the translational start site, and TGA termination codon fused 3' to SEQ ID NO:12. The resulting sequence was operably linked to the maize ubiquitin promoter (SEQ ID NO: 7) and a transcription terminator sequence from a rice (SEQ ID NO:64). To determine transformation efficiency, 3 ug of GFP internal control plasmid was transformed along with test constructs. Following transformation, the corn protoplasts were incubated in the dark and harvested after 48 hours. Genomic DNA was extracted and assayed for integration of the dsDNA fragment. Integration of the dsDNA fragment into the genomic DNA was detected by standard PCR and agarose gel electrophoresis to assess PCR amplicons. The dsDNA fragment may have integrated in either a 5' or 3' orientation with respect to the 5'- and 3'-ends of the DSB. Therefore, two PCR primer sets were run for the target site where the primer sets contained a primer specific to the dsDNA fragment and a primer specific to either the 5' side or the 3' side of the DSB at TS11. The PCR amplicons were separated using standard agarose gel electrophoresis and the size of the amplicon was confirmed by comparison to a molecular weight marker. The presence of a band of expected size was indicative of site-directed integration of the donor oligo at the ZmTS9 site following FnCpf1 mediated dsDNA cleavage. As shown in Table 12, expected bands were amplified from protoplasts expressing LbCpf1-CO2, FnCpf1-CO1, FnCpf1-CO2, FnCpf1-CO3, FnCpf1-CO4, FnCpf1-CO6, FnCpf1-CO7 along with the cognate gRNA cassette and ds DNA. Expected bands were not amplified from protoplasts expressing FnCpf1-CO5 or any of the negative controls.

TABLE 12

FNCPF1 MEDIATED SITE DIRECTED INTEGRATION OF DSDNA OLIGO AT ZMTS9 TARGET SITE.

| Assay | Nuclease Expression cassette | gRNA targeting ZmTS9 | Expected band amplified |
|---|---|---|---|
| 1 | $Prom_{Ubiq}$::NLS:LbCpf1-CO2:NLS::$Term_{Os}$ (Positive control) | + | Yes |
| 2 | $Prom_{35S}$::HIStag:NLS:FnCpf1Hs:mOrange:NLS::$Term_{NOS}$ | + | No |
| 3 | $Prom_{35S}$:: HIS tag:NLS:FnCpf1-CO1:mOrange:NLS::$Term_{NOS}$ | + | Yes |
| 4 | $Prom_{35S}$:: HIS tag:NLS:FnCpf1-CO2:mOrange:NLS::$Term_{NOS}$ | + | Yes |
| 5 | $Prom_{Ubiq}$::NLS:FnCpf1-CO3:NLS::$Term_{Os}$ | + | Yes |
| 6 | $Prom_{Ubiq}$::NLS:FnCpf1-CO4:NLS::$Term_{Os}$ | + | Yes |

TABLE 12-continued

FNCPF1 MEDIATED SITE DIRECTED INTEGRATION OF DSDNA OLIGO AT ZMTS9 TARGET SITE.

| Assay | Nuclease Expression cassette | gRNA targeting ZmTS9 | Expected band amplified |
|---|---|---|---|
| 7 | Prom$_{Ubiq}$::NLS:FnCpf1-CO5:NLS::Term$_{Os}$ | + | No |
| 8 | Prom$_{Ubiq}$::NLS:FnCpf1-CO6:NLS::Term$_{Os}$ | + | Yes |
| 9 | Prom$_{Ubiq}$::NLS:FnCpf1-CO7:NLS::Term$_{Os}$ | + | Yes |
| 10 | None | + | No |
| 11 | Prom$_{Ubiq}$::NLS:LbCpf1-CO2:NLS::Term$_{Os}$ | − | No |
| 12 | Prom$_{35S}$::HIStag:NLS:FnCpf1Hs:mOrange:NLS::Term$_{NOS}$ | − | No |
| 13 | Prom$_{35S}$:: HIS tag:NLS:FnCpf1-CO1:mOrange:NLS::Term$_{NOS}$ | − | No |
| 14 | Prom$_{35S}$:: HIS tag:NLS:FnCpf1-CO2:mOrange:NLS::Term$_{NOS}$ | − | No |
| 15 | Prom$_{Ubiq}$::NLS:FnCpf1-CO3:NLS::Term$_{Os}$ | − | No |
| 16 | Prom$_{Ubiq}$::NLS:FnCpf1-CO4:NLS::Term$_{Os}$ | − | No |
| 17 | Prom$_{Ubiq}$::NLS:FnCpf1-CO5:NLS::Term$_{Os}$ | − | No |
| 18 | Prom$_{Ubiq}$::NLS:FnCpf1-CO6:NLS::Term$_{Os}$ | − | No |
| 19 | Prom$_{Ubiq}$::NLS:FnCpf1-CO7:NLS::Term$_{Os}$ | − | No |

The invention claimed is:

1. A recombinant nucleic acid comprising the sequence of SEQ ID No: 38.

2. The recombinant nucleic acid of claim 1, further comprising one or more components selected from the group consisting of: a nucleic acid sequence encoding one or more nuclear localization signals, an operably linked promoter, one or more introns, one or more kozak sequences, one or more leader sequences, and one or more terminator sequences.

3. The recombinant nucleic acid of claim 2, wherein the promoter comprises a sequence selected from the group consisting of SEQ ID Nos: 7, 22, 27, and 32.

4. The recombinant nucleic acid of claim 1, wherein the recombinant nucleic acid comprises the sequence of SEQ ID No: 41.

5. A plant cell comprising the recombinant nucleic acid of claim 1.

6. A composition comprising: (a) the recombinant nucleic acid of claim 1, and (b) a recombinant nucleic acid encoding a guide RNA comprised of at least one crRNA and at least one spacer RNA sequence.

7. The composition of claim 6, wherein the composition is provided on a particle suitable for biolistic delivery to a plant cell.

8. A method for modifying a target sequence in the genome of a plant cell, comprising:
  a) introducing into the plant cell the recombinant nucleic acid of claim 1 operably linked to a promoter, and
  b) introducing into the plant cell a guide polynucleotide comprising a nucleic acid sequence that is complementary to a target sequence or a recombinant nucleic acid encoding the guide polynucleotide, wherein the guide polynucleotide and a Cpf1 nuclease expressed from the recombinant nucleic acid form a complex that can bind to and modify the target sequence.

9. The method of claim 8, wherein the promoter comprises a sequence selected from the group consisting of SEQ ID Nos: 7, 22, 27, and 32.

10. The method of claim 8, wherein the plant cell is a maize, cotton, soybean, canola, wheat, tomato, rice, brassica, melon, cucurbit, or lettuce cell.

11. The method of claim 8, further comprising introducing a donor DNA to the plant cell.

12. The method of claim 11, further comprising identifying at least one plant cell comprising in its genome the donor DNA, or a portion thereof, integrated into or near said target sequence.

13. A method for modifying a target sequence in the genome of a plant cell, the method comprising: introducing a guide polynucleotide comprising a nucleic acid sequence that is substantially complementary to the target sequence, or a recombinant nucleic acid encoding the guide polynucleotide, into a plant cell comprising in its genome the recombinant nucleic acid of claim 1 operably linked to a promoter, wherein the guide polynucleotide and a Cpf1 nuclease expressed from the recombinant nucleic acid form a complex that can bind to and modify the target sequence.

14. The method of claim 13, wherein the promoter comprises a sequence selected from the group consisting of SEQ ID Nos: 7, 22, 27, and 32.

15. The method of claim 13, wherein the plant cell is a maize, cotton, soybean, canola, wheat, tomato, rice, brassica, melon, cucurbit, or lettuce cell.

16. The method of claim 13, further comprising introducing a donor DNA to the plant cell.

17. The method of claim 16, further comprising identifying at least one plant cell comprising in its genome the donor DNA, or a portion thereof, integrated into or near said target sequence.

18. A kit for modifying a target sequence in the genome of a plant cell, the kit comprising a guide polynucleotide comprising a nucleic acid sequence that is complementary to a target sequence or a recombinant nucleic acid encoding the guide polynucleotide, and the recombinant nucleic acid of claim 1.

19. The kit of claim 18, wherein the recombinant nucleic acid comprises one or more sequences selected from the group consisting of SEQ ID Nos: 40 and 41.

20. The kit of claim 18, further comprising a recombinant nucleic acid encoding a selectable marker.

* * * * *

SEQUENCE LISTING

```
Sequence total quantity: 76
SEQ ID NO: 1                moltype = DNA  length = 3684
FEATURE                     Location/Qualifiers
misc_feature                1..3684
                            note = Synthetic polynucleotide. Codon optimized LbCpf1-CO1
source                      1..3684
                            mol_type = other DNA
                            organism = synthetic construct
SEQUENCE: 1
atgtccaagc ttgagaagtt tactaattgc tatagcctgt ctaagaccct tcgctttaag   60
gcgattcctg tgggcaagac gcaggaaaac atcgacaaca agcgactgct ggtggaagac  120
gagaagcgcg ctgaggacta aagggcgta aagaagctgc tcgatcggta ctacctgagt  180
tttatcaacg atgtgttgca ttccataaag ttgaagaatc ttaataacta catctccttg  240
tttcggaaaa agaccaggac cgagaaggag aataaagagt tggaaaatct ggagatcaac  300
ttgcgtaagg agatcgcgaa ggcgttcaag ggtaatgagg gttataagag tctcttttaaa  360
aaagatataa ttgaaacgat tctacccgaa tttctggatg ataaggatga gattgccctc  420
gtcaattcgt tcaatggctt tacaacagcg tttacaggtt tcttcgataa cagggaaaat  480
atgtttagcg aggaggcaaa gtcgacctct atcgcttttc gctgtataaa cgaaaattta  540
actcgatata tctccaatat ggatattttc gagaaagtcg atcgatctt tgataagcat  600
gaagtccagg agattaagga aaagattctt aattcagatt atgatgtgga agatttttc  660
gaaggtgagt tctttaactt cgtgcttacg caagaaggaa tcgacgttta caatgcaata  720
attggtgggt tgttactgga atctggtgaa aagatcaaag gcctcaatga gtacattaac  780
tgtacaatc agaagacgaa gcagaagtta ccaaaattca agccgctgta caagcaagtg  840
ttatctgaca gggaatcttt gtccttttac ggtgaaggat acacttctga tgaagagtg  900
cttgaggtct tcaggaatac actgaacaag aattctgaga tcttctcctc aattaagaaa  960
ctcgaaaaac ttttcaagaa ctttgatgaa tacagctctg ctggaatttt cgtaaagaat 1020
ggtcccgcca taagcactat ctcaaaggac atttttcggtg agtggaagtt tataagagat 1080
aaatggaatg cagagtacga cgatatccat ttgaagaaaa aggcggtagt taccgaaaag 1140
tacgaggatg acagaaggaa atcgttcaag aagattggct cattctccct ggagcagctt 1200
caggagtacg cggacgcgga cctttctgtt gttgaaaagc tcaaggagat catcataca  1260
aaggtagacg agatttataa ggtctatggg agctcagaga aattgttcga cgccgatttc 1320
gttttggaga agtcactgaa aaagaacgac gctgtcgtcg ctattatgaa agaccttttg 1380
gattctgtca agtcttttga gaactatatt aaggctttt tcggtgaggg taaggagacg 1440
aaccgcgacg agtcattcta cggagacttt gtactcgcat atgacatact gctcaaagtt 1500
gatcatattt atgacgcgat ccgcaattac gttacacaaa aaccatactc taaagataaa 1560
ttcaagctgt atttccaaaa cccgcaattc atgggggct gggataagga taaggaaacc 1620
gattataggg cgaccatatt gcgctacggg agcaagtatt acttagcgat catggataaa 1680
aaatacgcaa agtgtttgca aaagatagac aaggacgatg tcaatggcaa ttatgagaag 1740
attaactata agttgctgcc aggacccaat aagatgttgc ccaaagtttt ttctccaaa  1800
aaatgatgg cttattataa ccctagcgag gacatccaga aaatatacaa aaacggcaca 1860
tttaagaagg gggatatgtt caatcttaat gattgtcaca agctgataga ctttttcaag 1920
gactcaatct ctcggtatcc caagtggtcg aatgcgtacg atttaattt ttctgagacc 1980
gaaaagtaca aggatattgc aggcttttat cgcgaagtgg aggaacaagg ataccagtt 2040
tcattcgaat ccgcctcaaa aaggaggtc gacaaactcg gtaaaaccac taactgtaac 2100
atgttccaaa tttacaataa agactttca gacaaatcac acggaactcc taaccttcac 2160
acaatgtact ttaaattgct gttcgatgaa aataatcacg gtcaaattag gctgtcaggc 2220
ggagctgagc ttttcatgag gagggctagt ctgaagaaag aggagctggt ggtccatcct 2280
gcaaatagtc ccatagctaa taagaatcct gataacctca agaaaaccac cactctctcc 2340
tacgacgttt ataaggataa acggttcagt gaagatcagt atgagttgca tattcccatt 2400
gccataaata agtgccctaa gaacatcttc aaaattaaca cagaagtgag agttctcttg 2460
aaacacgatg ataatccata tgtgattggg atagataggg gagagcgtaa cctccttat  2520
attgtcgtgg ttgacggaaa gggtaacata gtggagcaat acagcctcaa tgaaattatt 2580
```

-continued

```
aacaacttta atggtattag aataaagact gactatcata gtctcttgga taaaaaagag  2640
aaggagaggt tcgaagctag gcagaattgg acgtctattg aaaatattaa agaactcaaa  2700
gcagggtaca ttagccaagt cgttcacaag atatgcgagt tggttgagaa atatgatgct  2760
gtcattgcac tggaggatct caatagcggt ttcaaaaaca gtcgtgttaa ggtggagaag  2820
caggtttacc agaaattcga gaagatgctg attgataagc ttaactatat ggtggacaaa  2880
aagtctaatc catgcgcgac cggtggcgca cttaagggct atcagatcac aaacaagttc  2940
gagtcgttta agtccatgtc aacacagaac ggtttcatct tctatatccc ggcatggctg  3000
acctcaaaaa ttgatcctag cacggggttc gtaaacttac ttaaaactaa atacacctca  3060
attgctgatt caaaaaagtt tatatcctca tttgaccgaa ttatgtatgt gcccgaggag  3120
gacctgttcg aattcgctct ggactataag aacttttcaa gaacagatgc ggattatatc  3180
aagaagtgga aactttacag ttatggtaac cgcattagga tattccggaa ccccaaaaaa  3240
aataatgtct tgattgggga ggaggtatgt ctgacgtctg cttataagga gctatttaat  3300
aagtacggca tcaattatca gcaggggac atccgcgcgc ttctctgcga gcaatccgat  3360
aaggctttct acagctcctt catgcgcttg atgagcctca tgctgcagat gagaaacagt  3420
atcacaggta gaacggacgt agacttccta atttctccag tgaagaattc agatggcatc  3480
ttctatgata gccgcaacta tgaggcacag gagaacgcca tcctgcccaa aaatgctgat  3540
gccaacggtg cgtataacat tgctaggaag gtcctctggg ccataggtca attcaagaaa  3600
gctgaagacg agaagctcga caaggtaaaa attgccatat ccaacaagga gtggctcgaa  3660
tatgcacaga cctctgtgaa gcat                                         3684

SEQ ID NO: 2             moltype = AA   length = 1228
FEATURE                  Location/Qualifiers
source                   1..1228
                         mol_type = protein
                         note = Lachnospiraceae bacterium ND2006
                         organism = unidentified
SEQUENCE: 2
MSKLEKFTNC YSLSKTLRFK AIPVGKTQEN IDNKRLLVED EKRAEDYKGV KKLLDRYYLS   60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNPQF MGGWDKDKET  540
DYRATILRYG SKYYLAIMDK KYAKCLQKID KDDVNGNYEK INYKLLPGPN KMLPKVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI AINKCPKNIF KINTEVRVLL KHDDNPYVIG IDRGERNLLY  840
IVVVDGKGNI VEQYSLNEII NNFNGIRIKT DYHSLLDKKE KERFEARQNW TSIENIKELK  900
AGYISQVVHK ICELVEKYDA VIALEDLNSG FKNSRVKVEK QVYQKFEKML IDKLNYMVDK  960
KSNPCATGGA LKGYQITNKF ESFKSMSTQN GFIFYIPAWL TSKIDPSTGF VNLLKTKYTS 1020
IADSKKFISS FDRIMYVPEE DLFEFALDYK NFSRTDADYI KKWKLYSYGN RIRIFRNPKK 1080
NNVFDWEEVC LTSAYKELFN KYGINYQQGD IRALLCEQSD KAFYSSFMAL MSLMLQMRNS 1140
ITGRTDVDFL ISPVKNSDGI FYDSRNYEAQ ENAILPKNAD ANGAYNIARK VLWAIGQFKK 1200
AEDEKLDKVK IAISNKEWLE YAQTSVKH                                    1228

SEQ ID NO: 3             moltype = DNA   length = 30
FEATURE                  Location/Qualifiers
source                   1..30
                         mol_type = unassigned DNA
                         organism = Lycopersicon esculentum
SEQUENCE: 3
ggatctaaga agagaagaat taaacaagat                                    30

SEQ ID NO: 4             moltype = DNA   length = 3750
FEATURE                  Location/Qualifiers
misc_feature             1..3750
                         note = Synthetic polynucleotide.NLS-LbCpf1-CO1-NLS
source                   1..3750
                         mol_type = other DNA
                         organism = synthetic construct
SEQUENCE: 4
atgggatcta agaagagaag aattaaacaa gatatgtcca agcttgagaa gtttactaat   60
tgctatagcc tgtctaagac ccttcgcttt aaggcgattc ctgtgggcaa gacgcaggaa  120
aacatcgaca acaagcgact gctggtggtg gacgagaagc gcgctgagga ctataagggc  180
gtaaagaagc tgctcgatcg gtactacctg agttttatca acgatgtgtt gcattccata  240
aagttgaaga tcttaataa ctacatctcc ttgtttcgga aaaagaccag gaccgagaag  300
gagaataaag agttggaaaa tctggagatc aactgtgcta aggagatcgc gaaggcgttc  360
aagggtaatg agggttataa gagtctcttt aaaaagata taattgaaac gattctaccc  420
gaatttctga tgataagga tgagattgcc ctcgtcaatt cgttcaatgg ctttacaaca  480
gcgtttacag gtttcttcga taacagggaa aatatgttta gcgaggaggc aaagtcgaca  540
tctatcgctt ttcgctgtat aaacgaaaat ttaactcgat atatctccaa tatggatatt  600
ttcgagaaaa tcgatgcgat cttttgataag catgaagtcc aggagattaa ggaaaagatt  660
cttaattcag attatgatgt ggaagatttt tcgaaggtg agttctttaa cttcgtgctt  720
acgcaagaag gaatcgacgt ttacaatgca ataattggtg ggtttgttac tgaatctggt  780
gaaaagatca aaggcctcaa tgagtacatt aacttgtaca atcagaagac gaagcagaag  840
```

```
ttaccaaaat tcaagccgct gtacaagcaa gtgttatctg acagggaatc tttgtccttt      900
tacggtgaag gatacacttc tgatgaagag gtgcttgagg tcttcaggaa tacactgaac      960
aagaattctg agatcttctc ctcaattaag aaactcgaaa aacttttcaa gaactttgat     1020
gaatacagct ctgctggaat tttcgtaaag aatggtcccg ccataagcac tatctcaaag     1080
gacattttcg gtgagtggaa tgttataaga gataaatgaa atgcagagta cgacgatatc     1140
catttgaaga aaaaggcggt agttaccgaa aagtacgagg atgacagaag gaaatcgttc     1200
aagaagattg gctcattctc cctggagcag cttcaggagt acgcggacgc ggacctttct     1260
gttgttgaaa agctcaagga gatcatcata caaaaggtag acgagattta taaggtctat     1320
gggagctcag agaaattgtt cgacgccgat ttcgttttgg agaagtcact gaaaaagacg     1380
gacgctgtcg tcgctattat gaaagacctt ttggattctg tcaagtcttt tgagaactat     1440
attaaggctt ttttcggtga gggtaaggag acgaaccgcg acgagtcatt ctacggagac     1500
tttgtactcg catatgacat actgctcaaa gttgatcata tttatgacgc gatccgcaat     1560
tacgttacac aaaaaccata ctctaaagat aaattcaagc tgtatttcca aaacccgcaa     1620
ttcatggggg gctgggataa ggataaggaa accgattata gggcgaccat attgcgctac     1680
gggagcaagt attacttagc gatcatggat aaaaaatacg caaagtgttt gcaaaagata     1740
gacaaggacg atgtcaatgg caattatgag aagattaact ataagttgct gccaggaccc     1800
aataagatgt tgcccaaagt tttttctcc aaaaaatgga tggcttatta taaccctagc     1860
gaggacatcc agaaaatata caaaaacggc acatttaaga aggggatat gttcaatctt     1920
aatgattgtc acaagctgat agactttttc aaggactcaa tctctcggta tcccaagtgg     1980
tcgaatgcgt acgattttaa ttttttctgag accgaaaagt acaaggatat tgcaggcttt     2040
tatcgcgaag tggaggaaca aggatacaag gtttcattcg aatccgcctc aaaaaaggag     2100
gtcgcaaact cgtcgaaga gggtaaactg tacatgttcc aaatttacaa taaagacttt     2160
tcagacaaat cacacggaac tcctaacctt cacacaatgt actttaaatt gctgttcgat     2220
gaaaataatc acggtcaaat taggctgtca ggcggagctg agcttttcat gagggagggct     2280
agtctgaaga aagaggagct ggtggtccat cctgcaaata gtcccatagc taataagaat     2340
cctgataacc ctaagaaaac caccactctc tcctacgaca tttataagga taacggttc       2400
agtgaagatc agtatgagtt gcatattccc attgccataa ataagtgccc taagaacatc     2460
ttcaaaatta acacagaagt gagagttctc ttgaaacacg atgataatcc atatgtgatt     2520
gggatagata ggggagagcg taacctcctt tatattgtcg tggttgacgg aaagggtaac     2580
atagtggagc aatacagcct caatgaaatt attaacaact ttaatggtat tagaataaag     2640
actgactatc atagtctctt ggataaaaaa gagaaggaga ggttcgaagc taggcagaat     2700
tggacgtcta ttgaaaatat taaagaactc aaagcagggt acattagcca agtcgttcac     2760
aagatatgcg agttggttga gaaatatgat gctgtcattg cactggagga tctcaatagc     2820
ggtttcaaaa acagtcgtgt taaggtggag aagcaggttt ccagaaatt cgagaagatg     2880
ttgattgata agcttaacta tatggtggac aaaaagtcta atccatgcgc gaccggtggc     2940
gcacttaagg gctatcagat cacaaacaag ttcgagtcgt ttaagtccat gtcaacacag     3000
aacgtttca tcttctatat cccggcatgg ctgacctcaa aaattgatcc tagcacgggg     3060
ttcgtaaact tacttaaac taaatacacc tcaattgctg attcaaaaaa gtttatatcc     3120
tcatttgacc gaattatgta tgtgcccgag gaggacctgt tcgaattcgc tctgactact    3180
aagaactttt caagaacaga tgcggattat atcaagaagt ggaaacttta cagttatggt    3240
aaccgcatta ggatattccg gaaccccaaa aaaaataatg tctttgattg ggaggaggta    3300
tgtctgacgt ctgcttataa ggagctattt aataagtacg gcatcaatta tcagcagggg    3360
gacatccgcg cgcttctctg cgagcaatcc gataaggctt tctacagctc cttcatgcga    3420
ttgatgagcc tcatgctgca gatgaaaac agtatcacag gtagaacgga cgtagacttc    3480
ctaatttctc cagtgaagaa ttcagatggc atcttctatg atagccgcaa ctatgaggca    3540
caggagaacg ccatcctgcc caaaaatgct gatgccaacg gtgcgtataa cattgctagg    3600
aaggtcctct gggccatagg tcaattcaag aaagctgaag acgagaagct cgacaaggta    3660
aaaattgcca tatccaacaa ggagtggctc gaatatgcac agacctctgt gaagcatgga    3720
tctaagaaga gaagaattaa acaagattga                                      3750
```

```
SEQ ID NO: 5            moltype = DNA   length = 189
FEATURE                 Location/Qualifiers
source                  1..189
                        mol_type = unassigned DNA
                        organism = Solanum tuberosum
SEQUENCE: 5
gtaagtttct gcttctacct ttgatatata taataatt atcattaatt agtagtaata        60
taatatttca aatattttt tcaaaataaa agaatgtagt atatagcaat tgcttttctg      120
tagtttataa gtgtgtatat tttaatttat aacttttcta atatatgacc aaaatttgtt    180
gatgtgcag                                                             189

SEQ ID NO: 6            moltype = DNA   length = 3939
FEATURE                 Location/Qualifiers
misc_feature            1..3939
                        note = Synthetic polynucleotide.NLS-
                        LbCpf15'-Intron-LbCpf13'-NLS
source                  1..3939
                        mol_type = other DNA
                        organism = synthetic construct
SEQUENCE: 6
atgggatcta agaagagaag aattaaacaa gatatgtcca agcttgagaa gtttactaat        60
tgctatagcc tgtctaagac ccttcgcttt aaggcgattc ctgtgggcaa gacgcaggaa      120
aacatcgaca acaagcgact gctggtgaaa gacgagaagc gcgctgagga ctataagggc      180
gtaaagaagc tgctcgatcg gtactacctg agttttatca acgatgtgtt gcattccata      240
aagttgaaga atcttaataa ctacatctcc ttgtttcgga aaaagaccag gaccgagaag      300
gagaataaag agttggaaaa tctggagatc aacttgcgta aggagatcgc gaaggcgttc      360
aagggtaatg agggttataa gagtctcttt aaaaagatat aattgaaac gattctaccc       420
gaatttctgg atgataagga tgagattgcc ctcgtcaatt cgtcaatgg ctttacaaca       480
gcgtttacag gtaagtttct gcttctacct ttgatatata taataatt atcattaatt       540
```

```
agtagtaata taatatttca aatattttt tcaaaataaa agaatgtagt atatatagcaat    600
tgcttttctg tagtttataa gtgtgtatat tttaatttat aacttttcta atatatgacc    660
aaaatttgtt gatgtgcagg tttcttcgat aacaggaaaa atatgtttag cgaggaggca    720
aagtcgacct ctatcgcttt tcgctgtata aacgaaaatt taactcgata tatctccaat    780
atggatattt tcgagaaagt cgatgcgatc tttgataagc atgaagtcga ggagattaag    840
gaaaagattc ttaattcaga ttatgatgtg aagatttt tcgaaggtga gttctttaac    900
ttcgtgctta cgcaagaagg aatcgacgtt tacaatgcaa taattggtgg gtttgttact    960
gaatctggtg aaaagatcaa aggcctcaat gagtacatta acttgtacaa tcagaagacg   1020
aagcagaagt taccaaaatt caagccgctg tacaagcaag tgttatctga cagggaatct   1080
ttgtcctttt acggtgaagg atacacttct gatgaagagg tgcttgaggt cttcaggaat   1140
acactgaaca agaattctga gatcttctcc tcaattaaga aactcgaaaa actttcaag   1200
aactttgatg aatacagctc tgctggaatt ttcgtaaaga atggtcccgc cataagcact   1260
atctcaaagg acattttcgg tgagtggaat gttataagag ataaatggaa tgcagagtac   1320
gacgatatcc atttgaagaa aaaggcggta gttaccgaaa agtacgagga tgacagaagg   1380
aaatcgttca agaagattgg ctcattctcc ctggagcagc ttcaggagta cgcggacgcg   1440
gacctttctg ttgttgaaaa gctcaaggag atcatctac aaaaggtaga cgagatttat   1500
aaggtctatg ggagctcaga gaaattgttc gacgccgatt tcgttttgga gaagtcactg   1560
aaaaagaacg acgctgtcgt cgctattatg aagaccttt tggattctgt caagtctttt   1620
gagaactata ttaaggcttt tttcggtgag ggtaaggaga cgaaccgcga cgagtcattc   1680
tacgagact ttgtactcgc atatgacata ctgctcaaag ttgatcatat ttatgacgcg   1740
atccgcaatt acgttacaca aaaaccatac tctaaagata aattcaagct gtatttccaa   1800
aacccgcaat tcatgggggg ctgggataag gataaggaaa cgattatag ggcgaccata   1860
ttgcgctacg ggagcaagta ttacttagcg atcatggata aaaatacgc aaagtgtttg   1920
caaaagatag acaaggacga tgtcaatggc aattatgaga agattaacta taagttgctg   1980
ccaggaccca ataagatgtt gcccaaagtt ttttctcca aaaatggat ggcttattat   2040
aaccctagcg aggacatcca gaaaatatac aaaaacgaca catttaagaa ggggatatg   2100
ttcaatctta atgattgtca caagctgata gactttttca aggactcaat ctctcggtat   2160
cccaagtggt cgaatgcgta cgattttaat tttctgaga ccgaaaagta caaggatatt   2220
gcaggctttt atcgcgaagt ggaggaacaa ggatacaagg tttcattcga atccgcctca   2280
aaaaaggagg tcgacaaact cgtcgaagag ggtaaactgt acatgttcca aatttacaat   2340
aaagacttt cagacaaatc acacggaact cctaacttc acacaatgta ctttaaattg   2400
ctgttcgatg aaaataatca cggtcaaatt aggctgtcag gcggagctga gcttttcatg   2460
aggagggcta gtctgaagaa agaggagctg gtggtccatc ctgcaaatag tcccatagct   2520
aataagaatc ctgataaccc taagaaaacc accactctct cctacgacgt ttataaggat   2580
aaacggttca gtgaagatca gtatgagttg catattccca ttgccataaa taagtgccct   2640
aagaacatct tcaaaattaa cacagaagtg agagttctct tgaaacacga tgataatcca   2700
tatgtgattg ggatagatag gggagagcgt aacctccttt atattgtcgt ggttgacgga   2760
aagggtaaca tagtggagca atacagcctc aatgaaatta ttaacaactt taatggtatt   2820
agaataaaga ctgactatca tagtctcttg gataaaaaag agaaggagag gttcgaagct   2880
aggcagaatt ggacgtctat tgaaaatatt aagaactca agcagggta cattagccaa   2940
gtcgttcaca agatatgcga gttggttgag aaatatgatg ctgtcattgc actgaggat   3000
ctcaatagcg gtttcaaaaa cagtcgtgtt aaggtggaga agcaggttta ccagaaattc   3060
gagaagatgc tgattgataa gcttaactat atggtgacaa aaagtctaa tccatgcgtg   3120
accggtggcg cacttaaggg ctatcagatc acaaacaagt cgagtcgtt taagtccatg   3180
tcaacacaga acgtttcat cttctatat ccggcatggc tgacctcaaa aattgatcct   3240
agcacggggt tcgtaaactt acttaaaact aaatacacct caattgctga ttcaaaaag   3300
tttatatcct catttgaccg aattatgtat gtgcccgagg aggacctgtt cgaattcgct   3360
ctggactata agaactttc aagaacagat gcggattata tcaagaagtg gaaactttac   3420
agttatggta accgcattag gatattccgg aaccccaaaa aaataatgt ctttgattgg   3480
gaggaggtat gtctgacgtc tgcttataag gagctattta ataagtacgg catcaattat   3540
cagcaggggg acatccgcgc gcttctctgc gagcaatccg ataaggcttt ctacagctcg   3600
ttcatggcat tgatgagcct catgctgcag atgagaaaca gtatcacagg tagaacggac   3660
gtagacttcc taatttctcc agtgaagaat tcagatggca tcttctatga tagccgcaac   3720
tatgaggcac aggagaacgc catcctgccc aaaaatgctg atgccaacgg tgcgtataac   3780
attgctagga aggtcctctg ggccataggt caattcaaga aagctgaaga cgagaagctc   3840
gacaaggtaa aaattgccat atccaacaag gagtggctcg aatatgcaca gacctctgtg   3900
aagcatggat ctaagaagag aagaattaca caagattga                          3939
```

SEQ ID NO: 7                moltype = DNA   length = 2008
FEATURE                 Location/Qualifiers
source                 1..2008
                        mol_type = unassigned DNA
                        organism = Zea mays
SEQUENCE: 7

```
gtcgtgcccc tctctagaga taaagagcat tgcatgtcta aagtataaaa aattaccaca     60
tatttttttg tcacacttat ttgaagtgta gtttatctat ctctatacat atatttaaac    120
ttcactctac aaataatata gtctataata ctaaataat attagtgttt tagaggatca    180
tataaataaa ctgctagaca tggtctaaag gataattgaa tatttgaca atctacagtt    240
ttatctttt agtgtgcatg tgatctctct gtttttttg caaatagctt gacctatata    300
atacttcatc cattttatta gtacatccat ttaggatttta gggttgatgg tttctataga    360
ctaattttta gtacatccat tttattcttt ttagtctcta aatttttaa aactaaaact    420
ctatttagt tttttattta ataatttaga tataaaatga aataaaataa attgactaca    480
aataaaacaa atacccttta agaaataaaa aaactaagca acattttc ttgtttcgag    540
tagataatga caggctgttc aacgccgtcg acgagtctaa cgagacacaa ccagcgaacc    600
agcagcgtcg cgtcgggcca agcgaagcag acgcacggc atctctgtag ctgcctctgg    660
accccctctcg agagttccgc tccaccgttg gactgctcc gctgtcggca tccgaaaatt    720
gcgtggcgga gcgcagacg tgaggcggca cggcaggcgg cctcttcctc ctctcacggc    780
accggcagct acggggggatt cctttcccac cgctccttcg ctttcccttc ctcgcccgcc    840
gtaataaata gacacccct ccacaccctc tttccccaac ctcgtgttcg ttcggagcgc    900
```

```
acacacacgc aaccagatct cccccaaatc cagccgtcgg cacctccgct tcaaggtacg    960
ccgctcatcc tccccccccc cctctctcta ccttctctag atcggcgatc cggtccatgg   1020
ttagggcccg gtagttctac ttctgttcat gtttgtgtta gagcaaacat gttcatgttc   1080
atgtttgtga tgatgtggtc tggttgggcg gtcgttctag atcggagtag gatactgttt   1140
caagctacct ggtggattta ttaattttgt atctgtatgt gtgtgccata catcttcata   1200
gttacgagtt taagatgatg gatgaaaata tcgatctagg ataggtatac atgttgatgc   1260
gggtttact  gatgcatata cagagatgct tttttctcg cttggttgtg atgatatggt   1320
ctggttgggc ggtcgttcta gatcggagta gaatactgtt tcaaactacc tggtggattt   1380
attaaaggat aaagggtcgt tctagatcgg agtagaatac tgtttcaaac tacctggtgg   1440
atttattaaa ggatctgtat gtatgtgcct acatcttcat agttacgagt ttaagatgat   1500
ggatggaaat atcgatctag gataggtata catgttgatg cgggttttac tgatgcatat   1560
acagagatgc ttttttcgc ttggttgtga tgatgtggtc tggttgggcg gtcgttctag   1620
atcggagtag aatactgttt caaactacct ggtggattta ttaattttgt atctttatgt   1680
gtgtgccata catcttcata gttacgagtt taagatgatg gatgaaaata ttgatctagg   1740
ataggtatac atgttgatgt gggttttact gatgcatata catgatggca tatgcggcat   1800
ctattcatat gctctaacct tgagtaccta tctattataa taaacaagta tgttttataa   1860
ttattttgat cttgatatac ttggatgatg gcatatgcag cagctatatg tggatttttt   1920
agccctgcct tcatacgcta tttatttgct tggtactgtt tcttttgtcc gatgctcacc   1980
ctgttgtttg gtgatacttc tgcaggtc                                     2008

SEQ ID NO: 8            moltype = DNA  length = 298
FEATURE                 Location/Qualifiers
source                  1..298
                        mol_type = unassigned DNA
                        organism = Oryza sativa
SEQUENCE: 8
taatcgatcc tccgatccct taattaccat accattacac catgcatcaa tatccatata    60
tatataaacc ctttcgcacg tacttatact atgttttgtc atacatatat atgtgtcgaa   120
cgatcgatct atcactgata tgatatgatt gatccatcag cctgatctct gtatcttgtt   180
atttgtatac cgtcaaataa aagtttcttc cacttgtgtt aataattagc tactctcatc   240
tcatgaaccc tatatataac tagtttaatt tgctgtcaat tgaacatgat gatcgatg     298

SEQ ID NO: 9            moltype = DNA  length = 200
FEATURE                 Location/Qualifiers
source                  1..200
                        mol_type = unassigned DNA
                        organism = Zea mays
SEQUENCE: 9
cggcgtatgt gccaaaaact tcgtcacaga gagggccata agaaacatgg cccacgccc     60
aatacgaagc accgcgacga agcccaaaca gcagtccgta ggtggagcaa agcgctgggt   120
aatacgcaaa cgttttgtcc caccttgact aatcacaaga gtggagcgta ccttataaac   180
cgagccgcaa gcaccgaatt                                               200

SEQ ID NO: 10           moltype = DNA  length = 3681
FEATURE                 Location/Qualifiers
misc_feature            1..3681
                        note = Synthetic polynucleotide.Codon optimized LbCpf1-CO2
source                  1..3681
                        mol_type = other DNA
                        organism = synthetic construct
SEQUENCE: 10
tcgaagctcg agaagttcac caactgctac tcgctgagca agacgctgcg gttcaaggcg    60
atccccgtcg ggaagaccca ggagaacatc gacaacaagc ggcctcctggt cgaggacgag   120
aagcgcgccg aggactacaa gggcgtcaag aagctgctgg accggtacta cctctccttc   180
atcaacgacg tcctgcactc gatcaagctc aagaacctga caactacat ctcgctgttc   240
cgcaagaaga cacggaccga aaggagaac aaggagctcg agaacctcga gatcaacctg   300
cgcaaggaga tcgcgaaggc gttcaagggc aacgaggggt acaagagcct gttcaagaaa   360
gacatcatcg agaccatcct gccggagttc ctggacgaca aggacgagat cgcgctggtg   420
aactcgttca acgggtttca cggccttca accgggtttt tcgacaaccg ggagaacatg   480
ttcagcgagg aggccaagtc gaccagcatc gccttccggt gcatcaacga gaacctcacc   540
cgctacatca gcaacatgga catcttcgag aaggtggacg ccatcttcga caagcacgag   600
gtccaggaga tcaaggaaaa gatcctgaac tcggactacg acgtggaaga cttctttgag   660
ggcgagttct tcaacttcgt cctcacccag gagggcatcg acgtctacaa cgccatcatc   720
ggcggcttcg tgacggagag cggccagaag atcaagggcc tcaacgagta catcaacctc   780
tacaaccaga agactaagca gaagctcccc aagttcaagc cgctgtacaa gcaagtcctg   840
agcgaccggg agtccctctc gttctacggc gagggctaca cgagcgacga ggaggtgctg   900
gaggtgttcc gcaacacgct gaacaagaac agcgagatct cagctcgat caagaaactc   960
gagaagctgt tcaagaactt cgacgagtac agcagcgcc gcatcttcgt caagaacggg  1020
cccgcgatca gcaccatcag caaggacatc ttcgggagt ggaactgtat ccgcgacac   1080
tggaacgccg agtacgacga catccactc aagaaaaagg cggtggtcac ggagaagtac  1140
gaggacgacc gccggaagtc cttcaagaaa tcgggagct tcagcctcga gcagctccag  1200
gagtacgcgg acgccgacct gagcgtggtg gagaagctca aggagatcat catccagaag  1260
gtcgacgaga tctacaaggt ctacggctcg agcgagaagc tgttcgacgc ggacttcgtg  1320
ctggaaagt ccctcaagaa gaacgacgcg gtggtgacga tcaagaaga tctgctcgag  1380
agcgtgaagt cgttcgagaa ctacatcaag gcattctttg gggagggcaa ggagacgaac  1440
cgggacgagt ccttctacgg ggactccgtg ctcgcgtacg acatcctcct gaaggtcgac  1500
cacatctacg acgcgatccg gaactacgtc acgcagaagc cctacagcaa ggacaagttc  1560
aagctctact ccagaacccc gcagttcatg ggcggtggg acaaggacaa ggagaccgac  1620
taccgggcca cgatcctgcg gtacgggtcc agtactacc tcgccatcat ggacaagaag  1680
```

```
tacgccaagt gcctccagaa gattgacaag gacgacgtga acgggaacta cgagaagatc   1740
aactacaagc tcctcccggg gcccaacaag atgctgccga aggtgttctt cagcaagaag   1800
tggatggcct actacaaccc ctcggaggac atccagaaga tatacaagaa cggcacgttc   1860
aaaaaggggg acatgttcaa cctgaacgac tgccacaagc tgatcgactt tttcaaggac   1920
agcatcagcc gctacccgaa gtggtcgaac gcctacgact tcaacttctc ggagacggag   1980
aagtacaagg acattgcggg cttctaccgg gaggtggagg agcagggcta caaggtctcc   2040
ttcgagagcg cctccaagaa agaggtggaa aagctcgtgg aggagggcaa gctgtacatg   2100
ttccagatct acaacaagga cttctcggac aagtcgcacg gcaccccgaa cctccacacg   2160
atgtacttca agctgctgtt cgacgagaac aaccacgcct cagcggcggg                 2220
gcggagctgt tcatgcgccg cgcgtccctc aagaaggagg agctggtcgt gcaccccgcc   2280
aactccccga tcgcgaacaa gaaccccgac aaccccaaga agacaaccac cctctcgtac   2340
gacgtctaca aggacaagcg gttctcggag gaccagtacg agctgcacat cccgatcgcc   2400
atcaacaagt gccccaagaa catcttcaag atcaacaccg aggtgcgggt gctgctcaag   2460
cacgacgaca accccacgt catcgggatc gaccgcggcg agcggaacct gctctacatc   2520
gtggtcgtgg acgggaaggg gaacatcgtg gagcagtaca gcctgaacga gatcatcaac   2580
aacttcaacg gcatccgcat caagacggac taccacagcc tcctggacaa gaaggagaag   2640
gagcggttcg aggcgcggca gaactggacc tccatcgaga acatcaagga gctgaaggcc   2700
ggctacatca gccaggtcgt gcacaagatc tgcgagctcg tggagaagta cgacgcgggtg   2760
atcgcgctgg aggacttgaa cagcgggttc aagaactccc gggtcaaggt cgagaagcag   2820
gtctaccaga agttcgagaa gatgctgatc gacaagctca actacatggt ggacaagaag   2880
tccaacccct cgccaccgg cggcgccctc aagggctacc agatcaccaa caagttcgag   2940
tccttcaagt cgatgtctac gcagaacggg ttcatttttc acatcccggc gtggctcacc   3000
agcaagatcg acccgagcac gggcttcgtc aacctcctga agaccaagta caccagcatc   3060
gcggacagca agaagttcat ctcctcgttc gaccgcatca tgtacgtccc cgaggaagac   3120
ctgttcgagt tcgccctcga ctacaagaac ttctcccgga cggacgccga ctacatcaaa   3180
aagtggaagc tctacagcta cggcaaccgg atccgcatct tccgcaacct caagaagaac   3240
aatgtgttcg actgggagga ggtgtgcctg acgagcgatt acaaggagct cttcaacaag   3300
tacggcatca actaccagca aggggacatc cgcgcgctgc tctgcgagca gtccgacaag   3360
gcgttctact cgtcgttcat ggccctgatg agcctcatgc tccagatgcg caacagcatc   3420
accggccgga cggacgtgga cttcctgatc agcccggtca agaacagcga cggcatttc   3480
tacgacagcc ggaactacga ggcccaggag aacgccatcc tccccaagaa cgccgacgcg   3540
aacggcgcct acaacatcgc gcggaaggtg ctgtgggcca tcggcagtt taaaaaggcg   3600
gaggacgaga agctggacaa ggtcaagatc gccatcagca acaaggagtg gctcgagtac   3660
gcgcagacga gcgtgaagca c                                              3681
```

SEQ ID NO: 11          moltype = DNA   length = 3681
FEATURE                Location/Qualifiers
misc_feature        1..3681
                       note = Synthetic polynucleotide.Codon optimized LbCpf1-Os
source               1..3681
                       mol_type = other DNA
                       organism = synthetic construct
SEQUENCE: 11

```
tccaagctgg agaagtttac aaactgttac agcctctcca aaaccctcag gtttaaagcg    60
atcccggtgg gcaagaccca ggagaacatc gacaacaaga ggctcctggt ggaagacgag   120
aagcgcgccg aagactacaa gggcgtgaag aagctgctcg ataggtacta cctcagcttt   180
attaacgaca tgctgcacag catcaaactc aagaatctca acaactactc ctccctcttc   240
cgcaaaaaga cccgcaccga aaggagaac aaggagctgg agaacctgga tcaacctc    300
cgcaaggaaa tcgccaaagc gttcaagggc aatgaaggt acaagagcct cttcaagaaa   360
gacatcatcg aaactatcct cccagagttt tcgatgaca aggacgagat cgcgctggtg   420
aactccttta cgggttcac aaccgcgttt accggctctc ttgataacag ggaaaatatg   480
ttctccgagg aggccaagtc caccagcatc gccttcaggt gtatcaacga aacctcacc    540
cgctacattt ccaatatgga cattttcgag aaggtggatg cgatcttcga taagcacgag   600
gtgcaggaga tcaagagaa gattctcaat tccgattatg acgtcgagga tttcttcgaa   660
ggggagttct ttaattttgt gctcacacaa gagggcattg acgtgtacaa cgcgattatc   720
gggggcttcg tcacagagtc cgggagaag attaagggc tgaatgagta catcaatctg   780
tacaatcaga agaccaagca gaaactgccg aaattcaagc cgctctacaa gcaagtcctg   840
tccgataggg aaagcctctc cttctacggc gagggctata ccagcgacga ggaggtgctg   900
gaagtcttcc gcaacacact gaataagaat agcgagattt tctcctcgaa caagaagctc   960
gagaagctct ttaagaactt tgacgagtac agctccgccg ggattttcgt gaagaacggg  1020
ccggcgatca gcaccatctc caaggacatc tttggcgagt ggaacgtcat cagggacaag  1080
tggaacgccg agtacgacga catccacctg aagaagaagg cggtgctgac cgagaagtat  1140
gaggacgatc gcaggaagtc cttcaaaaaa atcggctcct tcagcctcga acagctccag  1200
gagtatgcga atgcggatct gtccgtcgtc gagaacgtga aggaaatcat cattcagaag  1260
gtcgacgaga tctataaagt gtacgggtcc agcgagaagc tgttcgacgc cgactttgtg  1320
ctcgagaagt ccctcaaaaa gaatgacgcc gtggtggcca ttatgaaaga cctgctcgac  1380
tccgtgaagt ccttcgaaaa ttacattaaa gcgttctttg ggggagggaa ggaaactaac  1440
agggatgagt ccttctatgg cgactttgtc ctcgcgtacg acatcctgct gaaggtcgac  1500
cacatttacg acgcgatccg caactacgtg acacagaagc cgtactccaa agcaagttc   1560
aagctgtact tccagaaccc gcaatttatg gggggctggg acaaggataa agagacagac  1620
taccgcgcga caattctccg ctatggctcc aaatactatc tggccatcat ggacaagaag  1680
tacgcgaagt gcctgcagaa gatcgacaaa gacgacgtca tggcaacta tgaaaagatc  1740
aactacaagc tgctgccggg cccgaacaag atgctcccga aggtgttctt cagcaagaag  1800
tggatggcct actacaaatcc aagcgaggat atttcagaaaa tctataaaaa cgggaccttc  1860
aagaaggggg acatgttcaa cctcaacgac tgccacaagc tcattgattt cttcaaggat  1920
agcatttccc gctacccgaa atggtccaat gcgtacgatt taacttctc cgagacagaa  1980
aagtacaaag acatcgcggg cttttacagg gaggtggagg agcaagggta taaagttct   2040
tttgaatccg cgagcaagaa ggaagtcgac aagctcgtcg aggagggcaa gctctacatg  2100
ttccaaattt ataacaagga cttttccgac aagagccatg gaccccaaa cctccacacc  2160
```

```
atgtacttca aactgctctt tgacgagaac aaccacgggc aaatcaggct gagcggcggc 2220
gccgaattat tcatgcgcag ggcctccctc aagaaggaag agctggtcgt ccatccagcc 2280
aattccccga tcgcgaacaa gaacccggac aatccgaaaa agaccaccac cctgtcctac 2340
gacgtctaca aggacaaacg cttcagcgaa gaccagtacg aattacacat cccaattgcg 2400
attaataagt gcccaaagaa tatcttcaaa attaatacag aggtcagggt gctgctcaaa 2460
cacgacgaca atccgtatgt catcggcatt gacaggggcg agcgcaatct gctctatatc 2520
gtggtcgtgg atgggaaggg caatattgtg gagcagtact ccctgaacga gattatcaac 2580
aacttcaatg ggattaggat taagaccgac tatcacagcc tgctcgacaa gaaagaaaaa 2640
gagaggtttg aggcccgcca aaactggacc tccattgaga atatcaaaga attaaaggcc 2700
ggctatattt cccaagtcgt ccacaagatc tgcgagctgg tggagaaata tgacgccgtg 2760
attgcgctcg aagacttaaa ttctgggttc aagaactccc gcgtgaaggt ggaaaaacag 2820
gtgtatcaga aattcgagaa aatgctgatc gacaaactca attatatggt ggataagaag 2880
tccaacccgt gtgccacagg gggcgcgctg aagggctatc agatcaccaa caagttcgag 2940
agcttcaaga gcatgagcac ccagaacggg tttattttct acatcccggc gtggctcacc 3000
tccaagattg acccgagcac cggcttcgtg aacctcctga agacaaagta tacctccatt 3060
gccgacagca agaagtttat ctcctccttc gaccgcatta tgtatgtgcc ggaggaggac 3120
ctcttcgagt tcgccctcga ctacaaaaac ttcagccgca cagatgcgga ttacatcaag 3180
aagtggaagc tgtactccta cgggaacagg atccgcatct tcaggaatcc aaaaaaaaat 3240
aacgtctttg actgggagga agtgtgcctg acatccgcct acaaggaact gttcaataaa 3300
tacggcatca attaccagca gggcgacatt cgcgccctcc tctgtgagca gtccgacaaa 3360
gcgttttact ccagcttcat ggccctcatg tccctgatgc tccaaatgag gaatagcatc 3420
acagggcgca ccgacgtcga cttcctcatc agcccggtga agaactccga cgggatcttt 3480
tacgactccc gcaactatga ggcgcaagag aatgcgatcc tcccgaagaa cgccgatgcg 3540
aacgggccct ataatatcgc caggaaagtg ctctgggcca tcgggcagtt caaaaaggcg 3600
gaggatgaga agctcgacaa ggtgaaaatt gccatttcca acaaggagtg gctggagtac 3660
gcgcagacct ccgtgaagca c 3681

SEQ ID NO: 12         moltype = DNA   length = 3744
FEATURE               Location/Qualifiers
misc_feature          1..3744
                      note = Synthetic polynucleotide.NLS-LbCpf1-CO2-NLS
source                1..3744
                      mol_type = other DNA
                      organism = synthetic construct
SEQUENCE: 12
ggatctaaga agagaagaat taaacaagat tcgaagctcg agaagttcac caactgctac 60
tcgctgagca gacgctgcg gttcaaggcg atccccgtcg ggaagaccca ggagaacatc 120
gacaacaagc ggctcctggt cgaggacgag aagcgcgccg aggactacaa gggcgtcaag 180
aagctgctgg accggtacta cctctccttc atcaacgacg tcctgcactc gatcaagctc 240
aagaacctga caactacat ctcgctgttc cgcaagaaga cacggaccga gaaggagaac 300
aaggagctcg agaacctcga gatcaacctg cgcaaggaga tcgcgaaggc gttcaagggc 360
aacgagggg acaagagcct gttcaagaaa gacatcatcg agaccatcct gccggagttc 420
ctggacgaca aggacgagat cgcgctggtg aactcgttca acgggttcac cacggcctc 480
accgggtttt tcgacaaccg ggagaacatg ttcagcgagg aggccaagtc gaccagcatc 540
gccttccggt gcatcaacga gaacctcacc cgctacatca gcaacatgga catcttcgag 600
aaggtggacg ccatcttcga caagcacgag gtccaggaga tcaaggaaaa gatcctgaac 660
tcggactacg acgtggaaga cttctttgag ggcgagttct tcaacttcgt cctcacccag 720
gagggcatcg acgtctacaa cgccatcatc ggcggcttcg tgacggagag cggcgagaag 780
atcaagggcc tcaacgagta catcaaccte tacaaccaga gactaagca gaagctcccg 840
aagttcaagc cgctgtacaa gcaagtcctg agcgaccggg agtccctctc gttctacggc 900
gagggctaca cgagcgacga ggaggtgctg gaggtgttcc gcaacacgct gaacaagaac 960
agcgagatct tcagctcgat caagaaactc gagaagctgt tcaagaactt cgacgagtac 1020
agcagcgccg gcatcttcgt caagaacggg ccgcgatca gcaccatcag caaggacatc 1080
ttcgggagt ggaacgtgat ccgcgacaag tggaacgccg agtacgacga catccacctc 1140
aagaaaaagg cggtggtcac ggagaagtac gaggacgacc gccggaagtc cttcaagaaa 1200
atcgggagct tcagcctcga gcagctccaa gagtacgcgg acgccgacct gagcgtggtg 1260
gagaagctca aggagatcat catccagaag gtcgacgaga tctacaaggt ctacggctcg 1320
agcgagaagc tgttcgacgc ggacttcgtg ctggagaagt ccctcaagaa gaacgacgcc 1380
gtggtggcca tcatgaagga tctgctcgaa agcgtgaagt cgttcgagaa ctacatcaag 1440
gcattctttg ggagggcaa ggagacgaac cgggacgaat ccttctacgg ggacttcgtg 1500
ctcgcgtacg acatcctcct gaaggtcgac cacatctacg acgcgatccg gaactacgtc 1560
acgcagaagc cctacagcaa ggacaagttc aagctctact ccagaacccc gcagttcatg 1620
ggcggtgg acaaggacaa ggagaccgac taccgggcca cgatcctgcg gtacgggtcc 1680
aagtactacc tcgccatcat ggacaagaag tacgccaagg attgacaag 1740
gacgacgtga acgggaacta cgagaagatc aactacaagc tcctcccggg gcccaacaag 1800
atgctgccga aggtgttctt cagcaagaag tggatggcct actacaaccc tcggaggac 1860
atccagaaga tatacaagaa cggcacgttc aaaaaggggg acatgttcaa cctgaacgac 1920
tgccacaagc tgatcgactt ttcaaggac agcatcagcc gctacccgaa gtggtcgaac 1980
gcctacgact tcaacttctc ggacacggag aagtacaagg acattgcggg ttctacegg 2040
gaggtggagg agcagggcta caaggtctcc ttcgagagcg cctccaagaa agaggtggac 2100
aagctcgtgg aggagggcaa gctgtacatg ttccagatct caacaagga cttctcggac 2160
aagtcgcacg gcaccccgaa cctccacacg atgtacttca agctgctgtt cgacgagaac 2220
aaccacgggc agatccgcct cagcggcggg gcggagctgt tcatgcgccg cgcgtccctc 2280
aagaaggagg agctggtcgt gcaccccgcc aactcccgca tcgcgaacaa gaaccccgac 2340
aaccccaaga agacaaccac cctctcgtac gacgtctaca aggacaagcg gttctctgga 2400
gaccagtacg agctgcacat cccgatcgcc atcaacaagt gccccaagaa catcttcaag 2460
atcaacaccg aggtgcgggt gctgctcaag cacgacgaca cccccgtacgt catcgggatc 2520
gaccgcggcg agcggaacct gctctacatc gtggtcgtgg acgggaaggg gaacatcgtg 2580
gagcagtaca gcctgaacga gatcatcaac aacttcaacg gcatccgcat caagacggac 2640
```

-continued

```
taccacagcc tcctggacaa gaaggagaag gagcggttcg aggcgcggca gaactggacc    2700
tccatcgaga acatcaagga gctgaaggcc ggctacatca gccaggtcgt gcacaagatc    2760
tgcgagctcg tggagaagta cgacgcggtg atcgcgctgg aggacttgaa cagcgggttc    2820
aagaactccc gggtcaaggt cgagaagcag gtctaccaga agttcgagaa gatgctgatc    2880
gacaagctca actacatggt ggacaagaag tccaacccct gcgccaccgg cggcgccctc    2940
aagggctacc agatcaccaa caagttcgag tccttcaagt cgatgtctac gcagaacggg    3000
ttcattttct acatcccggc gtggctcacc agcaagatcg acccgagcac gggcttcgtc    3060
aacctcctga agaccaagta caccagcatc gcggacagca agaagttcat ctcctcgttc    3120
gaccgcatca tgtacgtccc cgaggaagac ctgttcgagt tcgccctcga ctacaagaac    3180
ttctcccgga cggacgccga ctacatcaaa aagtggaagc tctacagcta cggcaaccgg    3240
atccgcatct tccgcaaccc caagaagaac aatgtgttcg actgggagga ggtgtgcctg    3300
acgagcgcct acaaggagct cttcaacaag tacggcatca actaccagca aggggacatc    3360
cgcgcgctgc tctgcgagca gtccgacaag gcgttctact cgtcgttcat ggccctgatg    3420
agcctcatgc tccagatgcg caacagcatc accggccgga cggacgtgga cttcctgatc    3480
agccggtca gaacagcga cggcattttc tacgacagcc ggaactacga ggcccaggag    3540
aacgccatcc tccccaagaa cgccgacgcg aacggcgcct acaacatcgc gcggaaggtg    3600
ctgtgggcca tcggccagtt taaaaaggcg gaggacgaga agctggacaa ggtcaagatc    3660
gccatcagca acaaggagtg gctcgagtac gcgcagacga gcgtgaagca cggatctaag    3720
aagagaagaa ttaaacaaga ttga                                           3744
```

```
SEQ ID NO: 13              moltype = DNA     length = 12
FEATURE                    Location/Qualifiers
misc_feature               1..12
                           note = Synthetic polynucleotide.kozak sequence
source                     1..12
                           mol_type = other DNA
                           organism = synthetic construct
SEQUENCE: 13
gccgccatgg cg                                                        12

SEQ ID NO: 14              moltype = DNA     length = 3756
FEATURE                    Location/Qualifiers
misc_feature               1..3756
                           note = Synthetic polynucleotide.kozak-NLS-LbCpf1-CO2-NLS
source                     1..3756
                           mol_type = other DNA
                           organism = synthetic construct
SEQUENCE: 14
gccgccatgg cgggatctaa gaagagaaga attaaacaag attcgaagct cgagaagttc     60
accaactgct actcgctgag caagacgctg cggttcaagg cgatccccgt cgggaagacc    120
caggagaaca tcgacaacaa gcggctcctg gtcgaggacg agaagcgcgc cgaggactac    180
aagggcgtca agaagctgct ggaccggtac tacctctcct tcatcaacga cgtcctgcac    240
tcgatcaagc tcaagaacct gaacaactac atctcgctgt tccgcaagaa gacacggacg    300
gagaaggaga caaggagct cgagaacctc gagatcaacc tgcgcaagga gatcgcgaag    360
gcgttcaagg gcaacgaggg gtacaagagc ctgttcaaga agacatcat cgagaccatc    420
ctgccggagt tcctggacga caaggacgag atcgcgctgg tgaactcgtt caacgggttc    480
accacggcct tcaccgggtt tttcgacaac cgggagaacg tgttcagcga ggaggccaag    540
tcgaccagca tcgccttccg ggtgcatcaac gagaacctca cccgctacat cagcaacatg    600
gacatcttcg agaaggtgga cgccatcttc gacaagcacg aggtccagga gatcaaggaa    660
aagatcctga actcggacta cgacgtggaa gacttctttg agggcgagtt cttcaacttc    720
gtcctcaccc aggagggcat cgacgtctac aacgccatca tcggcggctt cgtgacggag    780
agcggcgaga agatcaaggg cctcaacgag tacatcaacc tctacaacca gaagactaag    840
cagaagctcc cgaagttcaa gccgctgtac aagcaagtcc tgagcgaccg ggagtccctc    900
tcgttctacg gcgagggcta cacgagcgac gaggaggtgc tggaggtgtt ccgcaacacg    960
ctgaacaaga acagcgagat cttcagctcg atcaagaaga tcgagaagct gttcaagaac    1020
ttcgacgagt acagcagcgc cggcatcttc gtcaagaacg gcccgcgat cagcaccatc    1080
agcaaggaca tcttcgggga gtggaacgtg atccgcgaca gtggaacgc cgagtacgac    1140
gacatccacc tcaagaaaaa ggcggtggtc acggagaagt acgaggacga ccgccggaag    1200
tccttcaaga aatcgggag cttcagcctc gagcagctcc aggagtacgc ggacgccgac    1260
ctgagcgtgg tggagaagct caaggagatc atcatccaga aggtcgacga gatctacaag    1320
gtctacggct cgagcgagaa gctgttcgac gcggacttcg tgctggagaa gtccctcaag    1380
aagaacgacg ccgtggtggc catcatgaag gatctgctcg acagcgtgaa gtcgttcgag    1440
aactacatca aggcattctt tgggggaggc aaggagacga accgggacga gtccttctac    1500
ggggacttcg tgctcgcgta cgacatcctc ctgaaggtcg accacatcta cgacgcgatc    1560
cggaactacg tcacgcagaa gccctacagc aaggacaagt tcaagctcta cttccagaac    1620
ccgcagttca tgggggcggtg gacaaggac aaggagaccg actaccgggc cacgatcctg    1680
cggtacgggt ccaagtacta cctcgccatc atggacaaga agtacgccaa gtgcctccag    1740
aagattgaca aggacgacgt gaacgggaac tacgagaaga tcaactacaa gctcctcccg    1800
gggcccaaca agatgctgcc gaaggtgttc ttcagcgaaa agtggatggc ctactacaac    1860
cctcggagg acatccagaa gatatacaag aacggcacgt tcaaaaaggg ggacatgttc    1920
aacctgaacg actgccacaa gctgatcgac tttttcaagg acagcatcag ccgctacccg    1980
aagtggtcga acgcctacga cttcaacttc tcggagacgg agaagtacaa ggacattgcg    2040
ggcttctacc gggaggtgga ggagcagggc tacaaggtc ccttcgagag cgcctccaag    2100
aaaagggtgg acaagctcgt ggaggagggc aagctgtaca tgttccagat ctacaacaag    2160
gacttctcgg acaagtcgca cggcaccccg aacctccaca cgatgtactt caagctgctg    2220
ttcgacgaga acaaccacgg gcagatccgc ctcagcggcg gggcggagct gttcatgcgc    2280
cgcgcgtccc tcaagaagga ggagctggtc gtgcaccccg ccaactcccc gatcgcgaac    2340
aagaaccccg acaaccccaa gaagacaacc ccctctcgt acgacgtcta caggggacaag    2400
cggttctcgg aggaccagta cgagctgcac atcccgatcg ccatcaacaa gtgccccaag    2460
```

-continued

```
aacatcttca agatcaacac cgaggtgcgg gtgctgctca agcacgacga caacccctac   2520
gtcatcggga tcgaccgcgg cgagcggaac ctgctctaca tcgtggtcgt ggacgggaag   2580
gggaacatcg tggagcagta cagcctgaac gagatcatca caaacttcaa cggcatccgc   2640
atcaagacgg actaccacag cctcctggac aagaaggaga aggagcggtt cgaggcgcgg   2700
cagaactgga cctccatcga gaacatcaag gagctgaaga ccggctacat cagccaggtc   2760
gtgcacaaga tctgcgagct cgtggagaag tacgacgcgg tgatcgcgct cgaggacttg   2820
aacagcgggt tcaagaactc ccgggtcaag gtcgagaagc aggtctacca gaagttcgag   2880
aagatgctga tcgacaagct caactacatg gtggacaaga agtccaaccc ctgcgccacc   2940
ggcggcgccc tcaagggcta ccagatcacc aacaagttcg agtccttcaa gtcgatgtct   3000
acgcagaacg ggttcatttt ctacatcccg gcgtggctca ccagcaagat cgacccgagc   3060
acgggcttcg tcaacctcct gaagaccaag tacaccagca tcgcggacag caagaagttc   3120
atctcctcgt tcgaccgcat catgtacgtc cccgaggaag acctgttcga gttcgccctc   3180
gactacaaga acttctcccg gacggacgcc gactacatca aaaagtggaa gctctacagc   3240
tgcaaacc ggatccgcat cttccgcaac cccaagaaga acaatgtgtt cgactgggag   3300
gaggtgtgcc tgacgagcgc ctacaaggag ctcttcaaca agtacggcat caactaccag   3360
caaggggaca tccgcgcgct gctctgcgag cagtccgaca aggcgttcta ctcgtcgttc   3420
atggccctga tgagcctcat gctccagatg cgcaacagca tcaccggccg gacggacgtg   3480
gacttcctga tcagcccggt caagaacagc gacggcattt tctacgacag ccggaactac   3540
gaggcccagg agaacgccat cctcccccaag aacgccgacg cgaacggcgc ctacaacatc   3600
gcgcggaagg tgctgtgggc catcggccag tttaaaaagg cggaggacga gaagctggac   3660
aaggtcaaga tcgccatcag caacaaggag tggctcgagt acgcgcagac gagcgtgaag   3720
cacggatcta agaagagaag aattaaacaa gattga                             3756
```

| SEQ ID NO: 15 | moltype = DNA length = 6062 |
|---|---|
| FEATURE | Location/Qualifiers |
| misc_feature | 1..6062 |
| | note = Synthetic polynucleotide.Expression Cassette comprising the ZmUbiqitin promoter cassette, koz-NLS-LbCpf1-CO2-NLS cassette andthe Oryza sativa LTP termination sequence |
| source | 1..6062 |
| | mol_type = other DNA |
| | organism = synthetic construct |

SEQUENCE: 15

```
gtcgtgcccc tctctagaga taaagagcat tgcatgtcta aagtataaaa aattaccaca     60
tatttttttg tcacacttat ttgaagtgta gtttatctat ctctatacat atatttaaac    120
ttcactctac aaataatata gtctataata ctaaaataat attagtgttt tagaggatca    180
tataaataaa ctgctagaca tggtctaaag gataattgaa tatttgaca atctacagtt    240
ttatctttttt agtgtgcatg tgatctctct gttttttttg caaatagctt gacctatata    300
atacttcatc cattttatta gtacatccat ttaggattta gggttgatgg tttctataga    360
ctaattttta gtacatccat tttattcttt ttagtctcta aattttttaa aactaaaact    420
ctatttagt ttttttattta ataatttaga tataaaatga aataaaataa attgactaca    480
aataaaacaa ataccctta agaaataaaa aaactaagca aacattttc ttgtttcgaa    540
tagataatga caggctgttc aacgccgtcg acgagtctaa cggacaccaa ccagcgaacc    600
agcagcgtcg cgtcgggcca agcgaagcag acggcacggc atctgctag ctgcctctgg    660
accccctctcg agagttccgc tccaccgttg gacttgctcc gctgtcggca tccagaaatt    720
gcgtggcgga gcgcagacg tgaggcggca cggcacggcg cctcttcctc ctctcacggc    780
accggcagct acgggggatt cctttcccac cgctccttcg cttttccctte ctcgcccgcc    840
gtaataaata gacaccccct ccacaccctc tttcccaac ctcgtgttcg ttcggagcgc    900
acacacacgc aaccagatct cccccaaatc cagccgtcgg cacctccgct tcaaggtacg    960
ccgctcatcc tccccccccc cctctctcta ccttctctag atcggcgatc cggtccatgg   1020
ttagggcccg gtagttctac ttctgttcat gtttgtgtta gagcaaacat gttcatgttc   1080
atgtttgtga tgatgtggtc tggttgggcg gtcgttctag atcggagtag gatactgttt   1140
caagctacct ggtggattta ttaattttgt atctgtatgt gtgtgccata catcttcata   1200
gttacgagtt taagatgatg gatggaaata tcgatctagg ataggtatac atgttgatgc   1260
gggttttact gatgcatata cagagatgct ttttttctcg cttggttgtg atgatattggt   1320
ctggttgggc ggtcgttcta gatcggagta gaatactgtt tcaaactacc tggtggattt   1380
attaaaggat aaagggtcgt tctagatcgg agtagaatac tgtttcaaac tacctggtgg   1440
atttattaaa ggatctgtat gtatgtgcct acatcttcat agttacgagt ttaagatgat   1500
ggatggaaat atcgatctag gataggtata catgttgatg cgggtttac tgatgcatat   1560
acagagatgc ttttttttcgc ttggttgtga tgatgtggtc tggttgggcg gtcgttctag   1620
atcggagtag aatactgttt caaactacct ggtggattta ttaattttgt atctttatgt   1680
gtgtgccata catcttcata gttacgagtt taagatgatg gatggaaata ttgatctagg   1740
ataggtatac atgttgatgt gggttttact gatcatata catgttgatgc tatgcggcat   1800
ctattcatat gctctaacct tgagtaccta tctattataa taaacaagta tgttttataa   1860
ttatttttgat cttgatatac ttggatgatg gcatatgcag cagctatatg tggattttttt   1920
agccctgcct tcatacgcta tttatttgct tggtactgtt tcttttgtcc gatgctcacc   1980
ctgttgtttg gtgatacttc tgcaggtcgc cgccatggcc ggatctaaga agaagaat   2040
taaacaagat tcgaagctac agaagttcac caactgctac tcgctgacag agacgctgcg   2100
gttcaaggcg atcccgtcg ggaagaccca ggagaacatc gacaacaagc ggctcctggt   2160
cgaggacgag aagcgcgccg aggactacaa gggcgtcaag aagctgctgg accggtacta   2220
cctctccttc atcaacgacg tcctgcactc gatcaagctc aagaacctga caactacat   2280
ctcgctgttc cgcaagaaga cacggaccga aaggagaac aaggagctcg agaacctcga   2340
gatcaacctg cggaaggaga tcgcaaggc gttcaaggc acagggggt acaagagcct   2400
gttcaagaaa gacatcatcg agaccatcct gccggagttc ctggacgaca aggacgagat   2460
cgcgctggtg aactcgttca acgggttcac cacggccttc accggttttt tcgcaaccg   2520
ggagaacatg ttcagcgagg aggccaagtc gaccagcatc gccttccggt gcatcaacga   2580
gaacctcacc cgctacatca gcaacatgga catcttcgaa aaggtggacg ccatcttcga   2640
caagcacgag gtccaggaga tcaaggaaaa gatcctgaac tcggactacg acgtggaaga   2700
```

-continued

```
cttctttgag ggcgagttct tcaacttcgt cctcacccag gagggcatcg acgtctacaa 2760
cgccatcatc ggcggcttcg tgacggagag cggcgagaag atcaagggcc tcaacgagta 2820
catcaacctc tacaaccaga agactaagca gaagctcccg aagttcaagc cgctgtacaa 2880
gcaagtcctg agcgaccggg agtccctctc gttctacggc gagggctaca cgagcgacga 2940
ggaggtgctg gaggtgttcc gcaacacgct gaacaagaac agcgagatct tcagctcgat 3000
caagaaactc gagaagctgt tcaagaactt cgacgagtac agcagcgccg gcatcttcgt 3060
caagaacggg cccgcgatca gcaccatcag caaggacatc ttcggggagt ggaacgtgat 3120
ccgcgacaag tggaacgccg agtacgacga catccacctc aagaaaaagg cggtggtcac 3180
ggagaagtac gaggacgacc gccggaagtc cttcaagaaa atcgggagct tcagcctcga 3240
gcagctccag gagtacgcgg acgccgacct gagcgtggtg gagagctcaa aggagatcat 3300
catccagaag gtcgacgaga tctacaaggt ctacggctcg agcgagagc tgttcgacgc 3360
ggacttcgtg ctggagaagt ccctcaagaa gaacgacgcc gtggtggcca tcatgaagga 3420
tctgctcgac agcgtgaagt cgttcgagaa ctacatcaag gcattctttg ggagggcaa 3480
ggagacgaac cgggacgagt ccttctacgg ggacttcgtg ctcgcgtacg acatcctcct 3540
gaaggtcgac cacatctacg acgcgatccg gaactacgtc acgcagaagc cctacagcaa 3600
ggacaagttc aagctctact ccagaaccc gcagttcatg ggcgggtggg acaaggacaa 3660
gggagaccgac taccggggcca cgatcctgcg gtacgggtcc aagtactacc tcgccatcat 3720
ggacaagaag tacgccaagt gcctccagaa gattgacaag gacgacgtga acggaaacta 3780
cgagaagatc aactcaaagc tcctcccggg gcccaacaag atgctgccga aggtgttctt 3840
cagcaagaag tggatggcct actacaaccc ctcggaggac atccagaaga tatacaagaa 3900
cggcacgttc aaaaagggg acatgttcaa cctgaacgac tgcccacaagc tgatcgactt 3960
tttcaaggac agcatcagcc agtacgaaca gtggtcgaca gcctacgact tcaacttctc 4020
ggagacggag aagtacaagg acattgcggg cttctaccgg gaggtggag agcagggcta 4080
caaggtctcc ttcgagagcg cctccaagaa agaggtggac aagctcgtgg aagagggcaa 4140
gctgtacatg ttccagatct acaacaagga cttctcggac aagtcgcacg caccccgaa 4200
cctccacacg atgtacttca agctgctgtt cgacgagaac aacacgggc agatccgcct 4260
cagcggcggg gcggagctgt tcatgcgccg cgcgtccctc aagaaggagg agctggtcgt 4320
gcaccccgcc aactccccga tcgcgaacaa gaaccccgac aaccccaaga agacaaccac 4380
cctctcgtac gacgtctaca aggacaagcg gttctcggag gaccagtacg agctgcacat 4440
cccgatccgc atcaacaagt gccccaagaa catcttcaag atcaacaccg aggtgcggt 4500
gctgctcaag cacgacgaca ccccctacgt catcggggatc gaccgcggcg agcggaacct 4560
gctctacatc gtggtcgtgg acgggaaggg gaacatcgtg gagcagtaca gcctgaacga 4620
gatcatcaac aacttcaacg gcatccgcat caagacggac taccacagcc tcctggacaa 4680
gaaggagaag gagcggttcg aggcgcggca gaactggacc tccatcgaga acatcaagga 4740
gctgaaggcc ggctactca gccaggtcgt gcacaagatc tgcgagctcg tggagaagta 4800
cgacgcggtg atcgcgctgg aggacttgaa cagcgggttc aagaactccc gggtcaaggt 4860
cgagaagcag gtctaccaga agttcgaaga gatgctgatc gacaagctca actacatggt 4920
ggacaagaag tccaaccct gcgccaccgg cggcgcctc aagggctacc agatcaccaa 4980
caagttcgag tccttcaagt cgatgtctac gcagaacggg ttcattttct acatcccggc 5040
gtggctcacc agcaagatcg acccgagcac gggcttcgtc aacctcctga agaccaagta 5100
caccagcatc gcggacagca agaagttcat ctcctcgttc gaccgcatca tgtacgtccc 5160
cgaggaagac ctgttcgagt tcgccctcga ctacaagaac ttctcccgga cggacgcga 5220
ctacatcaaa agtggaagc tctacagcta cggcaaccg atccgcatct tccgcaaccc 5280
caagaagaac aatgtgttcg actgggagga ggtgtgcctg acgagcgcct acaaggagct 5340
cttcaacaag tacggcatca actaccagca aggggacatc cgcgcgctgc tctgcagca 5400
gtccgacaag gcgttctact cgtcgttcat ggccctgatg agcctcatgc tccagatgcg 5460
caacagcatc accggccgga cggacgtgga cttcctgatc agccccggtc agaacagcga 5520
cggcattttc tacgacagcc ggaactacga ggcccaggag aacgccatcc tccccaagaa 5580
cgccgacgcg aacggcgcct acaacatcgc gcggaaggtg ctgtgggcca tcggccagtt 5640
taaaaggcg gaggacgaga agctggacaa ggtcaagatc gccatcagca acaaggagtg 5700
gctcgagtac gcgcagacga gcgtgaagca cggatcgaag aagagaagaa ttaaacaaga 5760
ttgataatcg atcctccgat cccttaatta ccataccatt acaccatgca tcaatatcca 5820
tatatatata aacccctttcg cacgtactta tactatgttt tgtcatacat atatatgtgt 5880
cgaacgatcg atctatcact gatatgatat gattgatcca tcagcctgat ctctgtatct 5940
tgttatttgt ataccgtcaa ataaaagttt cttccacttg tgttaataat tagctactct 6000
catctcatga acccctatata taactagttt aatttgctgt caattgaaca tgatgatcga 6060
tg                                                                 6062
```

SEQ ID NO: 16          moltype = DNA   length = 3744
FEATURE                Location/Qualifiers
misc_feature           1..3744
                       note = Synthetic polynucleotide.NLS-LbCpf1-Os-NLS
source                 1..3744
                       mol_type = other DNA
                       organism = synthetic construct

SEQUENCE: 16

```
ggatctaaga agagaagaat taaacaagat tccaagctgg agaagtttac aaactgttac  60
agcctctcca aaaccctcag gtttaaagcg atcccggtgg gcaagaccca ggagaacatc 120
gacaacaaga ggctcctggt ggaagacgag aagcgcgccg aagactacaa gggcgtgaag 180
aagctgctcg ataggtacta cctcagcttt attaacgacg tgctgcacag catcaaactc 240
aagaatctca caactacat ctcccctctttc cgcaaaaaga cccgcaccga aaggagaac 300
aaggagctga gaacctggaa gatcaacctc cgcaaggaaa tcgccaaagc gttcaagggc 360
aatgaagggt acaagagcct cttcaagaaa gacatcatcg aaactatcct cccagagttt 420
ctcgatgaca aggacgagat cgcgctggtg aactccttta accggttcac aaccgcgttt 480
accggcttct tgataacag ggaaaatatg ttctccgagg aggccaagtc caccagcatc 540
gccttcaggt gtatcaacga gaacctcacc gcgtacattt ccaatatgga cattttcgag 600
aagtggatg cgatcttcga taagcacgag gtgcaggaga tcaaagagaa gattctcaat 660
tccgattatg acgtcgagga tttcttcgaa ggggagttct taattttgt gctcacacaa 720
gagggcattg acgtgtacaa cgcgattatc gggggcttcg tcacagagtc cggggagaag 780
```

```
attaagggc tgaatgagta catcaatctg tacaatcaga agaccaagca gaaactgccg    840
aaattcaagc cgctctacaa gcaagtcctg tccgataggg aaagcctctc cttctacggc    900
gagggctata ccagcgacga ggaggtgctg gaagtcttcc gcaacacact gaataagaat    960
agcgagattt tctcctccat caagaagctc gagaagctct ttaagaactt tgacgagtac   1020
agctccgccg ggattttcgt gaagaacggg ccggcgatca gcaccatctc caaggacatc   1080
tttggcgagt ggaacgtcat cagggacaag tggaacgccg agtacgacga catccacctg   1140
aagaagaagg cggtggtgac cgagaagtat gaggacgatc gcaggaagtc cttcaaaaaa   1200
atcggctcct tcagcctcga acagctccag gagtatgccg atgcggatct gtccgtcgtc   1260
gagaagctga aggaaatcat cattcagaag gtcgagaga tctataaagt gtacgggtcc    1320
agcgaagc tgttcgacgc cgactttgtg ctcgagaagt ccctcaaaaa gaatgacgcc    1380
gtggtggcca ttatgaaaga cctgctcgac tccgtgaagt ccttcgaaaa ttacattaaa   1440
gcgttctttg gggaggggaa ggaaactaac agggatgagt ccttctatgg cgactttgtc   1500
ctcgcgtacg acatcctgct gaaggtcgac cacatttacg acgcgatccg caactcggtc   1560
acacagaagc cgtactccaa agacaagttc aagctgtact tccagaaccc gcaatttatg   1620
gggggctggg acaaggataa agagacagac taccgcgcga caattctccg ctatggctcc   1680
aaatactatc tggccatcat ggacaagaag tacgcgaagt gcctgcagaa gatcgacaaa   1740
gacgacgtca atggcaacta tgaaaagatc aactacaagc tgctgccggg cccgaacaag   1800
atgctcccga aggtgttctt cagcaagaag tggatggcct actacaatcc aagcgaggat   1860
attcagaaaa tctataaaaa cgggaccttc aagaaggggg acatgtttaa cctcaacgac   1920
tgccacaagc tcattgattt cttcaaggat agcatttccc gctacccgaa atggtccaat   1980
gcgtacgatt ttaacttctc cgagacagaa agtacaaaga catcgcgggg cttttacagg   2040
gaggtggagg agcaagggta taaagtttct tttgaatccg cggacgaaga gaagtcgac   2100
aagctcgtcg aggagggcaa gctctacatg ttccaaattt ataacaagga cttttccgac   2160
aagagccatg ggaccccaaa cctccacacc atgtacttca aactgctctt tgacgagaac   2220
aaccacgggg aaatcaggct gagcggcggc gccgaattat tcatgcgcag ggcctccctc   2280
aagaaggaag agctggtcgt ccatccagcc aattccccga tcgcgaacaa gaacctcgac   2340
aatccgaaaa agaccaccac cctgtcctac gacgtctaca aggacaaacg cttcagcgaa   2400
gaccagtacg aattacacat cccaattgcg attaataagt gcccaaagaa tatcttcaaa   2460
attaatacag aggtcagggt gctgctcaaa cacgacgaca atccgtatgt catcggcatt   2520
gacagggcgg agcgcaatct gctctatatc gtggtcgtgg atgggaaggg caatattgtg   2580
gagcagtact ccctgaacga gattatcaac aacttcaatg ggattaggat taagaccgac   2640
tatcacagcc tgctcgacaa gaaagaaaaa gagaggtttg aggcccgcca aaactggacc   2700
tccattgaga atatcaaaga attaaggcc ggctatattt cccaagtcgt ccacaagatc    2760
tgcgagctgg tggagaaata tgacgccgtg attgcgctcg aagacttaaa ttctgggttc   2820
aagaactccc gcgtgaaggt ggtgtatcga aattcgagaa aatgctgatc                2880
gacaaactca attatatggt ggataagaag tccaacccgt gtgccacagg gggcgcgctg   2940
aagggctatc agatcaccaa caagttcgag agcttcaaga gcatgagcac ccagaacggg   3000
tttatttttct acatcccggc gtggctcacc tccaagattg acccgagcac cggcttcgtg   3060
aacctcctga agacaaagta taccccatt gccgacagca agaagtttat ctcctcctc    3120
gaccgcatta tgtatgtgcc ggaggaggac ctcttcgagt cgccctcga ctacaaaaac    3180
ttcagccgca cagatgcgga ttacatcaag aagtggaagc tgtactccta cgggaacagg   3240
atccgcatct tcaggaatcc aaaaaaaaat aacgtctttg actgggagga agtgtgcctg   3300
acatccgcct acaaggaact gttcaataaa tacggcatca attccagca gggcgacatt    3360
cgcgccctcc tctgtgagca gtccgacaaa gcgttttact ccagcttcat ggccctcatg   3420
tccctgatgc tccaaatgag gaatagcatc acagggcgca ccgacgtcga cttcctcatc   3480
agcccggtga agaactccga cgggatcttt acgactccc gcaactatga ggcgcaagag   3540
aatgcgatcc tcccgaagaa cgccgatgcg aacggggcct ataatatcgc caggaaagtg   3600
ctctgggcca tcgggcagtt caaaaggcg gaggatgaga agctcgacaa ggtgaaaatt   3660
gccatttcca acaaggagtg gctggagtac gcgcagacct ccgtgaagca cggatctaag   3720
aagagaagaa ttaaacaaga ttga                                           3744
```

SEQ ID NO: 17          moltype = DNA   length = 3756
FEATURE                Location/Qualifiers
misc_feature           1..3756
                       note = Synthetic polynucleotide.kozak-NLS-LbCpf1-Os-NLS
source                 1..3756
                       mol_type = other DNA
                       organism = synthetic construct
SEQUENCE: 17

```
gccgccatgg cgggatctaa gaagagaaga attaaacaag attccaagct ggagaagttt     60
acaaactgtt acagcctctc caaaccctc aggtttaaag cgatcccggt gggcaagacc    120
caggagaaca tcgacaacaa gaggctcctg gtggaagacg agaagcgcgc cgaagactac    180
aagggcgtga agaagctgct cgataggtac tacctcagct ttattaacga cgtgctgcac    240
agcatcaaac tcaagaatct caacaactac atctcctct tccgcaaaaa gaccegcacc    300
gagaaggaga caaggagct ggagaacctg gagatcaacc tccgcaagga aatcgccaaa     360
gcgttcaagg gcaatgaagg gtacaagagc ctcttcaaga agacatcat cgaaactatc    420
ctcccagagt ttctcgatga caaggacgag atcgcgctgg tgaactcctt taacgggttc    480
acaaccgcgt ttaccggctt ctttgataac agggaaaata tgttctccga ggaggccaag   540
tccaccagca tcgccttcag gtgtatcaac gagaacctca cccgctact ttccaatatg   600
gacattttcg agaaggtgga tgcgatcttc gataagcacg aggtcagga gatcaaagag   660
aagattctca attccgatta tgcgtcgag gatttcttcg aaggggagtt ctttaattt    720
gtgctcacac aagagggcat tgacgtgtac aacgcgatta tcgggggctt cgtcacagag  780
tccgggagga agattaaggg gctgaatgag tacatcaatc tgtacaatca gaagaccaag   840
cagaaactga cgaaattcaa gccgctctac aagcaagttc tgtccgatag ggaaagcctc   900
tccttctacg gcgagggcta taccagcgac gaggaggtgc tggaagtctt ccgcaacaca    960
ctgaataaga atgcgagat tttctcctcc atcaagaagc tcgagaagct ctttaagaac   1020
tttgacgagt acagctccgc cgggattttc gtgaagaacg ggccggcgat cagcaccatc   1080
tccaaggaca tctttggcga gtggaacgtc atcagggaca gtggaacgc cgagtacgac   1140
gacatccacc tgaagaagaa ggcggtggtg accgagaagt atgaggacga tcgcaggaag   1200
```

```
tccttcaaaa aaatcggctc cttcagcctc gaacagctcc aggagtatgc cgatgcggat    1260
ctgtccgtcg tcgagaagct gaaggaaatc atcattcaga aggtcgacga gatctataaa    1320
gtgtacgggt ccagcgagaa gctgttcgac gccgactttg tgctcgagaa gtccctcaaa    1380
aagaatgacg ccgtggtggc cattatgaaa gacctgctcg actccgtgaa gtccttcgaa    1440
aattacatta aagcgttctt tggggagggg aaggaaacta acagggatga gtccttctat    1500
ggcgactttg tcctcgcgta cgacatcctg ctgaaggtcg accacattta cgacgcgatc    1560
cgcaactacg tgacacagaa gccgtactcc aaagacaagt tcaagctgta cttccagaac    1620
ccgcaattta tgggggctg ggacaaggat aaagagacag actaccgcgc gacaattctc    1680
cgctatggct ccaaatacta tctggccatc atggacaaga agtacgcgaa gtgcctgcag    1740
aagatcgaca aagacgacgt caatggcaac tatgaaaaga tcaactacaa gctgctgccg    1800
ggcccgaaca agatgctccc gaaggtgttc ttcagcaaga agtggatggc ctactacaat    1860
ccaagcgagg atattcagaa aatctataaa acgggacct caagaaggg ggacatgttt     1920
aacctcaacg actgccacaa gctcattgat ttcttcaagg atagcatttc ccgctacccg    1980
aaatggtcca atgcgtacga ttttaacttc tccgagcaag aaaagtacaa agacatcgcg    2040
ggctttaca gggaggtgga ggagcaaggg tataaagttt cttttcgaatc cgcgagcaag   2100
aaggaagtcg acaagctcgt cgaggagggc aagctctaca tgttccaaat ttataacaag    2160
gactttccg acaagagcca tgggacccca aacctccaca ccatgtactt caaactgctc    2220
tttgacgaga acaaccacgg gcaaatcagg ctgagcggcg cgccgaatt attcatgcgc    2280
agggcctccc tcaagaagga agagctggtc gtccatccag ccaattcccc gatcgcgaac    2340
aagaacccgg acaatccgaa aaagaccacc accctgtcct acgacgtcta caaggacaaa    2400
cgcttcagcg aagaccagta cgaattacac atcccaattg cgattaataa gtgcccaaag    2460
aatatcttca aaattaatac agaggtcagg gtgctgctca aacacgacga caatccgtat    2520
gtcatcggca ttgacagggg cgagcgcaat ctgctctata tcgtggtcgt ggatgggaag    2580
ggcaatattg tggagcagta ctccctgaac gagattatca caacttcaa tgggattagg    2640
attaagaccg actatcacag cctgctcgac aagaaagaaa aagagaggtt tgaggcccgc    2700
caaaactgga cctccattga gaatatcaaa gaattcaaag ccggctatat ttcccaagtc    2760
gtccacaaga tctgcgagct ggtggagaaa tatgacgccg tgattgcgct cgaagactta    2820
aattctgggt tcaagaactc ccgcgtgaag gtggaaaaac aggtgtatca gaaattcgag    2880
aaaatgctga tcgacaaact caattatatg gtggataaga agtccaaccc gtgtgccaca    2940
gggggcgcgc tgaagggcta tcagatcacc aacaagttcg agagcttcaa gagcatgacg    3000
acccagaacg ggtttatttt ctacatcccg gcgtggctca cctccaagat tgacccgagc    3060
accggcttcg tgaacctcct gaagacaaag tatacctcca ttgccgacag caagaagttt    3120
atctcctcct tcgaccgcat tatgtatgtg ccggaggagg acctcttcga gttcgccctc    3180
gactacaaaa acttcagccg cacagatgcg gattacatca agaagtggaa gctgtactcc    3240
tacgggaaca ggatccgcat cttcaggaat ccaaaaaaaa ataacgtctt tgactgggag    3300
gaagtgtgcc tgcatccgc ctacaaggaa ctgttcaata atacggcat caattaccag    3360
cagggcgaca ttcgcgccct cctctgtgag cagtccgaca agcgtttta ctccagcttc    3420
atggccctca tgtccctgat gctccaaatg aggaatagca tcacagggcg caccgacgtc    3480
gacttcctca tcagcccggt gaagaactcc gacgggatct tttacgactc ccgcaactac    3540
gaggcgcaag agaatgcgat cctcccgaag aacgccgatg cgaacggggc ctataatatc    3600
gccaggaaaa tgctctgggc catcgggcag ttcaaaaagg cggaggatga gaagctcgac    3660
aaggtgaaaa ttgccatttc caacaaggag tggctggagt acgcgcagac ctccgtgaag    3720
cacggatcta agaagagaag aattaaacaa gattga                            3756
```

SEQ ID NO: 18        moltype = DNA   length = 6062
FEATURE              Location/Qualifiers
misc_feature         1..6062
                     note = Synthetic polynucleotide.Expression Cassette
                     comprising the ZmUbiqitin promoter cassette,
                     koz-NLS-LbCpf1-Os-NLS cassette andthe Oryza sativa LTP
                     termination sequence
source               1..6062
                     mol_type = other DNA
                     organism = synthetic construct
SEQUENCE: 18

```
gtcgtgcccc tctctagaga taaagagcat tgcatgtcta agtataaaa aattaccaca     60
tattttttg tcacacttat ttgaagtgta gtttatctat ctctatacat atatttaaac    120
ttcactctac aaataatata gtctataata ctaaaataat attagtgttt tagaggatca    180
tataaataaa ctgctagaca tggtctaaag gataattgaa tatttgaca atctacagtt    240
ttatcttttt agtgtgcatg tgatctctct gttttttttg caaatagctt gacctatata    300
atacttcatc cattttatta gtacatccat ttaggattta gggttgatgg tttctataga    360
ctaatttta gtacatccat tttattcttt ttagtctcta aatttttaa aactaaaact    420
ctattttagt ttttattta ataatttaga tataaaatga aataaaataa attgactaca    480
aataaaacaa ataccctta agaaataaaa aaactaagca aacattttc ttgtttgaa    540
tagataatga caggctgttc aacgccgtcg acgagtctaa cggacaccaa ccagcgaacc    600
agcagcgtcg cgtcgggcca agcgaagcag acggcacggc atctctgtag ctgcctctgg    660
acccctctcg agagttccgc tccaccgttg gacttgctcc gctgtcggca tccagaaatt    720
gcgtggcgga gcggcagacg tgaggcggca cggcaggcgg cctcttcctc ctctcacggc    780
accggcagct acgggggatt cctttcccac cgctccttcg ctttcccttc ctcgcccgcc    840
gtaataaaata gacacccct ccacaccctc tttccccaac ctcgtgttcg ttcggagcgc    900
acacacgc aaccagatct cccccaaatc cagccgtcgg cacctccgct tcaaggtacg    960
ccgctcatcc tccccccccc cctctctcta ccttctctag atcggcgatc cggtccatgg   1020
ttaggccccg gtagttctac ttctgttcat gtttgtgtta gagcaaacat gttcatgttc   1080
atgtttgtga tgatgtggtc tggttgggcg tcgttctaa atcggagtag gatactgttt   1140
caagctaccg ggtggattta ttaatttgtt atctgtatgt gtgtgccata catcttcata   1200
gttacgagtt taagatgatg gatggaaata tcgatctagg ataggtatac atgttgatgc   1260
gggttttact gatgcatata cagagatgct tttttctcg cttggttgtg atgatatggt    1320
ctggttgggc ggtcgttcta gatcggagta gaatactgtt tcaaactacc tggtggattt   1380
attaaaggat aaagggtcgt tctagatcgg agtagaatac tgtttcaaac tacctggtgg   1440
```

```
atttattaaa ggatctgtat gtatgtgcct acatcttcat agttacgagt ttaagatgat 1500
ggatggaaat atcgatctag gataggtata catgttgatg cgggttttac tgatgcatat 1560
acagagatgc ttttttcgc ttggttgtga tgatgtggtc tggttgggcg gtcgttctag 1620
atcggagtag aatactgttt caaactacct ggtggattta ttaattttgt atctttatgt 1680
gtgtgccata catcttcata gttacgagtt taagatgaga gatggaaata ttgatctagg 1740
ataggtatac atgttgatgt gggttttact gatgcatata catgatggca tatgcggcat 1800
ctattcatat gctctaacct tgagtaccta tctattataa taaacaagta tgttttataa 1860
ttattttgat cttgatatac ttggatgatg gcatatgcag cagctatatg tggatttttt 1920
agccctgcct tcatacgcta tttatttgct tggtactgtt tcttttgtcc gatgctcacc 1980
ctgttgtttg gtgatacttc tgcaggtcgc cgccatggcg ggatctaaga agagaagaat 2040
taaacaagat tccaagctgg agaagtttac aaactgttac agcctctcca aaaccctcag 2100
gtttaaagcg atcccggtgg gcaagaccca ggagaacatc gacaacaaga ggctcctggt 2160
ggaagacgag aagcgcgccg aagactacaa gggcgtgaag aagtgctcg ataggtacta 2220
cctcagcttt attaacgacg tgctgcacag catcaaactc aagaatctca acaactacag 2280
ctccctcttc cgcaaaaaga cccgcaccga gaaggagaac aaggagctgg agaacctgga 2340
gatcaacctc cgcaaggaaa tcgccaaagc gttcaagggc aatgaagggt acaagagcct 2400
cttcaagaaa gacatcatcg aaactatcct cccagagttt ctcgatgaca aggacgagat 2460
cgcgctggtg aactcctta acgggttcac aaccgcgttt accggcttct ttgataacag 2520
ggaaaatatg ttctccgagg aggccaagtc caccagcatc gccttcaggt gtatcaacga 2580
gaacctcacc cgctacattt ccaatatgga cattttcgag aaggtggatg cgatcttcga 2640
taagcacgag gtgcaggaga tcaaagaaa gattctcaat tccgattatg acgtcgagga 2700
tttcttcgaa ggggagttct ttaattttgt gctcacacaa gagggcattg acgtgtacaa 2760
cgcgattatc gggggcttcg tcacagagtc cggggagaag attaagggg tgaatgagta 2820
catcaatctg tacaatcaga agaccaagca gaaactgccg aaattcaagc cgctctacaa 2880
gcaagtcctg tccgataggg aaagcctctc cttctacggc gagggctata ccagcgacga 2940
ggaggtgctg gaagtcttcc gcaacacact gaataagaat agcgagattt tctcctccat 3000
caagaagctc gagaagctct ttaagaactt tgacgagtac agctccgccg ggattttcgt 3060
gaagaacggg ccggcgatca gcaccatctc caaggacatc tttggcgagt ggaacgtcat 3120
cagggacaag tggaacgccg agtacgacga catccacctg aagaagaagg cggtggtgac 3180
cgagaagtat gaggacgatc gcaggaagtc cttcaaaaaa atcggctcct tcagcctcga 3240
acagctccag gagtatgccg atgcggatct gtccgtcgtc gagaagctga aggaaatcat 3300
cattcagaag gtcgacgaga tctataaagt gtacgggtcc agcgagagc tgttcgacgc 3360
cgactttgtg ctcgagaagt ccctcaaaaa gaatgacgcc gtggtggcca ttatgaaaga 3420
cctgctcgac tccgtgaagt ccttcgaaaa ttacattaaa gcgttctttg gggaggggaa 3480
ggaaactaac agggatgagt ccttctatgg cgactttgtc ctcgcgtacg acatcctgct 3540
gaaggtcgac cacatttacg acgcgatccg caactacgtg acacagaagc cgtactccaa 3600
agacaagttc aagctgtact ccagaaccc gcaatttatg gggggctggg acaaggataa 3660
agagacagac taccgcgcga caattctccg ctatggctcc aaatactatc tggccatcat 3720
ggacaagaag tacgcgaagt gcctgcagaa gatcgacaag gacgacgtca atggcaacta 3780
tgaaaagatc aactacaagc tgctgccggg cccgaacaag atgctcccga aggtgttctt 3840
cagcaagaag tggatggcct actacaatcc aagcgaggat attcagaaaa tctataaaaa 3900
cgggaccttc aagaagggg acatgtttaa cctcaacgac tgccacaagc tcattgattt 3960
cttcaaggat agcatttccc gctacccgaa atggtccaat ggctacgatt ttaacttctc 4020
cgagacagaa aagtacaaag acatcgcggg cttttacagg gaggtggagg agcaaggta 4080
taaagtttct tttgaatccg cgagcaagaa ggaagtcgac aagctcgtcg aggagggcaa 4140
gctctacatg ttccaaattt ataacaagga cttttccgac aagagccatg ggaccccaaa 4200
cctccacacc atgtacttca aactgctctt tgacgagaac aaccacggga aaatcaggct 4260
gagcggcggc gccgaattat tcatgcgcag ggcctccctc aagaaggaag agctggtcgt 4320
ccatccagcc aattccccga tcgcgaacaa gaacccggac aatccgaaaa agaccaccac 4380
cctgtcctac gacgtctaca aggacaaacg cttcagcgaa gaccagtacg aattacacat 4440
cccaattgcg attaataagt gcccaaagaa tatcttcaaa attaatacag aggtcaggt 4500
gctgctcaaa cacgacgaca atccgtatgt catcggcatt gacaggggcg agcgcaatct 4560
gctctatatc gtggtcgtgg atgggaaggg caatattgtg gagcagtact ccctgaacga 4620
gattatcaac aacttcaatg ggattaggat taagaccgac tatcacagcc tgctcgacaa 4680
gaaagaaaaa gagaggtttg aggcccgcca aaactgaacc tccattgaga atatcaaaga 4740
attaaaggcc ggctatattt cccaagtcgt ccacaagatc tgcgagctgg tggagaaata 4800
tgacgccgtg attgcgctcg aagacttaaa ttctgggttc aagaactccc gcgtgaaggt 4860
ggaaaaacag gtgtatcaga aattcgaaaa aatgctgatc gacaaactca attatatggt 4920
ggataagaag tccaacccgt gtgccacagg gggcgcgctg aagggctatc agatcaccaa 4980
caagttcgag agcttcaaga gcatgagcac ccagaacggg tttattttct acatcccggc 5040
gtggctcacc tccaagattg acccgagcac cggcttcgtg aacctcctga agacaaagta 5100
tacctccatt gccgacagca agaagtttat ctcctccttc gaccgcatta tgtatgtgcc 5160
ggaggaggac ctcttcgagt tcgccctcga ctacaaaaac ttcagccgca cagatgcgga 5220
ttacatcaag aagtggaagc tgtactccta cgggaaccag atccgcatct tcgaaatgga 5280
aaaaaaaat aacgtctttg actgggagga agtgtgcctg acatccgcct acaaggaact 5340
gttcaataaa tacggcatca attaccagca gggcgacatt cgcgccctcc tctgtgagca 5400
gtccgacaaa gcgttttact ccagcttcat ggccctcatg tccctgatgc tccaaatgag 5460
gaatagcatc acagggcgca ccgacgtcga cttcctcatc agccggtga agaactcga 5520
cgggatcttt tacgactccc gcaactatga gcgcaagag aatgcgatcc tcccgaagaa 5580
cgccgatgcg aacggggcct ataatatcgc caggaaagtg ctctgggcca tcggcagtt 5640
caaaaaggcg gaggatgaga agctcgacaa ggtgaaaatt gccatttcca acaaggagtg 5700
gctggagtac gcgcagacct ccgtgaagca cggatctaag aagagaagaa ttaaacaaga 5760
ttgataatcg atcctccgat cccttaatta ccataccatt acaccatgca tcaatatcca 5820
tatatatata aacccctttg cacgtactta tgtcatacat atatatgtgt 5880
cgaacgatcg atctatcact gatatgatat gattgatcca tcagcctgat ctctgtatct 5940
tgttatttgt ataccgtcaa ataaaagttt cttccacttg tgtaataat tagctactct 6000
catctcatga acctatata taactagttt aatttgctgt caattgaaca tgatgatcga 6060
tg                                                                  6062
```

| SEQ ID NO: 19 | moltype = DNA length = 6072 |
|---|---|
| FEATURE | Location/Qualifiers |
| misc_feature | 1..6072 |
| | note = Synthetic polynucleotide.Expression Cassette comprising the ZmUbiqitin promoter cassette, NLS-LbCpf1-Os-NLS cassette and theOryza sativa LTP termination sequence |
| source | 1..6072 |
| | mol_type = other DNA |
| | organism = synthetic construct |

SEQUENCE: 19

```
gtcgtgcccc tctctagaga taaagagcat tgcatgtcta aagtataaaa aattaccaca    60
tattttttg tcacacttat ttgaagtgta gtttatctat ctctatacat atatttaaac   120
ttcactctac aaataatata gtctataata ctaaaatat attagtgttt tagaggatca   180
tataaataaa ctgctagaca tggtctaaag gataattgaa tattttgaca atctacagtt   240
ttatcttttt agtgtgcatg tgatctctct gtttttttg caaatagctt gacctatata   300
atacttcatc cattttatta gtacatccat ttaggattta gggttgatgg tttctataga   360
ctaattttta gtacatccat tttattcttt ttagtctcta aatttttaa aactaaaact   420
ctattttagt tttttattta ataatttaga tataaaatga aataaaataa attgactaca   480
aataaaaacaa atacccttta agaaataaaa aaactaagca aacatttttc ttgtttcgag   540
tagataatga caggctgttc aacgccgtcg acgagtctaa cggacaccaa ccagcgaacc   600
agcagcgtcg cgtcgggcca agcgaagcag acggcacggc atctctgtag ctgcctctgg   660
acccctctcg agagttccgc tccaccgttg gacttgctcc gctgtcggca tccagaaatt   720
gcgtggcgga gcgcagacg tgaggcggca cggcaggcgg cctcttcctc ctctcacggc   780
accggcagct acggggatt cctttcccac cgctccttcg cttcccttc ctcgcccgcc   840
gtaataaata gacaccccct ccacacccctc tttccccaac ctcgtgttcg ttcggagcgg   900
acacacacgc aaccagatct ccccccaaatc cagccgtcgg cacctccgct tcaaggtacg   960
ccgctcatcc tccccccccc cctctctcta ccttctctag atcggcgatc cggtccatgg  1020
ttagggcccg gtagttctac ttctgttcat gtttgtgtta gagcaaacat gttcatgttc  1080
atgttttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatggaaata tcgatctagg ataggtatac atgttgatgc  1260
gggttttact gatgcatata cagagatgct tttttcttcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc ttttttctcg cttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggatttttt  1920
agccctgcct tcatacgcta tttatttgct tggtactgtt tctttttgtcc gatgctcacc  1980
ctgttgtttg gtgatacttc tgcaggtccg gtaccatggg atctaagaag agaagaatta  2040
aacaagatat gtccaagctg gagaagttta caaactgtta cagcctctcc aaaaccctca  2100
ggttttaaagc gatcccggtg ggcaagaccc aggagaacat caacaacaag aggctcctgg  2160
tggaagacga gaagcgcgcc gaagactaca agggcgtgaa gaagctgctc gataggtact  2220
acctcagctt tattaacgac gtgctgcaca gcatcaaact caagaatctc aacaactaca  2280
tctccctctt ccgcaaaaag acccgcaccg agaaggagaa caaggagctg gagaacctgg  2340
agatcaacct ccgcaaggaa atcgccaaag cgttcaaggg caatgaaggg tacaagagcc  2400
tcttcaagaa agacatcatc gaaactatcc tcccagagtt tctcgatgac aaggacgaga  2460
tcgcgctggt gaactccttt aacgggttca caaccgcgtt taccggcttc tttgataaca  2520
gggaaaaatat gttctccgag gaggccaagt ccaccagcat cgccttcagg tgtatcaacg  2580
agaacctcac ccgctacatt tccaatatgg acatttttga gaaggtggat gcgatcttcg  2640
ataagcacga ggtgcaggag atcaaagaga gattctcaa ttccgattat gacgtcgagg  2700
atttcttcga aggggagttc tttaatttg tgctcacaca agagggcatt gacgtgtaca  2760
acgcgattat cggggcttc gtcacagagt ccggggagaa gattaagggg ctgaatgagt  2820
acatcaatct gtacaatcag aagaccaagc agaaactgcc gaaattcaag ccgctctaca  2880
agcaagtcct gtccgatagg gaaagcctct ccttctacgg cgagggctat accagcgacg  2940
aggaggtgct ggaagtcttc gcaacacac tgaataagaa tagcgagatt ttctcctcca  3000
tcaagaagct cgagaagctc tttaagaact tgacgagta cagctccgcc gggatttcg  3060
tgaagaacgg gccggcgatc agcaccatct ccaaggacat ctttgcgag tggaacgtca  3120
tcagggacaa gtggaacgcc gagtacgacg acatccatct gaagaagaag gcggtggtga  3180
ccgagaagta tgaggacgat cgcaggaagt ccttcaaaaa aatcggctcc ttcagcctcg  3240
aacagctcca ggagtatgcc gatgcggatc tgtccgtcgt cgagaagctg aaggaaatca  3300
tcattcagaa ggtcgacgag atctataaag tgtacgggtc cagcgagaag ctgttcgacg  3360
ccgactttgt gctcgagaag tccctcaaaa agaatgacgc cgtggtggcc attatgaaag  3420
acctgctcga ctccgtgaag agcttcgaga attatattaa ggctttgctt gggaagggga  3480
aggaaactaa cagggatgag tccttctatg gcgactttgt cctcgcgtac gacatcctgc  3540
tgaaggtcga ccatttta gacgcgatcc gcaactacgt gacacagaag ccgtactcca  3600
aagacaagtt caagctgtac ttccagaacc cgcaattat ggggggctgg gacaaggata  3660
aagagacaga ctaccgcgcg caattctccg gctatgcgct caaatactat cggccatca  3720
tggacaagaa tgcgcgaag tgcctgcaga gagatcgcaa agcgacgtc aatgcaact  3780
atgaaaagat caactacaag ctgctgcgg gccgaacaa gatgctccg aaggtgttct  3840
tcagcaagaa gtgatggcc tactacaatc aagcgagga tattcagaaa atctataaa  3900
acgggacctt caaagagggg gacatgttta acctcaacga ctgccacaag ctcattgatt  3960
tcttcaagga tagcatttcc cgctacccga aatggtccaa tgcgtacgat tttaacttct  4020
ccgagacaga aaagtacaaa gacatcgcgg gcttttcag ggaggtggag gagcaaggt  4080
```

```
ataaagtttc ttttgaatcc gcgagcaaga aggaagtcga caagctcgtc gaggagggca  4140
agctctacat gttccaaatt tataacaagg acttttccga caagagccat gggaccccaa  4200
acctccacac catgtacttc aaactgctct tgacgagaa caaccacggg caaatcaggc   4260
tgagcggcgg cgccgaatta ttcatgcgca gggcctccct caagaaggaa gagctggtcg  4320
tccatccagc caattcccg atcgcgaaca agaacccgca caatccgaaa aagaccacca   4380
ccctgtccta cgacgtctac aaggacaaac gcttcagcga agaccagtac gaattacaca  4440
tcccaattgc gattaataag tgcccaaaga atatcttcaa aattaataca gaggtcaggg  4500
tgctgctcaa acacgacgac aatccgtatg tcatcggcat tgacagggc gagcgcaatc   4560
tgctctatat cgtggtcgtg gatgggaagg gcaatattgt ggagcagtac tccctgaacg  4620
agattatcaa caacttcaat gggattagga ttaagaccga ctatcacagc ctgctcgaca  4680
agaaagaaaa agagaggttt gaggcccgcc aaaactggac ctccattgag aatatcaaag  4740
aattaaaggc cggctatatt tcccaagtcg tccacaagat ctgcgagctg gtggagaaat  4800
atgacgccgt gattgcgctc gaagacttaa attctgggtt caagaactcc cgcgtgaagg  4860
tggaaaaaca ggtgtatcag aaattcgaga aaatgctgat cgacaaactc aattatatgt  4920
tggataagaa gtccaacccg tgtgccacag gggcgcgct gaagggctat cagatcacca   4980
acaagtcga gagcttcaag agcatgagca cccagaacgg gtttattttc tacatcccga   5040
cgtggctcac ctccaagatt gacccgagca ccggcttcgt gaacctcctg aagacaaagt  5100
ataccctccat tgccgacagc aagaagttta tctcctcctt cgaccgcatt atgtatgtgc  5160
cggaggagga cctcttcgag ttcgccctcg actacaaaaa cttcagccgc acagatgcgg  5220
attacatcaa gaagtggaag ctgtactcct acgggaacag gatccgcatc ttcaggaatc  5280
caaaaaaaaa taacgtcttt gactgggagg aagtgtgcct gacatccgcc tacaaggaac  5340
tgttcaataa atacggcatc aattaccagc agggcgaact cgcgccctc ctctgtgacg   5400
agtccgacaa agcgttttac tccagcttca tggccctcat gtccctgatg ctccaaatga  5460
ggaatagcat cacagggcgc accgacgtcg acttcctcat cagcccggtg aagaactccg  5520
acgggatctt ttacgactcc cgcaactatg aggcgcaaga aatgcgatc ctcccgaaga   5580
acgccgatgc gaacggggcc tataatatcg ccaggaagct gctctgggcc atcgggcagt  5640
tcaaaaaggc ggaggatgag aagctcgaca aggtgaaaat tgccattcc aacaaggagt   5700
ggctggagta cgcgcagacc tccgtgaagc acggatctaa gaagagaaga attaaacaag  5760
attgattaat taatcgatcc tccgatccct taattaccat gccattacac catgcatcaa  5820
tatccatata tatataaacc ctttcgcacg tacttatat atgtttttgtc atacatatat  5880
atgtgtcgaa cgatcgatct atcactgata tgatatgatt gatccatcag cctgatctct  5940
gtatcttgtt atttgtatac cgtcaaataa aagtttcttc cacttgtgtt aataattagc  6000
tactctcatc tcatgaaccc tatatataac tagtttaatt tgctgtcaat tgaacatgat  6060
gatcgatgcc tg                                                       6072
```

| SEQ ID NO: 20   | moltype = DNA  length = 5091 |
|---|---|
| FEATURE | Location/Qualifiers |
| misc_feature | 1..5091 |
| | note = Synthetic polynucleotide.Expression Cassette comprising the DaMVpromoter cassette, NLS-LbCpf1-CO2-NLS cassette and a Medicagotruncatula termination sequence |
| source | 1..5091 |
| | mol_type = other DNA |
| | organism = synthetic construct |

SEQUENCE: 20

```
agacatcctg gaccaatatg ctgaagatta tgctacctac accaggatag gacttgaagc   60
acttaacctt gaagattggt tcgaagaacc agaacccgat ccacctaacc ctgtggaccg   120
ccagaggata gaggacatcc tggacctact gaacgtcagc aatgacgact gaaagattcc   180
caggacaccg cgcggaagtgg tggacccagt ctaggtgcga tgcttagtcg cgcacgatga   240
ctatgtcgga aggcatcttt gctttcggca aactttagta atactttaag gaaagtattg   300
tacaagttag gtgcagagac aataatgcac ccagctttag ctttgtttat ggaattattg   360
tgtcggttgc attattggat gcctgcgtgc accctaagca atcaacggag aaacaaagat   420
aaaaatcaat tactcacatg aaagagtatt gatcacgagt cactatggag cgacaatctc   480
cagacaggat gtcagcatct tatcttcctt tgaagaaagc atcatcaata acgatgtaat   540
ggtggggaca tccactaagt tattgctctg caaacagctc aaaaagctac tggccgacaa   600
tcataattgc tcggcatgtg caggtggggc ctccactagc aataatacaa gctttacagc   660
ttgcagtgac tcatcctcca ataatggaga aaaagacgtc agcagtgacg aacaagggtc   720
gaaagacttg cctatataag ggcattctcc cctcagttga agatcatcga aagttggagc   780
aataaactct ctcttcaaca aatctatctt ttatctttta tcggtaccaa aaatggcggt   840
gatctaagaa gagaagaatt aaacaagatt cgaagctcga gaagttcacc aactgctctt   900
cgctgagcaa gacgctgcgg ttcaaggcga tcccgtcgg gaaagacccag gagaacatcg   960
acaacaagcg gctcctggtc gaggacgaga gcgcgccga ggactacaag ggcgtcaaga   1020
agctgctgga ccggtactac ctctccttca tcaacgacgt cctgcactcg atcaagctca   1080
agaacctgaa caactacatc tcgctgttcc gcaagaagac acggaccgga aaggagaaca  1140
aggagctcga gaacctcgag atcaacctgc gcaaggagat cgcgaaggcg ttcaaggca    1200
acgagggta caagagcctg ttcaagaaag acatcatcga gaccatcctg ccggagttcc   1260
tggacgacaa ggacgagatc gcgctggtga actcgttcaa cgggttcacc acggccttca  1320
ccgggttttt cgacaaccgg gagaacatgt tcagcgagga ggccaagtcg accagcatcg  1380
ccttccggtg catcaacgag aacctcaccc gctcatcagc caacatggac atcttcgaga  1440
aggtggacgc catcttcgac aagcacgagg tccaggagat caaggaaaag atcctgaact  1500
cggactacga cgtggaagac ttctttgagg gcgagttctt caacttcgtc ctcacccagg  1560
agggcatcga cgtctacaac gccatcatcg gcggcttcgt gacggagagc ggcgagaaga  1620
tcaagggcct caacgagtac atcaacctct acacaacaga gactaagcag aagctcccga  1680
agttcaagcc gctgtacaag caagtcctga gcgacgggga gtccctctcg ttctacggga  1740
agggctacac gagcgacgag gaggtgctgg aggtgttccg caacacgctg aacaagaaca  1800
gcgagatctt cagctcgatc aagaaactcg agaagctgtt caagaacttc gacgagtaca  1860
gcagcgccgg catcttcgtc aagaacgggc ccgatcag caccatcagc aaggacatct   1920
tcgggggagtg gaacgtgatc gcgcgacagt ggaacgccga gtacgacgac atccacctca  1980
agaaaaaggc ggtggtcacg gagaagtacg aggacgaccg ccgggaagtcc ttcaagaaaa  2040
```

```
tcgggagctt cagcctcgag cagctccagg agtacgcgga cgccgacctg agcgtggtgg    2100
agaagctcaa ggagatcatc atccagaagg tcgacgagat ctacaaggtc tacggctcga    2160
gcgagaagct gttcgacgcg gacttcgtgc tggagaagtc cctcaagaag aacgacgccg    2220
tggtggccat catgaaggat ctgctcgaca gcgtgaagtc gttcgagaac tacatcaagg    2280
cattctttgg ggagggcaag gagacgaacc gggacgagtc cttctacggg gacttcgtgc    2340
tcgcgtacga catcctcctg aaggtcgacc acatctacga cgcgatccgg aactacgtca    2400
cgcagaagcc ctacagcaag gacaagttca agctctactt ccagaacccg cagttcatgg    2460
gcgggtggga caaggacaag gagaccgact accgggccac gatcctgcgg tacgggtcca    2520
agtactacct cgccatcatg gacaagaagt acgccaagtg cctccagaag attgacaagg    2580
acgacgtgaa cgggaactac gagaagatca actacaagct cctcccgggg cccaacaaga    2640
tgctgccgaa ggtgttcttc agcaagaagt ggatggccta ctacaacccc tcggaggaca    2700
tccagaagat atacaagaac ggcacgttca aaaagggga catgttcaac ctgaacgact    2760
gccacaagct gatcgacttt tcaaggaca gcatcagccg ctacccgaag tggtcgaacg    2820
cctacgactt caacttctcg gagacggaga agtacaagga cattgcgggc ttctaccggg    2880
aggtggagga gcagggctac aaggtctcct tcgagagcgc ctccaagaaa gaggtggaca    2940
agctcgtgga ggagggcaag ctgtacatgt tccagatcta caacaaggac ttctcggaca    3000
agtcgcacgg caccccgaac ctccacacga tgtacttcaa gctgctgttc gacgagaaca    3060
accacgggca gatccgcctc agcggcgggg cggagctgtt catgcgccgc gcgtccctca    3120
agaaggagga gctggtcgtg cacccgcca actcccgat cgcgaacaag aacccgaca    3180
acccaagaa gacaaccacc ctctcgtacg acgtctacaa ggacaagcgg ttctcggagg    3240
accagtacga gctgcacatc ccgatcgcca tcaacaagtg ccccaagaac atcttcaaga    3300
tcaacacgga ggtgcgggtg ctgctcaagc acgacgaca cccctacgtc atcgggatcg    3360
accgcggcga gcggaacctg ctctacatcg tggtcgtgga cgggaagggg aacatcgtgt    3420
agcagtacag cctgaacgag atcatcaaca acttcaacgg catccgcatc aagacggact    3480
accacagcct cctggacaag aaggagaagg agcggttcga ggcgcggcag aactggacct    3540
ccatcgagaa catcaaggag ctgaaggccg gctacatcag ccaggtcgtg cacaagatct    3600
gcgagctcgt ggagaagtac gacgcggtga tcgcgctgga ggacttgaac agcgggttca    3660
agaactcccg ggtcaaggtc gagaagcagg tctaccagaa gttcgagaag atgctgatcg    3720
acaagctcaa ctacatggtg gacaagaagt ccaaccctg cgccaccggc ggcgcctca    3780
agggctacca gatcaccaac aagttcgagt ccttcaagtc gatgtctcg cagaacgggt    3840
tcatttcta catcccggcg tggctcacca gcaagatcga cccgagcacg ggcttcgtca    3900
acctcctgaa gaccaagtac accagcatcg cggacagcaa gaagttcatc tcctcgttcg    3960
accgcatcat gtacgtcccc gaggaagacc tgttcgagtt cgccctcgac tacaagaact    4020
tctcccggac ggacgccgac tacatcaaaa agtggaagct ctacagctac ggcaaccgga    4080
tccgcatctt ccgcaacccc aagaagaaca atgtgttcga ctgggaggag gtgtgcctga    4140
cgagcgccta caaggagctc ttcaacaagt acggcatcaa ctaccagcaa ggggacatcc    4200
gcgcgctgct ctgcgagcag tccgacaagg cgttctact cgtcgttcatg gccctgatga    4260
gcctcatgct ccagatgcgc aacagcatca ccggccggac ggacgtggac ttcctgatca    4320
gccgggtcaa gaacagcgac ggcattttct acgacgcccg gaactacgag gccaggaga    4380
acgccatcct ccccaagaac gccgacgcga acgcgccta caacatcgcg cggaaggtgc    4440
tgtgggccat cggccagttt aaaaaggcgg aggacgagaa gctggacaag gtcaagatcg    4500
ccatcagcaa caaggagtgg ctcgagtacg cgcagacgag cgtgaagcac ggatctaaga    4560
agagaagaat taaacaagat tgacttaatt aaagggctct ctgtcatgat ttcatacttt    4620
cattattgag ctctgtaatt acaattatga ccatgagaac atctcttatt gtgtggcctt    4680
ttaattgctg atgttagtac tgaaccaaag cttatcgtga tgatgtaaaa gcaataagta    4740
cttgtttgta gcttcttgt gtctccttt gggcttaata catctgttta gtgttgtggc    4800
tttggcatag acttcttcttg gtaataatgc cttgcaatgc aaaattcaa ttatcaaatt    4860
ctattatgtt ctcaccttat ggtaacagct taccctgtgg aagatgagat tcttgagttg    4920
agtcattgcc aattttggc attagctttt gaattagtga attttgacaa aaattaccgt    4980
gacactgatt tgttgaagc tcttaagtgt agtttttaca aaatttcagt ggctcgttgt    5040
gattatgtca aactcacggc gaatgtagtt cttacagaat ttcagtggct c             5091

SEQ ID NO: 21         moltype = DNA   length = 5091
FEATURE               Location/Qualifiers
misc_feature          1..5091
                      note = Synthetic polynucleotide.Expression Cassette
                      comprising the DaMVpromoter cassette, NLS-LbCpf1-Os-NLS
                      cassette and a Medicagotruncatula termination sequence
source                1..5091
                      mol_type = other DNA
                      organism = synthetic construct
SEQUENCE: 21
agacatcctg gaccaatatg ctgaagatta tgctacctac accaggatag gacttgaagc    60
acttaacctt gaagattggt tcgaagaacc agaacccgat ccactaacc ctgtgaccgt    120
ccagaggata gaggacatcc tggacctact gaacgtcagc aatgacgact gaaagattcc    180
caggacaccg gcggaagtgg tggacccagt ctaggtgcga tgcttagtcg cgcacgatga    240
ctatgtcgga aggcatcttt gctttcggca actttagta atactttaag gaaagttattg    300
tacaagttag gtgcagagac aataatgcac ccagcttttag ctttgtttat ggaattattg    360
tgtcggttgc attattggat gcctgcgtgc accctaagca atcaacggaa aaacaaagat    420
aaaaatcaat tactcacatg aaagagtatt gatcacgagt cactatggag cgacaatctc    480
cagacaggat gtcagcatct tatcttcctt tgaagaaagc atcatcaata acgatgtaat    540
ggtggggaca tccactaagt tattgctctg caaacagctc aaaaagctac tggccgacaa    600
tcataattgc tcggcatgtg caggtgggc ctccactagc aataatacaa gctttacagc    660
ttgcagtgac tcatcctcca ataatgaga aaagacgct agcagtgacg aacaagggtc    720
gaaagacttg cctatataag ggcattctcc cctcagttga agatcatcga agttggagc    780
aataaactct ctcttcaaca aatctatctt ttatctttta tcggtaccaa aaaatggcgg    840
gatctaagaa gagaagaatt aaacaagatt ccaagctgga gaagttaca aactgttaca    900
gcctctccaa aaccctcagg tttaaagcga tcccggtggg caagacccag agaacatcg    960
acaacaagag gctcctggtg gaagacgaga agcgcgccga agactacaag ggcgtgaaga   1020
```

```
agctgctcga taggtactac ctcagcttta ttaacgacgt gctgcacagc atcaaactca   1080
agaatctcaa caactacatc tccctcttcc gcaaaaagac ccgcaccgag aaggagaaca   1140
aggagctgga gaacctggag atcaacctcc gcaaggaaat cgccaaagcg ttcaagggca   1200
atgaagggta caagagcctc ttcaagaaag acatcatcga aactatcctc ccagagtttc   1260
tcgatgacaa ggacgagatc gcgctggtga actcctttca cgggttcaca accgcgttta   1320
ccggcttctt tgataacagg gaaaatatgt tctccgagga ggccaagtcc accagcatcg   1380
ccttcaggtg tatcaacgag aacctcaccc gctacatttc caatatggac attttcgaga   1440
aggtggatgc gatcttcgat aagcacgagg tgcaggagat caaagagaag attctcaatt   1500
ccgattatga cgtcgaggat ttcttcgaag gggagttctt taattttgtg ctcacacaag   1560
agggcattga cgtgtacaac gcgattatcg ggggcttcgt cacagagtcc ggggagaaga   1620
ttaaggggct gaatgagtac atcaatctgt acaatcagaa gaccaagcag aaactgccga   1680
aattcaagcc gctctacaag caagtcctgt ccgatgggaa aagcctctcc ttctacggcg   1740
agggctatac cagcgacgag gaggtgctgg aagtcttccg caacacactg aataagaata   1800
gcgagatttt ctcctccatc aagaagctcg agaagctctt taagaacttt gacgagtaca   1860
gctccgccgg gattttcgtg aagaacgggc cggcgatcag caccatctcc aaggacatct   1920
ttggcgagtg gaacgtcatc agggacaagt ggaacgccga gtacgacgac atccacctga   1980
agaagaaggc ggtggtgacc gagaagtatg aggacgatcg caggaagtcc ttcaaaaaaa   2040
tcggctcctt cagcctcgaa cagctccagg agtatgccga tgcggatctg tccgtcgtcg   2100
agaagctgaa ggaaatcatc attcagaagg tcgacgagat ctataaagtg tacgggtcca   2160
gcgagaagct gttcgacgcc gactttgtgc tcgagaagtc cctcaaaaag aatgacgccg   2220
tggtggccat tatgaaagac ctgctcgact ccgtgaagtc cttcgaaaat tacattaaag   2280
cgttctttgg ggaggggaag gaaactaaca gggatgagtc cttctatgcg gactttgtcc   2340
tcgcgtacga catcctgctg aaggtcgacc acatttacga cgcgatccgc aactacgtga   2400
cacagaagcc gtactccaaa gacaagttca agctgtactt ccagacccgc aatttatgg    2460
ggggctggga caaggataaa gagacagact accgcgcgac aattctccgc tatggctcca   2520
aatactatct ggccatcatg gacaagaagt acgcgaagtc cctgcagaag atcgacaaag   2580
acgacgtcaa tggcaactat gaaaagatca actacaagct gctgccgggc ccgaacaaga   2640
tgctcccgaa ggtgttcttc agcaagaagt ggatggccta ctacaatcca agcgaggata   2700
ttcagaaaat ctataaaaac gggaccttca gaaggggga catgtttaac ctcaacgact   2760
gccacaagct cattgatttc ttcaaggata gcatttcccg ctacccgaaa tggtccaatg   2820
cgtacgattt taacttctcc gagacagaaa agtacaaaga catcgcgggc ttttacaggg   2880
aggtggagga gcaagggtat aaagtttctt ttgaatccgc gagcaagaag gaagtcgaca   2940
agctcgtcga ggagggcaag ctctacatgt tccaaattta taacaaggac ttttccgaca   3000
agagccatgg gaccccaaac ctccacacca tgtacttcaa actgctcttt gacgagaaca   3060
accacgggca aatcaggctg agcggcggcg ccgaattatt catgcgcagg gcctccctca   3120
agaaggaaga gctggtcgtc catccagcca attcccgat cgcgaacaag aacccggaca    3180
atccgaaaaa gaccaccacc ctgtcctacg acgtctacaa ggacaaacgc ttcagcgaag   3240
accagtcgaa attcacacatc ccaattgcga ttaataagtg cccaaagaat atcttcaaaa   3300
ttaatacaga ggtcagggtg ctgctcaaac acgacgacaa tccgtatgtc atcggcattg   3360
acaggggcga gcgcaatctg ctctatatcg tggtcgtgaa tgggaagggc aatattgtgg   3420
agcagtactc cctgaacgag attatcaaca acttcaatgg gattaggatt aagaccgact   3480
atcacagcct gctcgacaag aaagaaaaag agaggtttga ggcccgccaa aactggacct   3540
ccattgagaa tatcaaagaa ttaaaggccg gctatatttc ccaagtcgtc cacaagatct   3600
gcgagctggt ggagaaatat gacgccgtga ttgcgctcga agacttaaat tctgggttca   3660
agaactcccg cgtgaaggtg gaaaaacagg tgtatcagaa attcgagaaa atgctgatcg   3720
acaaactcaa ttatatggtg gataagaagt ccaaccccgtg tgccacaggg ggcgcgctga   3780
agggcatca gatcaccaac aagttcgaga gcttcaagag catgagcacc cgaaccgggt   3840
ttattttcta catcccggcg tggctcacct ccaagattga cccgagcacc ggcttcgtga   3900
acctcctgaa gacaaagtat acctccattg ccgacagcaa gaagtttatc tcctccttcg   3960
accgcattat gtatgtgccg gaggaggacc tcttcgagtt cgccctcgac tacaaaaact   4020
tcagccgcac agatgcggat tacatcaaga agtggaagct gtactcctac ggaaccagga   4080
tccgcatctt caggaatcca aaaaaaaata acgtctttga ctgggaggaa gtgtgcctga   4140
catccgccta caaggaactg ttcaataaat acggcatcaa ttaccagcag ggcgacattc   4200
gcgcccctcct ctgtgagcag tccgacaaag cgttttactc cagcttcatg gccctcatgt   4260
ccctgatgct ccaaatgagg aatagcatca cagggcgcac cgacgtcgac ttcctcatca   4320
gcccggtgaa gaactccgac gggatctttt acgactcccg caactatgag gcgcaagaga   4380
atgcgatcct cccgaagaac gccgatgcga acgggggcta aatatcgcc aggaaagtgc    4440
tctgggccat cggggcagtt caaaaaggcgg aggatgagaa gctcgacaag gtgaaaattg   4500
ccatttccaa caaggagtgg ctggagtacg cgcagaccctc cgtgaagcac ggatctaaga   4560
agagaagaat taaacaagat tgacttaatt aaagggctct ctgtcatgat ttcatacttt   4620
cattattgag ctctgtaatt acaattatga ccatgagaac atctcttatt gtgtggcctt   4680
ttaattgctg atgttagtac tgaaccaaag cttatcgtga tgatgtaaaa gcaataagta   4740
cttgtttgta gcttctttgt gtctcccttt gggcttaata catctgttta gtgttgtggc   4800
tttggcatag acttctcttg gtaataatgc cttgcaatgc aaaatttcaa ttattcaaatt   4860
ctattatgtt ctcaccttat ggtaacagct taccctgtgg aagatgagat tcttgagttg   4920
agtcattgcc aatttttggc attagctttt gaattagtga attttgacaa aaattaccgt   4980
gacactgatt tgttgaagc tcttaagtgt agttttttaca aaatttcagt ggctcgttgt    5040
gattatgtca aactcacggc gaatgtagtt cttacagaat ttcagtggct c             5091

SEQ ID NO: 22        moltype = DNA   length = 1000
FEATURE              Location/Qualifiers
source               1..1000
                     mol_type = unassigned DNA
                     organism = Medicago truncatula
SEQUENCE: 22
actgttaata atttttaaac gtcagcgcac taaaaaacg aaaagacgga cacgtgaaaa      60
taaaaaacac acactagttt atgacgcaat actattttac ttatgatttg ggtacattag   120
acaaaaccgt gaaagagatg tatcagctat gaaacctgta tacttcaata cagagacgta   180
ctcatatcgg atacgtacgc acgaagtatc atattaatta ttttaatttt taataaatat   240
```

-continued

```
tttatcggat acttatgtga tactctacat atacacaagg atatttctaa gatactttat    300
agatacgtat cctagaaaaa catgaagagt aaaaagtga  acaatgttg  taaaaattca    360
ttataaatgt atatgattca attttagata tgcatcagta taattgattc tcgatgaaac    420
acttaaaatt atatttcttg tggaagaacg tagcgagaga ggtgattcag ttagacaaca    480
ttaaataaaa ttaatgttaa gttcttttaa tgatgtttct ctcaatatca catcatatga    540
aaatgtaata tgatttataa gaaaattttt aaaaaattta ttttaataat cacatgtact    600
attttttaaa aattgtatct tttataataa tacaataata aagagtaatc agtgttaatt    660
tttcttcaaa tataagtttt attataaatc attgttaacg tatcataagt cattaccgta    720
tcgtatctta attttttttt aaaaaccgct aattcacgta cccgtattgt attgtaccog    780
cacctgtatc acaatcgatc ttagttagaa gaattgtctc gaggcggtgc aagacagcat    840
ataatagacg tggactctct tataccaaac gttgtcgtat cacaaagggt taggtaacaa    900
gtcacagttt gtccacgtgt cacgttttaa ttggaagagc tgccgttggc gtaatataac    960
agccaatcga ttttgctat  aaaagcaaat caggtaaact                         1000

SEQ ID NO: 23           moltype = DNA   length = 92
FEATURE                 Location/Qualifiers
source                  1..92
                        mol_type = unassigned DNA
                        organism = Medicago truncatula
SEQUENCE: 23
aaacttcttc attcttttct tccccatcgc tacaaaaccg gttcctttgg aaaagagatt     60
cattcaaacc tagcacccaa ttccgtttca ag                                   92

SEQ ID NO: 24           moltype = DNA   length = 499
FEATURE                 Location/Qualifiers
source                  1..499
                        mol_type = unassigned DNA
                        organism = Medicago truncatula
SEQUENCE: 24
gtataatcta ctttctattc ttcgattatt ttattattat tagctactat cgtttaatcg     60
atctttttct ttgatccgtc aaatttaaat tcaattaggg ttttgttctt ttctttcatc    120
tgattgaaat ccttctgaat tgaaccgttt acttgatttt actgtttatt gtatgattta    180
atcctttgtt tttcaaagac agtctttaga ttgtgattag gggttcatat aaattttag    240
atttggattt ttgtattgta tgattcaaaa aatacgtcct ttaattagat tagtacatgg    300
atatttttta cccgatttat tgattgtcag ggagaatttg atgagcaagt tttttttgatg    360
tctgttgtaa attgaattga ttataattgc tgatctgctg cttccagttt tcataaccca    420
tattctttta accttgttgt acacacaatg aaaaattggt gattgattca tttgttttc    480
tttgttttgg attatacag                                                 499

SEQ ID NO: 25           moltype = DNA   length = 500
FEATURE                 Location/Qualifiers
source                  1..500
                        mol_type = unassigned DNA
                        organism = Medicago truncatula
SEQUENCE: 25
ttaatcatct gaaactgttc accatgcatg caatcttgtg aaatatatgg ttttaattag     60
acttcaatct tatgttggct attgtactaa taaaagcatg tcatgttatt ttcatttgat    120
tttatctgta ctttggtttg tttgaagaat aaagatgagc ttgctatgca tgcatgcatg    180
ccatcgatta tcagggtttc ctttttttctt ttctggcttc ccatcaattt ggtgtgaatt    240
agtgtgtgtg atatattata ttatgctatt tatgaaataa attgttggtt atatttgatc    300
tacaatctac atacatgtga tttttatcaa caaaatatct cgggaaacaa tacctttttg    360
gtagcaaaat tcaaataata ctattttaaa taaatcaaag ttaaccaata ccttattcaa    420
gttggagggg tctcaaacaa gcaaaagaat tcaagttgtt aatgaacttc ggttaatgat    480
aaaagaattc gcatttaaaa                                                500

SEQ ID NO: 26           moltype = DNA   length = 5856
FEATURE                 Location/Qualifiers
misc_feature            1..5856
                        note = Synthetic polynucleotide.Expression cassette
                         comprising Medicagotruncatula promoter cassette,
                         NLS-LbCpf1-CO2-NLS and Medicagotruncatula termination
                         sequence
source                  1..5856
                        mol_type = other DNA
                        organism = synthetic construct
SEQUENCE: 26
actgttaata atttttaaac gtcagcgcac taaaaaaacg aaaagacgga cacgtgaaaa     60
taaaaaacac acactagttt atgacgcaat actatttttac ttatgatttg ggtacattag    120
acaaaaccgt gaaagagatg tatcagctat gaaacctgta tacttcaata cagagacgta    180
ctcatatcgg atacgtacgc acgaagtatc atattaatta ttttaatttt taataaaatat    240
tttatcggat acttatgtga tactctacat atacacaagg atatttctaa gatactttat    300
agatacgtat cctagaaaaa catgaagagt aaaaagtga  acaatgttg  taaaaattca    360
ttataaatgt atatgattca attttagata tgcatcagta taattgattc tcgatgaaac    420
acttaaaatt atatttcttg tggaagaacg tagcgagaga ggtgattcag ttagacaaca    480
ttaaataaaa ttaatgttaa gttcttttaa tgatgtttct ctcaatatca catcatatga    540
aaatgtaata tgatttataa gaaaattttt aaaaaattta ttttaataat cacatgtact    600
attttttaaa aattgtatct tttataataa tacaataata aagagtaatc agtgttaatt    660
tttcttcaaa tataagtttt attataaatc attgttaacg tatcataagt cattaccgta    720
tcgtatctta attttttttt aaaaaccgct aattcacgta cccgtattgt attgtaccog    780
```

-continued

```
cacctgtatc acaatcgatc ttagttagaa gaattgtctc gaggcggtgc aagacagcat    840
ataatagacg tggactctct tataccaaac gttgtcgtat cacaaagggt taggtaacaa    900
gtcacagttt gtccacgtgt cacgttttaa ttggaagagc tgccgttggc gtaatataac    960
agccaatcga ttttgctat aaaagcaaat caggtaaact aaacttcttc attctttct    1020
tcccatcgc tacaaaaccg gttccttttgg aaaagagatt cattcaaacc tagcacccaa   1080
ttccgtttca aggtataatc tactttctat tcttcgatta ttttattatt attagctact   1140
atcgtttaat cgatcttttc ttttgatccg tcaaatttaa attcaattag ggttttgttc   1200
ttttctttca tctgattgaa atccttctga attgaaccgt ttacttgatt ttactgttta   1260
ttgtatgatt taatcctttg ttttcaaag acagtctta gattgtgatt aggggttcat    1320
ataaattttt agatttggat tttgtattg tatgattcaa aaaatacgtc ctttaattag   1380
attagtacat ggatatttt tacccgattt attgattgtc agggagaatt tgatgagcaa   1440
gttttttga tgtctgttgt aaattgaatt gattataatt gctgatctgc tgcttccagt   1500
tttcataacc catattcttt taaccttgtt gtacacacaa tgaaaaattg gtgattgatt   1560
catttgtttt tctttgttt ggattataca gggtaccaaa aatggcggg atctaagaag    1620
agaagaatta aacaagattc gaagctcgag aagttcacca actgctactc gctgagcaag   1680
acgctgcgt tcaaggcgat ccccgtcggt aagacccagg agaacatcga caacaagcgg    1740
ctcctggtcg aggacgagaa gcgcgccgag gactacaagg gcgtcaagaa gctgctggac   1800
cggtactacc tctccttcat caacgacgtc ctgcactcga tcaagctcaa gaacctgaac   1860
aactacatct cgctgttccg caagaagaca cggaccgaga aggagaacaa ggagctcgag   1920
aacctcgaga tcaacctgcg caaggagatc gcgaaggcgt tcaagggcaa cgaggggtac   1980
aagagcctgt tcaagaaaga catcatcgag accatcctgc cggagttcct ggacgacaag   2040
gacgagatcg cgctggtgaa ctcgttcaac gggttcacca cggccttcac cgggtttttc   2100
gacaaccggg agaacatgtt cagcgaggag gccaagtcga ccagcatcgc cttccggtgt   2160
atcaacgaga acctcacccg ctacatcagc aacatggaca tcttcgagaa ggtgacgcc    2220
atcttcgaca agcacgaggt ccaggagatc aaggaaaaga tcctgaactc ggactacgac   2280
gtggaagact tctttgaggg cgagttcttc aacttcgtcc tcaccagga gggcatcgac    2340
gtctacaacg ccatcatcgg cggcttcgtg acggagagcg gcgagaagat caagggcctc   2400
aacgagtaca tcaacctcta caaccagaag actaagcaga agctcccgaa gttcaagccg   2460
ctgtacaagc aagtcctgag cgaccggag tccctctcgt tctacggcga gggctacacg   2520
agcgacgagg aggtgctga ggtgttccgc aacacgctga acaagaacag cgagatcttc    2580
agctcgatca agaaactcga gaagctgttc aagaacttcg acgagtacag cagcgccggc   2640
atcttcgtca agaacgggcc cgcgatcagc accatcagca aggacatctt cggggagtgg   2700
aacgtgatcc gcgacaagtg gaacgccgag tacgacgaca tccacctcaa gaaaaaggcg   2760
gtggtcacgg agaagtacga ggacgaccgc cggaagtcct tcaagaaaat cgggagcttc   2820
agcctcgagc agctccagga gtacgcggac gccgacctga gcgtggtgga caagctcaag   2880
gagatcatca tccagaaggt cgacgagatc tacaagtct acggctcgag cgagaagctg    2940
ttcgacgcgg acttcgtgct ggagaagtcc ctcaagaaga acgacgccgt ggtggccatc   3000
atgaaggatc tgctcgacag cgtgaagtcg ttcgagaact acatcaaggc attctttggg   3060
gagggcaagg agacgaaccg ggacgagtcc ttctacgagg acttcgtgct cgcgtacgac   3120
atcctcctga aggtcgacca catctacgac gcgatccgga actacgtcac gcagaagccc   3180
tacagcaagg acaagttcaa gctctacttc cagaacccgc agttcatggg cgggtgggac   3240
aaggacaagg agaccgacta ccgggccacg atcctgcggt acgggtccaa gtactacctc   3300
gccatcatgg acaagaagta cgccaagtgc ctccagaaac ttgacaagga cgacgtgaac   3360
gggaactacg agaagatcaa ctacaagctc ctccgggggc ccaacaagat gctgccgaag   3420
gtgttcttca gcaagaagtg gatggcctac tacaacccct cggaggacat ccagaagata   3480
tacaagaacg gcacgttcaa aaagggggac atgttcaacc tgaacgactg ccacaagctg   3540
atcgactttt tcaaggacag catcagccgc taccgaagt ggtcgaacgg ctacgacttc    3600
aacttctcgg agacggagaa gtacaaggac attgcgggct tctaccggga ggtggaggag   3660
cagggctaca aggtctcctt cgagagcgcc tccaagaaag aggtggacaa gctcgtggag   3720
gagggcaagc tgtacatgtt ccagatctac aacaaggact tctcggacaa gtcgcacggc   3780
accccgaacc tccacacgat gtacttcaag ctgctgttcg acgagaacaa ccacgggcag   3840
atccgcctca gcggcgggc ggagctgttc atgcgccgcg cgtccctcaa gaaggaggag   3900
ctggtcgtgc acccgccaa ctcccgatc gcgaacaaga accccgacaa ccccaagaag    3960
acaaccaccc tctcgtacga cgtctacaag gacaagcggt tctcggagga ccagtacgag   4020
ctgcacatcc cgatcgccat caacaagtgc cccaagaaca tcttcaagat caacaccgag   4080
gtgcgggtgc tgctcaagca cgacgacaac ccctacgtca cgggatcga ccgcggcgaa    4140
cggaacctgc tctacatcgt ggtcgtggac gggaagggga acatcgtgga gcagtacagc   4200
ctgaacgaga tcatcaacaa cttcaacggc atccgcatca gacggactta ccacagcctc   4260
ctggacaaga aggagaagga gcggttcgag gcgcggcaga actggaccc catcgagaac   4320
atcaaggagc tgaaggccgg ctacatcagc caggtcgtgc acaagatctg cgagctcgtg   4380
gagaagtacg acgcggtgat cgcgctggag gacttgaaca gcgggttcaa gaactcccgg   4440
gtcaaggtcg agaagcaggt ctaccagaag ttcgagaaga tgctgatcga caagctcaac   4500
tacatggtgg acaagaagtc caacccctgc gccaccggcg gcgccctcaa gggctaccag   4560
atcaccaaca agttcgagtc cttcaagtcg atgtctac gaaacgggtt cattttctac    4620
atccggcgt ggctcaccag caagatcgac ccgagcacgg gcttcgtcaa cctcctgaag   4680
accaagtaca ccagcatcgc ggacagcaag aagttcatct cctcgttcga ccgcatcatg   4740
tacgtcccg aggaagacct gttcgagttc gccctcgact acaagaactt ctcccggacg   4800
gacgccgact acatcaaaaa gtggaagctc tacagctacg gcaaccggat ccgcatcttc   4860
cgcaacccca agaagaacaa tgtgttcgac tgggaggagg tgtgcctgac gagcgcctac   4920
aaggagctct tcaacaagta cggcatcaac taccagcaag gggacatccg cgcgctgctc   4980
tgcgagcagt ccgacaaggc gttctactcg tcgttcatgg ccctgatgag cctcatgctc   5040
cagatgcgca acagcatcac cggccggacg gacgtggact tcctgatcag cccggtcaag   5100
aacagcgacg gcattttcta cgacagccgg aactacgagg cccaggagaa cgccatcctc   5160
cccaagaacg ccgacgcaa cggcgcctac aacatcgccc gcaaggtgct gtgggccatc   5220
ggccagttta aaaggcgga ggacgagaag ctggacaagg tcaagatcgc catcagcaac   5280
aaggagtggc tcgagtacgc gcagacgagc gtgaagcacg atctaagaa gagaagaatt   5340
aaacaagatt gattaattaa tcatctgaaa ctgttcacca tgcatgcaat cttgtgaaat   5400
atatggttt aattagactt caatcttatg ttggctattg tactaataaa agcatgtcat    5460
gttattttca tttgatttta tctgtacttt ggtttgtttg aagaataaag atgagcttgc   5520
```

-continued

```
tatgcatgca tgcatgccat cgattatcag ggtttccttt tttcttttct ggcttcccat   5580
caatttggtg tgaattagtg tgtgtgatat attatattat gctatttatg aaataaattg   5640
ttggttatat ttgatctaca atctacatac atgtgatttt tatcaacaaa atatctcggg   5700
aaacaatacc tttttggtag caaaattcaa ataatactat tttaaataaa tcaaagttaa   5760
ccaataccct attcaagttg gaggggtctc aaacaagcaa aagaattcaa gttgttaatg   5820
aacttcggtt aatgataaaa gaattcgcat ttaaaa                             5856

SEQ ID NO: 27           moltype = DNA  length = 617
FEATURE                 Location/Qualifiers
source                  1..617
                        mol_type = unassigned DNA
                        organism = Cucumis melo
SEQUENCE: 27
aaatttaatt aattaaaatg aacaattttt caagagtaat agagtttgag agatgtcaga   60
gaagtttgag gaagaagata acaagtggga gaagagaata agtttgttgt gtgaaagaga   120
aggggaaatt tcattcaagg gtatattgaa cttttactc aaatttttgta agtctatttt    180
ttccgatcaa tcctaaaatc acacacaccc ttaaaaatg gattatattt ggcaatttc    240
catgataaac tcattttaa tttagagtta tttttcaac gagatattaa cagttttagt    300
tcatatacta attgtaagaa tagtttcttt taagttgaat agaattttg aaactttaa    360
tagttcaaaa ggtattttg aaacaaaata agaatgtttt tgaacttttt ataaaaagaa   420
ttgagatttt tttgaaattt ttgataaaga gaaagaaaa gaagaaagaa aaagaaaaa    480
caagtttgta gaactccgtg ggaaaatcgt cgagggcct gtgaaggaat tttgaatta    540
taatgagggt attttcgtca acaagggaat ttagacatcg tatataagca tcctcaaacc   600
ctataattaa gcccttc                                                 617

SEQ ID NO: 28           moltype = DNA  length = 54
FEATURE                 Location/Qualifiers
source                  1..54
                        mol_type = unassigned DNA
                        organism = Cucumis melo
SEQUENCE: 28
aatccaattg ccattctcca tctctcgccg caagggttta agagcagctt ctct          54

SEQ ID NO: 29           moltype = DNA  length = 545
FEATURE                 Location/Qualifiers
source                  1..545
                        mol_type = unassigned DNA
                        organism = Cucumis melo
SEQUENCE: 29
cctcaggttg gggtttcccc ctatcttctt cattcttcct cttctcgatt tctttcttct   60
atttgctcga tagtctctta tttcttgagc ttttgctgtt tttctcctgt acatcctaac   120
atgaattata acttggtttt gatttgtct tttacttctg tattaaacaa cttttcttac    180
cctttattc ttctcttt cttcgtgtcc ctgcccttt gttttatgc taattttagt      240
tttctgttta tcaatctatc gaggcgtgac ctgtcgttct tccaatagcg tagatctgca   300
cttaatctat tctagctgat tggattggtc gttttttcgtt ttttaattt attttctctg   360
ttctagttcc gataaatttt tttatatata attaacaagt tctccagcca aaagggttaa   420
tattgcgttg gatattttaa ttttacgtt atttagatgt gtgaatctaa taaaattagg    480
gttattcata aatttcagta atgatatttt ggttatctgt tcttgctgtt cctgtttcgc   540
agttc                                                              545

SEQ ID NO: 30           moltype = DNA  length = 19
FEATURE                 Location/Qualifiers
source                  1..19
                        mol_type = unassigned DNA
                        organism = Cucumis melo
SEQUENCE: 30
ttttacctaa tattcaagc                                                19

SEQ ID NO: 31           moltype = DNA  length = 5500
FEATURE                 Location/Qualifiers
misc_feature            1..5500
                        note = Synthetic polynucleotide.Expression cassette
                        comprising Cucumismelo EF1a promoter cassette,
                        NLS-LbCpf1-CO2-NLS and Medicagotruncatula termination
                        sequence
source                  1..5500
                        mol_type = other DNA
                        organism = synthetic construct
SEQUENCE: 31
aaatttaatt aattaaaatg aacaattttt caagagtaat agagtttgag agatgtcaga   60
gaagtttgag gaagaagata acaagtggga gaagagaata agtttgttgt gtgaaagaga   120
aggggaaatt tcattcaagg gtatattgaa cttttactc aaatttttgta agtctatttt    180
ttccgatcaa tcctaaaatc acacacaccc ttaaaaatg gattatattt ggcaattttc    240
catgataaac tcattttaa tttagagtta tttttcaac gagatattaa cagttttagt    300
tcatatacta attgtaagaa tagtttcttt taagttgaat agaattttg aaactttaa    360
tagttcaaaa ggtattttg aaacaaaata agaatgtttt tgaacttttt ataaaaagaa   420
ttgagatttt tttgaaattt ttgataaaga gaaagaaaa gaagaaagaa aaagaaaaa    480
caagtttgta gaactccgtg ggaaaatcgt cgagggcct gtgaaggaat tttgaatta    540
taatgagggt attttcgtca acaagggaat ttagacatcg tatataagca tcctcaaacc   600
```

```
ctataattaa gcccttcaat ccaattgcca ttctccatct ctcgccgcaa gggtttaaga    660
gcagcttctc tcctcaggtt ggggtttccc cctatcttct tcattcttcc tcttctcgat    720
ttctttcttc tatttgctcg atagtctctt atttcttgag cttttgctgt ttttctcctg    780
tacatcctaa catgaattat aacttggttt tgattttgtc ttttacttct gtattaaaca    840
acttttctta ccctttattt cttctctttct tcttcgtgtc cctgcccttt tgttttttatg   900
ctaattttat gtttctgttt atcaatctat cgaggcgtga cctgtcgttc ttccaatagc    960
gtagatctgc acttaatcta ttctagctga ttggattggt cgttttttcgt ttttttaatt   1020
tattttctct gttctagttc cgataaattt tttttatatat aattaacaag ttctccagcc   1080
aaaagggtta atattgcgtt ggatatttta attttacgt tatttagatg tgtgaatcta     1140
ataaaattag ggttattcat aaatttcagt aatgatattt tggttatctg ttcttgctgt    1200
tcctgtttcg cagttctttt acctaatatt caagcggtac caaaaaatgg cgggatctaa    1260
gaagagaaga attaaacaag attcgaagct cgagaagttc accaactgct actcgctgag    1320
caagacgctg cggttcaagg cgatcccgt cgggaagacc caggagaaca tcgacaacaa     1380
gcggctcctg gtcgaggacg agaagcgcgc cgaggactac aagggcgtca agaagctgct    1440
ggaccggtac tacctctcct tcatcaacga cgtcctgcac tcgatcaagc tcaagaacct    1500
gaacaactac atctcgctgt tccgcaagaa gacacggacc gagaaggaga caaggagct    1560
cgagaacctc gagatcaacc tgcgcaagga gatcgcgaag gcgttcaagg caacgaggg    1620
gtacaagagc ctgttcaaga aagacatcat cgagaccatc ctgccggagt tcctggacga   1680
caaggacgag atcgcgctgg tgaactcgtt caacgggttc accacggcct tcaccgggtt    1740
tttcgacaac cgggagaaca tgttcagcga ggaggcaag tcgaccagca tcgccttccg    1800
gtgcatcaac gagaacctca cccgctacat cagcaacatg gacatcttcg agaaggtgga    1860
cgccatcttc gacaagcacg aggtccagga gatcaaggaa aagatcctga actcggacta    1920
cgacgtggaa gacttctttg agggcgagtt cttcaacttc gtcctcaccc aggagggcat    1980
cgacgtctac aacgccatca tcggcggctt cgtgacggag agcggcgaga agatcaaggg    2040
cctcaacgag tacatcaacc tctacaacca gaagactaag cagaagctcc cgaagttcaa    2100
gccgctgtac aagcaagtcc tgagcgaccg ggagtccctc tcgttctacg gcgagggcta    2160
cacgagcgac gaggaggtgc tggaggtgtt ccgcaacacg ctgaacaaga acagcgagat    2220
cttcagctcg atcaagaaac tcgagaagct gttcaagaac ttcgacgagt acagcagcgc    2280
cggcatcttc gtcaagaacg ggcccgcgat cagcaccatc agcaaggaca tcttcggga    2340
gtggaagctg atccgcgaca agtggaacgc cgagtacgac gacatcccca tcaagaaaaa    2400
ggcggtggtc acggagaagt acgaggacga ccgccggaag tccttcaaga aaatcgggag    2460
cttcagcctc gagcagctcc aggagtacgc ggacgccgac ctgagcgtgg tggagaagct    2520
caaggagatc atcatccaga aggtcgacga gatctacaag gtctacgct cgagcgagaa    2580
gctgttcgac gcggacttcg tgctggagaa gtccctcaag aagaacgacg ccgtggtggc    2640
catcatgaag gatctgctcg acagcgtgaa gtccgttcga aactacatca aggcattctt    2700
tgggagggc aaggagacga accgggacga gtccttctac ggggacttcg tgctcgcgta    2760
cgacatcctc ctgaaggtcg accacatcta cgacgcgatc cggaactacg tcacgcagaa    2820
gccctacagc aaggacaagt tcaagctcta cttccagaac ccgcagttca tgggcgggtg    2880
ggacaaggac aaggagaccg actaccgggac cacgatcctg cggtacgggt ccaagtacta    2940
cctcgccatc atggacaaga gtacgccaa gtgcctccag aagattgaca aggacgacgt    3000
gaacgggaac tacgagaaga tcaactacaa gctcctcccg gggcccaaca agatgctgcc    3060
gaaggtgttc ttcagcaaga gtggatggc ctactacaac ccctcggagg acatccgaaa    3120
gatatacaag aacggcacgt tcaaaaaggg ggacatgttc gaagctgacg actgccacaa    3180
gctgatcgac ttttttcaagg acagcatcag ccgctacccg aagtggtcga acgcctacga    3240
cttcaacttc tcggagacgg agaagtacaa ggacattgcg ggcttctacc gggaggtgga    3300
ggagcagggc tacaaggtct ccttcgagag cgcctcaag aaaggtgg acaagctcgt    3360
ggaggaggc aagctgtaca tgttccagat ctacaacaag gacttctcga caagtcgca    3420
cggcaccccg aacctccaca cgatgtactt caagctgctg ttcgacgaga caaccacgg    3480
gcagatccgc ctcagcggcg gggcggagct gttcatgcgc cgcgcgtccc tcaagaagga    3540
ggagctggtc gtgcaccccg ccaactcccc gatcgcgaac aagaacccgg caaccccaa    3600
gaagacaacc acccctctcg tacgacgcta caaggacaag cggttctcg aggaccagta    3660
cgagctgcac atcccgatcg ccatcaacaa gtgcccaag aacatcttca agatcaacac    3720
cgaggtgcgg gtgctgctca agcacgacga caaaccctac gtcatcggga tcgaccgcgg    3780
cgagcggaac ctgctctaca tcgtggtcgt ggacgggaag gggaacatcg tggagcagta    3840
cagccggaac gagatcatca acaacttcaa cggcatccgc atcaagacgg actaccacag    3900
cctcctggac aagaaggaga aggagcggtt cgaggcgcgg cagaactgga cctccatcga    3960
gaacatcaag gagctgaagg ccggctacat cagccaggtc gtgcacaaga tctgcgagct    4020
cgtggagaag tacgacgcgg tgatcgcgct ggaggacttg aacagcgggt tcaagaactc    4080
ccgggtcaag gtcgagaagc aggtctacca gaagttcgag aagatgctga tcgacaagct    4140
caactacatg gtgacaagaa gtccaaccc ctgcgccacc ggccggcgcc tcaagggcta    4200
ccagatcacc aacaagttcg agtccttcaa gtccgatgtct acgcagaacg ggttcatttt    4260
ctacatcccg cgctggctca ccagcaagat cgacccgagc acgggcttcg tcaacctcct    4320
gaagaccaag tacaccagca tcgcggacag caagaagttc atctcctcgt tcgaccgcat    4380
catgtacgtc cccgaggaag acctgttcga gttcgccctc gactacaaga acttctccg    4440
gacgacgcc gactacatca aaaagtggaa gctctacagc tacggcaacc ggatccgat    4500
cttccgcaac cccaagaaga caatgtgtt cgactgggag gaggtgtgcc tgacgagcgc    4560
ctacaaggag ctcttcaaca agtacggcat caactaccag caaggggaca tccgcgcgct    4620
gctctgcgag cagtccgaca aggcgttcta ctcgtcgttc atggcccctga tgagcctcat    4680
gctccagatg cgcaacagca tcaccggccg gacggacgtg gacttcctga tcagcccggt    4740
caagaacagc gacggcattt tctacgacag ccggaactac gaggcccagg agaacgccat    4800
cctccccaag aacgccacg cgaacggcgc ctacaacatc gcgcggaagg tgctgtggg    4860
catcggccga tttaaaaagg cggaggacga gaagctggac aaggtcaaga tcgccatcag    4920
caacaaggag tggctcgagt acgcgcagac gagcgtgaag cacggatcta agagagaag    4980
aattaaacaa gattgattaa ttaatcatct gaaactgttc accatgcatg caatcttgtg   5040
aaatatatgg ttttaattag acttcaatct tatgttggct attgtactaa taaaagcatg    5100
tcatgttatt tcatttgat tttatctgta ctttggtttg tttaagaat aaagatgagc     5160
ttgctatgca tgcatgcatg ccatcgatta tcagggttc ctttttttctt ttctggcttc   5220
ccatcaattt ggtgtgaatt agtgtgtgtg atatattata ttatgctatt tatgaaataa   5280
attgttggtt atatttgatc tacaatctac atacatgtga ttttatcaa caaaatatct   5340
```

```
cgggaaacaa tacctttttg gtagcaaaat tcaaataata ctattttaaa taaatcaaag   5400
ttaaccaata ccttattcaa gttggagggg tctcaaacaa gcaaaagaat tcaagttgtt   5460
aatgaacttc ggttaatgat aaaagaattc gcatttaaaa                         5500

SEQ ID NO: 32          moltype = DNA   length = 829
FEATURE                Location/Qualifiers
source                 1..829
                       mol_type = unassigned DNA
                       organism = Arabidopsis thaliana
SEQUENCE: 32
gttttgtgta tcattcttgt tacattgtta ttaatgaaaa aatattattg gtcattggac   60
tgaacacgag tgttaaatat ggaccaggcc ccaaataaga tccattgata tatgaattaa   120
ataacaagaa taaatcgagt caccaaacca cttgcctttt ttaacgagac ttgttcacca   180
acttgataca aaagtcatta tcctatgcaa atcaataatc atacaaaaat atccaataac   240
actaaaaaat taaaagaaat ggataatttc acaatatgtt atacgataaa gaagttactt   300
ttccaagaaa ttcactgatt ttataagccc acttgcatta gataaatggc aaaaaaaaac   360
aaaaaggaaa agaaataaag cacgaagaat tctagaaaat acgaaatacg cttcaatgca   420
gtgggaccca cggttcaatt attgccaatt ttcagctcca ccgtatattt aaaaaataaa   480
acgataatgc taaaaaaata taaatcgtaa cgatcgttaa atctcaacgg ctggatctta   540
tgacgaccgt tagaaattgt ggttgtcgac gagtcagtaa taaacggcgt caaagtggtt   600
gcagccggca cacgagtc gtgtttatca actcaaagca caaatacttt tcctcaacct   660
aaaaataagg caattagcca aaaacaactt tgcgtgtaaa cacgctcaa tacacgtgt   720
attttattat tagctattgc ttcaccgcct tagctttctc gtgacctagt cgtcctcgtc   780
ttttcttctt cttcttctat aaaacaatac ccaaagagct cttcttctt                829

SEQ ID NO: 33          moltype = DNA   length = 67
FEATURE                Location/Qualifiers
source                 1..67
                       mol_type = unassigned DNA
                       organism = Arabidopsis thaliana
SEQUENCE: 33
cacaattcag atttcaattt ctcaaaatct taaaaacttt ctctcaattc tctctaccgt   60
gatcaag                                                              67

SEQ ID NO: 34          moltype = DNA   length = 306
FEATURE                Location/Qualifiers
source                 1..306
                       mol_type = unassigned DNA
                       organism = Arabidopsis thaliana
SEQUENCE: 34
gtaaatttct gtgttcctta ttctctcaaa atcttcgatt ttgttttcgt tcgatcccaa   60
tttcgtatat gttctttggt ttagattctg ttaatcttag atcgaagacg attttctggg   120
tttgatcgtt agatatcatc ttaattctcg attagggttt catagatatc atccgatttg   180
ttcaaataat ttgagttttg tcgaataatt actcttcgat ttgtgatttc tatctagatc   240
tggtgttagt ttcagtttg tgcgatcgaa tttgtcgatt aatctgagtt tttctgatta   300
acaggt                                                               306

SEQ ID NO: 35          moltype = DNA   length = 315
FEATURE                Location/Qualifiers
source                 1..315
                       mol_type = unassigned DNA
                       organism = Gossypium barbadense
SEQUENCE: 35
accatatgac actggtgcat gtgccatcat catgcagtaa tttcatggta tatcttaatt   60
atatggttaa taaaaaaaag atggtgagtg aataatgtgc gtgcattcct ccatgcacca   120
atggtgaatc tctttgcata catgagagatt ctgaatgatt atagtttatg ttgtagtgaa   180
attaattttg aatgttgttt ttaaatttta atgtcacttg gcttgattta tgttttaacg   240
aagcttatgt tatgtatttt actttaatga tattgcatgt attgttaatt taacattgct   300
tgatcagtat actct                                                     315

SEQ ID NO: 36          moltype = DNA   length = 5292
FEATURE                Location/Qualifiers
misc_feature           1..5292
                       note = Synthetic polynucleotide.Expression cassette
                       comprisingArabidopsis thaliana Ubiquitin promoter
                       cassette,NLS-LbCpf1-CO2-NLS and Gossypium barbadense
                       termination sequence.
source                 1..5292
                       mol_type = other DNA
                       organism = synthetic construct
SEQUENCE: 36
gttttgtgta tcattcttgt tacattgtta ttaatgaaaa aatattattg gtcattggac   60
tgaacacgag tgttaaatat ggaccaggcc ccaaataaga tccattgata tatgaattaa   120
ataacaagaa taaatcgagt caccaaacca cttgcctttt ttaacgagac ttgttcacca   180
acttgataca aaagtcatta tcctatgcaa atcaataatc atacaaaaat atccaataac   240
actaaaaaat taaaagaaat ggataatttc acaatatgtt atacgataaa gaagttactt   300
ttccaagaaa ttcactgatt ttataagccc acttgcatta gataaatggc aaaaaaaaac   360
aaaaaggaaa agaaataaag cacgaagaat tctagaaaat acgaaatacg cttcaatgca   420
gtgggaccca cggttcaatt attgccaatt ttcagctcca ccgtatattt aaaaaataaa   480
```

```
acgataatgc taaaaaaata taaatcgtaa cgatcgttaa atctcaacgg ctggatctta    540
tgacgaccgt tagaaattgt ggttgtcgac gagtcagtaa taaacggcgt caaagtggtt    600
gcagccggca cacacgagtc gtgtttatca actcaaagca caaatacttt tcctcaacct    660
aaaaataagg caattagcca aaaacaactt tgcgtgtaaa caacgctcaa tacacgtgtc    720
attttattat tagctattgc ttcaccgcct tagctttctc gtgacctagt cgtcctcgtc    780
ttttcttctt cttcttctat aaaacaatac ccaaagagct cttcttcttc acaattcaga    840
tttcaatttc tcaaaatctt aaaaactttc tctcaattct ctctaccgtg atcaaggtaa    900
atttctgtgt tccttattct ctcaaaatct tcgattttgt tttcgttcga tcccaatttc    960
gtatatgttc tttggtttag attctgttaa tcttagatcg aagacgattt tctgggtttg   1020
atcgttagat atcatcttaa ttctcgatta gggtttcata gatatcatcc gatttgttca   1080
aataatttga gttttgtcga ataattactc ttcgatttgt gatttctatc tagatctggt   1140
gttagtttct agtttgtgcg atcgaatttg tcgattaatc tgagtttttc tgattaacag   1200
gtggtaccaa aaaatggcgg gatctaagaa gagaagaatt aaacaagatt cgaagctcga   1260
gaagttcacc aactgctact cgctgagcaa gacgctgcgg ttcaaggcga tccccgtcga   1320
gaagacccag gagaacatcg acaacaagcg gctcctggtc gaggacgaga agcgcgccga   1380
ggactacaag ggcgtcaaga agctgctgga ccggtactac ctctccttca tcaacgacgt   1440
cctgcactcg atcaagctca agaacctgaa caactacatc tcgctgttcc gcaagaagac   1500
acggaccgag aaggagaaca aggagctcga gaacctgcag atcaacctgc gcaaggagat   1560
cgcgaaggcg ttcaagggca cgagggggta caagagcctg ttcaagaaag acatcatcga   1620
gaccatcctg ccggagttcc tggacgacaa ggacgagatc gcgctggtga actcgttcaa   1680
cggggttcacc acgccttca ccgggttttt cgacaaccgg gagaacatgt tcagcgagga   1740
ggccaagtcg accagcatcg ccttccggtg catcaacgag aacctcaccc gctacatcag   1800
caacatggac atcttcgaga aggtggacgc catcttcgac aagcacgagg tccaggagat   1860
caaggaaaag atcctgaact cggactacga cgtggaagac ttctttgagg gcgagttctt   1920
caacttcgtc ctcacccagg agggcatcga cgtctacaac gccatcatcg gcggcttcgt   1980
gacggagagc ggcgagaaga tcaagggcct caacgagtac atcaacctct acaaccagaa   2040
gactaagcag aagctcccga agttcaagcc gctgtacaag caagtcctga gcgaccggga   2100
gtccctctcg ttctacggcg agggctacac gagcgacgag gaggtgctgg aggtgttccg   2160
caacacgctg aacaagaaca gcgagatctt cagctcgatc aagaaactcg agaagctgtt   2220
caagaacttc gacgagtaca gcagcgccgg catcttcgtc aagaacgggc ccgcgatcag   2280
caccatcagc aaggacatct tcggggagtg gaacgtgatc cgcgacaagt ggaacgccga   2340
gtacgacgac atccacctca agaaaaaggc ggtggtcacg gagaagtacg aggacgaccg   2400
ccggaagtcc ttcaagaaaa tcgggagctt cagcctcgag cagctccagg agtacgcgga   2460
cgccgcctcg agcgtggtgg agaagctcaa ggagatcatc atccagaagg tcgacgagat   2520
ctacaaggtc tacggctcga gcgagaagct gttcgacgcg gacttcgtgc tggagaagtc   2580
cctcaagaag aacgacgccg tggtggccat catgaaggat ctgctcgaca gcgtgaagtc   2640
gttcgagaac tacatcaagg cattctttgg ggagggcaag gagacgaacc gggacgagtc   2700
cttctacggg gacttcgtgc tcgcgtacga catcctcctg aaggtcgacc acatctacga   2760
cgcgatccgg aactacgtca cgcagaagcc ctacagcaag gacaagttca agctctactt   2820
ccagaacccg cagttcatgg gcgggtggga caaggacaag gagaccgact accgggccac   2880
gatcctgcgg tacgggtcca agtactacct cgccatcatg gacaagaagt acgccaagtg   2940
cctccagaag attgacaagg acgacgtgaa cgggaactac gagaagatca actacaagct   3000
cctcccgggg cccaacaaga tgctgccgaa ggtgttcttc agcaagaagt ggatggccta   3060
ctacaaccc tcggaggaca tccagaagat atacaagaac ggcacgttca aaaaggggga   3120
catgttcaac ctgaacgact gccacaagct gatcgacttt ttcaaggaca gcatcagccg   3180
ctacccgaag tggtcgaacg cctacgactt caacttctcg gagacggaga agtacaagga   3240
cattgcggc ttctaccggg aggtggaga gcagggctac aaggtctcct tcgagagcgc   3300
ctccaagaaa gaggtggaca agtcgtgga ggagggcaag ctgtacatgt tccagatcta   3360
caacaaggac ttctcggaca agtcgcacgg caccccgaac ctccacacga tgtacttcaa   3420
gctgctgttc gacgagaaca ccacgggca gatccgcctc agcggcgggg cggagctgtt   3480
catgcgccgc gcgtccctca agaaggagga gctggtcgtg caccccgcca actcccgat   3540
cgcgaacaag aaccccgaca cccaagaa gacaaccacc ctctcgtacg acgtctacaa   3600
ggacaagcgg ttctcggagg accagtacga gctgcacatc ccgatcgcca tcaacaagtg   3660
ccccaagaac atcttcaaga tcaacaccga ggtgcgggtg ctgctcaagc acgacgacaa   3720
ccctacgtc atcgggatcg accgcggcga gcggaacctg ctctacatcg tggtcgtgga   3780
cgggaagggg aacatcgtgg agcagtacag cctgaacgag atcatcaaca acttcaacgg   3840
catccgcatc aagacggact accacagcct cctggacaag aaggagaagg agcggttcga   3900
ggcgcggcag aactggacct ccatcgaaa catcaaggag ctgaaggccg gctacatcag   3960
ccaggtcgtg cacaagatct gcgagctcgt ggagaagtac gacgcggtga tcgcgctgga   4020
ggacttgaac agcggggttca agaactcccg ggtcaaggtc gagaagcagg tctaccagaa   4080
gttcgagaag atgctgatcg acaagctcaa ctacatggtg gacaagaagt ccaaccctg   4140
cgccaccggc ggcgccctca gggctacca gatcaccaac aagttcgagt ccttcaagtc   4200
gatgtctacg cagaacgggt tcattttcta catcccggct tggctcacca gcaagatcga   4260
cccgagcacg ggcttcgtca acctcctgaa gaccaagtac accagcatcg cggacagcaa   4320
gaagttcatc tcctcgttcg accgcatcat gtacgtcccc gaggaagacc tgttcgagtt   4380
cgccctcgac tacaagaact tctcccggac ggacgccgac tacatcaaaa agtgaaagct   4440
ctacagctac ggcaaccgga tccgcatctt ccgcaacccc aagaagaaca atgtgttcga   4500
ctgggaggag tgtgcctga cgagcgccta caaggagctc ttcaacaagt acggcatcaa   4560
ctaccagcaa ggggacatcc gcgcgctgct ctgcgacaag tccgacaagg cgttctactc   4620
gtcgttcatg gccctgatga gcctcatgct ccagatgcgc aacagcatca ccggccggac   4680
ggacgtggac ttcctgatca gccggtcaa gaacagcgac ggcattttct acgacagccg   4740
gaactacgag gcccaggaga acgccatcct ccccaagaac gccgacgcga acggcgccta   4800
caacatcgcg cggaaggtgc tgtgggccat cggccagtt aaaaaggcgg aggacgagaa   4860
gctggacgga gtcaagatcg ccatcagcaa caagggagt ctcgagtcg cgcagacgag   4920
cgtgaagcac ggatctaaga agagaagaat taaacaagat tgattaatta agggcccacc   4980
atatgacact ggtgcatgtg ccatcatcat gcagtaattt catggtatat cttaattata   5040
tggttaataa aaaaaagatg gtgagtgaat aatgtgcgtg cattcctcca tgcaccaatg   5100
gtgaatctct ttgcatacat agagattctg aatgattata gttatgttg tagtgaaatt   5160
aattttgaat gttgttttta aattttaatg tcacttggct tgatttatgt tttaacgaag   5220
```

```
cttatgttat gtattttact ttaatgatat tgcatgtatt gttaatttaa cattgcttga   5280
tcagtatact ct                                                      5292

SEQ ID NO: 37           moltype = DNA   length = 822
FEATURE                 Location/Qualifiers
misc_feature            1..822
                        note = Synthetic polynucleotide.Chimeric promoter cassette
                         comprisingthe enhancer sequence from the Banana Streak
                         Virus strainAcuminata Vietnam fused to apromoter sequence
                         fromDahliaMosaic Virus (DaMV).
source                  1..822
                        mol_type = other DNA
                        organism = synthetic construct
SEQUENCE: 37
agacatcctg gaccaatatg ctgaagatta tgctacctac accaggatag gacttgaagc   60
acttaacctt gaagattggt tcgaagaacc agaacccgat ccacctaacc ctgtggaccg   120
ccagaggata gaggacatcc tggacctact gaacgtcagc aatgacgact gaaagattcc   180
caggacaccg gcggaagtgg tggacccagt ctaggtgcga tgcttagtcg cgcacgatga   240
ctatgtcgga aggcatcttt gctttcggca aactttagta atactttaag gaaagtattg   300
tacaagttag gtgcagagac aataatgcac ccagctttag ctttgtttat ggaattattg   360
tgtcggttgc attattggat gcctgcgtgc accctaagca atcaacggag aaacaaagat   420
aaaaatcaat tactcacatg aaagagtatt gatcacgagt cactatggag cgacaatctc   480
cagacaggat gtcagcatct tatcttcctt tgaagaaagt atcatcaata acgatgtaat   540
ggtgggaca tccactaagt tattgctctg caaacagctc aaaaagctac tggccgacaa   600
tcataattgc tcggcatgtg caggtggggc ctccactagc aataatacaa gctttacagc   660
ttgcagtgac tcatcctcca ataatggaga aaaagacgtc agcagtgacg aacaagggtc   720
gaaagacttg cctatataag ggcattctcc cctcagttga agatcatcga aagttggagc   780
aataaactct ctcttcaaca aatctatctt ttatctttta tc                    822

SEQ ID NO: 38           moltype = DNA   length = 3681
FEATURE                 Location/Qualifiers
misc_feature            1..3681
                        note = Synthetic polynucleotide.Codon optimized LbCpf1(TYC)
                         -CO2
source                  1..3681
                        mol_type = other DNA
                        organism = synthetic construct
SEQUENCE: 38
tcgaagctcg agaagttcac caactgctac tcgctgagca agacgctgcg gttcaaggcg   60
atccccgtcg ggaagaccca ggagaacatc gacaacaagc ggctcctggt cgaggacgag   120
aagcgcgccg aggactacaa gggcgtcaag aagctgctgg accggtacta cctctccttc   180
atcaacgacg tcctgcactc gatcaagctc aagaacctga caactacat ctcgctgttc   240
cgcaagaaga cacggaccga gaaggagaac aaggagctcg agaacctcaa gatcaacctg   300
cgcaaggaga tcgcgaaggc gttcaagggc aacgaggggt acaagagcct gttcaagaaa   360
gacatcatcg agaccatcct gccggagttc ctggacgaca ggacgagat cgcgctggtg   420
aactcgttca cgggttcac cacggccttc accgggttttt tcgacaaccg ggagaacatg   480
ttcagcgagg aggccaagtc gaccagcatc gccttccggg gcatcaacga gaacctcacc   540
cgctacatca gcaacatgga catcttcgag aaggtggacg ccatcttcga caagcacgag   600
gtccaggaga tcaaggaaaa gatcctgaac tcggactacg acgtgaaga cttctttgag   660
ggcgagttct tcaacttcgt cctcacccag gagggcatcg acgtctacaa cgccatcatc   720
ggcggcttcg tgacggagag cggcgagaag atcaaggcgc tcaacgagta catcaacctc   780
tacaaccaga agactaagca gaagctcccg aagttcaagc cgctgtacaa gcaagtcctg   840
agcgaccggg agtccctctc gttctacggc gagggctaca gagcgacga ggaggtgctg   900
gaggtgttcc gcaacacgct gaacaagaac agcgagatct tcagctcgat caagaaactc   960
gagaagctgt tcaagaactt cgacgagtac agcagccgg gcatcttcgt caagaacgtg  1020
cccgcgatca gcaccatcag caaggacatc ttcggggagt ggaacgtgat ccgcgacaag  1080
tggaacgccg agtacgacga catccaccc aagaaaaagg cggtggtcac ggagaagtac  1140
gaggacgacc gccggaagtc cttcaagaaa tcgggagct tcagcctcga gcagctccag  1200
gagtacgcgg acgccgacct gagcgtggtg gagaagctca aggagatcat catccagaag  1260
gtcgacgagt ctacaaggt ctacggctcg agcgagagc tgttcgacgc ggacttcgtg  1320
ctggagaagt ccctcaagaa gaacgacgcc gtggtggca tcatgaagga tctgctcgac  1380
agcgtgaagt cgttcgagaa ctacatcaag gcattctttg ggagggcaa ggagacgaac  1440
cgggacgagt ccttctacgg ggacttcgtg ctcgcgtacg acatcctcct gaaggtcgac  1500
cacatctacg acgcgatccg gaactacgtc acgcagaagc cctacagcaa ggacaagttc  1560
aagctctact ccagaaccc gcagttcatg cgcgggtggg acaaggacaa ggaagaccgac  1620
taccgggcca cgatcctgcg gtacgggtcc aagtactacc tcgccatcat ggacaagaag  1680
tacgccaagt gcctccagaa gattgacaag gacgacgtga cgggaacta cgagaagatc  1740
aactacaagc tcctcccggg gcccaacaag atgctgccga gggtgttctt cagcaagaag  1800
tggatggcct actacaaccc ctcggaggac atccagaaga tacaagaa cggcacgttc  1860
aaaaaggggg acatgttcaa cctgaacgac tgccacaagc tgatcgactt tttcaaggac  1920
agcatcagcc gctacccgaa gtggtcgaac gcctacgact tcaacttctc ggagacggag  1980
aagtacaagg acattgcggg cttctaccgg gaggtggagg gcagggcta aggtctcc  2040
ttcgagagcg cctccaagga gaggtggac aagtcgtgg aggagggcaa gctgtacatg  2100
ttccagatct acaacaagga cttctcgac aagtcccgaa gccccgaa cctccacacg  2160
atgtacttca agctgctgtt cgacgagaac aaccacggc agatccgcct cagcggcggg  2220
gcggagctgt tcatgcgccg cgcgtccctc aagaaggagg agctggtcgt gcaccccgcc  2280
aactccccga tcgcgaacaa gaaccccgac aaccccaaga gacaaccac cctccgtac  2340
gacgtctaca ggacaagcg gttctcggag gaccagtacg agctgcacat cccgatcgcc  2400
atcaacaagt gccccaagaa catcttcaag atcaacaccc aggtgcgggt gctgctcaag  2460
```

```
cacgacgaca accectacgt catcgggatc gaccgcggcg agcggaacct gctctacatc    2520
gtggtcgtgg acgggaaggg gaacatcgtg gagcagtaca gcctgaacga gatcatcaac    2580
aacttcaacg gcatccgcat caagacggac taccacagcc tcctggacaa gaaggagaag    2640
gagcggttcg aggcgcggca gaactggacc tccatcgaga acatcaagga gctgaaggcc    2700
ggctacatca gccaggtcgt gcacaagtgc tgcgagctcg tggagaagta cgacgcggtg    2760
atcgcgctgg aggacttgaa cagcgggttc aagaactccc gggtcaaggt cgagaagcag    2820
gtctaccaga agttcgagaa gatgctgatc gacaagctca actacatggt ggacaagaag    2880
tccaaccccct gcgccaccgg cggcgccctc aagggctacc agatcaccaa caagttcgag    2940
tccttcaagt cgatgtctac gcagaacggg ttcattttct acatccccgg cgtggctcacc    3000
agcaagatcg acccgagcac gggcttcgtc aacctcctga agaccaagta caccagcatc    3060
gcggacagca gaagttcat ctcctcgttc gaccgcatca tgtacgtccc cgaggaagac    3120
ctgttcgagt cgccctcga ctacaagaac ttctcccgga cggacgccga ctacatcaaa    3180
aagtggaagc tctacagcta cggcaaccgg atccgcatct tccgcaaccc caagaagaac    3240
aatgtgttcg actgggagga ggtgtgcctg acgagcgcct acaagagct cttcaacaag    3300
tacggcatca actaccagca aggggacatc cgcgcgctgc tctgcgagca gtccgacaag    3360
gcgttctact cgtcgttcat ggccctgatg agcctcatgc tccagatgcg caacagcatc    3420
accggccgga cggacgtgga cttcctgatc agcccggtca gaacagcga cggcattttc    3480
tacgacagcc ggaactacga ggccaggag aacgccatcc tccccaagaa cgccgacgcg    3540
aacgcgcct acaacatcgc gcggaaggtg ctgtgggcca tcggccagtt taaaaaggcg    3600
gaggacgaga gctggacaa ggtcaagatc gccatcagca acaaggagtg gctcgagtac    3660
gcgcagacga gcgtgaagca t                                              3681

SEQ ID NO: 39           moltype = AA  length = 1227
FEATURE                 Location/Qualifiers
REGION                  1..1227
                        note = Synthetic polypeptide.LbCpf1(TYC) variant
                          comprisingG532R andK595R substitutions
source                  1..1227
                        mol_type = protein
                        organism = synthetic construct
SEQUENCE: 39
SKLEKFTNCY SLSKTLRFKA IPVGKTQENI DNKRLLVEDE KRAEDYKGVK KLLDRYYLSF     60
INDVLHSIKL KNLNNYISLF RKKTRTEKEN KELENLEINL RKEIAKAFKG NEGYKSLFKK    120
DIIETILPEF LDDKDEIALV NSFNGFTTAF TGFFDNRENM FSEEAKSTSI APRCINENLT    180
RYISNMDIFE KVDAIFDKHE VQEIKEKILN SDYDVEDFFE GEFFNFVLTQ EGIDVYNAII    240
GGFVTESGEK IKGLNEYINL YNQKTKQKLP KFKPLYKQVL SDRESLSFYG EGYTSDEEVL    300
EVFRNTLNKN SEIFSSIKKL EKLFKNFDEY SSAGIFVKNG PAISTISKDI FGEWNVIRDK    360
WNAEYDDIHL KKKAVVTEKY EDDRRKSFKK IGSFSLEQLQ EYADADLSVV EKLKEIIIQK    420
VDEIYKVYGS SEKLFDADFV LEKSLKKNDA VVAIMKDLLD SVKSFENYIK AFFGEGKETN    480
RDESFYGDFV LAYDILLKVD HIYDAIRNYV TQKPYSKDKF KLYFQNPQFM RGWDKDKETD    540
YRATILRYGS KYYLAIMDKK YAKCLQKIDK DDVNGNYEKI NYKLLPGPNK MLPRVFFSKK    600
WMAYYNPSED IQKIYKNGTF KKGDMFNLND CHKLIDFFKD SISRYPKWSN AYDFNFSETE    660
KYKDIAGFYR EVEEQGYKVS FESASKKEVD KLVEEGKLYM FQIYNKDFSD KSHGTPNLHT    720
MYFKLLFDEN NHGQIRLSGG AELFMRRASL KKEELVVHPA NSPIANKNPD NPKKTTTLSY    780
DVYKDKRFSE DQYELHIPIA INKCPKNIFK INTEVRVLLK HDDNPYVIGI DRGERNLLYI    840
VVVDGKGNIV EQYSLNEIIN NFNGIRIKTD YHSLLDKKEK ERFEARQNWT SIENIKELKA    900
GYISQVVHKI CELVEKYDAV IALEDLNSGF KNSRVKVEKQ VYQKFEKMLI DKLNYMVDKK    960
SNPCATGGAL KGYQITNKFE SFKSMSTQNG FIFYIPAWLT SKIDPSTGFV NLLKTKYTSI   1020
ADSKKFISSF DRIMYVPEED LFEFALDYKN FSRTDADYIK KWKLYSYGNR IRIFRNPKKN   1080
NVFDWEEVCL TSAYKELFNK YGINYQQGDI RALLCEQSDK AFYSSFMALM SLMLQMRNSI   1140
TGRTDVDFLI SPVKNSDGIF YDSRNYEAQE NAILPKNADA NGAYNIARKV LWAIGQFKKA   1200
EDEKLDKVKI AISNKEWLEY AQTSVKH                                       1227

SEQ ID NO: 40           moltype = DNA  length = 6080
FEATURE                 Location/Qualifiers
misc_feature            1..6080
                        note = Synthetic polynucleotide.Expression cassette
                          comprising Zea maysUbiquitin promoter cassette,
                          NLS-LbCpf1(TYC)-CO2-NLS and an Oryzasativa transcription
                          termination sequence
source                  1..6080
                        mol_type = other DNA
                        organism = synthetic construct
SEQUENCE: 40
gtcgtgcccc tctctagaga taaagagcat gcatgtcta aagtataaaa aattaccaca      60
tatttttttg tcacacttat ttgaagtgta gtttatctat ctctatacat atatttaaac    120
ttcactctac aaataatata gtctataata ctaaaataat attagtgttt tagaggatca    180
tataaataaa ctgctagaca tggtctaaag gataattgaa tattttgaca atctacagtt    240
ttatctttt agtgtgcatg tgatctctct gttttttttg caaatagctt gacctata     300
atacttcatc cattttatta gtacatccat ttaggatttta gggttgatgg tttctataga    360
ctaattttta gtacatccat tttattcttt ttagtctcta aattttttaa aactaaaact    420
ctattttagt ttttttatta ataatttaga tataaaatga aataaaataa attgactaca    480
aatataaaacaa ataaccettta agaaataaaa aaactaagca aacatttttc ttgtttcgag    540
tagataatga caggctgttc aacgccgtcg acagtctaa cagacaccaa ccagcgaacc    600
agcagcgtcg cgtcgggcca agcgaagcag acgcacggc atctctgtag ctgcctctgg    660
acccctctcg agagttccgc tccaccgttg gacttgctcc gctgtcggca tccagaaatt    720
gcgtggcgga gcgcagacg tgaggcgca cggcaggcgg cctcttcctc ctctcacggc    780
accggcagct acggggatt cctttcccac cgctccttcg ctttcccttc ctcgcccgcc    840
gtaataaaata gacacccccct ccacaccctc tttcccaac ctcgtgttcg ttcggagcgc    900
```

```
acacacacgc aaccagatct cccccaaatc cagccgtcgg cacctccgct tcaaggtacg   960
ccgctcatcc tccccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatgaaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc ttttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatgaaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggattttt   1920
agccctgcct tcatacgcta tttatttgct tggtactgtt tcttttgtcc gatgctccac  1980
ctgttgtttg gtgatacttc tgcaggtccg gtacctcagc atgggtagca aaaagaggcg  2040
tatcaagcag gacgcgtcga agctcgagaa gttcaccaac tgctactcgc tgagcaagac  2100
gctgcggttc aaggcgatcc ccgtcgggaa gacccaggag aacatcgaca caagcggct   2160
cctggtcgag gacgagaagc cgccgaagca ctacaaggcc gtcaagaagc tgctggaccg  2220
gtactacctc tccttcatca acgacgtcct gcactcgatc aagctcaaga acctgaacaa  2280
ctacatctcg ctgttccgca agaagacacg gaccgagaag gagaacaagg agctcgagaa  2340
cctcgagatc aacctgcgca aggagatcgc gaaggcgttc aagggcaacg aggggtacaa  2400
gagcctgttc aagaaagaca tcatcgagac cgagttcctgg acgacaagga  2460
cgagatcgcg ctggtgaact cgttcaacgg gttcaccacg gccttcaccg gttttttcga  2520
caaccgggag aacatgttca gcgaggaggc caagtcgacc agcatcgcct tccggtgcat  2580
caacgagaac ctcacccgct acatcagcaa catggacatc ttcgagaagg tggacgccat  2640
cttcgacaag cacgaggtcc aggatcaaa ggaaaagatc ctgaactcgg actacgacgt  2700
ggaagacttc tttgagggcg agttcttcaa cttcgtcctc acccaggagg gcatcgacgt  2760
ctacaacgcc atcatcggcg gcttcgtgac ggagagcggc gagaagatca agggcctcaa  2820
cgagtacatc aacctctaca accagaagac taagcagaag ctcccgaagt tcaagccgct  2880
gtacaagcaa gtcctgagcg accgggagtc cctctcgttc tacggcgagg gctacacgag  2940
cgacgaggag gtgctggagg tgttccgcaa cacgctcaag aagaacagcg agatcttcag  3000
ctcgatcaag aaactcgaga agctgttcaa gaacttcgac gagtacagca gcgccggcat  3060
cttcgtcaag aacgggcccg cgatcagcac catcagcaag gacatcttcg gggagtggaa  3120
cgtgatccgc gacaagtgga acgccgagta cgacgacatc cacctcaaga aaaaggcggt  3180
ggtcacggag aagtacgagg acgaccgccg gaagtccttc aagaaaatcg ggagcttcag  3240
cctcgagcag ctccaggagt acgcggacgc cgacctgagc gtggtggaga agctcaagga  3300
gatcatcatc cagaaggtcg acgagatcta caaggtctac ggctcgagcg agaagctgtt  3360
cgacgcggac ttcgtgctgg agaagtccct caagaagaac gacgccgtgg tggccatcat  3420
gaaggatctcg ctcgacagcg tgaagtcgtt cgagaactac atcaaggcat tctttgggga  3480
gggcaaggag acgaaccggg acgagtccctt ctacggggac ttcgtgctcg cgtacgacat  3540
cctcctgaag gtcgaccaca tctacgacgg gatccggaac tacgtcacgc agaagcccta  3600
cagcaaggac aagttcaagc tctacttcca gaacccgcag ttcatgcgcg ggtgggacaa  3660
ggacaaggac accgactacc gggccacgat cctgcgggtac gggtccaagt actacctcgc  3720
catcatggac aagaagtacg ccaagtgcct ccagaagatt gacaaggacg acgtgaacgg  3780
gaactacgag aagatcaact acaagctcct cccgggggccc aacaagatgc tgccgagggt  3840
gttcttcagc aagaagtgga tggcctacta caacccctcg gaggacatcc agaagatata  3900
caagaacgac acgttcaaaa aggggacat gttcaacctg aacgactgcc acaagctgat  3960
cgactttttc aaggacagca tcagccgcta cccgaagtgg tcgaacgcct acgacttcaa  4020
cttctcggag acgagaagt acaaggacat tgcgggcttc taccgggagg tggaggagca  4080
gggctacaag gtctccttcg agagcgcctc caagaaagag gtgacaagc tcgtggagga  4140
gggcaagctg tacatgttcc agatctacaa caaggacttc tcggacagcc gcacggcac   4200
cccgaacctc cacacgatgt acttcaagct gctgttcgac gaacaacc acgggcagat   4260
ccgcctcagc ggcggggcgg agctgttcat gcgccgcgcg tccctcaaga aggaggagct  4320
ggtcgtgcac cccgccaact ccccgatcgc gaacaagaac cccgacaacc ccaagaagac  4380
aacccacctc tcgtacgacg tctacaagga caagcggttc tcggaggacc agtacgaact  4440
gcacatcccg atcgccatca caagtgccc caagaacatc ttcaagatca acacgcaggt  4500
gcgggtgctg ctcaagcacg acgacaaccc ctacgtcatc gggatcgacc gcggcgagcg  4560
gaacctgctc tacatcgtgg tcgtggacgg gaagggggaac atcgtggagc agtacagcct  4620
gaacgagatc atcaacaact tcaacggcat ccgcatcaag acggactacc acagcctcct  4680
ggacaaggag gagaaggagc ggttcgaggc gcggcagaac tggacctcca tcgagaacat  4740
caaggagctg aaggccggct acatcagcca ggtcgtgcac aagatctgcg agctcgtgga  4800
gaagtacgac gcggtgatcg cgctggagga cttgaacagc gggttcaaga actcccgggt  4860
caaggtcgag aagcaggtct accagaagtt cgagaagatg ctgatcgaca agctcaacta  4920
catggtggac aagaagtcca cccctcaagc gcaccggcgg cccctcaagg gctaccagat  4980
caccaacaag ttcgagtcgt tcaagtcgat gtctctacag aacgggttca ttttctacat  5040
cccggcgtgg ctcaccagca gatcgaccc gagcacgggc ttcgtcaacc tcctgaagac  5100
caagtacacc agcatcgcgg acagcaagaa gttcatctcc tcgttcgacc gcatcatgta  5160
cgtccccgag gaagacctgt tcgagttcgc cctcgactac aagaacttct cccggaacgg   5220
cgccgactac atcaaaaagt ggaagctcta cagctacggc aaccggatcc gcatcttccg  5280
caaccccaag aagaacaatg tgttcgactg gaggagtga gcgcctacaa  5340
ggagctcttc aacaagtacg gcatcaacta ccagcaaggg gacatccgcg cgctgctctg  5400
cgagcagtcc gacaaggcgt tctactcgtc gttcatggac ctgatgagcc tcatgctcca  5460
gatgcgcaac agcatcaccg gccggacgga cgtggacttc ctgatcagcc cggtcaagaa  5520
cagcgacggc atttttctacg acagccggaa ctacgaggcc caggagaacg ccatcctccc  5580
caagaacgcc gacgcgaacg gcgcctacaa catcgcgcgg aaggtgctgt gggccatcgg  5640
```

```
ccagtttaaa aaggcggagg acgagaagct ggacaaggtc aagatcgcca tcagcaacaa   5700
ggagtggctc gagtacgcgc agacgagcgt gaagcatgca ggatctaaga agcgtaggat   5760
caagcaagat taagaggtta attaatcgat cctccgatcc cttaattacc ataccattac   5820
accatgcatc aatatccata tatatataaa ccctttcgca cgtacttata ctatgttttg   5880
tcatacatat atatgtgtcg aacgatcgat ctatcactga tatgatatga ttgatccatc   5940
agcctgatct ctgtatcttg ttatttgtat accgtcaaat aaaagtttct tccacttgtg   6000
ttaataatta gctactctca tctcatgaac cctatatata actagtttaa tttgctgtca   6060
attgaacatg atgatcgatg                                              6080

SEQ ID NO: 41           moltype = DNA   length = 3753
FEATURE                 Location/Qualifiers
misc_feature            1..3753
                        note = Synthetic polynucleotide.NLS-LbCpf1(TYC)-CO2-NLS
source                  1..3753
                        mol_type = other DNA
                        organism = synthetic construct
SEQUENCE: 41
atgggtagca aaaagaggcg tatcaagcag gacgcgtcga agctcgagaa gttcaccaac    60
tgctactcgc tgagcaagac gctgcggttc aaggcgatcc ccgtcgggaa gacccaggag   120
aacatcgaca caaagcggct cctggtcgag gacgagaagc gcgccgagga ctacaagggc   180
gtcaagaagc tgctggaccg gtactacctc tccttcatca cgacgtcct gcactcgatc    240
aagctcaaga acctgaacaa ctacatctcg ctgttccgca agaagacactg gaccgagaag   300
gagaacaagg agctcgagaa cctcgagatc aacctgcgca aggagatcgc gaaggcgttc   360
aagggcaacag ggggtacaa gagcctgttc aagaaagaca tcatcgagac catccctgccg   420
gagttcctgg acgacaagga cgagatcgcg ctggtgaact cgttcaacgg gttcaccacg   480
gccttcaccg gttttttcga caaccgggag aacatgcttc gcgaggaggc caagtcgacc   540
agcatcgcct tccggtgcat caacgagaac ctcacccgct acatcagcaa catggacatc   600
ttcgagaagg tggacgccat cttcgacaag cacgaggtcc aggagatcaa ggaaaagatc   660
ctgaactcgg actacgacgt ggaagacttc tttgagggcg agttcttcaa cttcgtcctc   720
acccaggagg gcatcgacgt ctacaacgcc atcatcggcg gcttcgtgac ggagagcggc   780
gagaagatca agggcctcaa cgagtacatc aacctctaca accagaagac taagcagaag   840
ctcccgaagt tcaagccgct gtacaagcaa gtcctgagcg accgggagtc cctctcgttc   900
tacgcgagg gctacacgag cgacgaggag gtgctggagg tgttccgcaa cacgctgaac   960
aagaacagcg agatcttcag ctcgatcaag aaactcgaga agctgttcaa gaacttcgac  1020
gagtacagca gcgccggcat cttcgtcaag aacgggcccg cgatcagcac catcagcaag  1080
gacatcttcg gggagtggaa cgtgatccgc gacaagtgga acgccgagta cgacgacatc  1140
cacctcaaga aaaaggcggt ggtcacggag aagtacgagg acgaccgccg gaagtccttc  1200
aagaaaatcg ggagcttcag cctcgagcag ctccaggagt acgcggacgc cgacctgagc  1260
gtggtggaga agctcaagga gatcatcatc cagaaggtcg acgagatcta caaggtctac  1320
ggctcgagcg agaagctgtt cgacgcggac ttcgtgctgg agaagtccct caagaagaac  1380
gacgccgtgg tggccatcat gaaggatctg ctcgacagcg tgaagtcgtt cgagaactac  1440
atcaaggcat tctttgggga gggcaaggag acgaaccggg acgagtcctt ctacgggac   1500
ttcgtctcg cgtacgacat cctcctgaag gtcgaccaca tctacgacgc gatccggaag  1560
tacgtcacgc agaagcccta cagcaaggac aagttcaagc tctacttcca gaacccgcag  1620
ttcatgcgcg gtgggacaa ggacaaggag accgactacc gggccacgat cctgcggtac  1680
gggtccaagt actacctcgc catcatggac aagaagtacg ccaagtgcct ccagaagatt  1740
gacaaggacg acgtgaacgg gaactacgag aagatcaact acaagctcct cccggggccc  1800
aacaagatgc tgccgaaggt gttcttcagc aagaagtgga tggcctacta caaccccctcg  1860
gaggacatcc agaagatata caagaacggc acgttcaaaa aggggacat gttcaacctg  1920
aacgactgcc acaagctgat cgactttttc aaggacagca tcagccgcta cccgaagtgg  1980
tcgaacgcct acgacttcaa cttctcggag acggagaagt acaaggacat tgcgggcttc  2040
taccgggagg tggaggagca gggctacaag gtctccttcg agagcgcctc caagaaaagg  2100
gtggacaagc tcgtggagga gggcaagctg tacatgttcc agatctacaa caaggacttc  2160
tcggacaagt cgcacggcac cccgaacctc cacacgatgt acttcaagct gctgttcgac  2220
gagaacaacc acgggcagat ccgcctcagc ggcggggcgg agctgttcat gcgccgcgcg  2280
tccctcaaga aggaggagct ggtcgtgcac cccgccaact cccgatcgc gaacaagaac  2340
cccgacaacc caagaagac aaccaccctc tcgtacgacg tctacaagga caagcggttc  2400
tcggaggacc agtacgagct gcacatcccg atcgccatca caagtgccc caagaacatc  2460
ttcaagatca acaccgaggt gcgggtcctg ctcaagcacg acgaaaccc ctacgtcatc  2520
gggatcgacc gcggcgagcg gaacctgctc tacatcgtgt tcgtggacgg gaaggggaac  2580
atcgtggagc agtacagcct gaacgagatc atcaacaact tcaacggcat ccgcatcaag  2640
acggactacc acagcctcct ggacaagaag gagaaggagc ggttcgaggc gcggcagaac  2700
tggacctcca tcgagaacat caaggagctg aaggccggct acatcagcca ggtcgtgcac  2760
aagatctgcg agctcgtgga aagtacgac gcggttgatcg cgctggagca cttgaacagc  2820
gggttcaaga actcccgggt caaggtcgag aagcaggtct accagaagtt cgagaagatg  2880
ctgatcgaca agctcaacta catggtggac aagaagtcca ccccctgcgc caccggcggc  2940
gccctcaagg ctaccagat caccaacaag ttcgagtcct tcaagtcgat gtctacgcag  3000
aacgggttca ttttctacat cccggcgtgg ctcaccagca gatcgacccc gagcacgggc  3060
ttcgtcaacc tcctgaagac caagtacacc agcatcgcgg acagcaagaa gttcatctcg  3120
tcgttcgacc gcatcatgta cgtccccgag gaagacctgt cgagttcgc cctcgactac  3180
aagaacttct cccggacgga cgccgactac atcaaaaagt ggaagctcta cagctacggc  3240
aaccggatcc gcatcttccg caaccccaag aagaacaatg tgttcgactg ggaggaggtg  3300
tgcctgacga gcgcctacaa ggagctcttc aacaagtacg gcatcaacta ccagcaaggg  3360
gacatccgcg cgctcgtctg cgagcagtcc gacaaggcgt tctactcgtc cttcatggcc  3420
ctgatgagcc tcatgctcca gatgcgcaac agcatcaccg gccgactgga cgtggacttc  3480
ctgatcagcc cggtcaagaa cagcgacggc attttctacg acagccggaa ctacgaggcc  3540
caggagaacg ccatcctccc caagaacgcc gacgcgaacg gcgcctacaa catcgcgcgg  3600
aaggtgctgt gggccatcgg ccagtttaaa aaggcggagg acgagaagct ggacaaggtc  3660
aagatcgcca tcagcaacaa ggagtggctc gagtacgcgc agacgagcgt gaagcatgca  3720
```

-continued

```
ggatctaaga agcgtaggat caagcaagat taa                                3753

SEQ ID NO: 42          moltype = DNA  length = 33
FEATURE                Location/Qualifiers
source                 1..33
                       mol_type = unassigned DNA
                       organism = Solanum tuberosum
SEQUENCE: 42
atgggtagca aaaagaggcg tatcaagcag gac                                33

SEQ ID NO: 43          moltype = AA  length = 1300
FEATURE                Location/Qualifiers
source                 1..1300
                       mol_type = protein
                       note = subsp. novicida U112
                       organism = Francisella tularensis
SEQUENCE: 43
MSIYQEFVNK YSLSKTLRFE LIPQGKTLEN IKARGLILDD EKRAKDYKKA KQIIDKYHQF  60
FIEEILSSVC ISEDLLQNYS DVYFKLKKSD DDNLQKDFKS AKDTIKKQIS EYIKDSEKFK  120
NLFNQNLIDA KKGQESDLIL WLKQSKDNGI ELFKANSDIT DIDEALEIIK SFKGWTTYFK  180
GFHENRKNVY SSNDIPTSII YRIVDDNLPK FLENKAKYES LKDKAPEAIN YEQIKKDLAE  240
ELTFDIDYKT SEVNQRVFSL DEVFEIANFN NYLNQSGITK FNTIIGGKFV NGENTKRKGI  300
NEYINLYSQQ INDKTLKKYK MSVLFKQILS DTESKSFVID KLEDDSDVVT TMQSFYEQIA  360
AFKTVEEKSI KETLSLLFDD LKAQKLDLSK IYFKNDKSLT DLSQQVFDDY SVIGTAVLEY  420
ITQQIAPKNL DNPSKKEQEL IAKKTEKAKY LSLETIKLAL EEFNKHRDID KQCRFEEILA  480
NFAAIPMIFD EIAQNKDNLA QISIKYQNQG KKDLLQASAE DDVKAIKDLL DQTNNLLHKL  540
KIFHISQSED KANILDKDEH FYLVFEECYF ELANIVPLYN KIRNYITQKP YSDEKFKLNF  600
ENSTLANGWD KNKEPDNTAI LFIKDDKYYL GVMNKKNNKI FDDKAIKENK GEGYKKIVYK  660
LLPGANKMLP KVFFSAKSIK FYNPSEDILR IRNHSTHTKN GSPQKGYEKF EFNIEDCRKF  720
IDFYKQSISK HPEWKDFGFR FSDTQRYNSI DEFYREVENQ GYKLTFENIS ESYIDSVVNQ  780
GKLYLFQIYN KDFSAYSKGR PNLHTLYWKA LFDERNLQDV VYKLNGEAEL FYRKQSIPKK  840
ITHPAKEAIA NKNKDNPKKE SVFEYDLIKD KRFTEDKFFF HCPITINFKS SGANKFNDEI  900
NLLLKEKAND VHILSIDRGE RHLAYYTLVD GKGNIIKQDT FNIIGNDRMK TNYHDKLAAI  960
EKDRDSARKD WKKINNIKEM KEGYLSQVVH EIAKLVIEYN AIVVFEDLNF GFKRGRFKVE  1020
KQVYQKLEKM LIEKLNYLVF KDNEFDKTGG VLRAYQLTAP FETFKKMGKQ TGIIYYVPAG  1080
FTSKICPVTG FVNQLYPKYE SVSKSQEFFS KFDKICYNLD KGYFEFSFDY KNFGDKAAKG  1140
KWTIASFGSR LINFRNSDKN HNWDTREVYP TKELEKLLKD YSIEYGHGEC IKAAICGESD  1200
KKFFAKLTSV LNTILQMRNS KTGTELDYLI SPVADVNGNF FDSRQAPKNM PQDADANGAY  1260
HIGLKGLMLL GRIKNNQEGK KLNLVIKNEE YFEFVQNRNN                         1300

SEQ ID NO: 44          moltype = DNA  length = 3897
FEATURE                Location/Qualifiers
misc_feature           1..3897
                       note = Synthetic polynucleotide.Codon optimized FnCpf1-Hs
source                 1..3897
                       mol_type = other DNA
                       organism = synthetic construct
SEQUENCE: 44
agcatctacc aggagttcgt caacaagtat tcactgagta agacactgcg gttcgagctg  60
atcccacagg gcaagacact ggagaacatc aaggcccgag gcctgattct ggacgatgag  120
aagcgggcaa aagactataa gaaagccaag cagatcattg ataaatacca ccagttcttt  180
atcgaggaaa ttctgagctc cgtgtgcatc agtgaggatc tgctgcagaa ttactcagac  240
gtgtacttca agctgaagaa gagcgacgat gacaacctgc agaaggactt caagtccgcc  300
aaggacacca tcaagaaaca gattagcgag tacatcaagg actccgaaaa gtttaaaaat  360
ctgttcaacc agaatctgat cgatgctaag aaaggccagg agtccgacct gatcctgtgg  420
ctgaaacagt ctaaggacaa tggattgaa ctgttcaagg ctaactccga tatcactgat  480
attgacgagg cactggaaat catcaagagc ttcaagggat ggaccacata ctttaaaggc  540
ttccacgaga accgcaagaa cgtgtactcc agcaacgaca ttcctacctc catcatctac  600
cgaatcgtcg atgacaatct gccaaagttc ctggagaaca aggccaaata tgaatctctg  660
aaggacaaag ctcccgaggc aattaattac gaacagatca agaaagatct ggctgaggaa  720
ctgacattcg atatcgacta taagactagc gaggtgaacc agagggtctt ttccctggac  780
gaggtgtttg aaatcgccaa tttcaacaat tacctgaacc agtccggcat tactaaattc  840
aataccatca ttggcgggaa gtttgtgaac ggggagaata ccaagcgcaa gggaattaac  900
gaatacatca atctgtatag ccagcagatc aacgacaaaa ctctgaagaa atacaagatg  960
tctgtgctgt tcaaacagat cctgagtgat accgagtcca agtcttttgt cattgataaa  1020
ctggaagatg actcagacgt ggtcactacc atgcagagct tttatgagca gatcgccgct  1080
ttcaagacag tggaggaaaa atctattaag gaaactctga gtctgctgtt cgatgacctg  1140
aaagcccaga agctggacct gagtaagatc tacttcaaaa acgataagag tctgacagac  1200
ctgtcacagc aggtgtttga tgactattcc gtgattggga ccgccgtcct ggagtacatt  1260
acacagcaga tcgctccaaa gaacctggat aatccctcta agaaagagca ggaactgatc  1320
gctaagaaaa ccgagaaggc aaaatatctg agtctggaaa caattaagct ggcactggag  1380
gagttcaaca agcacaggga tattgacaaa cagtgccgct ttgaggaaat cctggccaac  1440
ttcgcagcca tccccatgat ttttgatgag atcgcccaga acaaagacaa tctggctcag  1500
atcagtatta agtaccagaa ccagggcaag aaagacctgc tgcaggcttc agcagaagat  1560
gacgtgaaag ccatcaagga tctgctggac cagaccaaca atctgctgca caagctgaaa  1620
atcttccata ttagtcagtc agaggataag gctaatatcc tggataaaga cgaacacttc  1680
tacctggtgt tcgaggaatg ttacttcgag ctggcaaaca ttgtccccct gtataacaag  1740
attaggaact acatcacaca gaagccttac tctgacgaga agtttaaact gaacttcgaa  1800
aatagtaccc tggccaacgg gtgggataag aacaaggagc ctgacaacac agctatcctg  1860
```

-continued

```
ttcatcaagg atgacaagta ctatctggga gtgatgaata agaaaaacaa taagatcttc  1920
gatgacaaag ccattaagga gaacaaaggg gaaggataca agaaaatcgt gtataagctg  1980
ctgcccggcg caaataagat gctgcctaag gtgttcttca gcgccaagag tatcaaattc  2040
tacaacccat ccgaggacat cctgcggatt agaaatcact caacacatac taagaacggg  2100
agcccccaga agggatatga gaaatttgag ttcaacatcg aggattgcag gaagtttatt  2160
gacttctaca agcagagcat ctccaaacac cctgaatgga aggattttgg cttccggttt  2220
tccgacacac agagatataa ctctatcgac gagttctacc gcgaggtgga aaatcagggg  2280
tataagctga cttttgagaa catttctgaa agttacatcg acagcgtggt caatcaggga  2340
aagctgtacc tgttccagat ctataacaaa gattttcag catacagcaa gggcagacca  2400
aacctgcata cactgtactg gaaggccctg ttcgatgaga ggaatctgca ggacgtggtc  2460
tataaactga acggagaggc cgaactgttt taccggaagc agtctattcc taagaaaatc  2520
actcacccag ctaaggaggc catcgctaac aagaacaagg acaatcctaa gaagagagc  2580
gtgttcgaat acgatctgat taaggacaag cggttccacg aagtaagtt cttttccat  2640
tgtccaatca ccattaactt caagtcaagc ggcgctaaca agttcaacga cgagatcaat  2700
ctgctgctga aggaaaaagc aaacgatgtg cacatcctga gcattgaccg aggagagcgg  2760
catctggcct actataccct ggtggatggc aaagggaata tcattaagca ggatacattc  2820
aacatcattg gcaatgaccg gatgaaaacc aactaccacg ataaactggc tgcaatcgag  2880
aaggatagag actcagctag gaaggactgg aagaaaatca acaacattaa ggagatgaag  2940
gaaggctatc tgagccaggt ggtccatgag attgcaaagc tggtcatcga atacaatgcc  3000
attgtggtgt tcgaggatct gaacttcggc tttaagaggg ggcgctttaa ggtgaaaaaa  3060
caggtctatc agaagctgga gaaaatgctg atcgaaaagc tgaattacct ggtgtttaaa  3120
gataacgact tcgacaaagac cggaggcgtc ctgagagccg acagctgaca agctccctt  3180
gaaactttca agaaaatggg aaaacagaca ggcatcatct actatgtgcc agccggattc  3240
acttccaaga tctgccccgt gaccggcttt gtcaaccagc tgtacctaaa atgagtca  3300
gtgagcaagt cccaggaatt tttcagcaag ttcgataaga tctgttataa tctggacaag  3360
gggtacttcg agttttcctt cgattacaag aacttcgtga caaggccgc taagggaaa  3420
tggaccattg cctccttcgg atctcgcctg atcaactttc gaattccga taaaaaccac  3480
aattgggaca ctaggaggt gtacccaacc aaggagctgg aaaagctgct gaaagactac  3540
tctatcgagt atggacatgg cgaatgcatc aaggcagcca tctgtggcga gagtgataag  3600
aaattttcg ccaagctgac ctcagtgctg aatacaatcc tgcagatgcg gaactcaaag  3660
accgggacag aactggacta tctgattagc ccgtggctg atgtcaacgg aaacttcttc  3720
gacagcagac aggcacccaa aaatatgcct caggatgcag acgccaacgg ggcctaccac  3780
atcgggctga agggactgat gctgctgggc cggatcaaga caatcagga ggggaagaag  3840
ctgaacctgg tcattaagaa cgaggaatac ttcgagtttg tccagaatag aaataac     3897
```

SEQ ID NO: 45          moltype = DNA   length = 3900
FEATURE                Location/Qualifiers
misc_feature           1..3900
                       note = Synthetic polynucleotide.Codon optimized FnCpf1-CO1
source                 1..3900
                       mol_type = other DNA
                       organism = synthetic construct
SEQUENCE: 45

```
atgtctatct atcaagagtt tgtcaacaag tacagcttaa gtaagacact tcgcttcgag   60
ttgatccctc aggggaagac actggaaaac atcaaggcga ggggcctta cctgacgac  120
gagaagcggg ctaagactac aaaaaagct aaacagataa ttgacaagta tcaccaattt  180
tttattgagg agatcctctc ctctgtgtgc ataagtgagg atctgctcca gaactattcg  240
gatgtttact taaactcaa gaagtccgat gatgacaacc ttcagaagga cttcaagtcc  300
gccaaagaca cgattaagaa acaaatcagt gagtacatca aggatagcga gaaattcaag  360
aacctgttca accagaactt aattgatgcc aaaaagggcc aagaatccga cctcatcctg  420
tggttaaagc aatctaaaga caacggtatt gagctgttca aggcaaacag cgacattaca  480
gacattgacg aggccctaga gatcatcaag tcattcaaag gctggacgac ttactttaaa  540
ggttttcacg agaaccgtaa gaatgtttac tcaagtaacg atataccaac gagcattatc  600
taccgaatag tggatgataa cctaccgaag ttccttgaga caaagcgaa gtacgagtct  660
ctcaaagaca aggccctgg gccatcaac tacgagcaga ttaagaagga tctcgccgag  720
gagctaaccct tcgacattga ctacaaaaca tcggaagtga atcagagggt gttctcgctt  780
gatgaagtat tcgagattgc taacttcaac aattacctga accagagtgg tattactaag  840
ttcaacacaa tcattggagg caaattcgtg acggcgaaa acacaaagcg aaagggata   900
aacgagtaca ttaacttgta cagccagcag atcaacgata agacactcaa gaagtataag  960
atgtctgtgc tgttcaaaca aatcttaagc gacacgaaa gcaagtcgtt cgtaattgac  1020
aagctggaag acgattctga cgtggttaca accatgcagt cctttacga gcagattgcc  1080
gcattcaaga ccgtggagga aaagtcgatc aaggaaacac tttcgttgct tttcgacgac  1140
cttaaagctc agaagctcga cttaagcaag atatactta agaacgataa gagcttgaca  1200
gacttgagcc agcaagtctt tgacgactac agcgttatcg cacgtgccgt tctgagtac  1260
ataacacagc agatcgcacc caagaacctt gacaacctt ccaagaaaga caagagttga  1320
atcgccaaga agactgaaaa ggctaagtac ctctctctgg agactatcaa gctcgctctt  1380
gaggagttta caagcacag ggacattgac aagcaatgcc gattcgagga atactggca   1440
aacttcgcag ccataccat gatattcgat gagatagccc aagcaaagga taacttggcc  1500
caaatctga ttaagtatca gaaccagggc aaaaaggacc ttctacaggc tagtgcagag  1560
gacgatgtga aggctattaa ggacttatta gatcagacaa acaaccttct gcataagctc  1620
aagatattcc atatctccca gtcagaggac aaggccaaca ttctgataa ggacgagcac  1680
ttctatctcg tattcgagga atgttacttt gagctggcca atatcgttcc cttgtacaac  1740
aaaatccgga actacatcac acagaagccc tacgtgatg agagttcaa attgaacttt  1800
caaaacttca acttgctga tggttgggac aagataaggg aaacctgcaa cactgccatc  1860
ctctttatta agatgataa gtactacctc ggggtgatga ataagaagaa caacaaaatc  1920
ttcgatgaca agctattaa ggagaacaaa ggtgaaggt acaagaagat tgtctacaaa  1980
ctgctgcctg gtgccaacaa aatgctacca aggtatttt tcagcgccaa atcattaag  2040
ttctacaatc caagcgagga tattctccgg atacggaatc actctacaca taccaagaat  2100
ggaagtccac aaaagggtta cgagaaattc gagttcaaca ttgaagactg ccggaaattc  2160
```

```
attgacttct acaagcaatc catctctaaa catcctgaat ggaaagactt cggtttccgc   2220
ttcagtgata ctcaacggta caattcaatt gacgaattct accgtgaggt tgagaaccag   2280
gggtacaaac tgaccttcga gaacatatca gagagctaca tcgactcagt ggttaatcag   2340
gggaagctat atctgtttca aatctacaac aaagacttta gtgcctactc taagggcgg   2400
ccaaacttac acacacttta ctggaaggca ctattcgacg aacgcaatct acaagatgta   2460
gtttacaaat tgaacggtga ggctgagttg ttctaccgta aacaatctat acccaagaag   2520
ataacacacc ctgctaaaga ggcaattgca aacaaaaaca aggataatcc caaaaaggag   2580
tctgtctttg agtatgacct cattaaggat aagcggttca cggaggacaa gttcttcttc   2640
cattgtccaa taaccatcaa cttcaaatca tccggcgcaa acaaattcaa tgacgagatc   2700
aacctgttac taaaggagaa ggctaacgat gttcacatct tatctattga tcgaggtgag   2760
agacacctag cctactacac tttagtggat gggaagggga acatcatcaa gcaagacacc   2820
ttcaacatca ttgggaacga caggatgaag actaactacc atgataagct cgccgctatt   2880
gaaaaggaca gggactctgc caggaaggac tggaaaaaaa ttaacaatat taaagagatg   2940
aaggagggct acctgagccg agtagtccat gagatagcaa aactggtgat tgagtacaac   3000
gcaatagtcg tattcgagga cttaaacttc ggcttcaaac gtgggcggtt taaggtggag   3060
aaacaagtct atcagaaatt ggagaagatg ctaatcgaga agctcaacta cctcgtgttt   3120
aaagacaacg agtttgacaa aactggagga gtcctgcggg cataccaact gaccgcaccc   3180
ttcgaacat tcaagaagat gggaaagcag actggcatca tctattacgt gccagcgggt   3240
tttacttcca aaatctgtcc agttacaggc ttcgtgaacc agttgtaccc gaagtacag   3300
tctgtttcca agtcacagga attcttctca agtttgaca agatatgtta caatctcgat   3360
aagggatact ttgagtttag tttcgactac aagaactttg gcgataaggc cgcaaaaggg   3420
aaatgacaa ttgcatcctt cgggtcacgc cttattactt ttcgtaactc agacaagaac   3480
cacaattggg acaccaggga ggtgtaccct actaaggagc tggagaagct acttaaagac   3540
tactcgattg agtacggaca tggagagtgc atcaaggcag caatatgtgg ggaatctgac   3600
aaaagttct ttgccaagct gacctctgta ctgaacacta ttctccaaat gagaaatagt   3660
aagactggca cagagttgga ctacctgatc tctccagtg ctgacgttaa tgggaatttt   3720
ttcgactcaa gacaagctcc caagaatatg ccacaggacg cagatgcaaa cggggcatat   3780
cacatcgggc ttaaaggact catgctacta gggcggatca agaataatca ggagggcaaa   3840
aagctgaacc tagtcatcaa gaacgaggag tacttcgaat tgtccagaa tcgtaacaac   3900
```

SEQ ID NO: 46          moltype = DNA  length = 3900
FEATURE                Location/Qualifiers
misc_feature           1..3900
                       note = Synthetic polynucleotide.Codon optimized FnCpf1-CO2
source                 1..3900
                       mol_type = other DNA
                       organism = synthetic construct
SEQUENCE: 46

```
atgtccatat accaggagtt cgtcaacaag tactcgctca gcaagacgct ccgcttcgag    60
ctgatccccc agggtaagac cctggagaac atcaaggcgc gcggactcat cctcgacgac   120
gagaagcggg ctaaggacta caaaaaggcc aagcagatca tcgacaagta ccaccagttc   180
ttcatcgagg agatcctctc ctccgtctgc atctccgagg acctcctcca gaactacagc   240
gacgtctact tcaagctcaa aaagtcggac gacgacacca tccagaagga cttcaagtcg   300
gcgaaggaca ccatcaagaa gcagatcagc gagtacatca aggactccga gaagttcaag   360
aacctgttca accagaacct gatcgacgcc aagaagggcc aggagtcgga cctgatcctg   420
tggctcaaga gagcaagga caacggcatc gagctcttca aggccaacag cgacatcacg   480
gacatcgaag aggccctgga gatcatcaag tcgttcaagg gctggaacga ctacttcaag   540
ggcttccacg agaaccgcaa gaacgtctat agctccaacg acatcccac ctcgatcatc   600
taccggatct ggacgacaa cctccccaag ttcctggaga caaggcgaa gtacgagtcg   660
ttgaaggaca aggcgccgga ggcgatcaac tacgagcaga tcaagaagga cctggccgag   720
gagctgacct tcgacatcga ctacaagacg tcggaggtga accagcgggt gttcagtcg   780
gacgaggtct tcgagatcgc gaacttcaac aactacctga accagtcggg gatcaccaag   840
ttcaacacga tcataggcgg caagttcgtg aacggcgaga acaccaagcg caaggggata   900
aacgagtaca tcaacctgta cagccagcag atcaacgaca gacgctcaa gaagtacaag   960
atgagcgtgc tcttcaagca gatcctcagt gacaccgagt ccaagagctt cgtgatcgac  1020
aagctggagg acgacagcga cgtcgtgaca accatgcaga gcttctacga gcagatcgcc  1080
gcgttcaaga ccgtcgagga gaagtcaatc aaggagacgc tctccttgct gttcgacgac  1140
ctgaaggcac aaaagctgga cctcagcaag atctacttca gaacgacaa gtccctgacc  1200
gacctgagcc agcaggtttt cgacgactac tccgtcatcg ggactgccgt cctggagtac  1260
atcacccagc agatcgctcc gaagaaccctc gacaacccgt ccaagagga gcagagctg  1320
attgcgaaga agacagagaa ggccaagtac ctctccctcg agaccatcaa gctcgccctg  1380
gaggagttca acaagcacag ggacattgac aagcagtgcc gtttcgagga gatcctggcc  1440
aacttcgcgc ccatccccat gatcttcgac gagatcgccc agaacaagga caacctggcg  1500
cagatctcta tcaagtacca gaaccagggg aagaaggact tgctccagcc ctcagcggag  1560
gacgacgtga aggccatcaa ggacctgctc gaccagacga caacttgct ccacaagctc  1620
aagatctttc acatcagcca gagcgaggac aaggccaaca tcctcgacaa ggacgagcac  1680
ttctacctcg tgttcgagga gtgctacttc gagctggcca catcgtgcc actttacaac  1740
aagatccgca actacatcac gcagaagcg tactccacg agaagttcaa gctgaacttc  1800
gagaactcca ccctcgccca cggctgggac aagaacaagg acggacaa caccgcgatc  1860
ctgttcatca aggacgacaa gtactacttg ggggtcatga caagaagaa caacaagata  1920
ttcgacgaca aggccatcaa ggagaacaag ggggaggct acaagaagat cgtctacaag  1980
ctcctccccg cgcgaacaa gatgctgcct aaggtcttct tttccgccaa gagtatcaag  2040
ttctacaacc cctccgagga catcctccgc atccggaacc acagcacgca cacaaagaac  2100
ggctcgctc agaagggcta cgagagtttc gagttcaaca tcaagagcgg ctgcgaagtc  2160
atcgacttct acaagcagag catctccaag cacccggagt ggaaggactt ggcttcagg  2220
ttctcagaca cccagcggta caactccatc gacgagttct accgcgaggt ggagaaccag  2280
ggctacaagc tgaccttcga gaatatatca gagtcgtaca tcgacagcgt ggtgaaccag  2340
gcaagttgt acctgttcca gatctacaac aaggacttct ccgcctactc aaggggcgt  2400
ccaaacctgc acacgctgta ctggaaggcg ctcttcgacg agcgcaacct acaagatgtt  2460
```

```
gtatacaagc tcaacggcga ggcggaactg ttctatagga agcagtcgat ccccaagaag  2520
attacgcacc cggctaagga ggccatcgcc aacaagaaca aggacaaccc caagaaggag  2580
tccgtgttcg agtacgacct catcaaggac aagaggttca cggaggacaa gttttcttc   2640
cactgcccaa tcactatcaa tttcaagtcg agcggagcca acaagttcaa cgacgagata  2700
aacctgctcc tcaaggagaa ggccaatgac gtgcacatcc tctccatcga ccggggcgag  2760
cggcacctgg cgtactacac gctggtggac ggcaagggca acatcatcaa gcaggacacc  2820
ttcaacatca tcgggaacga ccgcatgaag accaactacc acgacaagct cgccgccatc  2880
gagaaggaca gggactccgc gcgcaaggac tggaagaaga ttaacaacat caaggagatg  2940
aaggagggct acctcagcca ggtggtccac gagatcgcca agagctcgtc at tgagtacaac  3000
gccatcgtcg tcttcgagga cctgaatttc ggcttcaagc gcggccggtt caaggtggaa  3060
aagcaggtct accagaagct tgagaagatg ctgatcgaga agctgaacta cctggtgttc  3120
aaggacaacg agttcgacaa gaccggcgga gtgctgcgcg cctaccagct cacggcgcct  3180
ttcgagacgt tcaagaagat gggcaagcag acgggcatca tctactacgt gcccgccggc  3240
ttcacctcta agatctgccc agtgaccggc ttcgttaacc agctgtaccc gaagtacgag  3300
agcgtgtcca gtcccaggga gttcttctcc aagttcgaca agatttgtta caacctcgac  3360
aagggctact cgagttttc gttcgactac aagaactttg gcgacaaggc ggccaagggg  3420
aagtggacca tcgcctcttt cggcagcagg ctcatcaatt tccggaactc cgacaagaac  3480
cacaactggg acacgcgcga ggtgtacccg acgaaggagc tggagaagct gctcaaggac  3540
tactccatcg agtacggcca cggcgagtgc atcaaggcgg cgatctgcgg ggagagcgac  3600
aagaagttct tgccaagct gaccagcgtg ctgaacacca tcctccagat gcggaactcc  3660
aagaccggca ccgagctgga ctacctgatc tccccggtcg cggacgtcaa cgggaacttc  3720
ttcgactccc gacaggctcc caagaacatg cccaaggacg ccgagcgcga ggcgcgtac  3780
cacatccggcc tcaagggcct gatgctgctg gggcgcatca agaacaacca ggagggcaag  3840
aagctgaacc tcgtgatcaa gaacgaggaa tacttcgagt tcgtgcagaa ccgcaacaac  3900
```

```
SEQ ID NO: 47          moltype = DNA   length = 3900
FEATURE                Location/Qualifiers
misc_feature           1..3900
                       note = Synthetic polynucleotide.Codon optimized FnCpf1-CO3
source                 1..3900
                       mol_type = other DNA
                       organism = synthetic construct
SEQUENCE: 47
atgagcatct accaggagtt cgtgaacaag tacagcctgt cgaagaccct ccggttcgag  60
ctgatccctc aggggaagac gctggagaac atcaaggcgc gcggcctcat cctcgacgac  120
gagaagcggg cgaaggacta caaaaaggca aagcagatca tcgacaagta ccaccaattc  180
tttattgagg agatcctcag ctccgtctgc atcagcgagg acttgctcca gaactactcc  240
gacgtctatt tcaagctcaa gaagtcagac acgacaaacc tccagaagga cttcaagtcc  300
gcgaaggaca cgatcaaaaa gcagatcagc gagtacatcc aggagaagat caagaagttcaag  360
aacctcttca accagaacct gatcgacgcc aagaagggcc gggaatcgga cctcatcctg  420
tggctcaagc agtcgaagga caacggcatc gagctgttca aggccaactc cgacatcacc  480
gacatcgacg aggcgctgga gatcatcaag tcgttcaagg ggtggaccac ctacttcaag  540
ggcttccacg agaaccgcaa gaacgtttac tccagcaagg acatcccac ctcgatcatc  600
taccggatcg tggacgacaa cctgcccaag ttcctggaga caaggccaa gtacgagtcc  660
ctcaaggaca aggccccgga ggcgatcaac tacgagcaga ttaaaaagga ccttgctgag  720
gagctgacct tcgacatcga ctacaagacc tccgaggtga accagcgggt gttcagcctc  780
gacgaggtgt tcgagatcgc caacttcaac aactacctga accagtccgg gatcaccaag  840
ttcaacacga tcatcggcgg gaagttcgtc aacgcggaga acacgaagcg aagggcatc  900
aacgagtaca tcaacctcta cagccagcag atcaacgaca agaccctcaa aaaatacaaa  960
atgtcggtcc tgttcaagca gatcctgtcc gacaccgagt ccaagagctt cgtcatcgac  1020
aagctggaga acgactccga cgtcgtgacc accatgcagt ccttctacga gcagatcgct  1080
gccttcaaga ccgtggagga aggtccatc aaggagaccc tcagcctcct cttcgacgac  1140
ctcaaggcgc agaagctgga cctctccaag atatacttca gaacgacaa gagcctcacc  1200
gacctgtccc agcaagtatt cgacgactac agcgtgatcg gacggcggt gctggagtac  1260
atcccagcc agatagcgcc caagaacctg gacaaccccc tccaagaaaga acaggagctg  1320
attgctaaaa agaccgaaaa ggctaagtac ctgtccctgg agaccatcaa gctccgctg   1380
gaggagttca acaagcaccg ggacatcgac aagcagtgcc ggttcgagga gatcctagca  1440
aacttcgccg cgatccccat gatcttcgac gagatcgccc agaacaagga caacctggcc  1500
cagatcgaca tcaagtacca gaacccaggc aagaaggcc ttcttcaagc tagtgccgag  1560
gacgacgtga aggcgattaa ggatctgctc gaccagacca caacctgct ccacaagag  1620
aagatattcc acatctccca gtccgaggac aaggccaaca tcctggacaa ggacgagcac  1680
ttctacctgg tgttcgagga gtgctacttc gagctggcca acatcgtgcc gctgtacaac  1740
aagatccgga actacatcac ccagaagccc tactccgacg agagttcaa gctgaacttc  1800
gagaactcca ccctggccga cgggtgggac aagaacaggc cacgccatc                1860
ctcttcatca aggacgacaa atattatctg ggcgtcatga caaaaagaa caacaagata   1920
ttcgatgaca aggcgatcaa ggaaacaag gcgagggct acaagaaat agtatataaa     1980
ctactgcccg cgcgaacaa gatgctcccg aaggtgtttt ttagtgcaaa gtctattaag    2040
ttctacaacc ccagcgagga catcctccgc atccggaacc acgacacga caccaagaac   2100
ggcagcccac agaagggcta cgagaagttc gagttcaaca tcgaggactg ccgcaagttc  2160
atcgacttct acaagcagtc catctccaag caccccgagt ggaaggactt cgggttccgg   2220
ttcagcgaca cccagcgcta caacagcatc gacgagttct acgggaggt cgagaaccag    2280
gggtacaagc tgacgttcga gaacatctcc gagagctaca tcgacagcgt ggtgaaccag  2340
gggaagctgt acctgttca gatatacaac aaggacttct cagcctacag caaggggcgg   2400
ccgaacctga cacccctgta ctggaaggcc gtgttcgacg agcgaaactt ccaggagctc   2460
gtgtacaagc tcaacggcga ggcggagctg ttctaccgga agcagtccat ccccaaaaag  2520
attactcacc ccgcgaagga ggccatcgcc aacaagaaca aggacaaccc caaaaaggaa   2580
tcagtgttcg agtacgacct catcaaggac aagcgcttca ccgaggacaa attcttcttt  2640
cactgcccga tcacgatcaa cttcaagtcc tccggggcga caagttcaa cgacgagatc    2700
aacctgctgc tcaaggagaa ggccaacgac gtgcacatcc tcagcatcga ccggggcgag  2760
```

```
cgccacctgg cctactacac cctggtggac gggaagggca acatcataaa gcaagatacc 2820
ttcaacatca tcgggaacga ccggatgaag acgaactacc acgacaagct ggcggccatc 2880
gagaaggacc gggacagcgc ccgcaaggac tggaaaaaga taaacaacat taaggagatg 2940
aaggagggct acctgtccca ggtggtccac gagatcgcca agctcgtcat cgagtacaac 3000
gccatcgtcg tgttcgagga cttgaacttc ggggttcaag ggggccggtt caaggtggag 3060
aaacaagtct atcaaaagct ggagaagatg ctcatcgaga agctcaacta cctcgtgttc 3120
aaggacaacg agttcgacaa gaccggcggc gtcctgcggg cctaccagct caccgcgccg 3180
ttcgagacgt tcaagaagat ggggaagcag acggggatca tctactacgt ccccgccggg 3240
ttcaccagca agatatgccc ggtcacgggg ttcgtcaacc agctctaccc caagtacgag 3300
tcggtgagca agagccagga gttcttcagc aagttcgaca agatctgcta caacctggac 3360
aagggctact tcgagttctc gttcgactac aagaacttcg gggacaaggc ggcgaagggc 3420
aagtggacca tcgccagctt cggctcccgc ctcatcaact tccggaactc ggacaagaac 3480
cacaactggg acacccgcga ggtgtacccc acgaaggagc tggagaagct gctcaaggac 3540
tacagcatcg agtacgggca cggcgagtgc atcaaggccg ccatctgcgg ggagtccgac 3600
aagaaattct ttgccaagct gacctccgtg ctgaacacca tcctccagat gcggaacagc 3660
aagaccggga ccgagctgga ctacctgatc tccccggtcg ccgacgtcaa cggcaacttc 3720
ttcgattctc gccaggctcc caagaacatg ccccaggacg ccgacgccaa cggggcctac 3780
cacatcgggc tcaagggcct catgctgctc gggcggatca agaacaacca ggagggcaag 3840
aaactcaacc tggtcatcaa gaacgaggag tactttgagt tcgtccagaa ccggaacaac 3900
```

SEQ ID NO: 48  moltype = DNA  length = 3900
FEATURE        Location/Qualifiers
misc_feature   1..3900
               note = Synthetic polynucleotide.Codon optimized FnCpf1-CO4
source         1..3900
               mol_type = other DNA
               organism = synthetic construct
SEQUENCE: 48

```
atgagcatct accaggagtt cgtgaacaag tacagcctga gcaagaccct gcgcttcgag 60
ctgattcctc aggggaagac cctggagaac atcaaggcgc gcggcctgat cctggacgac 120
gagaagcggg cgaaggacta caaaaaggcg aagcagatca tcgacaagta ccatcagttt 180
ttcatcgagg agattctcag ctccgtgtgc atcagcgaag acctgctcca gaactacagc 240
gacgtttact tcaagctcaa gaaatcggac gacgacaacc tccagaagga cttcaagagc 300
gcgaaggaca cgattaagaa acagatcagc gagtacatca aggactccga gaagttcaag 360
aacctgttca accagaacct catcgacgcc aagaaaggcc aagagtcgga cctcatcctc 420
tggctcaagc agagcaagga caacggcatc gagctgttca aggcgaacag cgacatcacc 480
gacatcgacg aggcgctgga gatcatcaag tcgttcaagg gctggacgac ctacttcaag 540
ggcttccacg agaaccgcaa gaatgtctac tcgagcaacg acatccccac gtcgatcatc 600
taccgcatcg tggacgacaa cctcccgaag ttcctgaaga acaaggcgaa gtacgagagc 660
ctcaaggaca aggccccgga ggccatcaac tacgagcaga tcaaaaagga tttggctgag 720
gagctgacgt cgacatcga ctacaagacc tcgaggtga accagcgcgt cttcagcctc 780
gacgaggtgt tcgagatcgc caacttcaac aactacctca accagtcggg catcaccaag 840
ttcaacacca tcatcggcgg gaagttcgtc aacggcagaa acgaaggcg caaggggatc 900
aacgagtaca tcaacctgta cagccagcag atcaacgaca agaccctcaa gaagtataaa 960
atgtcggtgc tgttcaagca gatcctctcg gacaccgaga gcaagtcgtt cgtcatcgac 1020
aagctggagg acgacagcga cgtggtgacc accatgcaga gcttctacga gcagatcgcg 1080
gccttcaaga ccgtcgagga gaagtcgatc aaggagcgc tcagcctgct gttcgacgac 1140
ctcaaggccc agaagctcga cctgtccaag atatacttta agaacgacaa gagcctcacg 1200
gacctgtccc agcaggtatt cgacgactac agcgtgatcg ggacggccgt gctggagtac 1260
atcacccaac agatcgcgcc caagaacctg gacaacccgt ccaagaagga acaagagcta 1320
atcgccaaaa agactgagaa ggcgaagtac ctgtcgctgg agacgatcaa gctcgcgctt 1380
gaggagttta acaagcaccg cgacatcgac aagcagtgcc ggttcgagga gatcctggcc 1440
aacttcgcgg cgatcccgat gatcttcgac gagatcgccc agaacaagga caacctggcg 1500
cagatcagca tcaagtacca gaaccaggc aaaaagact tgctccaagc tagtgcggag 1560
gacgcgtga aggcgattaa ggatctgctg gaccagacta acatctgct gcacaagctc 1620
aagatctttc acatctctca gtcggaggac aaggcgaaca tcctggacaa ggacgagcac 1680
ttctacctag tgttcgagga gtgctacttc gagctggcga acatcgtgcc cctgtacaac 1740
aagatccgga actacatcac ccagaagccc tacagcgacg agaagttcaa gctgaacttc 1800
gagaacagca cgctggtgac cggggtgggac aagaacaagg agcccgacaa caccgccatc 1860
ctgttcatca aggacgacaa atattacctc gccgtcatga caaaaagaa taacaagata 1920
ttcgatgaca aggcgatcaa ggagaacaag ggcgagggct acaagaagat cgtatataaa 1980
ctcctgccgg gagcgaacaa gatgctcccg aaggttttct tagtgccaa gtccatcaag 2040
ttctacaacc cagcgagga catcctccgc atccggaacc actccaccca caccaagaac 2100
ggctcgccgc agaagggcta cgagaagttc gagttcaaca tcgagttcag cgacagcggc 2160
atcgacttct acaagcagtc catctccaag caccccgagt ggaaggactt cgggttccgg 2220
ttctccgaca cgcagcgcta caactccatc gacgagttct accgggaggt ggagaaccag 2280
ggctacaagc tgacgttcga gaacatctcg gagtcctaca tcgactccgt ggtcaaccag 2340
ggcaagctgt acctcttcca gatatacaat aaggacttct ccgcctacag caaggggcgg 2400
cccaacctcc acaccctgta ctggaaggcg ctcttcgacg aggaacct ccaggacgtc 2460
gtgtacaagc tgaacggcga ggcggagctg ttctaccgca agcagagcat ccccaagaag 2520
atcacgcacc ccgcgaagga ggccatcgcc aacaagaaca aggacaaccc caagaaggaa 2580
tcggtcttcg agtacgacct catcaaggac aagcggttca gaggacaa attctttttc 2640
cactgcccga tcactattaa cttcaagtcc agcggcgcga caagttcaa cgacgagatc 2700
aacctgctcc tcaaggagga ggcgaacgac gtgcacatct cagcatcga tgcggggagag 2760
cgccacctcg cctactacac gctggtggac gggaagggca acatcatcaa gcaagacacc 2820
ttcaacatca tcggcaacga ccggatgaag accaactacc acgacaagct ggccgccatc 2880
gagaaggacc gcgactcggc ccgcaaggac tggaaaaaga tcaacaatat caaggagatg 2940
aaggagggct acctgagcca agttgtccac gagatcgcca agctggtgat cgagtacaac 3000
gccatcgtcg tgttcgaaga cctgaacttc ggcttcaagc gcggccggtt caaggtcgag 3060
```

```
aaacaagtct atcagaaact tgagaagatg ctgatcgaga agctgaacta cctcgtcttc 3120
aaggacaacg agttcgacaa gaccggcggc gtcctccgcg cgtaccagct caccgcgccg 3180
ttcgagacgt tcaagaaaat gggcaagcag accggcatca tctactacgt gcccgccggg 3240
ttcacgagca aaatatgtcc cgtgaccggc ttcgtcaacc agctctaccc caagtacgag 3300
tccgtgtcga agtcccagga attcttcagc aagttcgaca agatatgcta caacctggac 3360
aagggctact tcgagttctc cttcgactac aagaacttcg gggacaaggc ggcgaagggg 3420
aagtggacca tcgcctcgtt cgggtcgcgc ctcatcaact tccggaacag cgacaagaac 3480
cacaactggg acacccgcga ggtgtacccg acgaaggagc tggagaagct cctcaaggac 3540
tacagcatcg agtacggcca cggggagtgc atcaaggcgc ccatctgcgg cgagtcggac 3600
aaaaagttct ttgccaaact cacctcggtc ctcaacacca tcctccagat gcggaacagc 3660
aagacgggca cggagctgga ctacctcatc agcccggtgg ccgacgtgaa cggcaatttc 3720
tttgactcac gccaggcccc taagaacatg ccccaggacg ccgacgccaa cggcgcgtac 3780
cacatcggcc tcaagggcct gatgctgctc ggccggatca gaacaaccag ggagggcaag 3840
aagctcaacc tggtcatcaa gaacgaggag tatttcgagt tcgtccagaa ccgcaacaac 3900
```

SEQ ID NO: 49          moltype = DNA   length = 3900
FEATURE                Location/Qualifiers
misc_feature           1..3900
                       note = Synthetic polynucleotide.Codon optimized FnCpf1-CO5
source                 1..3900
                       mol_type = other DNA
                       organism = synthetic construct
SEQUENCE: 49

```
atgtccatat accaggagtt tgttaataaa tatagcttgt ccaaaacccct gcggtttgaa 60
ctcatacctc aggggaagac tttgagaat atcaaagcgc ggggactgat actgacgac 120
gaaaagcgcg caaaagatta caagaaagcg aaacagatca tcgataaata ccatcaattt 180
ttcatagagg agattctcag ttctgtctgt atcagtgagg acctcctcca aaattattca 240
gacgtctatt ttaaactcaa gaagtcggac gacgacaacc ttcagaaaga tttaagtca 300
gcaaaagaca caatcaaaaa acaaatatcg gaatacataa aggactcaga aaagttcaag 360
aatcttttta accaaaatct gatagacgcg aagaaaggc aggaatctga tcttatactc 420
tggcttaagc agtctaaaga caacggcata gaactctttta aggcaaacag cgatataacc 480
gacatagatg aagccctcga gataattaag tccttcaaag gctggactac atattttaaa 540
gggttccatg agaataggaa gaacgtgtat tcctcgaatg atattcccac ctcgataatc 600
taccggattg tggatgataa tctgcctaaa tttttggaaa ataaagcgaa gtacgaaagt 660
ttgaaagata aagcaccaga agcaattaat tatgaacaaa ttaagaaaga tctggctgag 720
gaacttacgt tcgatatcga ttataaaaca tcagaagtta atcagcgggt ttttagcctg 780
gatgaagttt tgagatcgc caacttcaac aattatctta atcagagcgg gattaccaaa 840
ttcaacacta ttatcggtgg taaattcgtt aatggtgaga cacaaagag aaaaggtata 900
aacgaataca taaatttgta cagtcaacag attaacgata aacttttgaa aagtacaaag 960
atgtcagtgc ttttcaaaca aatcctttcc gacacagaat ccaaaagttt tgtgatagac 1020
aaattggaag atgatagcga cgtcgtacg accatgcaat catttttatga gcaaattgca 1080
gccttcaaga cggttgagga aaaaagtata aagaaacgt tgtcgctctt gttcgacgac 1140
ctgaaagcac agaaattgga tttgtctaag atatacttta aaaacgacaa atccctcacg 1200
gacttgtcgc agcaagtctt tgatgattat tcggtgattg ggacagccgt gctcgaatac 1260
atcacccagc aaatcgctcc gaaaaatctg gacaatccgt ctaaaaaga gcaagagctg 1320
atcgcaaaga aaaccgaaaa agcgaaatac ctgtctctgg agacaatcaa attggccttg 1380
gaagagttca ataagcacag agacattgat aaacaatgtc ggttgaggga aattcttgct 1440
aactttgccg ctatcccgat gatcttcgat gagattgcgc aaaataagga taatctggcc 1500
caaatctcga tcaagtatca aaatcagggt aagaaggacc tgcttcaagc atcggcggag 1560
gatgatgtga agcgattaa ggacttgttg atcagacca caatttgtt gcacaagctg 1620
aagatattcc acatctccca gagtgaggat aaggccaaca tcctggacaa ggatgaacat 1680
ttctatttgg tcttcgaaga gtgttatttt gaattggcca acatagttcc tcttataac 1740
aagatccgca attatattac acaaaagcct tattccgatg aaaaatttaa acttaacttc 1800
gaaaatagca cattggcgaa tggttgggat aaaaataagg agcctgacaa tactgctata 1860
cttttcatta aggacgataa gtactacctc ggcgttatga caagaagaa taataagatc 1920
tttgacgaca agcaatcaa agagaacaaa ggcgaaggtt acaaaaaaat cgtgtacaaa 1980
ctcctgcctg gcgcgaataa aatgcttccg aaggttttttt tcagtgcgaa gtccattaag 2040
tttttataacc cttccgagga tatttgaga attagaaatc actccaccca taccaagaat 2100
ggcagccccc agaagggta tgaaaagttc gaatttaata tcgaagactg ccgcaagttt 2160
atagactttt ataaacagtc catatctaaa catcccgaat ggaaagattt tggtttccgg 2220
ttttctgaca ctcagaggta caacagcata atgagttct accgcgaagt tgaaaaccaa 2280
ggctacaagc ttacattgga aacatcagc gagtcatata ttgactcagt cgttaatcag 2340
ggcaaacttt atttgttcca aatttacaac aaagacttttt cagcgtacag caaggagg 2400
ccaaatctcc atacactgta ttggaagcg tcgtttgacg acgtcaatct tcaagatgtt 2460
gtgtataaac tcaacgggga ggccgaattg ttctacagga agcaaagcat tcctaagaaa 2520
attacccacc ccgctaagga agcgatagca aataaaata aagacaatcc gaaaaagag 2580
agcgttttg agtacgacct tataaaggat aagagattca ccgaggataa gttttcttc 2640
cactgtccaa taactattaa ctttaaatcc tccggagcca acaagtttaa cgacgaaatt 2700
aatttgctgc tgaaagagaa ggcgaacgac gttcacattc tgtcaataga cagaggggag 2760
agacacttgg catactacac gctcgttgat ggaaagggta acattattaa gcaagatact 2820
ttcaacatca ttgggaatga cagaatgaaa acaaactatc acgataaact cgcggcaatt 2880
gagaaggacc gggattcggc gaggaagac tggaagaaaa tcaacaatat aaaggagatg 2940
aaggaaggat acctgtctca agtcgtccac gaaaatagcca agcttgttat agagtataat 3000
gcgattgtgg tcttttgaaga ccttaacttt ggatttaaac gcgcccggtt taagtcgag 3060
aaacaagtgt atcaaaact ggaaaaaatg ttgatcgaga aactgaatta tctcgtcttc 3120
aaggacaacg agttcgataa aaccggggc gtcttgcgcg cttatcaact gacggcaccg 3180
tttgaaactt tcaagaagat gggcaaacag actgggatta tctactacgt tcctgccgga 3240
ttcacctcca aaatatgccc agttactgga tttgttaacc agttgtaccc taagtacgaa 3300
tcagtcagca agtcccaaga gttttttctca aaatttgata agatctgcta taacctggac 3360
```

```
aaggggtact tcgagttttc cttcgactat aaaaatttcg gcgacaaggc agctaaaggt  3420
aaatggacga ttgcaagttt cggctccagg cttattaatt tcagaaacag cgacaaaaac  3480
cataactggg acacgcgcga ggtctaccct acgaaggaac tggaaaaact tctcaaggat  3540
tacagtatag aatacggaca cggggagtgt atcaaagctg cgatatgcgg agagtcggat  3600
aaaaagtttt tcgcaaagtt gacatcagtt ttgaacacta tcttgcagat gagaaattcc  3660
aagactggca cggagttgga ctaccttatt agcccagtgg cggatgtcaa cgggaacttt  3720
tttgattcga ggcaagcccc taagaatatg cctcaagacg ctgatgcaaa cggggcatat  3780
cacataggac tcaaagggtt gatgctgctg ggcagaatta agaacaacca ggaaggaaag  3840
aagctcaatc ttgttatcaa aaatgaagag tactttgaat tcgttcaaaa ccggaataac  3900
```

| | | |
|---|---|---|
| SEQ ID NO: 50 | moltype = DNA length = 3900 | |
| FEATURE | Location/Qualifiers | |
| misc_feature | 1..3900 | |
| | note = Synthetic polynucleotide.Codon optimized FnCpf1-CO6 | |
| source | 1..3900 | |
| | mol_type = other DNA | |
| | organism = synthetic construct | |

SEQUENCE: 50
```
atgagtattt atcaagagtt cgttaataag tacagtcttt ctaagacgct caggtttgag  60
ctcattccac aaggtaagac ccttgagaat attaaagccc gcggactgat cctggacgac  120
gagaagcgcg ccaaagacta taagaaggcg aaacagatca tagataagta tcaccaattc  180
ttcatagaag agatacttag ctctgtttgt atctcagagg atctgctcca gaactactcg  240
gatgtgtact ttaaactcaa gaagtctgac gatgacaatc tccagaagga ctttaagtcc  300
gccaaagaca caatcaagaa gcagatttcg gaatacataa aggacagtga gaagttcaag  360
aacttgttca accagaatct catagacgcc aagaagggtc aggagagcga tcttattctg  420
tggttgaaac aatcaaagga caacggtatt gagttgttta agcaaacctc tgacatcacc  480
gacattgacg aggctctgga gatcattaag agtttttaaag ggtggacaac ctactttaag  540
ggatttcatg agaatcgcaa gaacgtgtac tcgagcaatg acatacctac aagcataatc  600
tatcggatag tcgacgataa cctcccgaag ttcctcgaga ataaagcgaa gtacgaatcg  660
cttaaggata aggcgccgga ggcgataaac tatgaacaga ttaagaagga tctggctgaa  720
gaattgacct tgatattga ctataagacc agcgaagtca accaacgcgt ttcagcctg  780
gatgaagtgt ttgagatcgc caacttcaat aattacttga atcaatcggg gataacaaag  840
tttaatacga ttatcggcgg gaagtttgtc acgggggaga acacaaagag gaagggcata  900
aatgagtaca ttaatctcta tagtcaacag ataaatgaca agcgttgaa gaaatacaag  960
atgtcagtcc ttttcaagca gatcctgtct gacacagaat cgaagagctt cgtgatagat  1020
aagctggaag atgattccga cgttgtcaca accatgcaat cgttttacga gcagatcgcg  1080
gccttcaaga ccgttgagga agagtctatt aagagagatc tttctcttct gtttgatgac  1140
ttgaaggccc agaagcttga cttgtccaag atctacttca agaacgataa atctctgaca  1200
gatctcagcc agcaagtgtt tgacgactat tctgttatcg gaacggcgt gctggagtac  1260
atcacacagc agatcgcgcc taagaacctt gataatccga gcaagaaaga acaggagttg  1320
attgcaaaga agacagagaa ggccaaatac ctttctctgg agacaattaa acttgcactg  1380
gaagaattca ataagcacag agatatcgac aagcagtgtc gctttgagga gatcctggca  1440
aattttgctg ccatcccaat gatttttgat gagattgccc agaacaagga caatctcgga  1500
cagatatcaa tcaagtatca gaaccaaggc aagaaggacc tcctgcaagc ctcagccgaa  1560
gatgacgtta aggccataaa ggatctcctt gatcagacca ataacttgct gcacaagctg  1620
aagatctttc atatcagcca gtcggaagac aaagcaaata tccttgacaa ggacgagcat  1680
ttctatctgg tgttcgaaga aatgctatttc gagctgccca acgtc tctgtacaat  1740
aagatccgca attatatcac gcagaagccg tatagcgacg agaagttcaa gctgaatttc  1800
gagaactcca ccttggccaa tggttgggat aagaacaaag aaccggacaa tacggccatc  1860
ttgtttatca agatgacaa gtactatctg ggagtgatga ataagaagaa caataagatc  1920
ttcgatgaca aagccattaa ggagaataaa ggggaaggtt acaagaaagat tgtctataaa  1980
ctgctccccg gggccaacaa gatgctgccc aaagtttttt tcagtgccaa gagcatcaag  2040
tttttataatc cctcagaaga catactgaga atcagaaacc actcgaccca taccaagaac  2100
ggctctccgc agaaggggta cgagaaattc gaattcaaca tcgaagactg tagaaagttc  2160
atcgattttt acaagcaatc gatatcaaag caccctgaat ggaaggattt tggttttcgc  2220
tttagtgaca ctcagcggta taatagcatt gatgagttct accgcgaagt tgagaatcag  2280
ggatacaaat tgacattcga gaatatcagc gaatcgtaca ttgatagcgt cgtcaaccag  2340
gggaaacttt acctcttcca gatttataat aaagactt ct cggcgtactc caagggaaga  2400
ccaaatcttc atactcgtta ttggaaggca ctcttcgatg agaaaatct tcaggatgc  2460
gtttataaac ttaatgggga agcggagctg ttctaccgca agcagagcat ccctaagaag  2520
atcacgcacc ccgcgaagga ggcgatagcc aataagaaca aggataaccc gaagaaggag  2580
tccgtcttcg aatatgacct gatcaaggat aagagattca ctgaggacaa attcttcttc  2640
cattgcccta ttacgattaa ttttaaatcg agcggcgcga ataaattcaa cgacgagatc  2700
aaactgctcc tcaaagagaa ggccaatgat gtccacattc tctcaatcga cagaggggag  2760
aggcaccttg cctactatac gctcgttgat ggtaaaggta acatcattaa gcaggacacg  2820
ttcaacatca tcgggaacga ccgcatgaag acaaactatc tcgataaatt ggcggcaatc  2880
gagaaggatc gggatagtgc caggaaggac tggaagaaga ttaataacat caaggagatg  2940
aaggagggat atctttctca gtcgtccac gagatgcgca agctggttat cgatacaac  3000
gccatagtgg tcttcgaaga tctgaacttc ggattcaaga gagggagatt taaggtggac  3060
aagcaagttt atcagaaact ggagaagatg ctgatagaga gctcaacta cctcgtgttt  3120
aaagacaacg agtttgacaa gacagtgggg gtgttgaggg cctatcagct cacggccccc  3180
ttcgagacct tcaagaagat gggaaagcag acggggataa tctactacgt ccctgctggc  3240
ttcacttcga gatctgcccc agttacagga ttcgttaacc agttgtatcc caaatacgag  3300
tccgtctcaa agtcacaaga attcttttct aaattcgata agatctgcta caactggat  3360
aagggctact tcgagtttag ctttgactat aagaattcg gggacaaagc ggcaaggggg  3420
aagtggacaa tcgcaagttt tggctcccgg ctgattaact ttcggaattc tgacaagaat  3480
cacaactggg atactagaga ggtctatcca actaaagagt tggagaagtt gctcaaggac  3540
tactccattg aaatatggtc acggggaatgc attaaagcgg ccatctgcgg agagtccgat  3600
aagaagttct ttgccaaaact tacatcggtc ttgaacacca tactgcagat gcggaacagc  3660
```

```
aagacgggaa cggaactcga ctaccttatc tcacctgtgg cggatgttaa tggaaacttt     3720
ttcgattcga ggcaggcgcc caagaacatg ccgcaagatg cagatgccaa tggagcatat     3780
cacatcggtc ttaaagggct catgctgctt ggccgcatca agaacaacca agaggggaag     3840
aagttgaacc tggttattaa gaacgaagaa tacttcgaat tgtccagaa ccgcaacaac      3900
```

SEQ ID NO: 51          moltype = DNA   length = 3900
FEATURE                Location/Qualifiers
misc_feature       1..3900
                       note = Synthetic polynucleotide.Codon optimized FnCpf1-CO7
source               1..3900
                       mol_type = other DNA
                       organism = synthetic construct
SEQUENCE: 51
```
atgtccatct atcaggaatt tgttaacaag tactctctta gcaaaactct taggttcgaa       60
ttgataccte agggaaagac acttgagaat attaaggcgc gcgggctgat acttgatgat      120
gaaaagcggg caaggactca taagaaagct aagcaaataa ttgataagta ccaccagttt      180
tttattgaag agatcctgtc ctccgtttgt atatccgaag acttgcttca gaattactca      240
gatgtttatt ttaaattgaa gaaatctgac gatgataatc ttcaaaagga tttcaaatcg      300
gcaaaagaca caatcaaaaa acagattagc gagtacatca aggactccga aaagtttaag      360
aatctctttta tcagaatctt tatagacgca aagaaaggac aggaatcgga cttgattttg      420
tggttgaagc agtccaagga taacgggata gaactcttta agccaactc cgatataacg       480
gacatcgacg aagccctcga aatcattaag tcgtttaagg gttggaccac gtacttcaaa      540
ggattccacg agaacagaaa gaacgtttac tcgagcaacg acattcctac tagcatcata      600
tatagaaatg tggatgataa tttgcccaaa ttccttgaga caaggcaaa atatgaatcc       660
ctgaaagaca aggcgcccga agctatcaac tacgagcaga taagaaaga tctggctgag       720
gagctgacgt ttgacattga ttacaaaaca agcgaggtca accagaggt ttttttcgctg      780
gacgaggtt ttgaaatagc gaatttaat aactacctga ccaatccgg catcactaaa         840
tttaacacaa tcataggggg gaagttcgtg aacggagaga acacaaagcg caaagggatt      900
aatgagtaca tcaatttgta cagccagcag atcaatgaca aacgttgaa gaaatataag       960
atgagcgtct tgtttaagca gattctctcg gatacgagat ccaaatcatt cgtcattgac    1020
aagctggagg atgacagcga tgtggtgaca actatgcagt ccttctatga caaaattgca    1080
gcttttaaaa cggtcgaaga gaagtcgatt aagaaacgc tttcgctcct gttcgatgac     1140
ctgaaagcgc agaagctgga ccttttcgaag atatatttca aaaacgataa gtcactcacg    1200
gaccttagcc aacaggtttt cgatgactat tctgtcatag ggactgctgt gcttgagtat    1260
attactcagc aaaatagcccc caaaaacctg gacaacccgt ctaagaagga acaagagctg    1320
atagcgaaga aaacagagaa agctaaatat cttttcactt gaaactataa agcttgcactg    1380
gaggaattca caaacatcg cgacatcgac aagcagtgca gatttgagga gatcttggcc      1440
aacttcgcag ctattccaat gatttttgac gagatagcac agataaagga caacctggca    1500
cagattagca taaaatacca gaatcagggg aagaaggatc ttcttcaggc ttcggctgag    1560
gacgatgtca agccatcaa agatctgctc gaccagacca caatttgttt gcataaactc     1620
aagatcttcc acatatcgca gtccgaagat aaagcgaaca tacttgacaa agacgaacat    1680
tttttatcttg ttttcgagga gtgttatttt gagttggcaa acatcgttcc cctctacaac   1740
aaaattcgca actatataac tcagaagcc tattctgacg agaaattcaa acttaattc       1800
gaaaacagca ctctcgcaaa cggctgggat aaaaacaagg aacccgacaa caccgccata    1860
cttttttatta aggatgataa atattatttg gcgtgatga ataaaagaa caataaaata     1920
ttcgatgata aagcaattaa ggaaaataaa ggggaagggt atgaaaaaat cgtgtataag    1980
ctgcttccag gagctaataa aatgctgcca aaagtcttct tctctgccaa gtcgatcaag   2040
ttttacaatc cttctgaaga tatttgcgg atcagaaatc actctactca cactaaaaac   2100
ggttcacccc agaaaggata cgagaagttt gagttcaaca tcgaagactg tcggaagttt    2160
atcgactttt acaagcagtc tatatcaaaa caccccgaat ggaaagattt tggtttttcgg  2220
ttcagcgaca cgcagagata taattcaatt gatgagttct acagggaggt gggagaaccaa  2280
gggtataaac ttacttttga gaacatttcc gaatcctata ttgattcggt ggtcaatcag    2340
gggaaactgt acctgtttca gatatataac aaagactct ccgcgtattc taaaggacgg    2400
cccaatctcc atactcttta ttggaaggcg ctgtttgacg agcggaacct tcaggatgtt    2460
gtctataagt tgaacgggga agctgagctg ttctatcgga acagtctat tccaaaaaag   2520
ataacgcacc ccgcgaagga ggcaattgca aacaagaaca aagacaatcc aagaaggag   2580
tcggtgtttg agtacgatct gataaaagac aaaaggttta ccgaggacaa gttttttttc    2640
cactgtccga tcaccatcaa ttttaagtct tccggcgcca acaaattcaa tgacgaaata    2700
aatctgctgc tcaaggaaaa ggcaaatgat gttcatattc tgtcgataga ccgcgggaa    2760
agacacctcg cgtattac attggtcgat gggaaaggca atattatcaa acaagacacc     2820
ttcaatatca ttggtaacga taggatgaaa acgaactatc atgataaact tgcagctatt    2880
gaaaaggaca gagactcggc tcggaaagat tggaaaaaga tcaataacat caaggaaatg    2940
aaggaagggt atctctccca gtcgttcat gaaatcgcca aactggttat tgagtacaat   3000
gctatagtgg tttttgaaga tcttaatttt gggtttaaga gggagatt taaagtcgag    3060
aaacaggttt atcaaaaact tgaaaaaatg ttgatagaaa aattgaacta tcttgtgttt    3120
aaggacaatg agttcgataa accgggggg gttttgagag cttatcaact gacggctccc    3180
ttcgagacat tcaaaaaaat gggggaagcag accggcatca tttattatgt gccgcgcggc   3240
ttcacttcta aaatttgtcc tgtgacaggg ttcgtgaacc aattgtaccc caagtacgaa    3300
agcgtctcca gtcccaaga atctcttagc aagtttgaca aaatttgcta taacctggac    3360
aaagggtact tgagttttc ctttgattat aagaatttcg gggataaagc tgcgaaggt     3420
aagtggacga tagcctcttt cgggtcgcgc cttattaact tcaggaattc cgacaaaaac    3480
cataattggg acacccgcga ggtctaccct acaaggaac tcgaaaagtt gcttaaggat    3540
tattcaatag agtatggtca tggcgagtgt ttaaggctg ctatctgtgg tgagtcagat   3600
aagaaattct tcgcgaaatt gacatctgtt ttgaacactta tcctccaaat gaggaactct   3660
aaaacgggga cggagcttga ttatctcatc tcacccgttg ctgatgtgaa cggtaatttc    3720
tttgattcac gccaagcccc gaagaacatg cccaagacg ccgatgctaa cggcgctat     3780
catataggc tgaagggct catgcttctg gggcgcatca aaaataacca agaagggaag     3840
aaactcaatc tggttatcaa aaatgaggaa tatttcgaat tcgtgcaaaa ccgcaacaat    3900
```

| SEQ ID NO: 52 | moltype = DNA length = 705 |
|---|---|
| FEATURE | Location/Qualifiers |
| source | 1..705 |
| | mol_type = unassigned DNA |
| | organism = Entacmaea quadricolor |
| SEQUENCE: 52 | |

```
gtgagcaagg gcgaggagaa taacatggcc atcatcaagg agttcatgcg cttcaaggtg   60
cgcatggagg gctccgtgaa cggccacgag ttcgagatcg agggcgaggg cgagggccgc  120
ccctacgagg gctttcagac cgctaagctg aaggtgacca agggtggccc cctgcccttc  180
gcctgggaca tcctgtcccc tcatttcacc tacggctcca aggcctacgt gaagcacccc  240
gccgacatcc ccgactactt caagctgtcc ttccccgagg gcttcaagtg ggagcgcgtg  300
atgaactacg aggacggcgg cgtggtgacc gtgacccagg actcctccct gcaggacggg  360
gagttcatct acaaggtgaa gctgcgcggc accaacttcc cctccgacgg ccccgtgatg  420
cagaagaaga ccatgggctg ggaggcctcc tccgagcgga tgtaccccga ggacggtgcc  480
ctgaagggca agatcaagat gaggctgaag ctgaaggacg gcggccacta cacctccgag  540
gtcaagacca cctacaaggc caagaagccc gtgcagctgc ccggcgccta catcgtcgac  600
atcaagttgg acatcacctc ccacaacgag gactacacca tcgtggaaca gtacgaacgc  660
gccgagggcc gccactccac cggcggcatg gacgagctgt acaag            705
```

| SEQ ID NO: 53 | moltype = DNA length = 4674 |
|---|---|
| FEATURE | Location/Qualifiers |
| misc_feature | 1..4674 |
| | note = Synthetic polynucleotide.NLS-FnCpf1-CO1-mOR-NLS |
| source | 1..4674 |
| | mol_type = other DNA |
| | organism = synthetic construct |
| SEQUENCE: 53 | |

```
ggtagcaaaa agaggcgtat caagcaggac atgtctatct atcaagagtt tgtcaacaag   60
tacagcttaa gtaagacact tcgcttcgag ttgatccctc aggggaagac actggaaaac  120
atcaaggcga ggggccttat cctgaaggac gagaagcggg ctaaagacta caaaaaagct  180
aaacagataa ttgacaagta tcaccaattg tttattgagg atcctctctc tctgtgtgc   240
ataagtgagg atctgctcca gaactattcg gatgtttact ttaaactcaa gaagtccgat  300
gatgacaacc ttcagaagga cttcaagtcc gccaaagaca cgattaagaa acaaatcagt  360
gagtacatca aggatagcga gaaattcaag aacctgttca accagaactt aattgatgcc  420
aaaaagggcc aagaatccga cctcatcctg tggttaaagc aatctaaaga caacggtatt  480
gagctgttca aggcaaacag cgacattaca gacattgacg aggccctaga gatcatcaag  540
tcattcaaag gctggacgac ttactttaaa ggttttcacg agaaccgtaa gaatgtttac  600
tcaagtaacg atataccaac gagcattatc taccgaatag tggatgataa cctaccgaag  660
ttccttgaga acaaagcgaa gtacagtctc tcaaagaca aggccctga ggccatcaae  720
tacgagcaga ttaagaagga tctgccgag gagctaacct tcgacattga ctacaaaaca  780
tcggaagtga atcagagggt gttctcgctt gatgaagtat tcgagattgc taacttcaac  840
aattacctga ccagagtgg tattactaag ttcaacacaa tcattggagg caaattcgtg  900
aacggcgaa acacaaagcg aaaagggata aacgagtaca ttaacttgta cagccagcag  960
atcaacgata agacactcaa gaagtataag atgtctgtgc tgttcaaaca aatcttaagc 1020
gacacggaaa gcaagtcgtt cgtaattgac aagctggaag acgattctga cgtggttaca 1080
accatgcagt cctttacga gcagattgcc gcattcaaga ccgtggagga aaagtcgatc 1140
aaggaaacac tttcgttgct tttcgacgac ctaaagctc agaagctcga cttaagcaag 1200
atatacttta agaacgataa gagcttgaca gacttgagcc agcaagtctt tgacgactac 1260
agcgttatcg gaactgccgt tctggagtac ataacacagc agatcgcacc caagaacctt 1320
gacaaccctt ccaagaaga acaagagttg atcgccaaga gactgaaaa ggctaagtac 1380
ctctctctgg agactatcaa gctcgctctt gaggagttta acaagcacag ggacattgga 1440
aagcaatgcc gattcgagga atactggca aacttcgcag ccataccat gatattcgat 1500
gagatagccc agaacaagga taacttggcc caaatctcga ttaagtatca gaaccagggc 1560
aaaaaggacc ttctacaggc tagtgcagag gacgatgtga aggctattaa ggacttatta 1620
gatcagacaa acaaccttct gcataagctc aagatattcc atatctccca gtcagaggac 1680
aaggccaaca ttctggataa ggacgagcac ttctatctcg tattcgagga atgttactt 1740
gagctggcca atatcgttcc cttgtacaac aaaatccgga actacatcac acagaagccc 1800
tacagtgatg agaagttcaa attgaacttt gaaaactcaa cacttgctaa tggttgggac 1860
aagaataagg aacctgacaa cactgccatc ctctttatta aagatgataa gtactacctc 1920
ggggtgatga ataagaagaa caacaaaatc ttcgatgaca aagctattaa ggagaacaaa 1980
ggtgaagggt acaagaagat tgtctacaaa ctgctgcctg tgccaacaa aatgctacca 2040
aagtattttt tcagcgccaa atcatacaag ttctacaatc caagcgagga tattctccgg 2100
atacggaatc actctacaca taccaagaat ggaagtccac aaaagggtta cgagaaattc 2160
gagttcaaca ttgaagactg ccggaaatc attgacttct acagcaatc catctctaaa 2220
catcctgaat ggaaagactt cggtttccgc ttcagtgata tcaacggta caattcaatt 2280
gacgaattct accgtgaggt tgagaaccag gggtacaaac tgaccttcga aacatatca 2340
gagagctaca tcgactcagt ggttaatcag gggaagctat atctgtttca aatctacaac 2400
aaagacttta gtgcctactc taaagggcgg ccaaacttac acacactta ctgaaggca 2460
ctattcgacg aacgcaatct acaagatgta gtttcaaat tgaacggtga ggctgagttg 2520
ttctaccgta aacaatctat acccaagaag ataacacacc ctgctaaaga ggcaattgca 2580
aacaaaaca aggataatcc caaaaggag tctgtctttg agtatgacct cattaaggat 2640
aagcggttca cggaggacaa gttcttcttc cattgtccaa taccatcaa cttcaaatca 2700
tccggcgcaa acaaattcaa tgacgagatc aacctgttac taaggagaa ggctaacgat 2760
gttcacatct tatcttattga tcgagggag agacacctgg tttagtggat 2820
gggaaggga acatcatcaa gcaagacacc ttcaacatca ttgggaacga caggatgaag 2880
actactacc atgataagct cgccgctatt gaaaaggaca gggactctgc caggaaggac 2940
tggaaaaaa ttaacaatat taaagagatg aaggagggct accgtagcca agtagtccat 3000
gagatacgaa actggtgat tgagtacaac gcaatagcg tattcgagga cttaaactc 3060
ggcttcaaac gtgggcggtt taaggtggag aaacaagtct atcagaaatt ggagaagatg 3120
```

```
ctaatcgaga agctcaacta cctcgtgttt aaagacaacg agtttgacaa aactggagga  3180
gtcctgcggg cataccaact gaccgcaccc ttcgagacat tcaagaagat gggaaagcag  3240
actggcatca tctattacgt gccagcgggt tttacttcca aaatctgtcc agttacaggc  3300
ttcgtgaacc agttgtaccc gaagtacgag tctgtttcca agtcacagga attcttctca  3360
aagtttgaca agatatgtta caatctcgat aagggatact ttgagtttag tttcgactac  3420
aagaactttg gcgataaggc cgcaaaaggg aaatgggaca ttgcatcctt cgggtcacgc  3480
cttattaact ttcgtaactc agacaagaac cacaattggg acaccaggga ggtgtaccct  3540
actaaggagc tggagaagct acttaaagac tactcgattg agtacggaca tggagagtgc  3600
atcaaggcag caatatgtgg ggaatctgac aaaaagttct ttgccaagct gacctctgta  3660
ctgaacacta ttctccaaat gagaaatagt aagactggca cagagttgga ctacctgatc  3720
tctccagtgg ctgacgttaa tgggaatttt ttcgactcaa gacaagctcc caagaatatg  3780
ccacaggacg cagatgcaaa cggggcatat cacatcgggc ttaaaggact catgctacta  3840
gggcggatca agaataatca ggagggcaaa aagctgaacc tagtcatcaa gaacgaggag  3900
tacttcgaat ttgtccagaa tcgtaacaac ggatctgaca tgagcaaggg cgaggagaat  3960
aacatggcca tcatcaagga gttcatgcgc ttcaaggtgc gcatggaggg ctccgtgaac  4020
ggccacgagt tcgagatcga gggcgagggc gagggccgcc cctacgaggg ctttcagacc  4080
gctaagctga aggtgaccaa gggtggcccc ctgcccttcg cctgggacat cctgtcccct  4140
catttcacct acggctccaa ggcctacgtg aagcaccccg ccgacatccc cgactacttc  4200
aagctgtcct tccccgaggg cttcaagtgg gagcgcgtga tgaactacga ggacggcggc  4260
gtggtgaccg tgacccagga ctcctccctg caggacggcg agttcatcta caaggtgaag  4320
ctgcgcggca ccaacttccc ctccgacggc cccgtgatgc agaagaagac catgggctgg  4380
gaggcctcct ccgagcggat gtaccccgag gacggtgccc tgaagggcga gatcaagatg  4440
aggctgaagc tgaaggacgg cggccactac acctccgagg tcaagaccac ctacaaggcc  4500
aagaagcccg tgcagctgcc cggcgcctac atcgtcgaca tcaagttgga catcaccctc  4560
cacaacgagg actacaccat cgtggaacag tacgaacgcg ccgagggccg ccactccacc  4620
ggcggcatgg acgagctgta caaggatctc aagaagcgta ggatcaagca agat         4674
```

```
SEQ ID NO: 54           moltype = DNA  length = 33
FEATURE                 Location/Qualifiers
misc_feature            1..33
                        note = Synthetic polynucleotide.MGSS7H His tag comprising
                         sevenHistidine residues
source                  1..33
                        mol_type = other DNA
                        organism = synthetic construct
SEQUENCE: 54
atgggcagca gccatcatca ccaccatcac cat                                  33

SEQ ID NO: 55           moltype = DNA  length = 4710
FEATURE                 Location/Qualifiers
misc_feature            1..4710
                        note = Synthetic
                         polynucleotide.MGSS7H-NLS-FnCpf1-CO1-mOR-NLS
source                  1..4710
                        mol_type = other DNA
                        organism = synthetic construct
SEQUENCE: 55
atgggcagca gccatcatca ccaccatcac catatgggta gcaaaaagag gcgtatcaag     60
caggacatgt ctatctatca agagtttgtc aacaagtaca gcttaagtaa gacacttcgc   120
ttcgagttga tccctcaggg gaagacactg aaaacatca aggcgagggg ccttatcctg    180
gacgacgaga agcgggctaa agactacaaa aaagctaaac agataattga caagtatcac   240
caattttttta ttgaggagat cctctcctct gtgtgcataa gtgaggatct gctccagaac   300
tattcggatg tttactttaa actcaagaag tccgatgatg acaaccttca gaaggacttc   360
aagtccgcca agacacgat taagaaacaa atcagtgagt acatcaagga tagcgagaaa    420
ttcaagaacc tgttcaacca gaacttaatt gatgccaaag agggccaaga atccgacctc   480
atcctgtggt taaagcaatc taaagacaac ggtattgagc tgttcaaggc aaacagcgac   540
attacagaca ttgacgaggc cctagagatc atcaagtcat tcaagggctg gacgacttac   600
tttaaaggtt ttcacgagaa ccgtaagaat gtttactcaa gtaacgatat accaacgagc   660
attatctacc gaatagtgga tgataaccta ccgaagttcc ttgagaacaa agcgaagtac   720
gagtctctca aagacaaggc ccctgaggcc atcaactacg agcagattaa gaaggatctc   780
gccgaggagc taaccttcga cattgactac aaaaacatcg gaagtgaatca gagggtgttc   840
tcgcttgatg aagtattcga gattgctaac ttcaacaatt acctgaacca gagtggtatt   900
actaagttca cacaatcat ggaggcaaa ttcgtgaacg cgaaaacac aaagcgaaaa      960
gggataaacg agtacattaa cttgtacagc cagcagataa acgataggca actcaagaag  1020
tataagatgt ctgtgctgtt caaacaaatc ttaagcgaca cggaaagcaa gtcgttcgta  1080
attgacaagc tggaagacga ttctgacgtg gttacaacca tgcagtcctt ttacgagcag  1140
attgccgcat tcaagaccgt ggaggaaaag tcgatcaagg aaacactttc gttgcttttc  1200
gacgacttca agctcagaa gctcgactta agcaagatat actttaagaa cgataagagc  1260
ttgacagact gagccagca gtctttgac gactacagcg ttatcggaac tgccgttctg  1320
gagtacataa cacagcagat cgcacccaag aaccttgaca cccttccaa gaaagaacaa  1380
gagttgatcg ccaagaagac tgaaaaggct aagtacctct ctctggagac tatcaagctc  1440
gctcttgagg agtttaacaa gcacagggac attgacaagc aatgccgatt cgaggaaata  1500
ctggcaaact tcgcagatat acccatgata ttcgatgaga tagcccagaa caaggataac  1560
ttggccccaaa tctcgattaa gtatcagaac agggcaaaa aggacttct acaggctagt  1620
gcagaggacg atgtgaaggc tattaaggac ttattagatc agacaaacaa ccttctgcat  1680
aagctcaaga tattccatat ctcccagtca gaggacaagg ccaacattct ggataaggac  1740
gagcacttct atctcgtatt cgaggaatgt tactttgagc tggccaatat cgttcccttg  1800
tacaacaaaa tccggaacta catcacacag aagcctacta gtgatgagaa gttcaaattg  1860
aactttgaaa actcaacact tgctaatggt tgggacaaga taaggaacc tgacaacact  1920
```

```
gccatcctct ttattaaaga tgataagtac tacctcgggg tgatgaataa gaagaacaac  1980
aaaatcttcg atgacaaagc tattaaggag aacaaaggtg aagggtacaa gaagattgtc  2040
tacaaactgc tgcctggtgc caacaaaatg ctaccaaagg tattttttcag cgccaaatct  2100
attaagttct acaatccaag cgaggatatt ctccggatac ggaatcactc tacacatacc  2160
aagaatggaa gtccacaaaa gggttacgag aaattcgagt tcaacattga agactgccgg  2220
aaattcattg acttctacaa gcaatccatc tctaaacatc ctgaatggaa agacttcggt  2280
ttccgcttca gtgatactca acggtacaat tcaattgacg aattctaccg tgaggttgag  2340
aaccaggggt acaaactgac cttcgagaac atatcagaga gctacatcga ctcagtggtt  2400
aatcagggga agctatatct gttttcaaatc tacaacaaag actttagtgc ctactctaaa  2460
gggcggccaa acttacacac actttactgg aaggcactat tcgacgaacg caatctacaa  2520
gatgtagttt acaaattgaa cggtgaggct gagttgttct accgtaaaca atctataccc  2580
aagaagataa cacaccctgc taaagaggca attgcaaaca aaaacaagga taatcccaaa  2640
aaggagtctg tctttgagta tgacctcatt aaggataagc ggttcacgga ggacaagttc  2700
ttcttccatt gtccaataac catcaacttc aaatcatccg gcgcaaacaa attcaatgac  2760
gagatcaacc tgttactaaa ggagaaggct aacgatgttc acatcttatc tattgatcga  2820
ggtgagagac acctagccta ctacacttta gtggatggga aggggaacat catcaagcaa  2880
gacaccttca acatcattgg gaacgacagg atgaagacta actaccatga taagctcgcc  2940
gctattgaaa aggacaggga ctctgccagg aaggactgga aaaaaattaa caatattaaa  3000
gagatgaagg agggctacct gagccaagta gtccatgaga tagcaaaact ggtgattgag  3060
tacaacgcaa tagtcgtatt cgaggactta aacttcggct tcaaacgtgg gcggtttaag  3120
gtggagaaac aagtctatca gaaattggag aagatgctaa tcgagaagct caactacctc  3180
gtgtttaaag acaacgagtt tgacaaaact ggaggagtcc tgcgggcata ccaactgacc  3240
gcacccttcg agacattcaa gaagatggga aagcagactg gcatcatcta ttacgtgcca  3300
gcgggtttta cttccaaaat ctgtccagtt acaggcttcg tgaaccagtt gtacccgaag  3360
tacgagtctg tttccaagtc acaggaattc ttctcaaagt ttgacaagat atgttacaat  3420
ctcgataagg gatactttga gttttagtttc gactacaaga actttggcga taaggccgca  3480
aaagggaaat ggacaattgc atccttcggg tcacgcctta ttaactttcg taactcagac  3540
aagaaccaca attgggacac cagggaggtg taccctacta aggagctgga gaagctactt  3600
aaagactact cgattgagta cggacatgga gagtgcatca aggcagcaat atgtgggaa  3660
tctgacaaaa agttctttgc caagctgacc tctgtactga acactattct ccaaatgaa  3720
aatagtaaga ctggcacaga gttggactac ctgatctctc cagtggctga cgttaatggg  3780
aattttttcg actcaagaca agctcccaag aatatgccac aggacgcaga tgcaaacggg  3840
gcatatcaca tcgggcttaa aggactcatg ctactagggc ggatcaagaa taatcaggag  3900
ggcaaaaagc tgaacctagt catcaagaac gaggagtact tcgaatttgt ccagaatcgt  3960
aacaacggat ctggagtgag caagggcgag gagaataaca tggccatcat caaggagttc  4020
atgcgcttca aggtgcgcat ggagggctcc gtgaacggcc acgagttcga gatcgagggc  4080
gagggcgagg gccgccccta cgagggcttt cagaccgcta agctgaaggt gaccaagggt  4140
ggccccctgc ccttcgcctg gacatcctg tcccctcatt tcacctacgg ctccaaggcc  4200
tacgtgaagc accccgccga catccccgac tacttcaagc tgtccttccc cgagggcttc  4260
aagtgggagc gcgtgatgaa ctacgaggac ggcggcgtgg tgaccgtgac ccaggactcc  4320
tccctgcagg acggcgagtt catctacaag gtgaagctgc gcggcaccaa cttcccctcc  4380
gacggccccg tgatgcagaa gaagaccatg ggctgggagg cctcctccga gcggatgtac  4440
cccgaggacg gtgccctgaa gggcgaagatc aagatgaagc tgaagctgaa ggacggcggc  4500
cactacaccct ccgaggtcaa gaccacctac aaggccaaga gcccgtgca gctgcccggc  4560
gcctacatcg tcgacatcaa gttggacatc acctcccaca acgaggacta caccatcgtg  4620
gaacagtacg aacgcgccga gggccgccac tccaccggcg gcatggacga gctgtacaag  4680
ggatctaaga agcgtaggat caagcaagat                                    4710
```

SEQ ID NO: 56          moltype = DNA  length = 6465
FEATURE              Location/Qualifiers
misc_feature       1..6465
                     note = Synthetic polynucleotide.Expression cassette
                     comprising 35Spromoter cassette,
                     MGSS7H-NLS-FnCpf1-CO1-mOr-NLS and NOStranscription
                     termination sequence
source               1..6465
                     mol_type = other DNA
                     organism = synthetic construct
SEQUENCE: 56

```
ggtccgattg agacttttca acaaagggta atatccggaa acctcctcgg attccattgc   60
ccagctatct gtcactttat tgtgaagata gtggaaaagg aaggtggctc ctacaaatgc  120
catcattgcg ataaaggaaa ggccatcgtt gaagatgcct ctgccgacag tggtcccaaa  180
gatggacccc cacccacgag gagcatcgtg gaaaagaag acgttccaac cacgtcttca  240
aagcaagtga attgatgtga tggtccgatt gagactttc aacaaagggt aatatccgga  300
aacctcctcg gattccattg cccagctatc tgtcactttat tgtgaagat agtggaaaag  360
gaaggtggct cctacaaatg ccatcattgc gataaaggaa aggccatcgt tgaagatgcc  420
tctgccgaca gtggtcccaa agatggaccc ccacccacga ggagcatcgt ggaaaaagaa  480
gacgttccaa ccacgtcttc aaagcaagtg gattgatgtg atatctccac tgacgtaagg  540
gatgacgcac aatcccacta tccttcgcaa gacccttcct ctatataagg aagttcattt  600
catttggaga ggacacgctg acaagctgac tctagcagat ctaccgtctt cggtacgcgc  660
tcactccgcc ctctgccttt gttactgcca cgtttctctg aatgctctct tgtgtggtga  720
ttgctgagag tggtttagct ggatctgaaa ttacactctg aaatcgtgtt ctgcctgtgc  780
tgattacttg ccgtccttgt tagcagcaaa atatagggac atggtagtac gaaacgaaga  840
tagaacctac acagcaatac gagaaatgtg ttaatttggt cttagcggta tttatttaag  900
cacatgttgg tgttataggg cacttggatt cagaagtttg ctgttaattt aggcacaggc  960
ttcatactac atgggtcaat agtataggga ttcatattat aggcgatact ataataattt 1020
gttcgtctgc agagcttatt atttgccaaa attagatatt cctattctgt tttttgttgt 1080
gtgctgttaa attgttaacg cctgaaggaa taaatataaa tgacgaaatt ttgatgttta 1140
tctctgctcc tttattgtga ccataagtca agatcagatg cacttgtttt aaatattgtt 1200
```

```
gtctgaagaa ataagtactg acagtatttt gatgcattga tctgcttgtt tgttgtaaca   1260
aaatttaaaa ataaagagtt tccttttttgt tgctctcctt acctcctgat ggtatctagt   1320
atctaccaac tgacactata ttgcttctct ttacatacgt atcttgctcg atgcctttctc   1380
cctagtgttg accagtgtta ctcacatagt ctttgctcat ttcattgtaa tgcagatacc   1440
aagcggcctc tagaggatcc aggagcaacc atgggcgcca gccatcatca ccaccatcac   1500
catatgggta gcaaaaagag gcgtatcaag caggacatgt ctatctatca agagtttgtc   1560
aacaagtaca gcttaagtaa gacacttcgc ttcgagttga tccctcaggg gaagacactg   1620
gaaaacatca aggcgagggg ccttatcctg gacgacgaga agcgggctaa agactacaaa   1680
aaagctaaac agataattga caagtatcac caattttttta ttgaggagat cctctcctct   1740
gtgtgcataa gtgaggatct gctccagaac tattcggatg tttacttaa actcaagaag   1800
tccgatgatg acaaccttca gaaggacttc aagtccgcca agacacgat taagaaacaa   1860
atcagtgagt acatcaagga tagcgagaaa ttcaagaacc tgttcaacca gaacttaatt   1920
gatgccaaaa agggccaaga atccgacctc atcctgtggt taaagcaatc taaagacaac   1980
ggtattgagc tgttcaaggc aaacagcgac attacagaca ttgacgagc cctagagatc   2040
atcaagtcat tcaaaggctg gacgacttac tttaaaggtt ttcacgagaa ccgtaagaat   2100
gtttactcaa gtaacgatat accaacgagc attatctacc gaatagtgga tgataaccta   2160
ccgaagttcc ttgagaacaa agcgaagtac gagtctctca aagacaaggc ccctgaggcc   2220
atcaactacg agcagattaa gaaggatctc gccgaggagc taaccttcga cattgactac   2280
aaaacatcgg aagtgaatca gagggtgttc tcgcttgatg aagtattcga gattgctaac   2340
ttcaacaatt acctgaacca gagtggtatt actaagttca acacaatcat tggaggcaaa   2400
ttcgtgaacg gcgaaaacac aaagcgaaaa gggataaacg agtacattaa cttgtacagc   2460
cagcagatca acgataagac actcaagaag tataaagatc ctgtgctgtt caaacaaatc   2520
ttaagcgaca cggaaagcaa gtcgttcgta attgacaagc tggaagacga ttctgacgtg   2580
gttacaacca tgcagtcctt ttacgagcag attgccgcat tcaagaccgt ggaggaaaag   2640
tcgatcaagg aaacactttc gttgcttttc gacgaccttta agctcagaa gctcgactta   2700
agcaagatat actttaagaa cgataagagc ttgacagct tgagccagca agtctttgag   2760
gactacagcg ttatcggaac tgccgttctg gagtacataa cacagcagat cgcacccaag   2820
aaccttgaca acccttccaa gaagaacaa gagttgatcg ccaagaagac tgaaaaggct   2880
aagtacctct ctctggagac tatcaagctc gctcttgagg agttttaacaa gcacagggac   2940
attgacaagc aatgccgatt cgaggaaata ctggcaaact tcgcagccat acccatgata   3000
ttcgatgaga tagcccgaaa caaggataac ttggcccaaa tctcgattaa gtatcagaac   3060
cagggcaaaa aggaccttct acaggctagt gcagaggacg atgtgaaggc tattaaggac   3120
ttattagatc agacaaacaa ccttctgcat aagctcaaga tattccatat ctcccagtca   3180
gaggacaagg ccaacattct ggataaggac gagcacttct atctcgtatt cgaggaatgt   3240
tactttgagc tggccaatat cgttcccttg tacaacaaaa tccggaacta catcacacag   3300
aagccctaca gtgatgagaa gttcaaattg aactttgaaa actcaacact tgctaatggt   3360
tgggacaaga ataaggaacc tgacaacact gccatcctct ttattaaaga tgataagtac   3420
tacctcgggg tgatgaataa gaagaacaac aaaatcttcg atgacaaagc tattaaggag   3480
aacaaaggtg aagggtacaa gaagattgtc tacaaactgt gcctggtgc caacaaaatg   3540
ctaccaaagg tattttttcag cgccaaatct attaagttct acaatccaag cgaggatatt   3600
ctccggatac ggaatcactc tacacatacc aagaatggaa gtccacaaaa gggttacgag   3660
aaattcgagt tcaacattga agactgccgg aaattcattg acttctacaa gcaatccatc   3720
tctaaacatc ctgaatggaa agacttcggt ttccgcttca gtgatactca acggtacaat   3780
tcaattgacg aatttaccg tgaggttgag aaccagggga acaaactgac cttcgagaac   3840
atatcagaga gctacatcga ctcagtggtt aatcaggggga agctatatct gtttcaaatc   3900
tacaacaaag actttagtgc ctactctaaa gggcggccaa acttacacac actttactgg   3960
aaggcactat tcgacgaacg caatctacaa gatgtagttt acaaattgaa cggtgaggct   4020
gagttgttct accgtaaaca atctataccc aagaagataa cacacccctgc taaagaggca   4080
attgcaaaca aaaacaagga taatcccaaa aaggagtctg tctttgagta tgacctcatt   4140
aaggataagc ggttcacgga ggacaagttc ttcttccatt gtccaataac catcaacttc   4200
aaatcatccg gcgcaaacaa attcaatgac gagatcaaac tgttactaaa gggagaggct   4260
aacgatgttc acatcttatc tattgatcga ggtgagagac acctagccta ctacacttta   4320
gtggatggga agggaacat catcaagcaa gacaccttca acatcattgg aacgacagg   4380
atgaagacta actaccatga taagctcgcc gctattgaaa aggacaggga ctctgccagg   4440
aaggactgga aaaaaattaa caatattaaa gagatgaagg agggctaccct gagccaagta   4500
gtccatgaga tagcaaaact ggtgattgag tacaacgcaa tagtcgtatt cggagactta   4560
aacttcggct tcaaacgtgg gcggtttaag gtggagaaac aagtctatca gaaattggag   4620
aagatgctaa tcgagaagct caactacctc gtgtttaaag acaacgagtt tgacaaaact   4680
ggaggagtcc tgcgggcata ccaactgacc gcacccttcg agacattcaa gaagatggga   4740
aagcagactg gcatcatcta ttacgtgcca gcggggtttta cttccaaaat ctgtccagtt   4800
acaggcttcg tgaaccagtt gtacccgaag tacgagtctg tttccaagtc acaggaattc   4860
ttctcaaagt ttgacaagat atgttacaat ctcgataagg gatactttga gtttagtttc   4920
gactacagaa actttggcga taaggccgca aagggaaat ggacaattgc atccttcggg   4980
tcacgcctta ttaactttcg taactcagac aagaaccaca attgggacac cagggaggtg   5040
taccctacta aggagctgga gaagctactt aaagactact cgattgagta cggacatgga   5100
gagtgcatca aggcagcaat atgtgggaa tctgacaaaa agttcttgc caagctgacc   5160
tctgtactga acactattct ccaaatgaga aatagtaaga ctggcacaga gttggactac   5220
ctgatctctc cagtggctga cgttaatggg aattttttcg actcaagaca agctcccaag   5280
aatatgccac aggacgcaga tgcaaacggg gcatatccca tcgggcttaa aggactcatg   5340
ctactagggc ggatcaagaa taatcaggag ggcaaaagc tgaacctagt catcaagaac   5400
gaggagtact tcgaatttgt ccagaatcgt aacaacggat ctggagtgag caagggcgag   5460
gagaataaca tggccatcat caaggagttc atgcgcttca aggtgcgcat ggagggctcc   5520
gtgaacggcc acgagttcga gatcgagggc gagggcgagg ccgcccccta cgagggcttt   5580
cagaccgcta agctgaaggt gaccaagggt ggccccctgc cctttcgctg ggacatcctg   5640
tccctctcatt tcacctacgg ctccaaggcc tacgtgaagc accccgccga catccccgac   5700
tacttcaagc tgtccttccc cgagggcttc aagtgggagc gcgtgatgaa ctacgaggac   5760
ggcggcgtgg tgaccgtgac ccaggactcc tccctgcagg acggcgagtt catctacaag   5820
gtgaagctgc gcggcaccaa cttcccctcc gacgccccg tgatgcagaa gaagaccatg   5880
ggctggggagg cctcctccga gcggatgtac cccgaggacg gtgccctgaa gggcaagatc   5940
```

```
aagatgaggc tgaagctgaa ggacggcggc cactacacct ccgaggtcaa gaccacctac 6000
aaggccaaga agcccgtgca gctgccggc gcctacatcg tcgacatcaa gttggacatc 6060
acctcccaca acgaggacta caccatcgtg aacagtacg aacgcgccga gggccgccac 6120
tccaccggcg gcatggacga gctgtacaag ggatctaaga agcgtaggat caagcaagat 6180
tagaacccag cggtactcgc tgaggaattc gcgatcgttc aaacatttgg caataaagtt 6240
tcttaagatt gaatcctgtt gccggtcttg cgatgattat catataattt ctgttgaatt 6300
acgttaagca tgtaataatt aacatgtaat gcatgacgtt atttatgaga tgggttttta 6360
tgattagagt cccgcaatta tacatttaat acgcgataga aaacaaaata tagcgcgcaa 6420
actaggataa attatcgcgc gcggtgtcat ctatgttact agatc       6465

SEQ ID NO: 57           moltype = DNA   length = 4674
FEATURE                 Location/Qualifiers
misc_feature            1..4674
                        note = Synthetic polynucleotide.NLS-FnCpf1-CO2-mOR-NLS
source                  1..4674
                        mol_type = other DNA
                        organism = synthetic construct
SEQUENCE: 57
ggtagcaaaa agaggcgtat caagcaggac atgtccatat accaggagtt cgtcaacaag  60
tactcgctca gcaagacgct ccgcttcgag ctgatccccc agggtaagac cctggagaac 120
atcaaggcgc gcggactcat cctcgacgac gagaagcggg ctaaggacta caaaaaggcc 180
aagcagatca tcgacaagta ccaccagttc ttcatcgaag atcctctc ctccgtctgc 240
atctccgagg acctcctcca gaactacagc gacgtctact tcaagctcaa aaagtcggac 300
gacgacaacc tccagaagga cttcaagtcg gcgaaggaca ccatcaagaa gcagatcagc 360
gagtacatca aggactccga gaagttcaag aacctgttca accagaacct gatcgacgcc 420
aagaagggcc aggagtcgga cctgatcctg tggctcaaga agcaagga caaggcatc 480
gagctcttca aggccaacag cgacatcacg gacatcgacg aggccctgga gatcatcaag 540
tcgttcaagg gctggacgac ctacttcaag ggcttccacg agaaccgcaa gaacgtctat 600
agctccaacg acatccccac ctcgatcatc taccggatcg tggacgacaa cctccccaag 660
ttcctggaga acaaggcgaa gtacgagtcg ttgaaggaca aggcgccgga ggcgatcaac 720
tacgagcaga tcaagaagga cctggccgag gagctgacct tcgacatcga ctacaagacg 780
tcggaggtga accagcgggt gttcagtctg gacgaggtct tcgagatcgc gaacttcaac 840
aactacctga ccagtcgggg gatcaccaag ttcaacacga tcataggcgg caagttcgtg 900
aacgcgaga acaccaagcg caaggggata aacgagtaca tcaacctgta cagccagcag 960
atcaacgaca agacgctcaa gaagtcaagca gagagcgtgc tcttcaagga gatcctcagt 1020
gacaccgagt ccaagagctt cgtgatcgac aagctggagg acgacagcga cgtcgtgaca 1080
accatgcaga gcttctacga gcagatcgcc gcgttcaaga ccgtcgagga agtcaatc 1140
aaggagacgc tctccttgct gttcgacgac ctgaaggcac aaaaggtgga cctcagcaag 1200
atctacttca agaacgacaa gtccctgacc gacctgagcg agcaggtttt cgacgactac 1260
tccgtcatcg ggactgccgt cctggagtac atcacccagc agatcgctcc gaagaacctc 1320
gacaacccgt ccaagaagga gcaggagctg attgcgaaga agcagagaa ggccaagtac 1380
ctctcccctg agaccatcaa gctcgccctg gaggagttca acaagcacag ggacattgac 1440
aagcagtgcc gtttcgagga gatctggcc aacttcgtcg ccatccccat gatcttcgag 1500
gagatcgccc agaacaagga caacctggcc cagatctcta tcaagtacca gaaccagggg 1560
aagaaggact gctccaggc ctcagcggag gacgacgtga aggccatcaa ggacctgctc 1620
gaccagacga acaacttgct ccacaagctc aagatctttc acatcagcca gagcgaggac 1680
aaggccaaca tcctcgacaa ggacgccaca ttctacctcg tgttcgagga gtgctacttc 1740
gagctggcca acatcgtgcc actttacaac aagatccgca actacatcac gcagaagccg 1800
tactccgacg agaagttcaa gctgaacttc gagaactcca ccctcgccaa cggctgggac 1860
aagaacaagg agccggacaa caccgcgatc ctgttcataa aggacgacaa gtactacttg 1920
ggggtcatga acaagaagaa caacaagata ttcgacgaca aggccatgaa gaacaaag 1980
ggggagggct acaagaagat cgtctacaag ctcctccccg gcgcgaacaa gatgctgcct 2040
aaggtcttct tttccgccaa gagtatcaag ttctacaacc cctccgagga catcctccgc 2100
atccggaacc acagcacgca cacaaagaac ggctcgcctc agaagggcta cgagaagttc 2160
gagttcaaca tcgaggactg ccggaagttc atcgacttct acaagcagag catctccaag 2220
caccccggagt ggaaggactt tggcttcagg ttctcagaca cccagcggta caactccatc 2280
gacgagttct accgcgaggt ggagaaccag ggctacaagc tgaccttcga gaatatatca 2340
gagtcgtaca tcgacagcgt ggtgaaccag ggcaagttgt acctgttcca gatctacaac 2400
aaggacttct ccgcctactc aaaggggcgt ccaaacctgc aacgctgta ctggaaggcg 2460
ctcttcgacg agcgcaacct acaagatgtt gtatacaagc tcaacggcga ggcggaactg 2520
ttctatagga gcagtcgat ccccaagaag attacgcacc cggctaagga ggccatcgcc 2580
aacaagaaca aggacaaccc caagaaggag tccgtgttcg agtacgacct catcaaggac 2640
aagaggttca cggaggacaa gttttctctc cactgcccaa tcactatcaa tttcaagtcg 2700
agcggagaca acaagttcaa cgacgagata aacctgctcc tcaaggagaa cgaccaatgg 2760
gtgcacatcc tctccatcga ccggggcgag cggcacctgg cgtactacac gctggtggac 2820
ggcaagggca acatcatcaa gcaggacacc ttcaacatca tcgggaacga ccgcatgaag 2880
accaactacc acgacaagct cgccgccatc gagaaggaca gggactccgc gcgcaaggac 2940
tggaagaaga ttaacaacat caaggagatg aaggagggcc acctcagcca ggtggtccac 3000
gagatcgcca gctcgtcat ttagtacaac gccatcgtcg tcttccgagga cctgaattc 3060
ggcttcaagc gcggccggtt caaggtggag aagcaggtct accagaagct tgagaagatg 3120
ctgatcgaga agctgaacta cctggtgttc aaggacaacg agttcgacaa gaccggcgga 3180
gtgctgcgcg cctaccagct cacggcgcct tcgagacgt tcaagaagat gggcaagcag 3240
acgggcatca tctactacgt gcccgccggc ttcacctcta agatctgccc agtgaccggc 3300
ttcgttaacc agctgtaccc gaagtacgaa agcgtgtcca gttcttctcc 3360
aagttcgaca agatttgtta caacctcgac aagggctact cgagttttc gttcgactac 3420
aagaactttg cgacaaggc ggccaagggg aagtggacca tcgcctcttt cggcagcagg 3480
ctcatcaatt tccggaactc cgacaagaac acaactggg acacgcgcga ggtgtacccg 3540
acgaaggagc tggagaagct gctcaaggac tactccatcg agtacggcca cggcgagtgc 3600
atcaaggcg cgatctgcgg ggagagcgac aagaagttcc ttgccaagct gaccagcgtg 3660
```

```
ctgaacacca tcctccagat gcggaactcc aagaccggca ccgagctgga ctacctgatc   3720
tccccggtcg cggacgtcaa cgggaacttc ttcgactccc gacaggctcc aagaacatg    3780
ccccaggacg ccgacgcgaa cggcgcgtac cacatcggcc tcaagggcct gatgctgctg   3840
gggcgcatca agaacaacca ggagggcaag aagctgaacc tcgtgatcaa gaacgaggaa   3900
tacttcgagt tcgtgcagaa ccgcaacaac ggatctggag tgagcaaggg cgaggagaat   3960
aacatggcca tcatcaagga gttcatgcgc ttcaaggtgc gcatggaggg ctccgtgaac   4020
ggccacgagt tcgagatcga gggcgagggc gagggccgcc cctacgaggg cttccagacc   4080
gctaagctga aggtgaccaa gggtggcccc ctgcccttcg cctgggacat cctgtcccct   4140
catttcacct acggctccaa ggcctacgtg aagcaccccg cgacatccc cgactacttc   4200
aagctgtcct tccccgaggg cttcaagtgg gagcgcgtga tgaactacga ggacggcggc   4260
gtggtgaccg tgacccagga ctcctccctg caggacggcg agttcatcta caaggtgaag   4320
ctgcgcggca ccaacttccc ctccgacggc cccgtgatgc agaagaagac catgggctgg   4380
gaggcctcct ccgagcggat gtaccccgag gacggtgccc tgaagggcaa gatcaagatg   4440
aggctgaagc tgaaggacgg cggccactac acctccgagg tcaagaccac ctacaaggcc   4500
aagaagcccg tgcagctgcc cggcgcctac atcgtcgaca tcaagttgga catcaccctcc  4560
cacaacgagg actacaccat cgtggaacag tacgaacgcg ccgagggccg ccactccacc   4620
ggcggcatgg acgagctgta caaggggatct aagaagcgta ggatcaagca agat         4674

SEQ ID NO: 58           moltype = DNA   length = 4710
FEATURE                 Location/Qualifiers
misc_feature            1..4710
                        note = Synthetic polynucleotide.
                        MGSS7H-NLS-FnCpf1-CO2-mOR-NLS
source                  1..4710
                        mol_type = other DNA
                        organism = synthetic construct
SEQUENCE: 58
atgggcagca gccatcatca ccaccatcac catatgggta gcaaaaagag gcgtatcaag     60
caggacatgt ccatatacca ggagttcgtc aacaagtact cgctcagcaa gacgctccgc   120
ttcgagctga tccccagggt aagaccctg gagaacatca aggcgcgcaag actcatcctc   180
gacgacgaga gcgggctaa ggactacaaa aaggccaagc agatcatcga caagtaccac   240
cagttcttca tcgaggagat cctctcctcc gtctgcatct ccgaggacct cctccagaac   300
tacagcgacg tctacttcaa gctcaaaaag tcggacgacg acaacctcca gaaggacttc   360
aagtcggcga aggacaccat caaggacag atcagcgagt acatcaagga ctccgagaag   420
ttcaagaacc tgttcaacca gaacctgatc gacgccagaa agggccagga gtcggacctg   480
atcctgtggc tcaagcagag caaggacaac ggcatcgagc tcttcaaggc caacagcgac   540
atcacggaca tcgacgaggc cctggagatc atcaagtcgt tcaagggctg gacgacctac   600
ttcaagggct tccacgagaa ccgcaagaac gtctatagct ccaacgacat ccccacctcg   660
atcatctacc ggatcgtgga cgacaatcctc cccaagttcc tggagaacaa ggcgaagtac   720
gagtcgttga aggacaaggc gccggaggcg atcaactacg agcagatcaa gaaggacctg   780
gccgaggagc tgaccttcga catcgactac aagacgtcgg aggtgaacca gcgggtgttc   840
agtctggacg aggtcttcga gatcgcgaac ttcaacaact acctgaacca gtcggggatc   900
accaagttca acacgatcat aggcgcgaag ttcgtgaacg gcgagaacac caagcgcaag   960
gggataaaacg agtacatcaa cctgtacagc cagcagatca cgacaagac gctcaagaag  1020
tacaagatga gcgtgctctt caagcagatc ctcagtgaca ccgagtccaa gagcttcgtg  1080
atcgacaagc tggaggacga cagcgacgtc gtgacaacca tgcagagctt ctacgagcag  1140
atcgccgcgt tcaagaccgt cgaggaggaag tcaatcaagg agacgctctc cttgctgttc  1200
gacgacctga aggcacaaaa gctggacctc agcaagatct acttcaaggaa cgacaagtcc  1260
ctgaccgacc tgagccagca ggttttcgac gactactccg tcatcgggac tgccgtcctg  1320
gagtacatca cccagcagat cgctccgaag aacctcgaca cccgtccaa gaaggagcag  1380
gagctgattg cgaagaagac agagaaggcc aagtacctct ccctcgagac catcaagctg  1440
gccctggagg agttcaacaa gcacaggac attgacaagc agtgccgttt cgaggagatc  1500
ctggccaact cgcggccat ccccatgatc ttcgacgaga tcgcccagaa caaggacaac  1560
ctggcgcaga tctctatcaa gtaccagaac cagggggaaga aggacttgct ccaggcctca  1620
gcgcaggacg acgtgaaggc catcaaggac ctgctcgacc agacgaacaa cttgctccac  1680
aagctcaaga tctttcacat cagccagagc gaggacaagg ccaacatcct cgacaaggac  1740
gagcacttct acctcgtgtt cgaggagtgc tacttcgagc tggccaacat cgtgccactt  1800
tacaacaaga tccgcaacta catcacgcag aagccgtact ccgacgagaa gttcaagctg  1860
aacttcgaga actccaccct cgccaacggc tgggacaaga acaaggagcc ggacaacaac  1920
gcgatcctgt tcataaagga cgacaagtac tacttggggg tcatgaacaa gaagaacaac  1980
aagatattcg acgacaaggc catcaaggag aacaaggggg aggctacaa gaagatcgtc  2040
tacaagctcc tccccggcgc gaacaagatg ctgcctaagg tcttcttttc cgccaagagt  2100
atcaagttca caacccctc cgaggacatc ctccgcatcc ggaaccacag cacgcacaca  2160
aagaacgggc tcgcctcagaa gggctacgag aagttcgagt tcaacatcga ggactgccgg  2220
aagttcatcg acttctacaa gcagagcatc tccaagcacc cggagtggaa ggacttggcc  2280
ttcaggttct cagacaccca gcggtacaac tccatcgacg agttctaccg cgaggtggag  2340
aaccagggct acaagctgac cttcgagaat atatcagagt cgtacatcga cagcgtggtg  2400
aaccagggca agttgtacct gttccagatc tacaacaagg acttctccgc ctactcaaag  2460
gggtccaa acctgcacac gctgtactgg aaggcgctct cgacggtaca caacctacaa  2520
gatgttgtat acaagctcaa cggcgaggcg gaactgttct ataggaagca gtcgatcccc  2580
aagaagatta cgcacccggc taaggaggcc atcgccaaca gaacaagga caaccccaag  2640
aaggagtccg tgttcgagta cgacctcatc aaggacaaga ggttcacgga ggacaagttt  2700
ttcttccact gcccaatcac tatcaatttc aagtcgagcg gagcatcaaca agttcaacgac  2760
gataaaacc tgctcctcaa ggagaaggcc aatcctctcg catcgaccgg  2820
ggcgagcggc acctggcgta ctacgctg tggacggca agggcaacat catcaagcag  2880
gacaccttca acatcatcgg gaacgaccgc atgaagacca actaccgacga caagctcgcc  2940
gccatcgaga aggacaggga ctccgcgcgc aaggactgga gaagattaa caacatcaag  3000
gagatgaagg agggctacct cagccaggtg gtccacgaga tcgccaagct cgtcattgag  3060
tacaacgcca tcgtcgtctt cgaggacctg aatttcggct tcaagcgcgg ccggttcaag  3120
```

```
gtggagaagc aggtctacca gaagcttgag aagatgctga tcgagaagct gaactacctg 3180
gtgttcaagg acaacgagtt cgacaagacc ggcggagtgc tgcgcgccta ccagctcacg 3240
gcgccttttcg agacgttcaa gaagatgggc aagcagacgg gcatcatcta ctacgtgccc 3300
gccggcttca cctctaagat ctgcccagtg accggcttcg ttaaccagct gtacccgaag 3360
tacgagacg tgtccaagtc ccaggagttc ttctccaagt tcgacaagat ttgttacaac 3420
ctcgacaagg gctacttcga gttttcgttc gactacaaga actttggcga caaggcggcc 3480
aaggggaagt ggaccatcgc ctctttcggc agcaggctca tcaatttccg gaactccgac 3540
aagaaccaca actgggacac gcgcgaggtg tacccgacga aggagctgga gaagctgctc 3600
aaggactact ccatcgagta cggccacggc gagtgcatca aggcggcgat ctgcggggag 3660
agcgacaaga agttctttgc caagctgacc agcgtgctga acaccatcct ccagatgcgg 3720
aactccaaga ccggcaccga gctgactacc tgatctccc cggtcgcgga cgtcaacggg 3780
aacttcttcg actcccgaca ggctcccaag aacatgcccc aggacgccga cgcgaacggg 3840
gcgtaccaca tcggcctcaa gggcctgatg ctgctggggc gcatcaagaa caaccaggag 3900
ggcaagaagc tgaacctcgt gatcaagaac gaggaatact tcgagttcgt gcagaaccgc 3960
aacaacggat ctggagtgag caagggcgag gagaataaca tggccatcat caaggagttc 4020
atgcgcttca aggtgcgcat ggagggctcc gtgaacggcc acgagttcga gatcgagggc 4080
gagggcgagg gccgccccta cgagggcttt cagaccgcta agctgaaggt gaccaagggt 4140
ggccccctgc ccttcgcctg ggacatcctg tcccctcatt tcacctacgg ctccaaggcc 4200
tacgtgaagc accccgccga catccccgac tacttcaagc tgtccttccc cgagggcttc 4260
aagtgggagc gcgtgatgaa ctacgaggac ggcggcgtgg tgaccgtgac ccaggactcc 4320
tccctgcagg acggcgagtt catctacaag gtgaagctgc gcggcaccaa cttcccctcc 4380
gacggccccg tgatgcagaa gaagaccatg ggctgggaag cctcctccga gcggatgtac 4440
cccgaggacg gtgccctgaa gggcaagatc aagatgaggc tgaagctgaa ggacggcggc 4500
cactacacct ccgaggtcaa gaccacctac aaggccaaga gcccgtgca gctgcccggc 4560
gcctacatcg tcgacatcaa gttggacatc acctcccaca cgaggacta ccatcgtg 4620
gaacagtacg aacgcgccga gggccgcac tccaccggcg catggacga gctgtacaag 4680
ggatctaaga agcgtaggat caagcaagat                                  4710

SEQ ID NO: 59              moltype = DNA   length = 6465
FEATURE                    Location/Qualifiers
misc_feature               1..6465
                           note = Synthetic polynucleotide.Expression cassette
                              comprising 35Spromoter cassette,
                              MGSS7H-NLS-FnCpf1-CO2-mOr-NLS and NOStranscription
                              termination sequence
source                     1..6465
                           mol_type = other DNA
                           organism = synthetic construct
SEQUENCE: 59
ggtccgattg agactttca acaaagggta atatccggaa acctcctcgg attccattgc 60
ccagctatct gtcactttat tgtgaagata gtggaaaagg aaggtggctc ctacaaatgc 120
catcattgcg ataaaggaaa ggccatcgtt gaagatgcct ctgccgacag tggtcccaaa 180
gatggacccc cacccacgag gagcatcgtg gaaaaagaag acgttccaac cacgtcttca 240
aagcaagtgg attgatgtga tggtccgatt gagacttttc aacaaagggt aatatccgga 300
aacctcctcg gattccattg cccagctatc tgtcacttta ttgtgaagat agtgaaaag 360
gaaggtggcc cctacaaatg ccatcattgc gataaaggaa aggccatcgt tgaagatgcc 420
tctgccgaca gtggtcccaa agatggaccc ccacccacga ggagcatcgt ggaaaaagaa 480
gacgttccaa ccacgtcttc aaagcaagtg gattgatgtg atatctccac tgacgtaagg 540
gatgacgcac aatcccacta tccttcgcaa gaccttcct ctatataagg aagttcattt 600
catttggaga ggacacgctg acaagctgac tctagcagat ctaccgtctt cggtacgcgc 660
tcactccgcc ctctgccttt gttactgcca cgtttctctg aatgctctct tgtgtggtga 720
ttgctgagag tggtttagct ggatctagaa ttacactctg aaatcgtgtt ctgcctgtgc 780
tgattacttg ccgtcctttg tagcagcaaa atataggac atggtagtac gaaacgaaga 840
tagaacctac acagcaatac gagaaatgtg taatttggtg cttagcgta tttatttaag 900
cacatgttgg tgttatagg cacttggatt cagaagtttg ctgttaattt aggcacaggc 960
ttcatactac atgggtcaat agtatagga ttcatattat aggcgatact ataataattt 1020
gttcgtctgc agagcttatt attttgccaaa attagatatt cctattctgt ttttgtttgt 1080
gtgctgttaa attgttaacg cctgaaggaa taaatataaa tgacgaaatt ttgatgttta 1140
tctctgctcc tttattgtga ccataagtca agatcagatg cacttgtttt aaatattgtt 1200
gtctgaagaa ataagtactg acagtatttt gatgcattga tctgcttgtt tgttgtaaca 1260
aaatttaaaa ataaagagtt tcctttttgt tgctctcctt acctcctgat ggtatctagt 1320
atctaccaac tgacactata ttgcttctct ttacatacgt atcttgctcg atgccttctc 1380
cctagtgttg accagtgtta ctcacatagt ctttgctcat tcattgtaa tgcagatacc 1440
aagcggcctc tagaggatcc aggagcaacc atgggcaagc gccatcatca ccaccatcac 1500
catatgggta gcaaaaagag gcgtatcaag caggacatgt ccatataccc ggagttcgtc 1560
aacaagtact cgctcagcaa gacgtccgtc ttcgagctga tcccccaggg taagaccctg 1620
gagaacatca aggcgcgcgg actcatcctc gacgacgaga gcgggctaa ggactacaaa 1680
aaggccaagc agatcatcga caagtaccac cagttcttca tcgaggagat cctctcctcc 1740
gtctgcatct ccgaggacct tctccagaac tacagcgacg tctactttcaa gctcaaaaag 1800
tcggacgacg acaacctcca gaaggacttc aagtcggcga aggacaccat caagaagcag 1860
atcagcgagt acatcaagga ctccgagaag ttcaagaacc tgttcaacca gaacctgatc 1920
gacgccaaga agggccagga gtcggacctg atcctgtggc tcaagcagag caggacaac 1980
ggcatcgagc tcttcaaggc caacagcgac atcacggaca tcgacgaggc cctggagatc 2040
atcaagtcgt tcaagggctg gacgacctac ttcaaggcct tcaacgagaa ccgcaagaac 2100
gtctatagct ccaacgacat ccccacctcg atcatctacc ggatcgtgga cgacaactc 2160
cccaagttcc tggagaacaa ggcgaagtac gagtcgttga aggacaaggc gccgaggcg 2220
atcaactacg agcagatcaa gaaggacctg gccgaggagc tgaccttcga catcgactac 2280
aagacgtcgg aggtgaacca gcgggtgttc agtctgacg aggtcttcga gatcgcgaac 2340
ttcaacaact acctgaacca gtcggggatc accaagttca acacgatcat aggcggcaag 2400
```

```
ttcgtgaacg gcgagaacac caagcgcaag gggataaacg agtacatcaa cctgtacagc    2460
cagcagatca acgacaagac gctcaagaag tacaagatga gcgtgctctt caagcagatc    2520
ctcagtgaca ccgagtccaa gagcttcgtg atcgacaagc tggaggacga cagcgacgtc    2580
gtgacaacca tgcagagctt ctacgagcag atcgccgcgt tcaagaccgt cgaggagaag    2640
tcaatcaagg agacgctctc cttgctgttc gacgacctga aggcacaaaa gctggacctc    2700
agcaagatct acttcaagaa cgacaagtcc ctgaccgacc tgagccagca ggttttcgac    2760
gactactccg tcatcgggac tgccgtcctc gagtacatca cccagcagat cgctcccaag    2820
aacctcgaca acccgtccaa gaaggagcag gagctgattg cgaagaagac agagaaggcc    2880
aagtacctct ccctcgagac catcaagctc gccctggagg agttcaacaa gcacagggac    2940
attgacaagc agtgccgttt cgaggagatc ctggccaact tcgcggccat ccccatgatc    3000
ttcgacgaga tcgcccagaa caaggacaac ctggcgcaga tctctatcaa gtaccagaac    3060
caggggaaga aggacttgct ccaggcctca gcggaggacg acgtgaaggc catcaaggac    3120
ctgctcgacc agacgaacaa cttgctccac aagctcaaga tctttcacat cagccagagc    3180
gaggacaagg ccaacatcct cgacaaggac gagcacttct acctcgtgtt cgaggagtgc    3240
tacttcgagc tggccaacat cgtgccactt tacaacaaga tccgcaacta catcacgcag    3300
aagccgtact ccgacgagaa gttcaagctg aacttcgaga actccaccct cgccaacggc    3360
tgggacaaga acaaggagcc ggacaacacc gcgatcctgt tcataaagga cgacaagtac    3420
tacttggggg tcatgaacaa gaagaacaac aagtattcg acgacaaggc catcaaggag    3480
aacaaggggg agggctacaa gaagatcgtc tacaagctcc tccccggcgc gaacaagatg    3540
ctgcctaagg tcttcttttc cgccaagagt atcaagttct acaaccctc cgaggacatc    3600
ctccgcatcc ggaaccacag cacgcacaca aagaacggcc gcctcagaa gggctacgag    3660
aagttcgagt tcaacatcga ggactgccgg aagttcatcg acttctacaa gcagagcatc    3720
tccaagcacc cggagtggaa ggactttggc ttcaggttct cagacaccca gcggtacaac    3780
tccatcgacg agttctaccg cgaggtggag aaccagggct acaagctgac cttcgagaat    3840
atatcagagt cgtacatcga cagcgtggtg aaccagggca agttgtacct gttccagatc    3900
tacaacaagg acttctccgc ctactcaaag gggcgtccaa acctgcacac gctgtactgg    3960
aaggcgctct tcgacgagcg caacctacaa gatgttgtat acaagctcaa cggcgaggcg    4020
gaactgttct ataggaagca gtcgatcccc aagaagatta cgcacccggc taaggaggcc    4080
atcgccaaca gaacaaggga caaccccaag aaggagtccg tgttcgagta cgacctcatc    4140
aaggacaaga ggttccacga ggacaagttt ttcttccact gcccaatcac tatcaatttc    4200
aagtcgagcg gagccaacaa gttcaacgac gagataaacc tgctcctcaa ggagaaggcc    4260
aatgacgtgc acatcctctc catcgaccgg ggcgagcggc acctggcgta ctacacgctg    4320
gtggacggca agggcaacat catcaagcag gacaccttca acatcatcgg gaacgaccgc    4380
atgaagacca actaccacga caagctcgcc gccatcgaga aggacaggga ctccgcgcgc    4440
aaggactgga aagattaa caacatcaag gagatgaagg agggctacct cagccagtg    4500
gtccacgaga tcgccaagct cgtcattgag tacaacgcca tcgtcgtctt cgaggacctg    4560
aatttcggct tcaagcgcgg ccggttcaag gtggagaagc aggtctacca gaagcttgag    4620
aagatgctga tcgagaagct gaactacctg gtgttcaagg acaacgagtt cgacaagacc    4680
ggcggagtgc tgcgcgccta ccagctcacg cgccttcg aagttcaa gaagatggc     4740
aagcagacgg gcatcatcta ctacgtgccc gccggcttca cctctaagat ctgcccagtg    4800
accggcttcg ttaaccagct gtacccgaag tacgagagcg tgtccaagtc ccaggagttc    4860
ttctccaagt tcgacaagat tgttacaac ctcgacaagg gctacttcga gttttcgttc    4920
gactacaaga actttggcga caagcggcc aaggggaag aggaccatgc ctctttcggc    4980
agcaggctca tcaatttccg gaactccgac aagaaccaca actgggacac gcgcgaggtg    5040
tacccgacga aggagctgga gaagctgctc aaggactact ccatcgagta cggccacggc    5100
gagtgcatca aggcggcgat ctgcggggag agcgacaaga agttctttgc caagctgacc    5160
agcgtgctga acaccatcct ccagatgcgg aactccaaga ccggcaccga gctggactac    5220
ctgatctccc cggtcgcgga cgtcaacggg aacttcttcg actcccgaca ggctcccaag    5280
aacatgcccc aggacgccga cgcgaacggc gcgtaccaca tcggcctcaa gggcctgatg    5340
ctgctggggc gcatcaagaa caaccaggag ggcaagaagc tgaacctcgt gatcaagaac    5400
gaggaatact tcgagttcgt gcagaaccgc aacaacgat ctggagtgag aagggcgag    5460
gagaataaca tggccatcat caaggagttc atgcgcttca aggtgcgcat ggagggctcc    5520
gtgaacggcc acgagttcga gatcgagggc gaggcgagg gccgcccta cgaggctttg    5580
cagaccgcta agctgaaggt gaccaaggt ggccccctgc ccttcgcctg gacatcctg    5640
tccctcatt tcacctacgg ctccaaggcc tacgtgaagc accccgaca catcccaga    5700
tacttcaagc tgtccttccc cgagggcttc aagtgggag gcgtgatgaa ctacgaggac    5760
ggcggcgtgg tgaccgtgac ccaggactcc tccctgcagg acggcgagtt catctacaag    5820
gtgaagctgc gcggcaccaa cttcccctcc gacggcccg tgatgcagaa gaagaccatg    5880
ggctgggagg cctcctccga gcggatgtac cccgaggacg gtgccctgaa gggcaagtc    5940
aagatgctga tgaagctgaa ggacggcggc cactacacct ccgaggtcaa gaccacctac    6000
aaggccaaga gcccgtgca gctgcccggc gcctacatcg tcgacatcaa gttggacatc    6060
acctcccaca acgaggacta ccatcgtg aacagtacg aacgcgccga gggccgccac    6120
tccaccggcg gcatggacga gctgtacaag ggatctaaga gcgtaggat caagcaagat    6180
tagaacccag cggtactcgc tgaggaattc gcgatcgttc aaacattgg caataagtt    6240
tcttaagatt gaatcctgtt gccggtcttg cgatgattat catataaattt ctgttgaatt    6300
acgttaagca tgtaataatt aacatgtaat gcatgacgtt attatgaga tgggttttta    6360
tgattagagt cccgcaatta tacatttaat acgcgataga aaacaaaata tagcgcgcaa    6420
actaggataa attatcgcgc gcggtgtcat ctatgttact agatc              6465
```

| SEQ ID NO: 60 | moltype = DNA  length = 4671 |
|---|---|
| FEATURE | Location/Qualifiers |
| misc_feature | 1..4671 |
| | note = Synthetic polynucleotide.NLS-FnCpf1-Hs-mOR-NLS |
| source | 1..4671 |
| | mol_type = other DNA |
| | organism = synthetic construct |

SEQUENCE: 60
```
ggtagcaaaa agaggcgtat caagcaggac agcatctacc aggagttcgt caacaagtat      60
tcactgagta agacactgcg gttcgagctg atcccacagg gcaagacact ggagaacatc     120
```

```
aaggcccgag gcctgattct ggacgatgag aagcgggcaa aagactataa gaaagccaag    180
cagatcattg ataaatacca ccagttcttt atcgaggaaa ttctgagctc cgtgtgcatc    240
agtgaggatc tgctgcagaa ttactcagac gtgtacttca agctgaagaa gagcgacgat    300
gacaacctgc agaaggactt caagtccgcc aaggacacca tcaagaaaca gattagcgag    360
tacatcaagg actccgaaaa gttaaaaat ctgttcaacc agaatctgat cgatgctaag    420
aaaggccagg agtccgacct gatcctgtgg ctgaaacagt ctaaggacaa tgggattgaa    480
ctgttcaagg ctaactccga tatcactgat attgacgagg cactggaaat catcaagagc    540
ttcaagggat ggaccacata cttaaaggc ttccacgaga accgcaagaa cgtgtactcc    600
agcaacgaca ttcctacctc catcatctac cgaatcgtcg atgacaatct gccaaagttc    660
ctgggagaaca aggccaaata tgaatctctg aaggacaaag ctcccgaggc aattaattac    720
gaacagatca agaaagatct ggctgaggaa ctgacattcg atatcgacta taagactagc    780
gaggtgaacc agagggtctt ttccctggac gaggtgtttg aaatcgccaa tttcaacaat    840
tacctgaacc agtccggcat tactaaattc aataccatca ttggcgggaa gtttgtgaac    900
ggggagaata ccaagccgca gggaattaac gaatacatca atctgtatag ccagcagatc    960
aacgacaaaa ctctgaagaa atacaagatg tctgtgctgt tcaaacagat cctgagtgat   1020
accgagtcca agtcttttgt cattgataaa ctggaagatg actcagacgt ggtcactacc   1080
atgcagagct tttatgagca gatcgccgct ttcaagacag tggaggaaaa atctattaag   1140
gaaactctga gtctgctgtt cgatgacctg aaagcccaga agctggacct gagtaagatc   1200
tacttcaaaa acgataagag tctgacagac ctgtcacagc aggtgtttga tgactattcc   1260
gtgattggga ccgccgtcct ggagtacatt acacagcaga tcgctccaaa gaacctggat   1320
aatccctcta agaagagca ggaactgatc gctaagaaaa ccgagaaggc aaaatatctg   1380
agtctggaaa caattaagct ggcactggag gagttcaaca agcacaggga tattgacaaa   1440
cagtgccgct ttgaggaaat cctggccaac ttcgcagcca tccccatgat ttttgatgag   1500
atcgcccaga acaaagacaa tctggctcag atcagtatta agtaccgaaa ccagggcaag   1560
aaagacctgc tgcaggcttc agcagaagat gacgtgaaag ccatcaagga tctgctggac   1620
cagaccaaca atctgctgca caagctgaaa atcttccata ttagtcagtc agaggataag   1680
gctaatatcc tggataaaga cgaacacttc tacctggtgt tcgaggaatg ttacttcgag   1740
ctggcaaaca ttgtccccct gtataacaag attaggaact acatcacaca gaagccttac   1800
tctgacgaga gtttaaact gaacttcgaa atagtaccc tggccaacgg gtgggataag   1860
aacaaggagc ctgacaacac agctatcctg ttcatcaagg atgacaagta ctatctggga   1920
gtgatgaata agaaaaacaa taagatcttc gatgacaaag ccattaagga gaacaaaggg   1980
gaaggataca gaaaatcgt gtataagctg ctgcccggcg caaataagat gctgcctaag   2040
gtgttcttca gcgccaagag tatcaaattc tacaacccat ccgaggacat cctgcggatt   2100
agaaatcact caacacatac taagaacggg agcccccaga agggatatga gaaatttgaa   2160
ttcaacatcg aggattgcag gaagtttatt gacttctaca agcagagcat ctccaaacac   2220
cctgaatgga aggattttgg cttccggttt tccgacacac agagatataa ctctatcgac   2280
gagttctacc gcgaggtgga aaatcagggg tataagctga cttttgagaa catttctgaa   2340
agttacatcg acagcgtggt caatcaggga aagctgtacc tgttccagat ctataacaaa   2400
gattttcag catacagcaa gggcagacca aacctgcata cactgtactg gaaggccctg   2460
ttcgatgaga ggaatctgca ggacgtggtc tataaactga acggagaggc cgaactgttt   2520
taccggaagc agtctattcc taagaaaatc actcacccag ctaaggaggc catcgctaac   2580
aagaacaagg acaatcctaa gaaagagagc gtgttcgaat acgatctgat taggacaag   2640
cggttcacgg aagataagtt cttttcccat tgtccaatca ccattaactt caagtcaagc   2700
ggcgctaaca agttcaacga cgagatcaat ctgctgctga aggaaaaagc aaacgatgtg   2760
cacatcctga gcattgaccg aggagagcgg catctggcct actataccct ggtggatggc   2820
aaagggaata tcattaagca ggatacattc aacatcattg gcaatgaccg gatgaaaacc   2880
aactaccacg ataaactggc tgcaatcgag aaggataga aaccagctag gaaggactgg   2940
aagaaaatca caacattaa ggagatgaag gaaggctatc tgagccaggt ggtccatgag   3000
attgcaaagc tggtcatcga atacaatgcc attgtggtgt cgaggatct gaacttcggc   3060
tttaagaggg ggcgctttaa ggtggaaaaa caggtctatc agaagctgga gaaaatgctg   3120
atcgaaaagc tgaattacct ggtgtttaaa gataacgagt tcgacaagac cggaggcgtc   3180
ctgagagcct accagctgac agctcccttt gaaactttca gaaaatggg aaaacagaca   3240
ggcatcatct actatgtgcc agccggattc acttccaaga tctgcccgt gaccggcttt   3300
gtcaaccagc tgtaccctaa atatgagtca gtgagcaagt cccaggaatt tttcagcaag   3360
ttcgataaga tctgttataa tctggaacaa gggtacttcg agttttccttt cgattacaag   3420
aacttcggcg acaaggccgc taaggggaaa tggaccattg cctccttcgg atctcgcctg   3480
atcaactttc gaattccga taaaaaccac aattgggaca ctagggaggt gtacccaacc   3540
aaggagctga aaaagctgct gaaagactac tctatcgagt atggacatgg cgaatgcatc   3600
aaggcagcca tctgtggcga gagtgataag aaattttcg ccaagctgac ctcagtgctg   3660
aatacaatcc tgcagatgcg gaactcaaag accgggacag aactggacta tctgattagc   3720
cccgtggctg atgtcaacgg aaacttcttc gacagcagac aggcacccaa aaatatgcct   3780
caggatgcag acgccaacgg ggcctaccac atcgggctga agggactgat gctgctgggc   3840
cggatcaaga caatcaggag ggggaagaag ctgaacctgg tcattaagaa cgaggaatac   3900
ttcgagtttg tccagaatag aaataacgga tctggagtga gaaggggcga ggggctgaag   3960
atggccatca tcaaggagtt catgcgcttc aaggtgcgca tggagggctc cgtgaacggc   4020
cacgagttcg agatcgaggg cgagggcgag ggccgcccct acgagggctt cagaccgct   4080
aagctgaagg tgaccaaggg tggccccctg cccttcgcct gggacatcct gtcccctcat   4140
ttcacctacg gctccaaggc ctacgtgaag caccccgccg acatcccga ctacttcaag   4200
ctgtccttcc ccgagggctt caagtgggag cgcgtgatga actacgagga cggcggcgtg   4260
gtgaccgtga cccaggactc ctccctgcag gacggcgagt tcatctacaa ggtgaagctg   4320
cgcggcacca acttccccst cgacggcccc gtgatgcaga agaagaccat gggctgggag   4380
gcctcctccg agcggatgta ccccgaggac ggtgccctga gggcaagat caagatgagg   4440
ctgaagctga aggacggcgg ccactacacc tccgaggtca agaccaccta caaggccaag   4500
aagcccgtgc agctgcccgg ngccatatca gtcgacatca gttggaacat cacctcccac   4560
aacgaggact acaccatcgt ggaacagtac gaacgcgccg agggccgcca ctccaccggc   4620
ggcatggacg agctgtacaa gggatctaag aagcgtagga tcaagcaaga t            4671

SEQ ID NO: 61      moltype = DNA   length = 4707
FEATURE            Location/Qualifiers
```

| misc_feature | 1..4707 |
| --- | --- |
|  | note = Synthetic polynucleotide.MGSS7H-NLS-FnCpf1-Hs-mOR-NLS |
| source | 1..4707 |
|  | mol_type = other DNA |
|  | organism = synthetic construct |

SEQUENCE: 61

```
atgggcagca gccatcatca ccaccatcac catatgggta gcaaaaagag gcgtatcaag    60
caggacagca tctaccagga gttcgtcaac aagtattcac tgagtaagac actgcggttc   120
gagctgatcc cacagggcaa gacactggag aacatcaagg cccgaggcct gattctggac   180
gatgagaagc gggcaaaaga ctataagaaa gccaagcaga tcattgataa ataccaccag   240
ttctttatcg aggaaattct gagctccgtg tgcatcagtg aggatctgct gcagaattac   300
tcagacgtgt acttcaagct gaagaagagc gacgatgaca acctgcagaa ggacttcaag   360
tccgccaagg acaccatcaa gaaacagatt agcgagtaca tcaaggactc cgaaaagttt   420
aaaaaatctgt tcaaccagaa tctgatcgat gctaagaaag gccaggagtc cgacctgatc   480
ctgtggctga acagtctaa ggacaatggg attgaactgt tcaaggctaa ctccgatatc   540
actgatattg acgaggcact ggaaatcatc aagagcttca agggatggac cacatacttt   600
aaaggcttcc acgagaaccg caagaacgtg tactccagca cgacattcc tacctccatc   660
atctaccgaa tcgtcgatga caatctgcca aagttcctgg agaacaaggc caaatatgaa   720
tctctgaagg acaaagctcc cgaggcaatt aattacgaac agatcaagaa agatctggct   780
gaggaactga cattcgatat cgactataag actagcgagg tgaaccagag ggtcttttcc   840
ctggacgagg tgtttgaaat cgccaatttc aacaattacc tgaaccagtc cggcattact   900
aaattcaata ccatcattgg cgggaagttt gtgaaccggg agaataccaa gcgcaaggga   960
attaacgaat acatcaatct gtatagccag cagatcaacg acaaaactct gaagaaatac  1020
aagatgtctg tgctgttcaa acagatcctg agtgataccg agtccaagtc ttttgtcatt  1080
gataaactga agatgactca agacgtggtc actaccatgc agagctttta tgagcagatc  1140
gccgcttttca agacagtgga ggaaaaatct attaaggaaa ctctgagtct gctgttcgat  1200
gacctgaaag cccagaagct ggacctgagt aagatctact tcaaaaacga taagagtctg  1260
acagaccgtg tcacagcaggt gtttgatgac tattccgtga ttgggaccgc cgtcctggag  1320
tacattacac agcagatcgc tccaaagaac ctggataatc cctctaagaa agagcaggaa  1380
ctgatcgcta agaaaaccga gaaggcaaaa tatctgagtc tggaaacaat taagctgagc  1440
ctggaggagt tcaacaagca cagggatatt gacaaacagt gccgctttga ggaaatcctg  1500
gccaacttcg cagccatccc catgattttt gatgagatcg cccagaacaa agacaatctg  1560
gctcagatca gtattaagta ccagaaccag ggcaagaaag acctgctgca ggcttcagca  1620
gaagatgacg tcaaggatct ctggacccaga ccaacaatct gctgcacaag  1680
ctgaaaatct tccatattag tcagtcagag gataaggcta atatcctgga taaagacgaa  1740
cacttctacc tggtgttcga ggaatgttac tccgagctgg caaacattgt ccccctgtat  1800
aacaagatta ggaactacat cacacagaag ccttactctg acgagaagtt taaactgaac  1860
ttcgaaaata gtacccctggc caacgggtgg ataagaaca aggagcctga caacacagct  1920
atcctgttca tcaaggatga caagtactat ctgggagtga tgataagaa aaacaataag  1980
atcttcgatg acaaagccat taaggagaac aaagggaag gatacaagaa aatcgtgtat  2040
aagctgctgc ccgcgcaaa taagatgctg cctaaggtgt cttcagcgc caagagtatc  2100
aaattctaca acccatccga ggacatcctg cggattgaga atcactcaac acatactaag  2160
aacggagcc cccagaaggg atatgagaaa tttgagttca acatcgagga ttgcaggaag  2220
tttattgact tctacaagca gagcatctcc aaacaccctg aatggaagga ttttggcttc  2280
cggttttccg cacacagag atataactct atcgacgagt tctaccgcga ggtgaaaat  2340
cagggggtata agctgacttt tgagaacatt tctgaaagtt acatcgacag cgtggtcaat  2400
cagggaaagc tgtacctgtt ccagatctat cacaaagatt tttcagcatc cagcaagggc  2460
agaccaaacc tgcatacact gtactggaag gccctgttcg atgagaggaa tctgcaggac  2520
gtggtctata aactgaacgg agaggccgaa ctgttttacc ggaagcagtc tattcctaag  2580
aaaatcactc acccagctaa ggaggccatc gctaacaaga caaggacaa tcctaagaaa  2640
gagagcgtgt tcgaatacga tctgattaag gacaagcagt tcaccgaaga taagttctttt  2700
ttccattgtc caataccat taacttcaag tcaagcggcg ctaacaagtt caacgacgag  2760
atcaatctgc tgctgaagga aaagcaaac gatgtgcaca tcctgagcat tgaccgagga  2820
gagcggcatc tggcctacta tacccctggtg gatggcaaag gaatatcat taagcaggat  2880
acattcaaca tcattggcaa tgaccggatg aaaaccaact accacgataa actggctgaa  2940
atcgagaagg atagactca gctaggagg gactgaaga aaatcaacaa cattaaggag  3000
atgaaggaag gctatctgag ccaggtggtc catgagattg caaagctggt catcgaatac  3060
aatgccattg tggtgttcga ggatctgaac ttcggctttta gaggggggcg ctttaaggtg  3120
gaaaaacagg tctatcgaaa gctggaaga atgctgaaa ttaccttggtg  3180
tttaaagata acgagttcga caagaccgga ggcgtcctga gagcctacca gctgacagct  3240
cccttttgaaa ctttcaagaa aatgggaaaa cagacaggca tcatctacta tgtgccagcc  3300
ggattcactt ccaagatctg cccgtgcacc ggctttgtca accagctgta ccctaaatat  3360
gagtcagtga gcaagtccca ggattttttc agcaagtcg ataagatctg ttataatctg  3420
gacaaggggt acttcgagtt ttccttcgat tacaagaaact tcggccgaca ggccgctcaga  3480
gggaaatgga ccattgcctc cttcggatc cgcctgatca acttcgaaa ttccgataaa  3540
aaccacaatt gggacactag ggaggtgta ccaaccaagg agctgaaa gctgctgaaa  3600
gactactcta tcgagtatgg acatggcgaa tgcatcaagg cagccatctg tggcgagagt  3660
gataagaaat ttttcgccaa gctgacctca gtgctgaata caatcctgca gatgcggaac  3720
tcaaagaccg ggacagaact ggactatctg attagcccccg tggctgatgt caacggaaac  3780
ttcttcgaca gcagacaggc acccaaaaat atgcctcagg atgcagacgc caacggggcc  3840
taccacatcg ggctgaaggg actgatgctg ctgggccgga tcaagaacaa tcaggagggg  3900
aagaagctga acctggtcat taagaacgag gaatactcg agtttgtcca aatagaaat  3960
aacgggatctg gagtgagcaa gggcgaggag ataacatgg ccatcatcaa ggagttcatg  4020
cgcttcaagg tgcgcatgga gggctccgtg aacggccacg agttcgagat cgagggcgag  4080
ggcgagggcc gcccctacga gggctttcag accgctaagc tgaaggtgac caagggtggc  4140
cccctgccct tcgcctggga catcctgtcc cctcatttca cctacggctc aaggcctac  4200
gtgaagcacc ccgccgacat ccccgactac ttcaagctgt ccttcccga ggcttcaag  4260
tgggagcgcg tgatgaacta cgaggacggc ggcgtggtga ccgtgaccca ggactcctcc  4320
ctgcaggacg gcgagttcat ctacaaggtg aagctgcgcg gcaccaactt ccctccgac  4380
```

```
ggccccgtga tgcagaagaa gaccatgggc tgggaggcct cctccgagcg gatgtacccc   4440
gaggacggtg ccctgaaggg caagatcaag atgaggctga agctgaagga cggcggccac   4500
tacacctccg aggtcaagac cacctacaag gccaagaagc ccgtgcagct gcccggcgcc   4560
tacatcgtcg acatcaagtt ggacatcacc tcccacaacg aggactacac catcgtggaa   4620
cagtacgaac gcgccgaggg ccgccactcc accggcggca tggacgagct gtacaaggga   4680
tctaagaagc gtaggatcaa gcaagat                                       4707
```

| | |
|---|---|
| SEQ ID NO: 62 | moltype = DNA  length = 6462 |
| FEATURE | Location/Qualifiers |
| misc_feature | 1..6462 |
| | note = Synthetic polynucleotide.Expression cassette comprising 35Spromoter cassette, MGSS7H-NLS-FnCpf1-Hs-mOr-NLS and NOStranscription termination sequence |
| source | 1..6462 |
| | mol_type = other DNA |
| | organism = synthetic construct |

SEQUENCE: 62

```
ggtccgattg agacttttca acaaagggta atatccggaa acctcctcgg attccattgc     60
ccagctatct gtcactttat tgtgaagata gtggaaaagg aaggtggctc ctacaaatgc    120
catcattgcg ataaaggaaa ggccatcgtt gaagatgcct ctgccgacag tggtcccaaa    180
gatggacccc cacccacgag gagcatcgtg gaaaaagaag acgttccaac cacgtcttca    240
aagcaagtgg attgatgtga tggtccgatt gagacttttc aacaaagggt aatatccgga    300
aacctcctcg gattccattg cccagctatc tgtcacttta ttgtgaagat agtggaaaag    360
gaaggtggct cctacaaatg ccatcattgc gataaaggaa aggccatcgt tgaagatgcc    420
tctgccgaca gtggtcccaa agatggaccc ccacccacga ggagcatcgt ggaaaaagaa    480
gacgttccaa ccacgtcttc aaagcaagtg gattgatgtg atatctccac tgacgtaagg    540
gatgacgcac aatcccacta tccttcgcaa gacccttcct ctatataagg aagttcattt    600
catttggaga ggacacgctg acaagctgac tctagcagat ctaccgtctt cggtacgcgc    660
tcactccgcc ctctgccttt gttactgcca cgtttctctc aatgctctct tgtgtggtga    720
ttgctgagag tggtttagct ggatctagaa ttacactctg aaatcgtgtt ctgcctgtgt    780
tgattacttg ccgtcctttg tagcagcaaa atatagggac atggtagtac gaaacgaaga    840
tagaacctac acagcaatac gagaaatgtg taatttggtg cttagcggta tttatttaag    900
cacatgttgg tgttataggg cacttggatt cagaagtttg ctgttaattt aggcacaggc    960
ttcatactac atgggtcaat agtataggga ttcatattat aggcgatact ataataattt   1020
gttcgtctgc agagcttatt atttgccaaa attagatatt cctattcgtt ttttgtttgt   1080
gtgctgttaa attgttaacg cctgaaggaa taaatataaa tgacgaaatt ttgatgttta   1140
tctctgctcc tttattgtga ccataagtca agatcagatg cacttgtttt aaatattgtt   1200
gtctgaagaa ataagtactg acagtattt gatgcattga tctgcttgtt tgttgtaaca   1260
aaatttaaaa ataaagagtt tccttttgt gctctccttt acctcctgat ggtatctagt   1320
atctaccaac tgacactata ttgcttctct ttacatacgt atcttgctcg atgccttctc   1380
cctagtgttg accagtgtta ctcacatagt cttttgctcat tcattgtaa tgcagatacc   1440
aagcggcctc tagaggatcc aggagcaacc atgggacgga gccatcatca ccaccatcac   1500
catatgggta gcaaaaagag gcgtatcaag caggacagca tctaccagga gttcgtcaac   1560
aagtattcac tgagtaagac actgcggttc gagctgatcc cacagggcaa gacactggag   1620
aacatcaagc ccgaggcct gattctggac gatgagaagc gggcaaaaga ctataagaaa   1680
gccaagaca tcattgataa ataccaccag ttctttatcg aggaaattc gagctccgtg   1740
tgcatcagtg aggatctgct gcagaattac tcagacgtgt acttcaagct gaagaagagc   1800
gacgatgaca acctgcagaa ggacttcaag tccgccaagg acaccatcaa gaaacagatt   1860
agcgagtaca tcaaggactc cgaaaagttt aaaaaatctgt tcaaccagaa tctgatcgat   1920
gctaagaaag gccaggagtc cgacctgatc ctgtggctga acagtctaa ggacaatgag   1980
attgaactgt tcaaggctaa ctccgatatc actgatatg acgaggcact ggaaatcatc   2040
aagagcttca agggatggac cacatacttt aaagcttcc acgagaaccg caagaacgtg   2100
tactccagca cgacattcc tacctccatc atctaccgaa tcgtcgatga caatctgcca   2160
aagttcctgg agaacaaggc caaatatgaa tctctgaagg acaaagctcc cgaggcaatt   2220
aattacgaac agatcaagaa agatctggct gaggaactga cattcgatat cgactataag   2280
actagcgagg tgaaccagag ggtctttttcc ctggacgagg tgtttgaaat cgccaatttc   2340
aacaattacc tgaaccagtc cggcattact aaattcaata ccatcattgg cgggaagttt   2400
gtgaacgggg agaataccaa gcgcaaggga attaacgaat acatcaatct gtatagccag   2460
cagatcaacg acaaaactct gaagaaatac aagatgtctg tgctgttcaa acagatcctg   2520
agtgataccg agtccaagtc ttttgtcatt gataaactgg aagatgactc agacgtggtc   2580
actaccatgc agagctttta tgagcagatc gccgctttca gacagtgga ggaaaaatct   2640
attaaggaaa ctctgagtct gctgttcgat gacctgaaag cccagaagct ggacctgagt   2700
aagatctact tcaaaaacga taagtctctg acagacctgg agcagctggc gtttgatgac   2760
tattccgtca ttgggaccgc cgtcctggag tacattacac agcagatcgc tccaaagaac   2820
ctggataatc cctctaagaa agagcaggaa ctgatcgcta gaaaccgga aggcaaaa     2880
tatctgagtc tggaaacaat taagctgca ctggaggagt tcaacaagca cagggatatt   2940
gacaaacagt gccgcttga ggaaatcctg gccaactcg cagccatccc catgattttt   3000
gatgagatcg cccagaacaa agacctcagt cctatcgtc atggcaga   3060
ggcaagaaag acctgctgca ggcttcagca gaagatgacg tgaaagccat caaggatctg   3120
ctggaccaga ccaacaatct gctgcacaag ctgaaaatct tccatattag tcagtcagag   3180
gataaggcta atatcctgga taagacgaa cacttctacc tggtgttcga ggaatgttac   3240
ttcgagctgg caaacattgt cccccgtat aacaagatta ggaactacat cacacagaag   3300
ccttactctg acgagaagtt taaactgaac ttcgaaaatt cgacctggcc cacgggtgg   3360
gataagaaca aggagcctga caacacagct atcctgttca tcaaggatga caagtactat   3420
ctgggagtga tgaataagaa aaacaataag atcttcgatg acaaagccat taaggagaac   3480
aaaggggaag gatacaagaa aatcgtgtat aagctgctgc ccggcgcaaa taagatgctg   3540
cctaaggtg tcttcagcgc caagagtatc aatttctaca acccatccga ggacatcctg   3600
cggattagaa atcactcaac acatactaag aacgggagcc cccagaaggg atatgagaaa   3660
```

```
tttgagttca acatcgagga ttgcaggaag tttattgact tctacaagca gagcatctcc 3720
aaacaccctg aatggaagga tttttggcttc cggttttccg acacacagag atataactct 3780
atcgacgagt tctaccgcga ggtggaaaat caggggtata agctgacttt tgagaacatt 3840
tctgaaagtt acatcgacag cgtggtcaat cagggaaagc tgtacctgtt ccagatctat 3900
aacaaagatt tttcagcata cagcaagggc agaccaaacc tgcatacact gtactggaag 3960
gccctgttcg atgagaggaa tctgcaggac gtggtctata aactgaacgg agaggccgaa 4020
ctgtttttacc ggaagcagtc tattcctaag aaaatcactc acccagctaa ggaggccatc 4080
gctaacaaga acaaggacaa tcctaagaaa gagagcgtgt tcgaatacga tctgattaag 4140
gacaagcggt tcaccgaaga taagttcttt ttccattgtc caatcaccat taacttcaag 4200
tcaagcggcg ctaacaagtt caacgacgag atcaatctgc tgctgaagga aaaagcaaac 4260
gatgtgcaca tcctgagcat tgaccgagga gagcggcatc tggcctacta taccctggtg 4320
gatggcaaag ggaatatcat taagcaggat acattcaaca tcattggcaa tgaccggatg 4380
aaaaccaact accacgataa actggctgca atcgagaagg atagagactc agctaggaag 4440
gactggaaga aaatcaacaa cattaaggag atgaaggaag gctatctgag ccaggtggtc 4500
catgagattg caaagctggt catcgaatac aatgccattg tggtgttcga ggatctgaac 4560
ttcggcttta agaggggggcg ctttaaggtg gaaaaacagg tctatcagaa gctggagaaa 4620
atgctgatcg aaaagctgaa ttacctggtg tttaaagata acgagttcga caagaccgga 4680
ggcgtgctga gagcctacca gctgacagct cccttttgaaa aatgggaaaa 4740
cagacaggca tcatctacta tgtgccagcc ggattcactt ccaagatctg ccccgtgacc 4800
ggctttgtca accagctgta ccctaaatat gagtcagtga gcaagtccca ggaattttc 4860
agcaagttca ataagatctg ttataatctg acaaggggg acttcgagtt ttccttcgat 4920
tacaagaact tcggcgacaa ggccgctaag gggaaatgga ccattgcctc cttcggatct 4980
cgcctgatca actttcgaaa ttccgataaa aaccacaatt gggacactag ggaggtgtac 5040
ccaaccaagg agctggaaaa gctgctgaaa gactactcta tcgagtatgg acatggcgaa 5100
tgcatcaagg cagccatctg tggcgagagt gataagaaat ttttcgccaa gctgacctca 5160
gtgctgaata caatcctgca gatgcggaac tcaaagaccg ggacagaact ggactatctg 5220
attagccccg tggctgatgt caacggaaac ttcttcgaca gcagacaggc acccaaaaat 5280
atgcctcagg atgcagacgc caacgggccc taccacatcg gctgaaggg actgatgctg 5340
ctgggccgga tcaagaacaa tcaggagggg aagaagctga acctggtcat taagaacgag 5400
gaatacttcg agtttgtcca gaataagaat aacggatctg ggtgagcaa gggcgaggag 5460
aataacatgg ccatcatcaa ggagttcatg cgcttcaagg tgcgcatgga gggctccgtg 5520
aacggccacg agttcgagat cgagggcgag ggcgagggcc gcccctacga gggctttcag 5580
accgctaagc tgaaggtgac caagggtggc ccctgccct tcgcctggga catcctgtcc 5640
cctcatttca cctacggctc caaggcctac gtgaagcacc ccgcgacat ccccgactac 5700
ttcaagctgt ccttcccga gggcttcaag tgggagcgcg tgatgaacta cgaggacgggc 5760
ggcgtggtga ccgtgaccca ggactcctcc ctgcaggacg gcgagttcat ctacaaggtg 5820
aagctgcgcg gcaccaactt cccctccgac ggccccgtga tgcagaagaa gaccatgggc 5880
tgggaggcct cctccgagcg gatgtacccc gaggacggtg ccctgaaggg caagatcaag 5940
atgaggctga agctgaagga cggcggccac tacacctccg aggtcaagac cacctacaag 6000
gccaagaagc ccgtgcagct gcccggcgcc tacatcgtcg acatcaagtt ggacatcacc 6060
tcccacaacg aggactacac catcgtggaa cagtacgaac gcgccgaggg ccgccactcc 6120
accggcggca tggacgagct gtacaaggga tctaagaagc gtaggatcaa gcaagattag 6180
aacccggtac tccgctgagg aattcgcgca atcgttcaca catttggcaa taaagtttct 6240
taagattgaa tcctgttgcc ggtcttgcga tgattatcat ataatttctg ttgaattacg 6300
ttaagcatgt aataattaac atgtaatgca tgacgttatt tatgagatgg gttttttatga 6360
ttagagtccc gcaattatac atttaatacg cgatagaaaa caaaatatag cgcgcaaact 6420
aggataaatt atcgcgcgcg gtgtcatcta tgttactaga tc 6462

SEQ ID NO: 63          moltype = DNA  length = 3960
FEATURE                Location/Qualifiers
misc_feature           1..3960
                       note = Synthetic polynucleotide.NLS-FnCpf1-CO3-NLS
source                 1..3960
                       mol_type = other DNA
                       organism = synthetic construct
SEQUENCE: 63
ggtagcaaaa agaggcgtat caagcaggac atgagcatct accaggagtt cgtgaacaag 60
tacagcctgt cgaagaccct ccggttcgag ctgatccctc aggggaagac gctggagaac 120
atcaaggcgc gcgccctcat cctcgacgac ggaagcgggg cgaaggacta caaaaaggca 180
aagcagatca tcgacaagta ccaccaattc tttattgagg agatcctcag ctccgtctgt 240
atcagcgagg acttgctcca gaactactcc gacgtctatt tcaagctcaa gaagtcagac 300
gacgacaacc tccagaagga cttcaagtcc gcgaaggaca cgatcaaaaa gcagatcagc 360
gagtacatca aggactccga gaagttcaag aaccttctca accagaacct gatcgacgcc 420
aagaaggcc gggaatcgga cctcatcctg tggctcaaga gtcgaagga caacgcatc 480
gagctgttca aggccaactc cgacatcacc gacatcgacg aggcgctgga gatcatcaag 540
tcgttcaagg ggtggaccac ctacttcaag ggcttccacg agaaccgcaa gaacgtttac 600
tccagcaacg acatcccac ctcgatcatc taccggatcg tggacgacaa cctgcccaag 660
ttcctggaga acaaggccaa gtacgagtcc ctcaaggaca ggccccgga ggcgatcaac 720
tacgacgtga ttaaaaagga ccttgctgag gagctgacct tcgacatcga ctacaagacc 780
tccgaggtga accagcgggt gttcagcctc gacgaggtgt tcgagatcgc caacttcaac 840
aactacctga ccagtccgg gatcaccaag ttcaacacga tcatcggcgg gaagttcgtc 900
aacggcgaga acacgaagcg gaagggcatc aacgagtaca tcaacctcta cagccagcag 960
atcaacgaca agaccctcaa aaaatacaaa atgtcggtcc tgttcaagca gatcctgtcc 1020
gacaccgagt ccaagagctt cgtcatcgac aagctggagg acgactccga cgtcgtgacc 1080
accatgcagt cctttacga gcagatcgcc gccttcaaga ccgtggagga agtccatc 1140
aaggagaccc tcagcctcct cttcgacgac ctcaaggcgc agaagctgga cctctccaag 1200
atatacttca agaacgacaa gagcctcacc gacctgtccc agcaagtatt cgacgactac 1260
agcgtgatcg gacggcggt gctggagtac atcacccagc agatagcgcc caagaacctg 1320
gacaaccctc caagaaaga acaggagctg attgctaaaa agaccgaaaa ggctaagtac 1380
```

```
ctgtccctgg agaccatcaa gctcgcgctg gaggagttca acaagcaccg ggacatcgac   1440
aagcagtgcc ggttcgagga gatcctagca aacttcgccg cgatccccat gatcttcgac   1500
gagatcgccc agaacaagga caacctggcc cagatcagca tcaagtacca gaaccagggc   1560
aagaaggacc ttcttcaagc tagtgccgag gacgacgtga aggcgattaa ggatctgctc   1620
gaccagacca acaacctgct ccacaagctc aagatattcc acatctccca gtccgaggac   1680
aaggccaaca tcctggacaa ggacgagcac ttctacctgg tgttcgagga gtgctacttc   1740
gagctggcca acatcgtgcc gctgtacaac aagatccgga actacatcac ccagaagccc   1800
tactccgacg agaagttcaa gctgaacttc gagaactcca ccctggcgaa cgggtgggac   1860
aagaacaagg agcccgacaa cacggccatc ctcttcatca aggacgacaa atattactg    1920
ggcgtcatga acaaaaagaa caacaagata ttcgatgaca aggcgatcaa ggagaacaag   1980
ggcgagggct acaagaaaat agtatataaa ctactgcccg cgcgcaacaa gatgctcccg   2040
aaggtgtttt ttagtgcaaa gtctattaag ttctacaacc ccagcgagga catcctccgc   2100
atccggaacc acagcacgca caccaagaac ggcagcccac agaagggcta cgagaagttc   2160
gagttcaaca tcgaggactg ccgcaagttc atcgacttct acaagcagtc catctccaag   2220
caccccgagt ggaaggactt cgggttccgg ttcagcgaca cccagcgcta caacagcatc   2280
gacgagttct accgggaggt cgagaaccag gggtacaagc tgacgttcga gaacatctcc   2340
gagagctaca tcgacagcgt ggtgaaccag gggaagctgt acctgtttca gatatacaac   2400
aaggacttct cagcctacag caaggggcgg ccgaacctgc acaccctgta ctggaaggcc   2460
ctgttcgacg agcggaacct ccaggacgtc gtgtacaagc tcaacggcga ggcggagctg   2520
ttctaccgga agcagtccat ccccaaaaag attactcacc ccgcgaagga ggccatcgcc   2580
aacaagaaca aggacaaccc caaaaggaa tcagtgttcg agtacgacct catcaaggac   2640
aagcgcttca ccgaggacaa attcttcttt cactgcccga tccgatcaa cttcaagtcc    2700
tccggggcga caagttcaa cgacgagatc aacctgctgc tcaaggagaa ggccaacgac    2760
gtgcacatcc tcagcatcga ccggggcgag cgccacctgg cctactacac cctggtggac   2820
gggaagggca acatcataaa gcaagatacc ttcaacatca tcgggaacga ccggatgaag   2880
acgaactacc acgacaagct ggcggccatc gagaaggaca gggacagcgc cgccaaggac   2940
tggaaaaaga taacaacat taaggagatg aaggagggct acctgtccca ggtggtccac    3000
gagatcgcca agctcgtcat cgagtacaac gccatcgtcg tgttcgagga cttgaacttc   3060
gggttcaagc ggggccggtt caaggtggag aaacaagtct atcaaaagct ggagaagatg   3120
ctcatcgaga agctcaacta cctcgtgttc aaggacaacg agttcgacaa gaccggcagc   3180
gtcctgcggg cctaccagct caccgcgccg ttcgagacgt tcaagaagat ggggaagcag   3240
acggggatca tctactacgt ccccgccggg ttcaccagca agatatgccc ggtcacgggg   3300
ttcgtcaacc agctctaccc caagtacgag tcggtgagca agagccagga gttcttcagc   3360
aagttcgaca agatctgcta caacctggac aagggcttct cgagttctc gttcgactac   3420
aagaacttcg gggacaaggc ggcgaagggc aagtggacca tcgccagctt cggctcccgc   3480
ctcatcaact tccggaactc ggacaagaac cacaactggg acaccgcga ggtgtacccc    3540
acgaaggagc tggagaagct gctcaaggac tacagcatcg agtacgggca cggcgagtgc   3600
atcaaggcca ccatctgcgg ggagtccgac aagaaattct ttgccaagct gacctccgtg   3660
ctgaacacca tcctccagat gcggaacagc aagaccggac ccgagctgga ctacctgcc    3720
tccccggtcg ccgacgtcaa cggcaacttc ttcgattctc gccaggctcc caagaacatg   3780
ccccaggacg ccgacgccaa cggggcctac cacatcgggc tcaagggcct catgctgctc   3840
gggcggatca agaacaacca ggagggcaag aaactcaacc tggtcatcaa gaacgaggag   3900
tactttgagt tcgtccagaa ccggaacaac ggatctaaga agcgtaggat caagcaagat   3960

SEQ ID NO: 64         moltype = DNA  length = 530
FEATURE               Location/Qualifiers
source                1..530
                      mol_type = unassigned DNA
                      organism = Oryza sativa
SEQUENCE: 64
atccaagtaa attaagttgg atcagtagag atgcatggtt ggtgttctca tgtggtctga    60
atctgtgttc tgtttcatct tttgtgtaag tgtgcaactt cgattctgta aaacttggca   120
agtagatgaa cgatgtcatt tatatgcgt tagcttgtca aaatacaaag tagaaacctg     180
tatctgaata agatggcatt catgaaataa tattatcgat tgaacgaacg aagcaacaga   240
atgatcttcc aaattgaagc aaaggaattg atggacaacg agttgctgta ctttggagct   300
gtaaatctgt agtacttctc aacgatgcta tggaccgtgg gccgtccata atcgctgggt   360
ggaatgagcc cactgtccat gtgcttctgc atttggcccg tgtacagccc atataatgtc   420
gaaaaaccta atacgcgcgc gccgccggcg cgcgtttcgg acccagaacg cctagcgccg   480
ctgcgccgac gtgcgcgcgt ctccactttt tttttcgttt tctttccatt                530

SEQ ID NO: 65         moltype = DNA  length = 6530
FEATURE               Location/Qualifiers
misc_feature          1..6530
                      note = Synthetic polynucleotide.Expression cassette
                      comprising Zea maysUbiquitin promoter cassette,
                      NLS-FnCpf1-CO3-NLS and an Oryzasativa transcription
                      termination sequence
source                1..6530
                      mol_type = other DNA
                      organism = synthetic construct
SEQUENCE: 65
gtcgtgcccc tctctagaga taaagagcat tgcatgtcta agtataaaa aattaccaca     60
tatttttttg tcacacttat ttgaagtgta gtttatctat ctctatacat atatttaaac   120
ttcactctac aaataatata gtctataata ctaaaataat attagtgttt tagaggatca   180
tataaataaa ctgctagaca tggtctaaag gataattgaa tatttttgaca atctacagtt   240
ttatctttt agtgtgcatg tgatctctct gttttttttg caaatagctt gacctatata     300
atacttcatc cattttatta gtacatccat ttaggattta gggttgatgg tttctataga   360
ctaattttta gtacatccat tttattcttt ttagtctcta aatttttttaa aactaaaact   420
ctattttagt ttttttattta ataatttaga tataaaatga aataaatataa attgactaca   480
```

```
aataaaacaa ataccctta agaaataaaa aaactaagca aacattttc ttgtttcgag    540
tagataatga caggctgttc aacgccgtcg acgagtctaa cggacaccaa ccagcgaacc   600
agcagcgtcg cgtcgggcca agcgaagcag acggcacggc atctctgtag ctgcctctgg   660
accccctctcg agagttccgc tccaccgttg gacttgctcc gctgtcggca tccagaaatt   720
gcgtggcgga gcggcagacg tgaggcggca cggcaggcgg cctcttcctc ctctcacggc   780
accggcagct acggggggatt cctttccac cgctccttcg cttttccctc ctcgcccgcc   840
gtaataaata gacacccct ccacaccctc ttccccaac ctcgtgttcg ttcggagcgc    900
acacacacgc aaccagatct cccccaaatc cagccgtcgg cacctccgct tcaaggtacg   960
ccgctcatcc tccccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc ttttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggattttt    1920
agccctgcct tcatacgcta tttatttgct tggtactgtt tctttgtcc gatgctcacc   1980
ctgttgttgg gtgatacttc tgcagcggac cgacggtacc atgggtagca aaaagaggcg   2040
tatcaagcag gacatgagca tctaccagga gttcgtgaac aagtacagcc tgtcgaagac   2100
cctccggttc gagctgatcc ctcagggaa gacgctggag aacatcaagg cgcgcggcct   2160
catcctcgac gacgagaagc gggcgaagga ctacaaaaag gcaaagcaga tcatcgacaa   2220
gtaccaccaa ttctttattg aggagatcct cagctccgtc tgcatcacgg aggacttgct   2280
ccagaactac tccgacgtct atttcaagct caagaagtca gacgacgaca acctccgaaa   2340
ggacttcaag tccgcgaagg acacgatcaa aaagcagatc agcgagtaca tcaaggactc   2400
cgagaagttc aagaacctct tcaaccagaa cctgatcgac gccaagaagg ccgggaatc    2460
ggacctcatc ctgtggctca agcagtcgaa ggacaacggc atcgagctgt tcaaggcgaa   2520
ctccgacatc accgacatcg acgaggcgct ggagatcatc aagtcgttca agggtggac    2580
cacctacttc aagggcttcc acgagaaccg caagaacgtt tactccagca acgacatccc   2640
cacctcgatc atctaccgga tcgtggacga caacctgccc aagttcctgg agaacaaggc   2700
caagtacgag tccctcaagg acaaggcccc ggaggcgatc aactacgagc agattaaaaa   2760
ggaccttgct gaggagctga cccttgacat cgactacaag acctccggac tgaaccagcg   2820
ggtgttcagc ctcgacgagg tgttcgagat cgccaacttc aacaactacc tgaaccagtc   2880
cgggatcacc aagttcaaca cgatcatcgg cgggaagttc gtcaacggcg agaacacgaa   2940
gcggaagggc atcaacgagt acatcaacct ctacagccag cagatcaacg acaagaccct   3000
caaaaaatac aaaatgtcgg tcctgttcaa gcagatcacc tccgacaacg agtccaagag   3060
cttcgtcatc gacaagctgg aggacgactc cgacgtcgtg accaccatgc agtccttcta   3120
cgagcagatc gccgccttca agaccgtgga ggagaagtcc atcaaggaga ccctcagcct   3180
cctcttcgac gacctcaagg cgcagaagct ggacctctcc aagatatact tcaagaacga   3240
caaggacctc accgacctgt cccagcaagt attcgacgac tacgcgtga tcgggacggc   3300
ggtgctggag tacatcaccc agcagatagc gcccaagaac ctggacaacc cctccaagaa   3360
agaacaggag ctgattgcta aaaagaccga aaaggctaag tacctgtccc tggagaccat   3420
caagctcgcg ctggaggagt tcaacaagca ccggacatc gacaagcagt gccggttcga    3480
ggagatccta gcaaacttcg ccgcgatccc catgatcttc gacgagatcg cccagaacaa   3540
ggacaacctg gcccagatca gcatcaagta ccagaaccag ggcaagaagg accttcttca   3600
agctagtgcc gaggacgacg tgaaggcgat taaggatctg ctcgaccaga ccaacaacct   3660
gctccacaag ctcaagatat tccacatctc ccagtccgag gacaaggcca acatcctgga   3720
caaggacgag cacttctacc tggtgttcga ggagtgctac ttcgagctgg ccaacatcgt   3780
gccgctgtac aacaagatcc ggaactacat cacccagaag ccctactccg acgagaagtt   3840
caagctgaac ttcgagaact ccaccctggc gaacggtgg gacaagaaca aggagcccga    3900
caacacggcc atcctcttca tcaaggacga caaatattat ctgggcgtca tgaacaaaaa   3960
gaacaacaag atattcgatg acaaggcgat caaggagaac aagggcgagg gctacaagaa   4020
aatagtatat aaactactgc ccggcgcgaa caagatgctc ccgaaggtgt ttttagtgg    4080
aaagtctatt aagttctaca accccagcga ggacatcctc cgcatccgga accacagcac   4140
gcacaccaag aacggcagcc cacagaaggg ctacgagaag ttcgagttca acatcgagga   4200
ctgccgcaag ttcatcgact tctacaagca gtccatctcc aagcaccccg agtggaagga   4260
cttcgggttc cggttcagcg acaccagcg ctacaacagc gtagaagtgc tgactccagg    4320
ggtcgagaac caggggtaca agctgacgtt cgagaacatc tccgagagct acatcgacag   4380
cgtggtgaac caggggaagc tgtacctgtt tcagatatac aacaaggact ctcagcctca   4440
cagcaagggg cggccgaacc tgcacaccct gtactgaag gccctgttcg acgagcgaa     4500
cctccaggac gtcgtgtaca agtcaacg cgaggcggag ctgttctacc ggaagcagtc     4560
catcccaaa aagattactc accccgcgaa ggaggccaac gaaccagta acaaggacaa     4620
ccccaaaaag gaatcagtgt tcgagtacga cctcatcaag gacaagcgct tcaccgagga    4680
caaattcttc tttcactgcc cgatcacgat caacttcaag tcctccgggg cgaacaagtt   4740
caacgacgag atcaacctgc tgctcaagga aaggccaac gacgtgcaca tcctcagcat    4800
cgaccggggc gagcgccacc tggcctacta caccctggtg gacgggaagg gcaacatcat   4860
aaagcaagat accttcaaca tcatcgggaa gcccagagcg aagacgaact accagacaa    4920
gctggcggcc atcgagaagg accgggacag cgcccgcaag gactgaaaa agataaacaa    4980
cattaaggag atgaaggagg gctacctgtc ccaggtggtc cacgagatcg ccaagctcgt   5040
catcgagtac aacgccatcg tcgtgttcga ggacttgaac ttcgggttca agcggggccg   5100
gttcaaggtg gagaaacaag tctatcaaaa gctggagaag atgctcatcg agaagctcaa   5160
ctacctcgtg ttcaaggaca acgagttcga caagaccgg ggcgtcctgc gggcctacca    5220
```

```
gctcaccgcg ccgttcgaga cgttcaagaa gatggggaag cagacgggga tcatctacta    5280
cgtccccgcc gggttcacca gcaagatatg cccggtcacg gggttcgtca accagctcta    5340
ccccaagtac gagtcggtga gcaagagcca ggagttcttc agcaagttcg acaagatctg    5400
ctacaacctg gacaagggct acttcgagtt ctcgttcgac tacaagaact tcggggacaa    5460
ggcggcgaag ggcaagtgga ccatcgccag cttcggctcc cgcctcatca acttccggaa    5520
ctcggacaag aaccacaact gggacacccg cgaggtgtac cccacgaagg agctggagaa    5580
gctgctcaag gactacagca tcgagtacgg cacggcgag tgcatcaagg ccgccatctg    5640
cggggagtcc gacaagaaat tctttgccaa gctgacctcc gtgctgaaca ccatcctcca    5700
gatgcggaac agcaagaccg ggaccgagct ggactacctg atctcccgg tcgccgacgt    5760
caacggcaac ttcttcgatt ctcgccaggc tcccaagaac atgccccagg acgccgacgc    5820
caacggggcc taccacatcg ggctcaaggg cctcatgctg ctcggcgga tcaagaacaa    5880
ccaggagggc aagaaactca acctggtcat caagaacgag gagtactttg agttcgtcca    5940
gaaccggaac aacggatcta agaagcgtag gatcaagcaa gattgattaa ttaagggccc    6000
atccaagtaa attaagttgg atcagtagag atgcatggt ggtgttctca tgtggtctga    6060
atctgtgttc tgtttcatct tttgtgtaag tgtgcaactt cgattctgta aaacttggca    6120
agtagatgaa cgatgtcatt tatatgcgtg tagcttgtca aaatacaaag tagaaacctg    6180
tatctgaata agatggcatt catgaaataa tattatcgat tgaacgaacg aagcaacaga    6240
atgatcttcc aaattgaagc aaaggaattg atggacaacg agttgctgta ctttggagct    6300
gtaaatctgt agtacttctc aacgatgcta tggaccgtgg gccgtccata atcgctgggt    6360
ggaatgagcc cactgtccat gtgcttctgc atttggcccg tgtacagccc atataatgtc    6420
gaaaaaccta atacgcgcgc gccgccgcg cgcgtttcgg acccagaacg cctagcgccg    6480
ctgcgccgac gtgcgcgcgt ctccactttt tttttcgttt tctttccatt                6530
```

SEQ ID NO: 66        moltype = DNA   length = 3960
FEATURE              Location/Qualifiers
misc_feature       1..3960
                       note = Synthetic polynucleotide.NLS-FnCpf1-CO4-NLS
source                 1..3960
                       mol_type = other DNA
                       organism = synthetic construct
SEQUENCE: 66

```
ggtagcaaaa agaggcgtat caagcaggac atgagcatct accaggagtt cgtgaacaag      60
tacagcctga gcaagaccct gcgcttcgag ctgattcctc aggggaagac cctggagaac     120
atcaaggcgc gcggcctgat cctggacgac gagaagcggg cgaaggacta caaaaaggcg     180
aagcagatca tcgacaagta ccatcagttt ttcatcgagg agattctcag ctccgtgtgc     240
atcagcgaag acctgctcca gaactacagc gacgtttact tcaagctcaa gaaatcggac     300
gacgacaacc tccagaagga cttcaagagc gcgaaggaca cgattaagaa acagatcagc     360
gagtacatca aggactccga gaagttcaag aacctgttca accagaacct catcgacgcc     420
aagaaaggcc aagagtcgga cctcatcctc tggctcaaga agagcaagga caacggcatg     480
gagctgttca aggcgaacag cgacatcacc gacatcgacg aggcgctgga gatcatcaag     540
tcgttcaagg gctggacgac ctacttcaag ggcttccacg agaaccgcaa gaatgtctac     600
tcgagcaacg acatccccac gtcgatcatc taccgcatcg tggacgacaa cctcccgaag     660
ttcctggaga acaaggcgaa gtacgagagc ctcaaggaca gcccccggc ggccatcgaa      720
tacgagcaga tcaaaaagga tttggctgag gagctgacgt tcgacatcga ctacaagacc     780
tccgaggtga accagcgcgt cttcagcctc gacgaggtgt cgagatcgc caacttcaac      840
aactacctca ccagtcgggg catcaccaag ttcaacacca tcatcggcgg gaagttcgtc     900
aacggcgaac acacgaagcg caaggggatc aacgagtaca tcaacctgta cagccagcag     960
atcaacgaca gaccctcaa gaagtataaa atgtcggtgc tgttcaagca gatcctctcg     1020
gacaccgaga gcaagtcgtt cgtcatcgac aagtcggagg acgacagcga cgtggtgacc    1080
accatgcaga gcttctacga gcagatcgcg gccttcaaga ccgtcgagga agtcgatc     1140
aaggagagca tcagcctgct gttcgacgac ctcaaggccc agaagctcga cctgtccaag    1200
atatacttta agaacgacaa gagcctcacg gacctgtccc agcaggtatt cgacgactac    1260
agcgtgatcg gacggccgt gctggagtac atcaccaac agatcgcgcc caagaacctg    1320
gacaaccgt ccaagaagga caagagcta atcgccaaaa gactgagaa ggcgaagtac      1380
ctgtcgctgg agacgatcaa gctcgcgctt gaggagttta acaagcaccg cgacatcgac    1440
aagcagtgcc ggttcgagga gatcctggcc aacttcgcgg cgatcccgat gatcttcgac    1500
gagatcgccc agaacaagga caacctggcg cagatcagca tcaagtacca gaaccagggc    1560
aaaaaagact tgctccaagc tagtgcggag gacgacgtga aggcgattaa ggatctgctg    1620
gaccagacta caatctgct gcacaagctc aagatctttc acatctctca gtcggaggac    1680
aaggcgaaca tcctggacaa ggacgagcac ttctaccatg tgttcgagga gtgctacttc    1740
gagctggcga acatcgtgcc cctgtacaac aagatccgga actacatcac ccagaagccc    1800
tacagcgacg agaagttcaa gctgaacttc gagaacagca cgctggcgaa cggtgggac    1860
aagaacaagg agcccgacaa caccgccatc ctgttcatca aggacgacaa atattacctc    1920
ggcgtcatga caaaaaagaa taacaagata ttcgatgaca aggcgatcaa ggagaacaag    1980
ggcgagggct acaagaagat cgtatataaa ctcctgccgg gagcgaacaa gatgctcccg    2040
aaggttttct ttagtgccaa gtccatcaag ttctacaacc cagcgagga catcctccgc    2100
atccggaacc actccaccca caccaagaac ggctcgccgc agaaggcta cgagaagttc    2160
gagttcaaca tcgaggactg ccgcaagttc atcgacttct acaagcagtc catctccaag    2220
caccccggag tggaaggactt cggttccga ttctccgaca gcagcgcta caactccatc    2280
gacgagttct accggggagt ggagaaccag ggctacaagc tgacgttcga aacatctcg    2340
gagtcctaca tcgactccgt ggtcaaccag ggcaagctgt acctcttcca gatatacaat    2400
aaggacttct ccgcctacag caaggggcgg cccaacctcc acaccctgta ctggaaggcg    2460
ctcttcgacg agcggaacct ccaggacgtc gtgtacaagc tgaacggcga ggcggagctg    2520
ttctaccgca agagcagcat cccccaagag atcacgcac aggccatccg                2580
aacaagaaca aggacaaccc caagaaggaa tcggtcttcg agtacgacct catcaaggac    2640
aagcggttca ccggaggacaa attctttttt cactgcccga tcactattaa cttcaagtcc    2700
agcggcgcga caagttcaa cgacgagatc aacctgctcc tcaaggagaa ggcgaacgac    2760
gtgcacatcc tcagcatcga ccggggcgag cgccaccctcg cctactacac gctggtggac    2820
gggaaggca acatcatcaa gcaagacacc ttcaacatca tcggcaacga ccggatgaag    2880
```

```
accaactacc acgacaagct ggccgccatc gagaaggacc gcgactcggc ccgcaaggac  2940
tggaaaaga tcaacaatat caaggagatg aaggagggct acctgagcca agttgtccac  3000
gagatcgcca agctggtgat cgagtacaac gccatcgtcg tgttcgaaga cctgaacttc  3060
ggcttcaagc gcggccggtt caaggtcgag aaacaagtct atcagaaact gagaagatg  3120
ctgatcgaga agctgaacta cctcgtcttc aaggacaacg agttcgacaa gaccggcgcc  3180
gtcctccgcg cgtaccagct caccgcgccc ttcgagacgt tcaagaaaat gggcaagcag  3240
accggcatca tctactacgt gcccgccggg ttcacgagca aaatatgtcc cgtgaccggc  3300
ttcgtcaacc agctctaccc caagtacgag tccgtgtcga agtcccagga attcttcagc  3360
aagttcgaca agatatgcta caacctggac aagggctact tcgagttctc cttcgactac  3420
aagaacttcg gggacaaggc ggcgaagggg aagtggacca tcgcctcgtt cgggtcgcg  3480
ctcatcaact tccggaacag cgacaagaac cacaactggg acaccgcga ggtgtacccg  3540
acgaaggagc tggagaagct cctcaaggac tacagcatcg agtacggcca cggggagtgc  3600
atcaaggcg ccatctgcgg cgagtcggac aaaaagttct tgccaaaact cacctcggtc  3660
ctcaacacca tcctccagat gcggaacgac aagacgggca cggagctgga ctacctcatc  3720
agcccggtgg ccgacgtgaa cggcaatttc tttgactcac gccaggcccc taagaacatg  3780
ccccaggacg ccgacgccaa cggcgcgtac cacatcggcc tcaagggcct gatgctgctc  3840
ggccggatca agaacaacca ggagggcaag aagctcaacc tggtcatcaa gaacgaggag  3900
tatttcgagt tcgtccagaa ccgcaacaac ggatctaaga agcgtaggat caagcaagat  3960

SEQ ID NO: 67           moltype = DNA  length = 6530
FEATURE                 Location/Qualifiers
misc_feature            1..6530
                        note = Synthetic polynucleotide.Expression cassette
                          comprising Zea maysUbiquitin promoter cassette,
                          NLS-FnCpf1-CO4-NLS and an Oryzasativa transcription
                          termination sequence
source                  1..6530
                        mol_type = other DNA
                        organism = synthetic construct
SEQUENCE: 67
gtcgtgcccc tctctagaga taaagagcat tgcatgtcta agtataaaa aattaccaca    60
tatttttttg tcacacttat ttgaagtgta gtttatctat ctctatacat atatttaaac   120
ttcactctac aaataatata gtctataata ctaaaataat attagtgttt tagaggatca   180
tataaataaa ctgctagaca tggtctaaag gataattgaa tattttgaca atctacagtt   240
ttatctttt agtgtgcatg tgatctctct gtttttttg caaatagctt gacctatata    300
atacttcatc cattttatta gtacatccat ttaggattta gggttgatgg tttctataga   360
ctaattttta gtacatccat tttattcttt ttagtctcta aattttttaa aactaaaact   420
ctattttagt ttttattta ataatttaga tataaaatga aataaaataa attgactaca   480
aataaaacaa ataccttta agaaataaaa aaactaagca aacattttc ttgtttcgag    540
tagataatga caggctgttc aacgccgtcg acgagtctaa cggacaccaa ccagcgaacc   600
agcagcgtcg cgtcgggcca agcgaagcag acggcacggc atctgtag ctgcctctgg    660
acccctctcg agagttccgc tccaccgttg gacttgctcc gctgtcggca tccagaaatt   720
gcgtggcgga gcggcagacg tgaggcggca cggcaggcgg cctcttcctc ctctcacgag   780
accggcagct acgggggatt cctttcccac cgctccttcg cttcccttc ctcgcccgcc    840
gtaataaata gacaccccct ccacacctc ttccccaac ctcgtgttcg ttcggagcgc     900
acacacgcg aaccagatct ccccaaatc cagccgtcgg cacctccgct tcaaggtacg    960
ccgctcatcc tccccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaatttgt atctgtatgt gtgtgccata catcttcata   1200
gttacgagtt taagatgatg gatgaaata tcgatctagg ataggtatac atgttgatgc   1260
gggttttact gatgcatata cagagatgct tttttctcg cttggttgtg atgatatggt   1320
ctggttgggc ggtcgttcta gatcggagta gaatactgtt tcaaactacc tggtggattt   1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc tttttttcgc ttggttgtga tgatgtggtc tggttgggcg gtcgttctag  1620
atcggagtag aatactgttt caaactacct ggtggattta ttaatttgt atctttatgt   1680
gtgtgccata catcttcata gttacgagtt taagatgatg gatggaaata ttgatctagg   1740
ataggtatac atgttgatgt gggttttact gatgcatata catgatggca tatgcggcat  1800
ctattcatat gctctaacct tgagtaccta tctattataa taaacaagta tgttttataa   1860
ttatttgat cttgatatac ttggatgatg gcatatgcag cagctatatg tggattttt   1920
agccctgcct tcatacgcta tttatttgct tggtactgtt tcttttgtcc gatgctcacc  1980
ctgttgttgg gtgatacttc tgcagcggac cgacggcagt aggtagca aaaagaggcg   2040
tatcaagcag gacatgagca tctaccagga gttcgtgaac aagtacagcc tgagcaagac   2100
cctgcgcttc gagctgattc ctcagggaa gaccctggag aacatcaagg cgcgcggcct   2160
gatcctggac gacgagaagc gggcgaagga ctacaaaaag gcgaagcaga tcatcgacaa   2220
gtaccatcag ttttttcatcg aggagattct cagctccgtg tgcatcacg aagacctgct    2280
ccagaactac agcgacgttt acttcaagct caagaaatcg gacgacgaaa acctccagaa   2340
ggacttcaag agcgcgaagg acacgattaa gaaacagatc agcgagtaca tcaaggactc   2400
cgagaagttc aagaacctgt tcaaccagaa cctcatcgac gccaagaag gccaagagtc    2460
ggacctcatc ctctgctca agcagagcaa ggacaacggc atcgagctgt tcaaggcgaa   2520
cagcgacatc accgacatcg acgaggcgct ggagatcatc aagtcgttca agggctggac   2580
gacctactc aagggcttcc acgagaaccg caagaatgtc tactcgagca acgacatccc   2640
cacgtcgatc atctaccgca tcgtggacga caacctcccg aagttcctgg agaacaaggc   2700
gaagtacgag agcctcaagg acaaggcccc ggaggccatc aactacgagc agatcaaaaa   2760
ggatttggct gaggagctga cgttcgacat cgactacaag acctccgagg tgaaccagcg   2820
cgtcttcagc ctcgacgagg tgtcgagat cgccaacttc aacaactacc tcaaccagtc   2880
gggcatcacc aagttcaaca ccatcatcgg cggaagttc gtcaacggcg agaacacgaa    2940
```

-continued

```
gcgcaagggg atcaacgagt acatcaacct gtacagccag cagatcaacg acaagaccct 3000
caagaagtat aaaatgtcgg tgctgttcaa gcagatcctc tcggacaccg agagcaagtc 3060
gttcgtcatc gacaagctgg aggacgacag cgacgtggtg accaccatgc agagcttcta 3120
cgagcagatc gcggccttca agaccgtcga ggagaagtcg atcaaggaga cgctcagcct 3180
gctgttcgac gacctcaagg cccagaagct cgacctgtcc aagatatact ttaagaacga 3240
caagagcctc acggacctgt cccagcaggt attcgacgac tacagcgtga tcggacggac 3300
cgtgctggag tacatcaccc aacagatcgc gcccaagaac ctggacaacc cgtccaagaa 3360
ggaacaagag ctaatcgcca aaaagactga gaaggcgaag tacctgtcgc tggagacgat 3420
caagctcgcg cttgaggagt ttaacaagca ccgcgacatc gacaagcagt gccggttcga 3480
ggagatcctg gccaacttcg cggcgatccc gatgatcttc gacgagatcg cccagaacaa 3540
ggacaacctg cgcgcagatca gcatcaagta ccagaaccag ggcaaaaaag acttgctcca 3600
agctagtgcg gaggacgacg tgaaggcgat taaggatctg ctggaccaga ctaacaatct 3660
gctgcacaag ctcaagatct ttcacatctc tcagtcggag gacaaggcga acatcctgga 3720
caaggacgag cacttctacc tagtgttcga ggagtgctac ttcgagctgg cgaacatcgt 3780
gccctgtac aacaagatcc ggaactacat cacccagaag ccctacagcg acgagaagtt 3840
caagctgaac ttcgagaaca gcacgctggc gaacgggtgg gacaagaaca aggagcccga 3900
caacaccgcc atcctgttca tcaaggacga caaatattac ctcggcgtca tgaacaaaaa 3960
gaataacaag atattcgatg acaaggcgat caaggagaac aaaggcgagg gctacaagaa 4020
gatcgtatat aaaactcctg ccgggagcga acaagatgctc ccgaaggttt tctttagtgc 4080
caagtccatc aagttctaca accccagcga ggacatcctc cgcatccgga accactccac 4140
ccacaccaag aacggctcgc cgcagaaggg ctacgagaag ttcgagttca acatcgagga 4200
ctgccgcaag ttcatcgact tctacagcga gtccatctcc aagcacccgg agtggaaga 4260
cttcgggttc cggttctccg acacgcagcg ctacaactcc atcgacgagt ctaccgggaa 4320
ggtgagaac cagggctaca agctgacgtt cgagaacatc tcggagtcct acatcgactc 4380
cgtggtcaac cagggcaagc tgtacctctt ccagatatac aataaggact tctccgccta 4440
cagcaagggg cggcccaacc tccacaccct gtactggaag gcgctcttcg acgagcggaa 4500
cctccaggac gtcgtgtaca agctgaacgg cgaggcggag ctgttctacc gcaagcagag 4560
catcccaag aagatcacgc accccgcgaa ggaggccatc gccaacaaga caaggacaa 4620
ccccaagaag gaatcggtct tcgagtacga cctcatcaag gacaagcggt tcacggagga 4680
caaattctt ttccactgcc cgatcactat taacttcaag tccaccggcg cgaacaagtt 4740
caacgacgag atcaacctgc tcctcaagga gaaggcgaac gacgtgcaca tcctcagcat 4800
cgaccggggc gagcgccacc tcgcctacta cacgctggtg gacgggaagg gcaacatcat 4860
caagcaagac accttcaaca tcatcggcaa cgaccggatg aagaccaact accacgacaa 4920
gctggccgcc atcgagaagg accgcgactc ggcccgcaag gactggaaaa agatcaacaa 4980
tatcaaggag atgaaggagg gctacctgag ccaagttgtc cacgagatcg ccagctggt 5040
gatcgagtac aacgccatcg tcgtgttcga gacctgaac ttcggcttca gcgcggccg 5100
gttcaaggtc gagaaacaag tctatcagaa acttgagaag atgctgatcg agaagctgaa 5160
ctacctcgtc ttcaaggaca acgagttcga caagaccggc ggcgtcctcc gcgcgtacca 5220
gctcaccgcg ccgttcgaga cgttcaagaa aatgggcaag cagaccggca tcatctacta 5280
cgtgcccgcc gggttcacga gcaaaatatg tccgtgacc ggcttcgtca ccagctcta 5340
ccccaagtac gagtccgtgt cgaagtccca ggaattcttc agcaagttcg acaagatatg 5400
ctacaacctg acaagggct acttcgagtt ctccttcgac tacaagaact cggggacaa 5460
ggcggcgaag gggaagtgga ccatcgcctc gttcgggtcg cgcctcatca acttccgaa 5520
cagcgacaag aaccaact gggacacccg cgaggtgtac ccgacgaagg agctgaaga 5580
gctcctcaag gactacagca tcgagtacgg ccacggggag tgcatcaagg cggccatctg 5640
cggcgagtcg gacaaaaagt tctttgccaa actcacctcg gtcctcaaca ccatcctcca 5700
gatgcggaac agcaagacgg gcacgagct ggactacctc atcagcccgg tggccgacgt 5760
gaacggcaat ttctttgact cacgccaggc ccctaagaac atgccccagg acgccgacgc 5820
caacggcgcg taccacatcg gcctcaaggg cctgatgctg ctcggccgga tcaagaacaa 5880
ccaggagggc aagaagctca acctggtcat caagaacgag gagtatttcg agttcgtcca 5940
gaaccgcaac aacggatcta agaagcgtag gatcaagcaa gattagttaa ttaagggcca 6000
atccaagtaa attaagttgg atcagtagag atgcatggtt ggtgttctca tgtggtctga 6060
atctgtgttc tgtttcatct tttgtgtaag tgtgcaactt cgattctgta aaacttggca 6120
agtagatgaa cgatgtcatt tatatgcgtg tagcttgtca aaatacaaag tagaaacctg 6180
tatctgaata agatgcatt catgaaataa tattatcgat tgaacgaacg aagcaacaga 6240
atgatcttcc aaattgaagc aaaggaattg atggacaacg agttgctgta ctttggagct 6300
gtaaatctgt agtacttctc aacgatgcta tggaccgtgg gccgtccata tcgctgggt 6360
ggaatgagcc cactgtccat gtgcttctgc atttggcccg tgtacagccc atataatgtc 6420
gaaaaacctg atacgcgcgc gccgccggcg cgcgtttcgg acccagaacg cctagccgcg 6480
ctgcgccgac gtgcgcgcgt ctccactttt tttttgtttt tctttccatt 6530
```

| SEQ ID NO: 68 | moltype = DNA length = 3960 |
|---|---|
| FEATURE | Location/Qualifiers |
| misc_feature | 1..3960 |
| | note = Synthetic polynucleotide.NLS-FnCpf1-CO5-NLS |
| source | 1..3960 |
| | mol_type = other DNA |
| | organism = synthetic construct |

SEQUENCE: 68

```
ggtagcaaaa agaggcgtat caagcaggac atgtccatat accaggagtt tgttaataaa 60
tatagcttgt ccaaaaccct gcggtttgaa ctcatacctc aggggaagac tttggagaat 120
atcaaagcgc ggggactgat actggacgac gaaaagcgcg caaagattaa caagaaagcg 180
aaacagatca tcgataaata ccatcaattt ttcatagagg agattctcag ttctgtctgt 240
atcagtgagg acctcctcca aaattattca gacgtctatt ttaaactcaa gaagtcggac 300
gacgacaacc ttcagaaaga tttttaagtca gcaaaagaca caatcaaaaa acaaatatcg 360
gaatacataa aggactcaga aaagttcaag aatcttttta accaaaatct gatagacgcg 420
aagaaagggc aggaatctga tcttatactc tggcttaagc agtctaaaga caacggcata 480
gaactcttta aggcaaacag cgatataacc gacatagatg aagccctcga taattaaga 540
tccttcaaag gctggactac atattttaaa gggttccatg agaataggaa gaacgtgtat 600
```

```
tcctcgaatg atattcccac ctcgataatc taccggattg tggatgaataa tctgcctaaa    660
tttttggaaa ataaagcgaa gtacgaaagt ttgaaagata aagcaccaga agcaattaat    720
tatgaacaaa ttaagaaaga tctggctgag gaacttacgt tcgatatcga ttataaaaca    780
tcagaagtta atcagcgggt ttttagcctg gatgaagttt ttgagatcgc caacttcaac    840
aattatctta atcagagcgg gattaccaaa ttcaacacta ttatcggtgg taaattcgtt    900
aatggtgaga acacaaagag aaaaggtata aacgaataca taaatttgta cagtcaacag    960
attaacgata aactttgaa aaagtacaag atgtcagtgc ttttcaaaca aatcctttcc   1020
gacacagaat ccaaaagttt tgtgatagac aaattggaag atgatagcga cgtcgtcacg   1080
accatgcaat cattttatga gcaaattgca gccttcaaga cggtcgaga aaaaagtata   1140
aaagaaacgt tgtcgctctt gttcgacgac ctgaaagcac agaaattgga tttgtctaag   1200
atatacttta aaaacgacaa atccctcacg gacttgtcgc agcaagtctt tgatgattat   1260
tcggtgattg gacagccgt gctcgaatac atcacccagc aaatcgctcc gaaaatctg   1320
gacaatccgt ctaaaaaaga gcaagagctg atcgcaaaga aaaccgaaaa agcgaaatac   1380
ctgtctctgg agacaatcaa attggccttg gaagagttca ataagcacag agacattgat   1440
aaacaatgtc ggtttgagga aattcttgct aactttgccg ctatcccgat gatcttcgat   1500
gagattgcgc aaaataagga taatctggcc caaatctcga tcaagtatca aaatcagggt   1560
aagaaggacc tgcttcaagc atcggcgag gatgatgtga aagcgattaa ggacttgttg   1620
gatcagacca acaatttgtt gcacaagctg aagatattcc acatctccca gagtgaggat   1680
aaggccaaca tcctggacaa ggatgaacat ttctatttgg tcttcgaaga gtgttatttt   1740
gaattggcca acatagttcc tctttataac aagatccgca attatattac acaaaagcct   1800
tattccgatg aaaaatttaa acttaacttc gaaaatagca cattggcgaa tggttgggat   1860
aaaaataagg agcctgcaa tactgctata cttttcatta aggacgataa gtactacctc   1920
ggcgttatga acaagaagaa taataagatc tttgacgaca aagcaatcaa agagaacaaa   1980
ggcgaaggtt acaaaaaat cgtgtacaaa ctcctgcctg gcgcgaataa aatgcttccg   2040
aaggtttttt tcagtgcgaa gtccattaag ttttataacc cttccgagga tattttgaga   2100
attagaaatc actccaccca taccaagaat ggcagccccc agaagggggta tgaaaagttc   2160
gaatttaata tcgaagactg ccgcaagttt atagactttt ataaacagtc catatctaaa   2220
catcccgaat ggaaagattt tggtttccgg ttttctgaca ctcagaggta caacagcata   2280
gatgagttct accgcgaagt tgaaaaccaa ggctacaagc ttacatttga gaacatcagc   2340
gagtcatata ttgactcagt cgttaatcag ggcaaacttt attttgttcca aatttacaac   2400
aaagactttt cagcgtacag caagggaagg ccaaatctcc atacactgta ttggaaggcg   2460
ctgtttgacg agcggaatct tcaagatgtt gtgtataaac tcaacgggga ggccgaattg   2520
ttctacagga agcaaagcat tcctaagaaa attccccacc ccgctaagga agcgatagca   2580
aataaaaata aagacattcc gaaaaaagag agcgttttg agtacgacct tataaaggat   2640
aagagattca ccgaggataa gtttttcttc cactgtccaa taactattaa ctttaaatcc   2700
tccggagcca acaagtttaa cgacgaaatt aatttgctgc tgaaagagaa ggcgaacgac   2760
gttcacattc tgtcaataga cagagggggg agacacttgg catactacac gctcgttgat   2820
ggaaaaggta acattattaa gcaagatact ttcaacatca ttgggaatga cagaatgaaa   2880
acaaactatc acgataaact cgcggcaatt gagaaggacc gggattcggc gaggaaagac   2940
tggaagaaaa tcaacaatat aaaggagatg aaggaaggat acctgtctca agtcgtccac   3000
gaaatagcca agcttgttat agagtataat gcgattgtgg tctttgaaga ccttaacttt   3060
ggatttaaac gcggccggtt taaagtcgag aaacaagtgt atcaaaaaact ggaaaaaatg   3120
ttgatcgaga aactgaatta tctcgtcttc aaggacaacg agttcgataa aaccgggggc   3180
gtcttgcgcg cttatcaact gacggcaccg tttgaaactt tcaagaagat gggcaaacag   3240
actgggatta tctactacgt tcctgccgga ttcacctcca aaatatgccc agttactgga   3300
tttgttaacc agttgtaccc taagtacgaa tcagtcagca agtcccaaga gttttttctca   3360
aaatttgata agatctgcta taacctggac aaggggtact tcgagttttc cttcgactat   3420
aaaaattctcg gcgacaaggc agctaaaggt aaatgggacga ttgcaagttt cggctccagg   3480
cttattaatt tcagaacag cgacaaaaac cataactggg acacgcgcga ggtctacccct   3540
acgaaggaac tggaaaaact tctcaaggat tacagtatag aatacggaca cggggagtgt   3600
atcaaagctg cgatatgcgg agagtcggat aaaaagttttt tcgcaaagtt gacatcagtt   3660
ttgaacacta tcttgcagat gagaaattcc aagactggca cggagttgga ctaccttatt   3720
agcccagtgg cggatgtcaa cgggaacttt tttgattcga ggcaagcccc taagaatatg   3780
cctcaagacg ctgatgcaaa cggggcatat cacataggac tcaaagggtt gatgctgctg   3840
ggcagaatta agaacaacca ggaaggaaag aagctcaatc ttgttatcaa aaatgaagag   3900
tactttgaat tcgttcaaaa ccggaataac ggatctaaga gcgtaggat caagcaagat   3960

SEQ ID NO: 69       moltype = DNA   length = 6530
FEATURE             Location/Qualifiers
misc_feature        1..6530
                    note = Synthetic polynucleotide.Expression cassette
                    comprising Zea maysUbiquitin promoter cassette,
                    NLS-FnCpf1-CO5-NLS and an Oryzasativa transcription
                    termination sequence
source              1..6530
                    mol_type = other DNA
                    organism = synthetic construct
SEQUENCE: 69
gtcgtgcccc tctctagaga taaagagcat tgcatgtcta aagtataaaa aattaccaca     60
tatttttttg tcacacttat ttgaagtgta gtttatctat ctctatacat atatttaaac    120
ttcactctac aaataatata gtctataata ctaaaataat attagtgttt tagaggatca    180
tataaataaa ctgctagaca tggtctaaag gataattgaa tattttgaca atctacagtt    240
ttatcttttt agtgtgcatg tgatctctct gtttttttg caaatagctt gacctatata    300
atacttcatc cattttatta gtacatccat ttaggattga gggttgatgg tttctataga    360
ctaatttttta gtacatccat tttattcttt ttagtctcta aatttttaa aactaaaact    420
ctatttttagt ttttattta ataatttaga tataaaatga aataaaataa attgactaca    480
aataaaacaa atacccttta agaaataaaa aaactaagca acattttttc ttgtttcgag    540
tagataatga caggctgttc aacgccgtcg acgagtctaa cggacaccaa ccagcgaacc    600
agcagcgtcg cgtcgggcca agcgaagcag acggcacggc atctctgtag ctgcctctgg    660
```

```
accccctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acgggggatt cctttcccac cgctccttcg cttteccttc ctcgcccgcc  840
gtaataaata gacaccccct ccacaccctc tttcccaac ctcgtgttcg ttcggagcgc  900
acacacacgc aaccagatct cccccaaatc cagccgtccg cacctccgct tcaaggtacg  960
ccgctcatcc tccccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc ttttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggattttt  1920
agccctgcct tcatacgcta tttattgct tggtactgtt tcttttgtcc gatgctcacc  1980
ctgttgttgg gtgatacttc tgcagccgac cgacgtacc atgggtagca aaaagaggcg  2040
tatcaagcag gacatgtcca tataccagga gtttgttaat aaatatagct tgtccaaaac  2100
cctgcggttt gaactcatac ctcaggggaa gactttggag aatatcaaag cgcgggact  2160
gatactggac gacgaaaagc gcgcaaaaga ttacaagaaa gcgaaacga tcatcgataa  2220
ataccatcaa tttttcatag aggagattct cagttctgtc tgtatcagtg aggacctcct  2280
ccaaaattat tcagacgtct atttttaaact caagaagtcg gacgacgaca accttcagaa  2340
agatttaag tcagcaaaag acacaatcaa aaaacaaata tcggaataca taaggactc  2400
agaaaagttc aagaatcttt ttaaccaaaa tctgatagac ggcgaagaaag ggcaggaatc  2460
tgatcttata ctctggctta agcagtctaa agacaacggc atagaactct ttaaggcaaa  2520
cagcgatata accgacatag atgaagcccct cgagataatt aagtccttca aaggctggac  2580
tacatatttt aaagggttcc atgagaatag gaagaacgtg tattcctcga atgatattcc  2640
cacctcgata atctaccgga ttgtggatga taatctgcct aaattttttgg aaaataaagc  2700
gaagtacgaa agtttgaaag ataaaagcacc agaagcaatt aattatgaac aaattaagaa  2760
agatctggct gaggaactta cgttcgatat cgattataaa acatcagaag ttaatcagcg  2820
ggttttagc ctgatgaag ttttttgagat cgccaacttc aacaattatc ttaatcagag  2880
cgggattacc aaattcaaca ctattatcgg tggtaaattc gttaatggtg agaacacaaa  2940
gagaaaaggt ataaacgaat acataaattt gtacagtcaa cagattaacg ataaaacttt  3000
gaaaaagtac aagatgtcag tgcttttcaa acaaatcctt tccgacacag aatccaaaag  3060
ttttgtgata gacaaattgg aagatgatag cgacgtcgtc acgaccatgc aatcattta  3120
tgagcaaatt gcagccttca agacggttga ggaaaaagt ataaagaaa cgttgtcgct  3180
cttgttcgac gacctgaaag cacagaaatt ggatttgtct aagatatact ttaaaaacga  3240
caaatccctc acggacttgt cgcagcaagt ctttgatgat tattcggtga ttgggacagc  3300
cgtgctcgaa tacatcaccc agcaaatcgc tccgaaaaat ctggacaatc cgtctaaaaa  3360
agagcaagag ctgatcgcaa agaaaccga aaaagcgaaa tacctgtctc tggagacaat  3420
caaattggcc ttggaagagt tcaataagca cagagacatt gataaacaat gtcggtttga  3480
ggaaattctt gctaactttg ccgctatccc gatgatcttc gatgagattg cgcaaaataa  3540
ggataatctg gcccaaatct cgatcaagta tcaaaatcag ggtaagaagg acctgcttca  3600
agcatcggcg gaggatgatg tgaaagcgat taaggacttg ttggatcaga ccaacaattt  3660
gttgcacaag ctgaagatat tccacatctc ccagagtgag gataaggcca acatcctga  3720
caaggatgaa catttctatt tggtcttcga agagtgttat tttgaattgg ccaacatagt  3780
tcctctttat aacaagatcc gcaattatat tacacaaaag ccttattccg atgaaaatt  3840
taaacttaac ttcgaaaata gcacattggc gaatggttgg ataaaaata aggagcctga  3900
caatactgct atactttca ttaaggacga taagtactac ctcggcgtta tgaacaagaa  3960
gaataataag atctttgacg acaaagcaat caaagagaac aaaggcgaag gttacaaaaa  4020
aatcgtgtac aaactcctgc ctggcgcgaa taaaatgctt ccgaaggttt ttttcagtgc  4080
gaagtccatt aagttttata acccttccga ggatattttg agaattagaa atcactccac  4140
ccataccaag aatggcagcc cccagaaggg gtatgaaaag ttcgaattta atatcgaaga  4200
ctgccgcaag tttatagact tttataaaca gtccatatct aaacatcccg aatgaaagaa  4260
ttttggtttc cggttttctg acactcagag gtacaacagc atagatgagt tctaccgcga  4320
agttgaaaac caaggctaca agcttacatt tgagaacatc agcgagtcat atattgactc  4380
agtcgttaat cagggcaaac tttatttgtt ccaaatttac aacaaagact tttcagcgta  4440
cagcaagggg aggccaaatc tccatacact gtattggacg gcgctgtttg acgagcggaa  4500
tcttcaagat gttgtgtata aactcaacgg ggaggccgaa ttgttctaca ggaagcaaag  4560
cattcctaag aaaattaccc accccgctaa ggaagcgata gcaataaaaa ataaagacaa  4620
tccgaaaaaa gagagcgttt ttgagtacga ccttataaag gataagagat tcaccgagga  4680
taagttttttc ttccactgtc caataactat taactttaaa tcctccggag ccaacaagtt  4740
taacgacgaa attaatttgc tgctgaaaga gaaggcaagc gacgttcaca ttctgtcaat  4800
agacagaggg gagagacact tggcatacta cacgctcgtt gatggaaaag gtaacattat  4860
taagcaagat acttttcaaca tcattgggaa tgacagaatg aaaacaaact atcacgataa  4920
actcgcggca attgagaagg accgggattc ggcgaggaaa gactggaaga aaatcaacaa  4980
tataaaggag atgaaggaag gatacctgtc tcaagtcgtc cacgaaatag ccaagcttgt  5040
tatagatgta aatgcgattg tggtcttgga agaccttaac tttgagttta aacgcggccg  5100
gtttaaagtc gagaaacaag tgtatcaaaa actggaaaaa atgttgatcg agaaactgaa  5160
ttatctcgtc ttcaaggaca acgagttcga taaaaccggg ggcgtcttgc gcgcttatca  5220
actgacggca ccgtttgaaa ctttcaagaa gatgggcaaa cagactggga ttatctacta  5280
cgttcctgcc ggattcacct ccaaaatatg cccagttact ggatttgtta accagttgta  5340
ccctaagtac gaatcagtca gcaagtccca agagttttc tcaaaatttg ataagatctg  5400
```

```
ctataacctg dacaagggt acttcgagtt ttccttcgac tataaaaatt tcggcgacaa    5460
ggcagctaaa ggtaaatgga cgattgcaag tttcggctcc aggcttatta atttcagaaa    5520
cagcgacaaa aaccataact gggacacgcg cgaggtctac cctacgaagg aactggaaaa    5580
acttctcaag gattacagta tagaatacgg acacggggga tgtatcaaag ctgcgatatg    5640
cggagagtcg gataaaaagt ttttcgcaaa gttgacatca gttttgaaca ctatcttgca    5700
gatgagaaat tccaagactg gcacggagtt ggactacctt attagcccag tggcggatgt    5760
caacgggaac ttttttgatt cgaggcaagc ccctaagaat atgcctcaag acgctgatgc    5820
aaacggggca tatcacatag gactcaaagg gttgatgctg ctgggcagaa ttaagaacaa    5880
ccaggaagga aagaagctca atcttgttat caaaaatgaa gagtactttg aattcgttca    5940
aaaccggaat aacggatcta agaagcgtag gatcaagcaa gattgattaa ttaagggccc    6000
atccaagtaa attaagttgg atcagtagag atgcatggtt ggtgttctca tgtggtctga    6060
atctgtgttc tgtttcatct tttgtgtaag tgtgcaactt cgattctgta aaacttggca    6120
agtagatgaa cgatgtcatt tatatgcgtg tagcttgtca aaatacaaag tagaaacctg    6180
tatctgaata agatggcatt catgaaataa tattatcgat tgaacgaacg aagcaacaga    6240
atgatcttcc aaattgaagc aaaggaattg atggacaacg agttgctgta ctttggagct    6300
gtaaatctgt agtacttctc aacgatgcta tggaccgtgg gccgtccata atcgctgggt    6360
ggaatgagcc cactgtccat gtgcttctgc atttggcccg tgtacagccc atataatgtc    6420
gaaaaaccta atacgcgcgc gccgccggcg cgcgtttcgg acccagaacg cctagcgccg    6480
ctgcgccgac gtgcgcgcgt ctccactttt tttttcgttt tctttccatt                6530

SEQ ID NO: 70          moltype = DNA  length = 3960
FEATURE                Location/Qualifiers
misc_feature           1..3960
                       note = Synthetic polynucleotide.NLS-FnCpf1-CO6-NLS
source                 1..3960
                       mol_type = other DNA
                       organism = synthetic construct
SEQUENCE: 70
ggtagcaaaa agaggcgtat caagcaggac atgagtattt atcaagagtt cgttaataag      60
tacagtcttt ctaagacgct caggtttgag ctcattccac aaggtaagac ccttgagaat     120
attaaagccc gcggactgat cctggacgac gagaagcgcg ccaaagacta taagaaggcg     180
aaacagatca tagataagta tcaccaattc ttcatagaag agatacttag ctctgtttgt     240
atctcagagg atctgctcca gaactactcg gatgtgtact ttaaactcaa gaagtctgac     300
gatgcaaatc tccagaagga cttttaagtcc gccaaagaca caatcaagaa gcagatttcg     360
gaatacataa aggacagtga gaagttcaag aacttgttca accagaatct catgacgcgc     420
aagaagggtc aggagagcga tcttattctg tggttgaaac aatcaaagga caacggtatt     480
gagttgttta aagcaaactc tgacatcacc gacattgacg aggctctgga gatcattaag     540
agttttaaag ggtggacaac ctacttttag ggatttcatg agaatcgcaa aacgtgtac     600
tcgagcaatg acatacctac aagcataatc tatcggataa tcgacgataa cctcccgaag     660
ttcctcgaga ataaagcgaa gtacgaatcg cttaaggata aggcgccgga ggcgataaac     720
tatgaacaga ttaagaagga tctggctgaa gaattgacct ttgatattga ctataagacc     780
agcgaagtca accaacgcgt tttcagcctg gatgaagtgt ttgagatcgc caacttcaat     840
aattacttga atcaatcggg gataacaaag tttaatacga ttatcggcgg gaagtttgtc     900
aacggggaga acacaaagag gaagggcata aatgagtaca ttaatctcta tagtcaacag     960
ataaatgaca agacgttgaa gaaatacaag atgtcagtcc ttttcaagca gatcctgtct    1020
gacacagaat cgaagagctt cgtgatagat aagctgaagg atgattccga cgttgtcaca    1080
accatgcaat cgttttacga gcagatgcgc gccttcaaga ccgttgagga gaagtctatt    1140
aaagagactc tttctcttct gtttgatgac ttgaaggccc agaagcttga cttgtccaag    1200
atctacttca agaacgataa atctctgaca gatctcagcc agcaagtgtt tgacgactat    1260
tctgttatcg gaacggccgt gctggagtac atcacacagc agatcgcgcc taagaaccct    1320
gataatccga gcaagaaaga acaggagttg attgcaaaga agacagagaa ggccaaatac    1380
ctttctctgg agacaattaa acttgcactg gaagaattca ataagcacag agatatcgac    1440
aagcagtgtc gctttgagga gatcctggca aatttttgctg ccatcccaat gattttttgat    1500
gagattgccc agaacaagga caatctgcgc agatatcaa tcaagtatca gaaccaaggc    1560
aagaaggacc tcctgcaagc tcagcgaaa gatgacgtta aggccataaa ggatctcctt    1620
gatcagacca taaacttgct gcacaagctg aagatctttc atatcagcca gtcggaagac    1680
aaagcaaata tccttgacaa ggacgagcat ttctatctgg tgttcgaaga atgctatttc    1740
gagctggcca atatcgtgcc tctgtacaat aagatccgca attatatcac gcagaagccg    1800
tatagcgacg agaagttcaa gctgaatttc gagaactcca ccttggccaa tggttgggat    1860
aagaacaaag aaccggacaa tacggccatc ttgtttatca agatgacaa gtactatctg    1920
ggagtgatga ataagaagaa caataagatc ttcgatgaca agccattaa ggagaataaa    1980
ggggaaggtt acaagaagat tgtctataaa ctgctccccg gggccaacaa gatgctgccc    2040
aaagtttttt tcagtgccaa gagcatcaag ttttataatc cctcagaaga catactgaga    2100
atcagaaacc actcgaccca taccagaac ggctctccga agaaggggta cgagaaattc    2160
gaattcaaca tcgaagactg tagaaagttc atcgatttttt acaagcaatc gatatcaaag    2220
caccctgaat ggaaggattt tggttttcgc tttagtgaca ctcagcggta taatagcatt    2280
gatgagttct accgcgaagt tgagaatcag ggatacaaat tgacattcga gaatatcagc    2340
gaatcgtaca ttgatagcgt cgtcaaccag gggaaacttt acctcttcca gatttataat    2400
aaagacttct cggcgtactc caagggaaga ccaaatcttc atactctgta ttggaaggca    2460
ctcttcgatg agagaaatct tcaggatgtc gtttataaac ttaatgggga agcggagctg    2520
ttctaccgca agcagagcat ccctaagaag atcacgcacc ccgcgaagga ggcgatagcc    2580
aataagaaca aggataaccc gaagaaggag tccgtcttcg aatatgacct gatcaaggat    2640
aagagattca ctgaggacaa attcttcttc cattgcccta ttacgattaa ttttaaatcg    2700
agcggcgcga ataattcaa gcacgaatc aacctgctcc tcaaagagaa gcccaatgat    2760
gtccacattc tctcaatcga cagagggag aggcaccttg cctactatac gctcgttgat    2820
ggtaaagta acatcattaa gcaggacacg ttcaacatca tcgggaacga ccgcatgaag    2880
acaaactatc acgataaatt ggcggcaatc gagaaggat gggatagtgc caggaaggac    2940
tggaagaaga ttaataacat caaggagatg aaggagggat atcttctca gtcgtccac    3000
gagatcgcga agctggttat cgagtacaac gccatagtgg tcttcgaaga tctgaacttc    3060
```

```
ggattcaaga gagggagatt taaggtggag aagcaagttt atcagaaact ggagaagatg   3120
ctgatagaga agctcaacta cctcgtgttt aaagacaacg agtttgacaa gacaggtggg   3180
gtgttgaggg cctatcagct cacggccccc ttcgagacct tcaagaagat gggaaagcag   3240
acggggataa tctactacgt ccctgctggc ttcacttcga agatctgccc agttacagga   3300
ttcgttaacc agttgtatcc caaatacgag tccgtctcaa agtcacaaga attcttttct   3360
aaattcgata agatctgcta caacctggat aagggctact tcgagtttag ctttgactat   3420
aagaatttcg gggacaaagc ggcaaggggg aagtggacaa tcgcaagttt ggctcccgg    3480
ctgattaact ttcggaattc tgacaagaat cacaactggg atactagaga ggtctatcca   3540
actaaagagt tggagaagtt gctcaaggac tactccattg aatatggtca cggggaatgc   3600
attaaagcgg ccatctgcgg agagtccgat aagaagttct ttgccaaact tacatcggtc   3660
ttgaacacca tactgcagat gcggaacagc aagacgggaa cggaactcga ctaccttatc   3720
tcacctgtgg cggatgttaa tggaaacttt tcgattcga ggcaggcgcc caagaacatg    3780
ccgcaagatg cagatgccaa tggagcatat cacatcggtc ttaaagggct catgctgctt   3840
ggccgcatca agaacaacca agaggggaag aagttgaacc tggttattaa gaacgaagaa   3900
tacttcgaat ttgtccagaa ccgcaacaac ggatcataga agcgtaggat caagcaagat   3960

SEQ ID NO: 71          moltype = DNA    length = 6530
FEATURE                Location/Qualifiers
misc_feature           1..6530
                       note = Synthetic polynucleotide.Expression cassette
                       comprising Zea maysUbiquitin promoter cassette,
                       NLS-FnCpf1-CO6-NLS and an Oryzasativa transcription
                       termination sequence
source                 1..6530
                       mol_type = other DNA
                       organism = synthetic construct
SEQUENCE: 71
gtcgtgcccc tctctagaga taaagagcat tgcatgtcta aagtatataaa aattaccaca   60
tattttttttg tcacacttat ttgaagtgta gtttatctat ctctatacat atatttaaac   120
ttcactctac aaataaatata gtctataata ctaaaataat attagtgttt tagaggatca   180
tataaataaa ctgctagaca tggtctaaag gataattgaa tattttgaca atctacagtt   240
ttatcttttt agtgtgcatg tgatctctct gttttttttg caaatagctt gacctatata   300
atacttcatc catttttatta gtacatccat ttaggattta gggttgatgg tttctataga   360
ctaattttta gtacatccat tttattcttt ttagtctcta aattttttaa aactaaaact   420
ctattttagt ttttttattta ataatttaga tataaaatga aataaaataa attgactaca   480
aataaaacaa ataccctta agaaataaaa aaactaagca aacatttttc ttgtttcgag    540
tagataatga caggctgttc aacgccgtcg acgagtctaa cggacaccaa ccagcgaacc   600
agcagcgtcg cgtcgggcca agcgaagcag acggcacggc atctctgtag ctgcctctgg   660
accccctcg agagttccgc tccaccgttg gacttgctcc gctgtcggca tccagaaatt   720
gcgtggcgga gcggcagacg tgaggcggca cggcaggcgg cctcttcctc ctctcacggg   780
accggcagct acgggggatt cctttcccac cgctccttcg ctttcccttc ctcgcccgcc   840
gtaataaaata gacaccccct ccacacctc tttccccaac ctcgtgttcg ttcggagcgc   900
acacacacgc aaccagatct cccccaaatc cagccgtccg cacctccgct tcaaggtacg   960
ccgctcatcc tccccccccc cctctctcta ccttctctag atcggcgatc cggtccatgg   1020
ttagggcccg gtagttctac ttctgttcat gtttgtgtta gagcaaacat gttcatgttc   1080
atgtttgtga tgatgtggtc tggttgggcg tcgttctag atcggagtag gatactgttt    1140
caagctacct ggtggattta ttaatttgt atctgtatgt gtgtgccata catcttcata   1200
gttacgagtt taagatgatg gatgaaata tcgatctagg ataggtatac atgttgatgc   1260
gggtttact gatgcatata cagagatgct tttttttctcg cttggttgtg atgatatggt   1320
ctggttgggc ggtcgttcta gatcggagta gaatactgtt tcaaactacc tggtggattt   1380
attaaaggat aaagggtcgt tctagatcgg agtagaatac tgtttcaaac tacctggtgg   1440
atttattaaa ggatctgtat gtatgtgcct acatcttcat agttacgagt ttaagatgat   1500
ggatggaaat atcgatctag ataggtata catgttgatg cgggttttac tgatgcatat   1560
acagagatgc tttttttcgc ttggttgtga tgatgtggtc tggttgggcg tcgttctag   1620
atcggagtag aatactgttt caaactacct ggtggattta ttaatttgt atctttatgt   1680
gtgtgccata catcttcata gttacgagtt taagatgatg gatgaaata ttgatctagg    1740
ataggtatac atgttgatgt gggttttact gatgcatata catgatggca tatgcggcat   1800
ctattcatat gctctaacct tgagtaccta tctattataa taaacaagta tgttttataa   1860
ttattttgat cttgatatac ttggatgatg gcatatgcag cagtatatg tggattttt    1920
agccctgcct tcatacgcta tttattttgct tggtactgtt tctttttgtcc gatgctcacc   1980
ctgttgttgg gtgatacttc tgcagcggac cgacggtacc atgggtagca aaaagaggcg   2040
tatcaagcag gacatgagta tttatcaaga gttcgttaat aagtacagtc tttctaagac   2100
gctcaggttt gagcttcattc cacaaggtaa gacccttgag aatattaaag cccgcggact   2160
gatcctggac gacgagaagc gcgccaaaga ctataagaag gcgaaacaga tcatagataa   2220
gtatcaccaa ttcttcatag aagagatact tagctctgtt tgtatctcag aggatctgct   2280
ccagaactac tcggatgtgt actttaaact caagaagtct gacatgaca atctccagaa   2340
ggactttaag tccgccaaag acacaatcaa gaagcagatt tcggaataca taaaggacag   2400
tgagaagttc aagaactgt tcaaccagaa tctcatagac gccaagaagg tcaggagag    2460
cgatcttatt ctgtggttga aacaatcaaa ggacaacggt attgagtttgt ttaaagcaaa   2520
ctctgacatc accgacattg acgaggctct ggagatcatt aagagtttta agggtggac    2580
aacctacttt aagggatttc atgagaatcg caagaacgtg tactcgagca atgacatacc   2640
tacaagcata atctatcgga tagtcgacga taacctcccg aagttcctcg agaataaagc   2700
gaagtacgaa tcgcttaagg ataaggcgcc ggaggcgata aactatgaac agattaagaa   2760
ggatctgcct gaagaattga atttgatat tgactataag accagcgaag tcaaccaacg   2820
cgttttcagc ctgatgaag tgtttgagat cgccaacttc aataattact gaatcaatc    2880
ggggataaca agttaata cgattatcgg cgggaagttt gtcaacgggg agaacacaaa    2940
gaggaagggc ataaatgagt acattaatct ctatagtcaa cagatcaatg acaagacgtt   3000
gaagaaaatac aagatgtcag tccttttcaa gcagatcctg tctgacacag aatcgaagag   3060
cttcgtgata gataagctgg aagatgattc cgacgttgtc acaaccatgc aatcgttta    3120
```

```
cgagcagatc gcggccttca agaccgttga ggagaagtct attaaagaga ctctttctct  3180
tctgtttgat gacttgaagg cccagaagct tgacttgtcc aagatctact tcaagaacga  3240
taaatctctg acagatctca gccagcaagt gtttgacgac tattctgtta tcggaacggc  3300
cgtgctggac tacatcacac agcagatcgc gcctaagaac cttgataatc cgagcaagaa  3360
agaacaggag ttgattgcaa agaagacaga gaaggccaaa tacctttctc tggagacaat  3420
taaacttgca ctggaagaat tcaataagca cagagatatc gacaagcagt gtcgctttga  3480
ggagatcctg gcaaattttg ctgccatccc aatgattttt gatgagattg cccagaacaa  3540
ggacaatctc gcgcagatat caatcaagta tcagaaccaa ggcaagaagg acctcctgca  3600
agcctcagcc gaagatgacg ttaaggccat aaaggatctc cttgatcaga ccaataactt  3660
gctgcacaag ctgaagatct ttcatatcga ccagtcggaa gacaaagcaa atatccttga  3720
caaggacgag catttctatc tggtgttcga agaatgctat ttcgagctgg ccaatatcgt  3780
gcctctgtac aataagatcc gcaattatat cacgcagaag ccgtatagcg acgagaagtt  3840
caagctgaat ttcgagaact ccaccttggc caatggttgg gataagaaca agaaccgga   3900
caatacggcc atcttgttta tcaaagatga caagtactat ctgggagtga tgaataagaa  3960
gaacaataag atcttcgatg acaaagccat taaggagaat aaaggggaag gttacaagaa  4020
gattgtctat aaactgctcc ccggggccaa caagatgctg cccaaagttt tttcagtgc   4080
caagagcatc aagttttata atccctcaga agacatactg agaatcagaa accactcgac  4140
ccatccaag  aacggctctc cgcagaaggg gtacgaaaa ttcgaattca acatcgaaga  4200
ctgtagaaag ttcatcgatt tttacaagca atcgatatca aagcaccctg aatggaagga  4260
ttttggttt cgctttagtg acactcagcg gtataatagc attgatgagt ctaccgcga   4320
agttgagaat cagggataca aattgacatt cgagaatatc agcgaatcgt acattgatag  4380
cgtcgtcaac caggggaaac tttacctctt ccagatttat aataaagact tctcggcgta  4440
ctccaaggga agaccaaatc ttcatactct gtattggaag gcactcttcg atgagagaaa  4500
tcttcaggat gtcgtttata aacttaatgg ggaagcggag ctgttctacc gcaagcgagg  4560
catccctaag aagatcacgc accccgcgaa ggaggcgata gccaataaga caaggataa   4620
cccgaagaag gagtccgtct tcgaaatatga cctgatcaag gataagagat tcactgagga  4680
caaattcttc ttccattgcc ctattacgat taattttaaa tcgagcggcg cgaataaatt  4740
caacgacgag atcaacctgc tcctcaaaga gaaggccaat gatgtccaca ttctctcaat  4800
cgacagaggg gagaggcacc ttgcctacta tacgctcgtt gatggtaaag gtaacatcat  4860
taagcgacac acgttcaaca tcatcggaa  cgaccgcatg aagacaaact atcacgataa  4920
attggcggca atcgagaagg atcgggatag tgccaggaag gactggaaga agattaataa  4980
catcaaggag atgaaggagg gatatctttc tcaagtcgtc cacgagatcg cgaagctggt  5040
tatcgagtac aacgccatag tggtcttcga agatctgaac ttcggattca agagagggag  5100
atttaaggtg gagaagcaag tttatcagaa actggagaag atgctgatag agaagctcaa  5160
ctacctcgtg tttaaagaca acgagtttga caagacaggt ggggtgttga gggcctatca  5220
gctcacggcc cccttcgaga ccttcaagaa gatgggaaag cagacgggga taatctacta  5280
cgtccctgct ggcttcactt cgaagatctg cccagttaca ggattcgtta accagttgta  5340
tcccaaatac gagtccgtct caaagtcaca agaattctttt tctaaattcg ataagatctg  5400
ctacaacctg gataagggct acttcgagtt tagctttgac tataagaatt tcggggacaa  5460
agcggcaaag gggaagtgga caatcgcaag ttttggctcc cggctgatta actttcggaa  5520
ttctgacaag aatcacaact gggatactag agaggtctat ccaactaaag agttggagaa  5580
gttgctcaag gactactcca ttgaatatgg tcacgggaa  tgcattaaag cggccatctg  5640
cggagagtcc gataagaagt tctttgccaa acttacatcg gtcttgaaca ccatactgca  5700
gatgcggaac agcaagacgg gaacggaact cgactacctt atctcacctg tggcggatgt  5760
taatggaaac tttttcgatt cgaggcaggc gcccaagaac atgccgcaag atgcagatgc  5820
caatggagca tatcacatcg gtcttaaagg gctcatgctg cttggccgca tcaagaacaa  5880
ccaagagggg aagaagttga acctggttat taagaaccgaa gaatacttcg aatttgtcca  5940
gaaccgcaac aacggatcta agaagcgtag gatcaagcaa gattgattaa ttaagggccc  6000
atccaagtaa attaagttgg atcagtagag atgcatggtt ggtgttctca tgtggtctga  6060
atctgtgttc tgtttcatct tttgtgtaag tgtgcaactt cgattctgta aaacttggca  6120
agtagatgaa cgatgtcatt tatatgcgtg tagcttgtca aaatacaaag tagaaacctg  6180
tatctgaata agatggcatt catgaaataa tattatcgat tgaacgaacg aagcaacaga  6240
atgatcttcc aaaattgaagc aaaggaattg atggacaacg agttgctgta ctttggagct  6300
gtaaatctgt agtacttctc aacgatgcta tggaccgtgg gccgtccata atcgctgggt  6360
ggaatgagcc cactgtccat gtgcttctgc atttggcccg tgtacagccc atataatgtc  6420
gaaaaaccta atacgcgcgc gccgccggcg cgcgtttcgg acccagaacg cctagcgccg  6480
ctgcgccgac gtgcgcgcgt ctccacttt tttttcgttt tctttccatt            6530
```

| SEQ ID NO: 72 | moltype = DNA length = 3960 |
|---|---|
| FEATURE | Location/Qualifiers |
| misc_feature | 1..3960 |
|  | note = Synthetic polynucleotide.NLS-FnCpf1-CO7-NLS |
| source | 1..3960 |
|  | mol_type = other DNA |
|  | organism = synthetic construct |

SEQUENCE: 72

```
ggtagcaaaa agaggcgtat caagcaggac atgtccatct atcaggaatt tgttaacaag   60
tactctctta gcaaaactct taggttcgaa ttgatacctc agggaaagac acttgagaat  120
attaaggcgc gcgggctgat acttgatgat gaaaagcggg caaggacta  taagaaagct  180
aagcaaataa ttgataagta ccaccagttt tttattgaag atcctgtc  ctccgttttgt  240
atatccgaag acttgcttca gaattactca gatgtttatt ttaaattgaa gaaatctgac  300
gatgataatc ttcaaaagga tttcaaatcg gcaaagaca  caatcaaaaa acagattagc  360
gagtacatca aggactccga aaagtttaag aatctctttta tcagaatct  tatagacgca  420
aagaaaggac aagaatcgga cttgattttg tggttgaaga gtccaagga taacgggata  480
gaactctttta aagccaactc cgatataacg gacatcgacg aagccctcga atcattaag  540
tcgtttaaag gttggaccac gtacttcaaa ggattccacg agaacagaaa gaacgtttac  600
tcgagcaaca acattcctac tagcatcata tatagaatag tggatgataa tttgcccaaa  660
ttccttgaga acaaggcaaa atatgaatcc ctgaaagaca aggcgcccga agctatcaac  720
tacgagcaga taaagaaaga tctggctgag gagctgacgt ttgacattga ttacaaaaca  780
```

-continued

```
agcgaggtca accagagggt tttttcgctg gacgaggttt ttgaaatagc gaattttaat    840
aactacctga accaatccgg catcactaaa tttaacacaa tcataggggg gaagttcgtg    900
aacggagaga acacaaagcg caaagggatt aatgagtaca tcaatttgta cagccagcag    960
atcaatgaca aaacgttgaa gaaatataag atgagcgtct tgtttaagca gattctctcg   1020
gatacggaat ccaaatcatt cgtcattgac aagctggagg atgacagcga tgtggtgaca   1080
actatgcagt ccttctatga acaaattgca gcttttaaaa cggtcgaaga gaagtcgatt   1140
aaagaaacgc tttcgctcct gttcgatgac ctgaaagcgc agaagctgga cctttcgaag   1200
atatatttca aaaacgataa gtcactcacg gaccttagcc aacaggtttt cgatgactat   1260
tctgtcatag ggactgctgt gcttgagtat attactcagc aaatagcccc caaaaacctg   1320
gacaacccgt ctaagaagga acaagagctg atagcgaaga aaacagagaa agctaaatat   1380
ctttcacttg aaactataaa gcttgcactg gaggaattca acaaacatcg cgacatcgac   1440
aagcagtgca gatttgagga gatcttggcc aacttcgcag ctattccaat gattttgac    1500
gagatagcac agaataagga caacctggca cagattagca taaaatacca gaatcagggg   1560
aagaaggatc ttcttcaggc ttcggctgag gacgatgtca aagccatcaa gatctgctc    1620
gaccagacca acaatttgtt gcataaactc aagatcttcc acatatcgca gtccgaagat   1680
aaagcgaaca tacttgacaa agacgaacat ttttatcttg ttttcgagga gtgttatttt   1740
gagttggcaa acatcgttcc cctctacaac aaaattcgca actatataac tcagaagccc   1800
tattctgacg agaaattcaa acttaatttc gaaaacagca ctctcgcaaa cggctgggat   1860
aaaaacaagg aacccgacaa caccgccata ctttttatta aggatgataa atattatttg   1920
ggcgtgatga ataaaaagaa caataaaata ttcgatgata agcaattaa ggaaaataaa    1980
ggggaagggt ataaaaaaat cgtgtataag ctgcttccag gagctaataa aatgctgcca   2040
aaagtcttct tctctgccaa gtcgatcaag ttttacaatc tcctgaaga tatttgcgg     2100
atcagaaatc actctactca cactaaaaac ggttcacccc agaaaggata cgagaagttt   2160
gagttcaaca tcgaagactg tcggaagttt atcgactttt acaagcagtc tatatcaaaa   2220
caccccgaat ggaaagattt tggttttcgg ttcagcgaca cgcagagata taattcaatt   2280
gatgagttct acagggaggt ggagaaccaa gggtataaac ttacttttga gaacatttcc   2340
gaatcctata ttgattcggt ggtcaatcag gggaaactgt acctgtttca gatatataac   2400
aaagacttct ccgcgtattc taaggacgg cccaatctcc atactcttta ttggaaggcg    2460
ctgtttgacg agcggaacct tcaggatgtt gtctataagt tgaacgggga agctgagctg   2520
ttctatcgga agcagtctat tccaaaaaag ataacgcacc ccgcgaagga ggcaattgca   2580
aacaagaaca aagacaatcc aaagaaggag tcggtgtttg agtacgatct gataaaagac   2640
aaaaggttta ccgaggacaa gttttttttc cactgtccga tcaccatcaa ttttaagtct   2700
tccgcgccca acaaattcaa tgacgaaata aatctgctgc tcaaggaaaa ggcaaatgat   2760
gttcatattc tgtcgataga ccgcgggga agacacctcg cgtattatac attggtcgat   2820
gggaaaggca atattatcaa acaagacacc ttcaatatca ttggtaacga taggatgaaa   2880
acgaactatc atgataaact tgcagctatt gaaaaggaca gagactcggc tcggaaagat   2940
tggaaaaaga tcaataacat caaggaaatg aaggaagggt atctctccca ggtcgttcat   3000
gaaatcgcca aactggttat tgagtacaat gctatagtgg ttttttgaaga tcttaattt   3060
gggtttaaga gagggagatt taaagtcgag aaacaggttt atcaaaaact tgaaaaaatg   3120
ttgatagaaa aattgaacta tcttgtgttt aaggacaatg agttcgataa aaccgggggg   3180
gttttgagag cttatcaact gacggctccc ttcgagacat tcaaaaaaat ggggaagcag   3240
accggcatca tttattatgt gcccgcgggc ttcacttcta aaatttgtcc tgtgacaggg   3300
ttcgtgaacc aattgtaccc caagtacgaa agcgtctcca gtcccaaga attcttttagc   3360
aagtttgaca aaatttgcta taacctggac aaagggtact tgagttttc ctttgattat    3420
aagaatttcg gggataaagc tgcgaaaggt aagtggacga tagcctcttt cgggtcgcgc   3480
cttattaact tcaggaattc cgacaaaaac cataattggg acaccgcga ggtctaccct    3540
acaaaggaac tcgaaaagtt gcttaaggat tattcaatag atatggtca tggcgagtgt    3600
attaaggctg ctatctgtgg tgagtcagat aagaaattct tcgcgaaatt gacatctgtt   3660
ttgaacacca tcctccaaat gaggaactct aaaacgggga cggagcttga ttatctcatc   3720
tcacccgttg ctgatgtgaa cggtaatttc tttgattcac gccaagcccc gaagaacatg   3780
ccccaagacg ccgatgctaa cggcgcttat catatagggt tgaaggggct catgcttctga  3840
gggcgcatca aaaataacca agaagggaag aaactcaatc tggttatcaa aaatgaggaa   3900
tatttcgaat tcgtgcaaaa ccgcaacaat ggatctaaga agcgtaggat caagcaagat   3960
```

```
SEQ ID NO: 73        moltype = DNA   length = 6530
FEATURE              Location/Qualifiers
misc_feature         1..6530
                     note = Synthetic polynucleotide.Expression cassette
                     comprising Zea maysUbiquitin promoter cassette,
                     NLS-FnCpf1-CO7-NLS and an Oryzasativa transcription
                     termination sequence
source               1..6530
                     mol_type = other DNA
                     organism = synthetic construct
SEQUENCE: 73
gtcgtgcccc tctctagaga taaagagcat gcatgtcta aagtataaaa aattaccaca     60
tattttttg tcacacttat ttgaagtgta gtttatctat ctctatacat atatttaaac    120
ttcactctac aaataatata gtctataata ctaaaataat attagtgttt tagaggatca   180
tataaataaa ctgctagaca tggtctaaag gataattgaa tattttgaca atctacagtt   240
ttatcttttt agtgtgcatg tgatctctct gtttttttg caaatagctt gacctatata    300
atacttcatc cattttatta gtacatccat ttaggattta gggttgatgg tttctataga   360
ctaattttta gtacatccat tttattcttt ttagtctcta aattttttaa aactaaaact   420
ctatttttagt tttttattta ataatttaga tataaaatga aataaaataa attgactaca   480
aataaaacaa ataccctta agaaatataa aaactaagca acattttt ttgtttcgaa      540
tagataatga caggctgttc aacgccgtcg acgagtctaa cggacaccaa ccagcgaacc   600
agcagcgtcg cgtcgggcca agcgaagcag acggcacggc atctgctag ctgcctctgg    660
accccctctcg agagttccgc tccacgttg gacttgctcc gctgtcggca tccagaaatt   720
gcgtggcgga gcggcagacg tgaggcggca cggcaggcgg cctcttcctc ctctcacggc   780
accggcagct acggggggatt cctttcccac cgctccttcg ctttccccttc ctcgcccgcc  840
```

```
gtaataaata gacacccct ccacaccctc tttccccaac ctcgtgttcg ttcggagcgc    900
acacacacgc aaccagatct cccccaaatc cagccgtcgg cacctccgct tcaaggtacg    960
ccgctcatcc tccccccccc cctctctcta ccttctctag atcggcgatc cggtccatgg   1020
ttagggcccg gtagttctac ttctgttcat gtttgtgtta gagcaaacat gttcatgttc   1080
atgtttgtga tgatgtggtc tggttgggcg gtcgttctag atcggagtag gatactgttt   1140
caagctacct ggtggattta ttaattttgt atctgtatgt gtgtgccata catcttcata   1200
gttacgagtt taagatgatg gatggaaata tcgatctagg ataggtatac atgttgatgc   1260
gggttttact gatgcatata cagagatgct ttttttctcg cttggttgtg atgatatggt   1320
ctggttgggc ggtcgttcta gatcggagta gaatactgtt tcaaactacc tggtggattt   1380
attaaaggat aaagggtcgt tctagatcgg agtagaatac tgtttcaaac tacctggtgg   1440
atttattaaa ggatctgtat gtatgtgcct acatcttcat agttacgagt ttaagatgat   1500
ggatggaaat atcgatctag gataggtata catgttgatg cgggttttac tgatgcatat   1560
acagagatgc ttttttctcg cttggttgtga tgatgtggtc tggttgggcg gtcgttctag   1620
atcggagtag aatactgttt caaactaccc ggtggattta ttaattttgt atctttatgt   1680
gtgtgccata catcttcata gttacgagtt taagatgatg gatggaaata ttgatctagg   1740
ataggtatac atgttgatgt gggttttact gatgcatata catgatggca tatgcggcat   1800
ctattcatat gctctaacct tgagtaccta tctattataa taaacaagta tgttttataa   1860
ttattttgat cttgatatac ttggatgatg gcatatgcag catgtcatatg tggattttt   1920
agccctgcct tcatacgcta tttatttgct tggtactgtt tcttttgtcc gatgctcacc   1980
ctgttgttgg gtgatacttc tgcagcggac cgacggtacc atgggtagca aaagaggcg   2040
tatcaagcag gacatgtcca tctatcagga atttgttaac aagtactctc ttagcaaaac   2100
tcttaggttc gaattgatac ctcagggaaa gacacttgaa aatattaagg cgcgcgggct   2160
gatacttgat gatgaaaagc gggcaaagga ctataagaaa gctaagcaaa taattgataa   2220
gtaccaccag tttttttattg aagagatcct gtcctccgtt tgtatatccg aagacttgct   2280
tcagaattac tcagatgttt attttaaatt gaagaaatct gacgatgata tcttcaaaa   2340
ggatttcaaa tcggcaaaag acacaatcaa aaaacagatt agcgagtaca tcaaggactc   2400
cgaaaagttt aagaatctct ttaatcagaa tcttatagac gcaaagaaag gacaggaatc   2460
ggacttgatt ttgtggttga agcagtccaa ggataacggg atagaactct ttaaagccaa   2520
ctccgatata acggacatcg acgaagccct cgaaatcatt aagtcgttta aaggttggac   2580
cacgtacttc aaaggattcc actgaacag aagaaccgtt tactccgagca acgacattcc   2640
tactagcatc atatatagaa tagtggatga taatttgccc aaattccttg agaacaaggc   2700
aaaaatatgaa tccctgaaag caaggcgcc cgaagctatc aactacgagc agataaagaa   2760
agatctggct gaggagctga cgtttgacat tgattacaaa acaagcgagg tcaaccagag   2820
ggttttttcg ctggacgagg tttttgaaat agcgaatttt aataactacc tgaaccaatc   2880
cggcatcact aaatttaaca caatcatagg ggggaagttc gtgaacggag agaacacaaa   2940
gcgcaaaggg attaatgagt acatcaattt gtacagccag cagatcaatg acaaaacgtt   3000
gaagaaatat aagatgagcg tcttgtttaa gcagattctc tcggatacgg aatccaaatc   3060
attcgtcatt gacaagctgg aggatgacag cgatgtggtg acaactatgc agtccttcta   3120
tgaacaaatt gcagctttta aaacggtcga agagaagtcg attaaagaaa cgctttcgct   3180
cctgttcgat gacctgaaag cgcagaagct ggaccttcg aagatatatt tcaaaacga   3240
taagtcactc acggaccta gccaacaggt tttcgatgac tattctgtca tagggactgc   3300
tgtgcttgag tatattactc agcaaatagc ccccaaaaac ctggacaacc cgtctaagaa   3360
ggaacaagag ctgatagcga agaaaacaga gaaagctaaa tatctttcac ttgaaactat   3420
aaagcttgca ctggaggaat tcaacaaaca tcgcgacatc gacaagcagt gcagatttga   3480
ggagatcttg gccaacttcg cagctattcc aatgattttt gacgagatag cacagaataa   3540
ggacaacctg gcacagatta gcataaaata ccagaatcag gggaagaagg atcttcttca   3600
ggcttcggct gaggacgatg tcaaagccat caaagatctg ctcgaccaga ccaacaattt   3660
gttgcataaa ctcaagatct tccacatatc gcagtccgaa gataaagcga acatacttga   3720
caaagacgaa cattttttatc ttgttttcga ggagtgttat tttgagttgg caaacatcgt   3780
tccctctac aacaaaattc gcaactatat aactcagaag ccctattctg acgagaaatt   3840
caaacttaat ttcgaaaaca gcactctcgc aaacgctgg gataaaaca aggaacccga   3900
caacaccgcc atacttttta ttaaggatga taaatattat ttgggcgtga tgaataaaaa   3960
gaacaataaa atattcgatg ataaagcaat taaggaaaat aaaggggaag gtataaaaaa   4020
aatcgtgtat aagctgcttc caggagctaa taaaatgctg ccaaaagtct tcttctctgc   4080
caagtcgatc aagtttttaca atccttctga agatattttg cggatcagaa atcactctac   4140
tcacactaaa aacggttcac cccagaaagg atacgagaag tttgagttca acatcgaaga   4200
ctgtcggaag tttatcgact tttacaagca gtctatatca aaacacccg aatggaaga   4260
tttttggtttt cggttcagcg acagcgagag atataattca attgatgagt ctacaggga   4320
ggtggagaac caagggtata aacttacttt tgagaacatt tccgaatcct atattgattc   4380
ggtggtcaat caggggaaac tgtacctgtt tcagatatat aacaaagact tctccgcta   4440
ttctaaagga cggcccaatc tccatactct ttattggaag gcgctgtttg acgagcggaa   4500
ccttcaggat gttgtctata gttgaacgg ggaagctgag ctgttctatc ggaagcagtc   4560
tattccaaaa aagataacgc acccccgcaa ggaggcaatt gcaaacaaga acaaagacaa   4620
tccaaagaag gagtcggtgt ttgagtacga tcagataaa gacaaaggt ttaccgagga   4680
caagttttttt ttccactgtc cgatcaccat caatttttaag tcttccggcg ccaacaaatt   4740
caatgacgaa ataaatctgc tgctcaagga aaaggcaaat gatgttcata ttctgtcgat   4800
agaccgcggg gaaagacacc tcgcgtatta cattggtc gatgggaaag gcaatattat   4860
caaacaagac accttcaata tcattggtaa cgataggat aaaacgaact atcatgataa   4920
acttgcagct attgaaaagg acagactc ggctcggaaa gattgaaaa agataactaa   4980
catcaaggaa atgaaggaag ggtatctctc ccaggtcgtt catgaaatcg ccaaactggt   5040
tattgagtac aatgctatag tggttttttga agatcttaat tttgggttta agagagggag   5100
atttaaagtc gagaaacagg tttatcaaaa acttgaaaaa atgttgatag aaaaattgaa   5160
ctatcttgtg tttaaggaca atgagttcga taaaccgggg ggggttttga gagcttatca   5220
actgacggct cccttcgaga cattcaaaaa aatgggggaag cagaccggca tcatttatta   5280
tgtgcccgcg ggcttcactt ctaaaatttg tcctgtgaca gggttcgtga accaattgta   5340
ccccaagtac gaaagcgtct ccaagtccca agaattcttt agcaagtttg acaaaatttg   5400
ctataacctg gacaaagggt actttgagtt ttccttttgat tataagaatt cggggataa   5460
agctgcgaaa ggtaagtgga cgatagcctc tttcgggtcg cgccttatta acttcaggaa   5520
ttccgacaaa accataatt gggacacccg cgaggtctac cctacaaagg aactcgaaaa   5580
```

```
gttgcttaag gattattcaa tagagtatgg tcatggcgag tgtattaagg ctgctatctg    5640
tggtgagtca gataagaaat tcttcgcgaa attgacatct gttttgaaca ccatcctcca    5700
aatgaggaac tctaaaacgg ggacggagct tgattatctc atctcacccg ttgctgatgt    5760
gaacggtaat ttctttgatt cacgccaagc cccgaagaac atgccccaag acgccgatgc    5820
taacggcgct tatcatatag ggctgaaggg gctcatgctt ctggggcgca tcaaaaataa    5880
ccaagaaggg aagaaactca atctggttat caaaaatgag gaatatttcg aattcgtgca    5940
aaaccgcaac aatggatcta agaagcgtag gatcaagcaa gattgattaa ttaagggccc    6000
atccaagtaa attaagttgg atcagtagag atgcatggtt ggtgttctca tgtggtctga    6060
atctgtgttc tgtttcatct tttgtgtaag tgtgcaactt cgattctgta aaacttggca    6120
agtagatgaa cgatgtcatt tatatgcgtg tagcttgtca aaatacaaag tagaaacctg    6180
tatctgaata agatggcatt catgaaataa tattatcgat tgaacgaacg aagcaacaga    6240
atgatcttcc aaattgaagc aaaggaattg atggacaacg agttgctgta ctttggagct    6300
gtaaatctgt agtacttctc aacgatgcta tggaccgtgg gccgtccata atcgctgggt    6360
ggaatgagcc cactgtccat gtgcttctgc atttggccg tgtacagccc tataatgtc     6420
gaaaaaccta atacgcgcgc gccgccggcg cgcgtttcgg acccagaacg cctagcgccg    6480
ctgccgccgac gtgcgcgcgt ctccactttt tttttcgttt tctttccatt              6530

SEQ ID NO: 74          moltype = DNA  length = 6062
FEATURE                Location/Qualifiers
misc_feature           1..6062
                       note = Synthetic polynucleotide.Expression cassette
                       comprising Zea maysUbiquitin promoter cassette,
                       NLS-LbCpf1-CO2-NLS and an Oryzasativa transcription
                       termination sequence
source                 1..6062
                       mol_type = other DNA
                       organism = synthetic construct
SEQUENCE: 74
gtcgtgcccc tctctagaga taaagagcat tgcatgtcta aagtataaaa aattaccaca      60
tatttttttg tcacacttat ttgaagtgta gtttatctat ctctatacat atatttaaac     120
ttcactctac aaataatata gtctataata ctaaaataat attagtgttt tagaggatca     180
tataaataaa ctgctagaca tggtctaaag gataattgaa tattttgaca atctacagtt     240
ttatcttttt agtgtgcatg tgatctctct gttttttttg caaatagctt gacctatata     300
atacttcatc cattttatta gtacatccat ttaggattag gggtgatgg tttctataga     360
ctaattttta gtacatccat tttattcttt ttagtctcta aatttttaa aactaaaact     420
ctattttagt tttttattta ataatttaga tataaaatga aataaaataa attgactaca     480
aataaaacaa atacccttta agaaatataaa aaactaagca acattttttc ttgtttcgag     540
tagataatga caggctgttc aacgccgtcg acgagtctaa cggacaccaa ccagcgaacc     600
agcagcgtcg cgtcgggcca agcgaagcag acggcacggc atctcgtag ctgcctctga     660
accctctcg agagttccgc tccaccgttg gacttgctcc gctgtcggca tccagaaatt     720
gcgtggcgga gcggcagacg tgaggcggca cggcaggcgg cctcttcctc ctctcacggc     780
accggcagct acggggatt cctttcccac cgctccttcg cttcccttc ctcgcccgcc     840
gtaataaaata gacaccccct ccacaccctc tttcccaac ctcgtgttcg ttcggagcgc    900
acacacacgc aaccagatct ccccccaaatc cagccgtcgg cacctccgct tcaaggtacg     960
ccgctcatcc tcccccccccc cctctctcta ccttctctag atcggcgatc cggtccatgg    1020
ttagggcccg gtagttctac ttctgttcat gttttgtgtta gagcaaacat gttcatgttc    1080
atgtttgtga tgatgcggtc tggttgggcg gtcgtttcta atcggagtgt gatactgttt    1140
caagctacct ggtggattta ttaattttgt atctgtatgt gtgtgccata catcttcata    1200
gttacgagtt taagatgatg gatggaaata tcgatctagg ataggtatac atgttgatgc    1260
gggttttact gatgcatata cagagatgct ttttttctcg cttggttgtg atgatatggt    1320
ctggttgggc ggtcgttcta gatcggagta gaatactgtt tcaaactacc tggtggattt    1380
attaaaggat aaagggtcgt tctagatcgg agtagaatac tgtttcaaac tacctggtgg    1440
atttattaaa ggatcgtgtat gtatgtgcct acatcttcat agttacgagt taagatgat    1500
ggatggaaat atcgatctag ataggtata catgttgatg cgggttttac tgatgcatat    1560
acagagatgc tttttttcgc ttggttgtga tgatgtgcg tggttgggcg gtcgttctag    1620
atcggagtag aatactgttt caaactacct ggtggattta ttaattttgt atctttatgt    1680
gtgtgccata catcttcata gttacgagtt taagatgatg gatggaaata ttgatctagg    1740
ataggtatac atgttgatgt gggttttact gatgcatata catgatggca tatgcggcat    1800
ctattcatat gctctaacct tgagtaccta tctattataa taaacaagta tgttttataa    1860
ttatttgat cttgatatac ttggatgatg gcatatgcag cagctatatg tggattttt    1920
agccctgcct tcatacgcta tttatttgct tggtactgtt tcttttgtcc gatgctcacc    1980
ctgttgtttg gtgatacttc tgcaggtcgc gccatggcg ggatctaaga agagaagaat    2040
taaacaagat tcgaagctcg agaagttcac caactgctac tcgctgagca agacgctgcg    2100
gttcaaggcg atcccgtcg ggaagcccca ggagaacatc gacaacaagc ggctcctgta    2160
cgaggacgag aagcgcgcc aggactacaa gggcgtcaag aagctgctgg accggtacta    2220
cctctccttc atcaacgacg tcctgcactc gatcaagctc aagaacctga caactacat    2280
ctcgctgttc cgcaagaaga cacggaccga gaaggagaac aaggagctcg agaacctcga    2340
gatcaacctg cgcaaggaga tcgcgaaggc gttcaagggc aacgagggt caagagcct    2400
gttcaagaaa gacatcatcg agaccatcct gccggagttc ctggacgaca aggacgagat    2460
cgcgctggtg aactcgttca acgggttcac cacggccttc accggttttt tcgacaaccg    2520
ggagaacatg ttcagcgagg aggccaagtc gaccagcatc gccttccggt gcatcaacga    2580
gaacctcacc cgctacatca gcaacatgga catcttcgag aaggtggacg ccatcttcga    2640
caagcacgag gtccaggaga tcaaggaaaa gatcctgaac tcggactacg acgtggaaga    2700
cttctttgag gcgagttct caacttcgt cctcacccag gaggcatcg acgtctacaa    2760
cgccatcatc ggcggcttcg tgacggagag cggcgagaag atcaagggcc tcaacgagta    2820
catcaaccta tacaaccaga gactaagca aagctcccg aagttcaagc cgctgtacaa    2880
gcaagtcctg agcgaccggg agtccctctc gttctacggc gagggctacac cgagcgacga    2940
ggaggtgctg gaggtgttcc gcaacacgct gaacaagaac agcgagatct tcagctcgat    3000
caagaaactc gagaagctgt tcaagaactt cgacgagtac agcagcgccg gcatcttcgt    3060
```

```
caagaacggg cccgcgatca gcaccatcag caaggacatc ttcggggagt ggaacgtgat 3120
ccgcgacaag tggaacgccg agtacgacga catccacctc aagaaaaagg cggtggtcac 3180
ggagaagtac gaggacgacc gccggaagtc cttcaagaaa atcgggagct tcagcctcga 3240
gcagctccag gagtacgcgg acgccgacct gagcgtggtg gagaagctca aggagatcat 3300
catccagaag gtcgacgaga tctacaaggt ctacggctcg agcgagaagc tgttcgacgc 3360
ggacttcgtg ctggagaagt ccctcaagaa gaacgacgcc gtggtggcca tcatgaagga 3420
tctgctcgac agcgtgaagt cgttcgagaa ctacatcaag gcattctttg ggagggcaa 3480
ggagacgaac cgggacgagt ccttctacgg ggacttcgtg ctcgcgtacg acatcctcct 3540
gaaggtcgac cacatctacg acgcgatccg gaactacgtc gcagaagcc cctacagcaa 3600
ggacaagttc aagctctact tccagaaccc gcagttcatg ggcgggtggg acaaggacaa 3660
ggagaccgac taccgggcca cgatcctgcg gtacgggtcc aagtactacc tcgccatcat 3720
ggacaagaag tacgccaagt gcctccagaa gattgacaag gacgacgtga acgggaacta 3780
cgagaagatc aactacaagc tcctcccggg gcccaacaag atgctgccga aggtgttctt 3840
cagcaagaag tggatggcct actacaaccc ctcggaggca atccagaaga tatacaagaa 3900
cggcacgttc aaaaggggg acatgttcaa cctgaacgac tgccacaagc tgatcgactt 3960
tttcaaggac agcatcagcc gctacccgaa gtggtcgaac gcctacgact caacttctc 4020
ggagacggag aagtacaagg acattgcggg cttctaccgg gaggtggagg agcagggcta 4080
caaggtctcc ttcgagagcg cctccaagaa agaggtggac aagctcgtgg aggagggcaa 4140
gctgtacatg ttccagatct acaacaagga cttctcggac aagtcgcacg gcaccccgaa 4200
cctccacacg atgtacttca agctgctgtt cgacgagaac aaccacgggc agatccgcct 4260
cagcggcggg gcggagctgt tcatgcgccg cgcgtccctc aagaaggagg agctggtcgt 4320
gcaccccgcc aactccccga tcgcaacaa gaaccccgac aaccccaaga agacaaccac 4380
cctctcgtac gacgtctaca aggacaagcg gttctcggag gaccagtacg agctgcacat 4440
cccgatcgcc atcaacaagt gccccaagaa catcttcaag atcaacaccg aggtgcgggt 4500
gctgctcaag cacgacgaca cccctacg catcgggatc gaccgcggcg agcggaacct 4560
gctctacatc gtggtcgtgg acgggaaggg gaacatcgtg gcagtaca gctgaacga 4620
gatcatcaac aacttcaacg gcatccgcat caagacggga taccacagcc tcctggacaa 4680
gaaggagaag gagcggttcg aggcgcggca gaactggacc tccatcgaga acatcaagga 4740
gctgaaggcc ggctacatca gccaggtcgt gcacaagatc tgcgagctcg tggagaagta 4800
cgacgcgggtg atcgcgctgg aggacttgaa cagcggggttc agaactccc gggtcaaggt 4860
cgagaagcag gtctaccaga agttcgagaa gatgctgatc gacaagctca actacatggt 4920
ggacaagaag tccaaccct gcgccaccgg cggcgccctc aagggctacc agatcaccaa 4980
caagttcgag tccttcaagt cgatgtctac gcagaacggg ttcattttct catcccggc 5040
gtggctcacc agcaagatcg acccgagcac ggggcttcgtc aacctcctga agaccaagta 5100
caccagcatc gcggacagca agaagttcat ctcctcgttc gaccgcatca tgtacgtccc 5160
cgaggaaagac ctgttcgagt tcgccctcga ctacaagaac tttctcccgga cggacgccga 5220
ctacatcaaa aagtggaagc tctacagcta cggcaaccgg atccgcatct tccgcaaccc 5280
caagaagaac aatgtgttcg actggggagga ggtgtgcctg acgagcgcct acaaggagct 5340
cttcaacaag tacggcatca actaccagca agggagcaagatg cgcgcgctgc tctgcgagca 5400
gtccgacaag gcgttctact cgtcgttcat ggccctgatg agcctcatgc tccagatgcg 5460
caacagcatc accggccgga cggacgtgga cttcctgatc agcccggtca gaacagcga 5520
cggcattttc tacgacagcc ggaactacga ggcccaggag aacgccatcc tcccaagaa 5580
cgccgacgcg aacggcgcct acaacatcgc gcggaaggtg ctgtgggcca tcggccaagt 5640
taaaaaggcg gaggacgaga agctggacaa ggtcaagatc gccatcagca acaaggagtg 5700
gctcgagtac gcgcagacga gcgtgaagca cggatctaag aagagaagaa ttaaacaaga 5760
ttgataatcg atcctccgat ccttaattta ccataccatt acaccatgca tcaatatcca 5820
tatatatat aaccctttcg cacgtactta tactatgttt tgtcatacat atatgtgt 5880
cgaacgatcg atctatcact gatatgatat gattgatcca tcagcctgat ctctgtatct 5940
tgttatttgt ataccgtcaa ataaaagttt cttccacttg tgttaataat tagctactct 6000
catctcatga accctatata taactagttt aatttgctgt caattgaaca tgatgatcga 6060
tg 6062
```

SEQ ID NO: 75           moltype = DNA   length = 3684
FEATURE                 Location/Qualifiers
misc_feature            1..3684
                        note = Synthetic polynucleotide.Codon optimized
                        LbCpf1(TAT)- CO2
source                  1..3684
                        mol_type = other DNA
                        organism = synthetic construct
SEQUENCE: 75

```
atgtcgaagc tcgagaagtt caccaactgc tactcgctga gcaagacgct gcggttcaag    60
gcgatccccg tcgggaagac ccaggagaac atcgacaaca gcggctcct ggtcgaggac    120
gagaagcgcc ccgaggacta caagggcgtc aagaagctgc tggaccggta ctacctctcc    180
ttcatcaacg acgtcctgca ctcgatcaag ctcaagaacc tgaacaacta catctcgctg    240
ttccgcaaga agacacggac cgagaaggag aacaaggagc tcgagaacct cgagatcaac    300
ctgcgcaagg agatcgcgaa ggcgttcaag gcaacgagg gtacaagag cctgttcaag    360
aaagacatca tcgagaccat cctgccggag ttcctggaca caaggacga gatcgcgctg    420
gtgaactcgt tcaacgggtt caccacggcc ttcaccgggt ttttcgacaa ccggggagaac    480
atgttcagcg aggaggccaa gtcgaccagc atcgccttcc ggtgcatcaa cgagaacctc    540
acccgctaca tcagcaacat ggacatcttc gagaaggtgg acgccatctt cgacaagcac    600
gaggtccagg agatcaagga aagatcctg aactcggact cgacgtgga gactttcttt    660
gagggcgagt cttcaactt cgtcctcacc caggaggca tcgacgtcta caacgccatc    720
atcggcggct tcgtgacgga gagcggcgag aagatcaag gcctcaacga gtacatcaac    780
ctctacaacc agaagactaa gcagaagctc ccgaagttca gccgctgta caagcaagtc    840
ctgagcgacc gggagtccct tcgttctac ggcgaggct acacgagcga cgaggagtg    900
ctggaggtgt ccgcaacac gctgaacaag acagcgaga tcttcagctc gatcaagaaa    960
ctcgagaagc tgttcaagaa cttcgacgag tacagcagcc ccggcatctt cgtcaagaac    1020
gggcccgcga tcagcaccat cagcaaggac atcttcgggg agtggaacgt gatccgcgac    1080
```

```
aagtggaacg ccgagtacga cgacatccac ctcaagaaaa aggcggtggt cacggagaag   1140
tacgaggacg accgccggaa gtccttcaag aaaatcggga gcttcagcct cgagcagctc   1200
caggagtacg cggacgccga cctgagcgtg gtggagaagc tcaaggagat catcatccag   1260
aaggtcgacg agatctacaa ggtctacggc tcgagcgaga gctgttcga cgcggacttc   1320
gtgctggaga agtccctcaa gaagaacgac gccgtgtgg ccatcatgaa ggatctgctc   1380
gacagcgtga agtcgttcga gaactacatc aaggcattct ttggggaggg caaggagacg   1440
aaccgggacg agtccttcta cggggacttc gtgctcgcgt acgacatcct cctgaaggtc   1500
gaccacatct acgacgcgat ccggaactac gtcacgcaga agcccacag caaggacaag   1560
ttcaagctct acttccagaa cccgcagttc atgcgcgggt gggacaagga cgtggagaag   1620
gaccgccggg ccacgatcct gcggtacggg tccaagtact acctcgccat catggacaag   1680
aagtacgcca agtgcctcca gaagattgac aaggacgacg tgaacgggaa ctacgagaag   1740
atcaactaca agctcctccc ggggcccaac aagatgctgc cgaaggtgtt cttcagcaag   1800
aagtggatgg cctactacaa ccctcggag gacatccaga agatatacaa gaacggcacg   1860
ttcaaaaagg gggacatgtt caacctgaac gactgccaca agctgatcga ctttttcaag   1920
gacagcatca gccgctaccc gaagtggtcg aacgcctacg acttcaactt ctcggagacg   1980
gagaagtaca aggacattgc gggcttctac cgggaggtgg aggagcaggg ctacaaggtc   2040
tccttcgaga gcgcctccaa gaaagaggtg gacaagctcg tggaggaggg caagctgtac   2100
atgttccaga tctacaacaa ggacttctcg gacaagtcgc acggcacccc gaacctccac   2160
acgatgtact tcaagctgct gttcgacgag aacaaccacg ggcagatccg cctcagcggc   2220
ggggcggagc tgttcatgcg ccgcgcgtcc ctcaagaagg aggagctggt cgtgcacccc   2280
gccaactccc cgatcgcgaa caagaacccc gacaacccca gaagacaac caccctctcg   2340
tacgacgtct acaaggacaa gcggttctcg gaggaccgat acgagctgca catcccgatc   2400
gccatcaaca agtgccccaa gaacatcttc aagatcaaca ccgaggtgcg ggtgctgctc   2460
aagcacgacg acaaccccta cgtcatcggg atcgaccgcg gcgagcggaa cctgctctac   2520
atcgtggtcg tggacgggaa ggggaacatc gtggagcagt acagcctgaa cgagatcatc   2580
aacaacttca acggcatccg catcaagacg gactaccaca gcctcctgga caagaaggag   2640
aaggagcggt tcgaggcgcg gcagaactgg acctccatcg agaacatcaa ggagctgaag   2700
gccggctaca tcagccaggt cgtgcacaag atctgcgagc tcgtggagaa gtacgacgcg   2760
gtgatcgcgc tggaggactt gaacagcggg ttcaagaact cccgggtcaa ggtcgagaag   2820
caggtctacc agaagttcga gaagatgctg atcgacaagc tcaactacat ggtggacaag   2880
aagtccaacc cctgcgccac cggcggcgcc ctcaagggct accagatcac caacaagttc   2940
gagtccttca gtcgatgtc tacgcagaac gggttcattt tctacatccc ggcgtggctc   3000
accagcaaga tcgacccgag cacgggcttc gtcaacctcc tgaagaccaa gtacaccagc   3060
atcgcggaca gcaagaagtt catctcctcg ttcgaccgca tcatgtacgt ccccgaggaa   3120
gacctgttcg agttcgccct cgactacaag aacttctccc ggacggacgc cgactacatc   3180
aaaaagtgga agctctacag ctacggcaac cggatccgca tcttccgcaa ccccaagaag   3240
aacaatgtgt tcgactggga ggaggtgtgc ctgacgagcg cctacaagga gctcttcaac   3300
aagtacggca tcaactacca gcaagggac atccgcgcgc tgctctgcga gcagtccgac   3360
aaggcgttct actcgtcgtt catggccctg atgagcctca tgctccagat gcgcaacagc   3420
atcaccggcc ggacggacgt ggacttcctg atcagcccgg tcaagaacag cgacggcatt   3480
ttctacgaca gccggaacta cgaggcccag gagaacgcca tcctcccaa gaacgccgac   3540
gcgaacggcg cctacaacat cgcgggaag gtgctgtggg ccatcggcca gtttaaaaag   3600
gcggaggacg agaagctgga caaggtcaag atcgccatca gcaacaagga gtggctcgag   3660
tacgcgcaga cgagcgtgaa gcac                                          3684

SEQ ID NO: 76          moltype = AA   length = 1228
FEATURE                Location/Qualifiers
REGION                 1..1228
                       note = Synthetic polypeptide.LbCpf1(TAT)-CO2
                       comprisingG532R/K538V/Y542R substitutions
source                 1..1228
                       mol_type = protein
                       organism = synthetic construct
SEQUENCE: 76
MSKLEKFTNC YSLSKTLRFK AIPVGKTQEN IDNKRLLVED EKRAEDYKGV KKLLDRYYLS    60
FINDVLHSIK LKNLNNYISL FRKKTRTEKE NKELENLEIN LRKEIAKAFK GNEGYKSLFK   120
KDIIETILPE FLDDKDEIAL VNSFNGFTTA FTGFFDNREN MFSEEAKSTS IAFRCINENL   180
TRYISNMDIF EKVDAIFDKH EVQEIKEKIL NSDYDVEDFF EGEFFNFVLT QEGIDVYNAI   240
IGGFVTESGE KIKGLNEYIN LYNQKTKQKL PKFKPLYKQV LSDRESLSFY GEGYTSDEEV   300
LEVFRNTLNK NSEIFSSIKK LEKLFKNFDE YSSAGIFVKN GPAISTISKD IFGEWNVIRD   360
KWNAEYDDIH LKKKAVVTEK YEDDRRKSFK KIGSFSLEQL QEYADADLSV VEKLKEIIIQ   420
KVDEIYKVYG SSEKLFDADF VLEKSLKKND AVVAIMKDLL DSVKSFENYI KAFFGEGKET   480
NRDESFYGDF VLAYDILLKV DHIYDAIRNY VTQKPYSKDK FKLYFQNPQF MRGWDKDVET   540
DRRATILRYG SKYYLAIMDK KYAKCLQKID KDDVNGNYEK INYKLLPGPN KMLPKVFFSK   600
KWMAYYNPSE DIQKIYKNGT FKKGDMFNLN DCHKLIDFFK DSISRYPKWS NAYDFNFSET   660
EKYKDIAGFY REVEEQGYKV SFESASKKEV DKLVEEGKLY MFQIYNKDFS DKSHGTPNLH   720
TMYFKLLFDE NNHGQIRLSG GAELFMRRAS LKKEELVVHP ANSPIANKNP DNPKKTTTLS   780
YDVYKDKRFS EDQYELHIPI AINKCPKNIF KINTEVRVLL KHDDNPYVIG IDRGERNLLY   840
IVVVDGKGNI VEQYSLNEII NNFNGIRIKT DYHSLLDKKE KERFEARQNW TSIENIKELK   900
AGYISQVVHK ICELVEKYDA VIALEDLNSG FKNSRVKVEK QVYQKFEKML IDKLNYMVDK   960
KSNPCATGGA LKGYQITNKF ESFKSMSTQN GFIFYIPAWL TSKIDPSTGF VNLLKTKYTS  1020
IADSKKFISS FDRIMYVPEE DLFEFALDYK NFSRTDADYI KKWKLYSYGN RIRIFRNPKK  1080
NNVFDWEEVC LTSAYKELFN KYGINYQQGD IRALLCEQSD KAFYSSFMAL MSLMLQMRNS  1140
ITGRTDVDFL ISPVKNSDGI FYDSRNYEAQ ENAILPKNAD ANGAYNIARK VLWAIGQFKK  1200
AEDEKLDKVK IAISNKEWLE YAQTSVKH                                    1228
```